(12) United States Patent
Zhang et al.

(10) Patent No.: US 10,189,819 B2
(45) Date of Patent: Jan. 29, 2019

(54) FACTOR IXA INHIBITORS

(71) Applicants: MERCK SHARP & DOHME CORP.; MOCHIDA PHARMACEUTICAL CO., LTD, Tokyo (JP)

(72) Inventors: Ting Zhang, Princeton Junction, NJ (US); Yi-Heng Chen, Whippany, NJ (US); Liangqin Guo, Edison, NJ (US); Alan Hruza, Hackettstown, NJ (US); Tianying Jian, Westfield, NJ (US); Bing Li, Towaco, NJ (US); Dongfang Meng, Morganville, NJ (US); Dann L. Parker, Cranford, NJ (US); Edward C. Sherer, Manville, NJ (US); Harold B. Wood, Westfield, NJ (US); Isao Sakurada, Tokyo (JP)

(73) Assignees: Merck Sharp & Dohme, Corp., Rahway, NJ (US); Mochida Paraceuticals Co., Ltd., Tokyo (JP)

( * ) Notice: Subject to any disclaimer, the term of this patent is extended or adjusted under 35 U.S.C. 154(b) by 0 days.

(21) Appl. No.: 15/534,029

(22) PCT Filed: Dec. 7, 2015

(86) PCT No.: PCT/US2015/064176
§ 371 (c)(1),
(2) Date: Jun. 8, 2017

(87) PCT Pub. No.: WO2016/094260
PCT Pub. Date: Jun. 16, 2016

(65) Prior Publication Data
US 2018/0030036 A1 Feb. 1, 2018

Related U.S. Application Data

(60) Provisional application No. 62/089,979, filed on Dec. 10, 2014.

(51) Int. Cl.
| | | |
|---|---|---|
| *C07D 403/12* | (2006.01) | |
| *C07D 401/14* | (2006.01) | |
| *C07D 401/12* | (2006.01) | |
| *C07D 471/04* | (2006.01) | |
| *C07D 413/14* | (2006.01) | |
| *C07D 413/12* | (2006.01) | |
| *C07D 417/12* | (2006.01) | |

(52) U.S. Cl.
CPC ......... *C07D 403/12* (2013.01); *C07D 401/12* (2013.01); *C07D 401/14* (2013.01); *C07D 413/12* (2013.01); *C07D 413/14* (2013.01); *C07D 417/12* (2013.01); *C07D 471/04* (2013.01)

(58) Field of Classification Search
CPC .................................................. C07D 403/12
See application file for complete search history.

(56) References Cited

U.S. PATENT DOCUMENTS

| | | | |
|---|---|---|---|
| 5,314,880 | A | 5/1994 | Whittaker et al. |
| 7,371,743 | B2 * | 5/2008 | Priepke ................ C07D 235/14 514/222.2 |
| 2005/0203078 | A1 * | 9/2005 | Priepke ................ C07D 235/14 514/211.08 |
| 2006/0205942 | A1 | 9/2006 | Kolesnikov et al. |
| 2010/0022506 | A1 | 1/2010 | Pinto et al. |
| 2014/0206706 | A1 | 7/2014 | Hangeland et al. |

FOREIGN PATENT DOCUMENTS

| | | | | |
|---|---|---|---|---|
| WO | WO-2005082895 A1 * | 9/2005 | ........... C07D 235/14 |
| WO | 2015160636 A1 | 10/2015 | |
| WO | WO2015160634 A1 | 10/2015 | |
| WO | 2016133793 A1 | 8/2016 | |

OTHER PUBLICATIONS

STN Chemical Database Entry for Benzamide, N-[2-(2-chlorophenyl)-2-(1H-indol-3-yl)ethyl]-4-(1H-1,2,4-triazol-1-yl)- RN 1016078-35-5 Supplier: Ambinter Entered STN: Apr. 21, 2008.*
Online "http://web.archive.org/web/20070202005900/http://www.ambinter.com/" dated Feb. 2, 2007, accessed Feb. 28, 2013.*
"Exploiting Chemical Diversity for Drug Discovery" Edited by Paul A Bartlett and Michael Entzeroth, The Royal Society of Chemistry, 2006, pp. 113-118.*
International Search Report and Written Opinion for PCT/US2015/064176—dated Feb. 11, 2016, 8 pages.
Pubchem-CID 46978227 Create Date Nov. 25, 2010.
Pubchem-CID 91799239 Create Date Jun. 4, 2015.
Extended European Search Report for 15866965.5, dated Jun. 2, 2018, 9 pages.
Parker, Dann L.; et al, Rapid development of two factor IXa inhibitors from hit to lead, Bioorganic & Medicinal Chemistry Letters, 2015, 2321-2325, vol. 25, No. 11.

(Continued)

*Primary Examiner* — David K O'Dell
(74) *Attorney, Agent, or Firm* — Nicole M. Beeler; John C. Todaro

(57) ABSTRACT

The present invention provides a compound of Formula I, and pharmaceutical compositions comprising one or more said compounds, and methods for using said compounds for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The compounds are selective Factor IXa inhibitors.

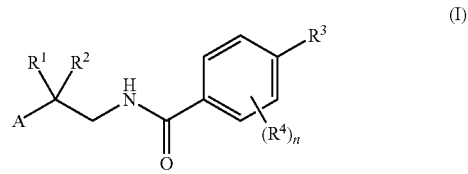

14 Claims, No Drawings

(56) References Cited

OTHER PUBLICATIONS

RN-1016078-35-5, ZREGISTRY, Entered STN: Apr. 21, 2008, downloaded Jun. 4, 2018.
RN-1277908-42-5 ZREGISTRY, Entered STN: Apr. 10, 2011, downloaded Jun. 4, 2018.
RN-129-4951-20-4, ZREGISTRY, Entered STN: May 15, 2011, downloaded Jun. 4, 2018.
RN-1370834-40-4 ZREGiSTRY, Entered STN: Apr. 29, 2012, downloaded Jun. 4, 2018.
RN-956182-82-4 ZREGISTRY, Entered STN: Nov. 28, 2007, downloaded Jun. 4, 2018.
Zhang, Ting; et al, Development of a novel class of potent and selective FIXa inhibitors, Bioorganic & Medicinal Chemistry Letters, 2015, 4945-4949, vol. 25, No. 21.

* cited by examiner

FACTOR IXA INHIBITORS

CROSS REFERENCE TO RELATED APPLICATIONS

This application is a U.S. National Phase application under 35 U.S.C. § 371 of PCT Application No. PCT/US2015/064176 filed Dec. 7, 2015, which claims priority from U.S. Provisional Application Ser. No. 62/089,979 filed Dec. 10, 2014.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijayku-mar et al., *Bioorganic & Medicinal Chemistry Letters* (2006), 16 (10), 2796-2799, discloses hydroxy pyrazole based factor IXa inhibitors.

SUMMARY OF THE INVENTION

The present invention relates to compounds of Formula I:

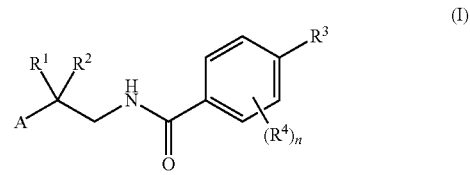

or pharmaceutically acceptable salts thereof. The compounds of Formula I are selective Factor IXa inhibitors, and as such may be useful in the treatment, inhibition or amelioration of one or more disease states that could benefit from inhibition of Factor IXa, including unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The compounds of this invention could further be used in combination with other therapeutically effective agents, including but not limited to, other drugs useful for the treatment of including unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

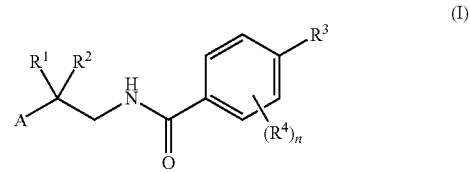

wherein A is selected from:

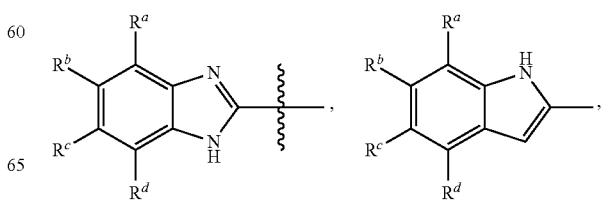

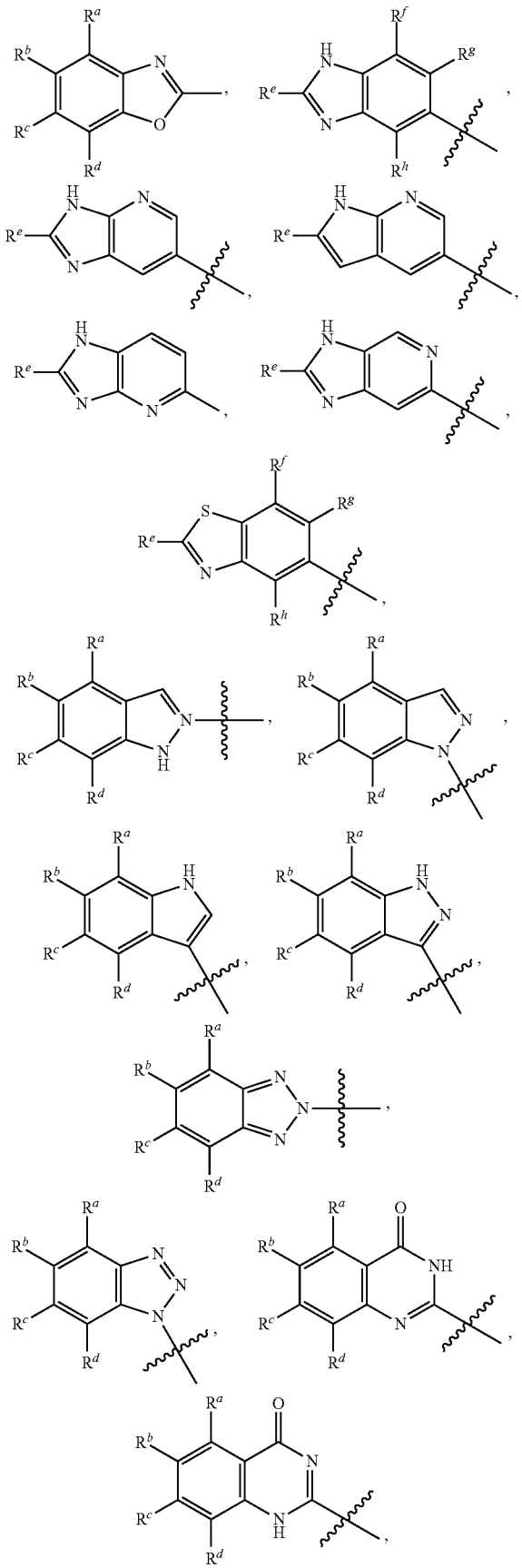

R[1] is phenyl, which is optionally substituted with halo, R[5], (C=O)OR[5], (C=O)NR[5]R[6] or $C_{1-3}$ alkyl(C=O)OR[5]; or heteroaryl, which is optionally substituted with one or two substituents independently selected from the group consisting of halo, oxo, R[5], OR[5], NR[5]R[6] and $C_{1-3}$ alkyl-NR[5]R[6];

R[2] is hydrogen or $C_{1-6}$ alkyl;

R[3] is heteroaryl, which is optionally substituted with one or two substituents independently selected from the group consisting of halo, oxo, cyclopropyl, R[5], OR[5], (C=O)OR[5] and $CH_2SO_2CH_3$;

each R[4] is independently selected from halo, R[5] or OR[5], each R[5] is hydrogen or $C_{1-6}$ alkyl, which is optionally substituted with one to three substituents independently selected from the group consisting of halo and hydroxy;

R[6] is hydrogen, cyclopropyl or $C_{1-6}$ alkyl, which is optionally substituted with one to three substituents independently selected from the group consisting of halo and hydroxy;

R[a] is hydrogen, halo, $C_{1-6}$ alkyl or O($C_{1-6}$ alkyl);
R[b] is hydrogen, halo, $C_{1-6}$ alkyl or O($C_{1-6}$ alkyl);
R[c] is hydrogen, halo, $C_{1-6}$ alkyl or O($C_{1-6}$ alkyl);
R[d] is hydrogen, halo, $C_{1-6}$ alkyl or O($C_{1-6}$ alkyl);
R[e] is hydrogen, halo, $C_{1-6}$ alkyl or O($C_{1-6}$ alkyl);
R[f] is hydrogen, halo, $C_{1-6}$ alkyl or O($C_{1-6}$ alkyl);
R[g] is hydrogen, halo, $C_{1-6}$ alkyl or O($C_{1-6}$ alkyl);
R[h] is hydrogen, halo, $C_{1-6}$ alkyl or O($C_{1-6}$ alkyl);
n is an integer between zero and two;
or a pharmaceutically acceptable salt thereof.

An embodiment of the present invention relates to compounds of Formula Ia:

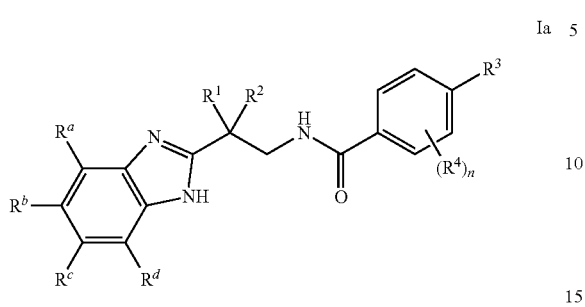

wherein $R^1$ is phenyl, which is optionally substituted with halo, $R^5$, (C=O)$OR^5$, (C=O)$NR^5R^6$ or $C_{1-3}$ alkyl(C=O)$OR^5$; or heteroaryl, which is optionally substituted with one or two substituents independently selected from the group consisting of halo, oxo, $R^5$, $OR^5$, $NR^5R^6$ or $C_{1-3}$ alkyl-$NR^5R^6$;
$R^2$ is hydrogen or $C_{1-6}$ alkyl;
$R^3$ is heteroaryl, which is optionally substituted with one or two substituents independently selected from the group consisting of halo, oxo, cyclopropyl, $R^5$, $OR^5$, (C=O)$OR^5$ and $CH_2SO_2CH_3$;
each $R^4$ is independently selected from halo, $R^5$ or $OR^5$,
$R^5$ is hydrogen or $C_{1-6}$ alkyl, which is optionally substituted with one to three substituents independently selected from the group consisting of halo and hydroxy;
$R^6$ is hydrogen, cyclopropyl or $C_{1-6}$ alkyl, which is optionally substituted with one to three substituents independently selected from the group consisting of halo and hydroxy;
$R^a$ is hydrogen, halo, $C_{1-6}$ alkyl or O($C_{1-6}$ alkyl);
$R^b$ is hydrogen, halo, $C_{1-6}$ alkyl or O($C_{1-6}$ alkyl);
$R^c$ is hydrogen, halo, $C_{1-6}$ alkyl or O($C_{1-6}$ alkyl);
$R^d$ is hydrogen, halo, $C_{1-6}$ alkyl or O($C_{1-6}$ alkyl);
$R^e$ is hydrogen, halo, $C_{1-6}$ alkyl or O($C_{1-6}$ alkyl);
$R^f$ is hydrogen, halo, $C_{1-6}$ alkyl or O($C_{1-6}$ alkyl);
$R^g$ is hydrogen, halo, $C_{1-6}$ alkyl or O($C_{1-6}$ alkyl);
$R^h$ is hydrogen, halo, $C_{1-6}$ alkyl or O($C_{1-6}$ alkyl);
n is an integer between zero and two;
or a pharmaceutically acceptable salt thereof.

In an embodiment of the invention, A is

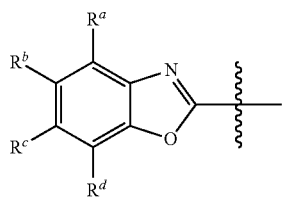

In another embodiment of the invention, A is

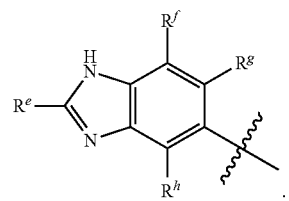

In another embodiment of the invention, A is

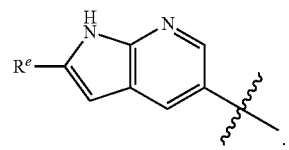

In another embodiment of the invention, A is

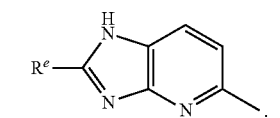

In another embodiment of the invention, A is

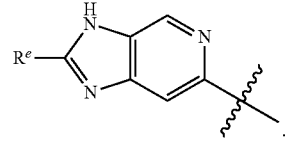

In another embodiment of the invention, A is

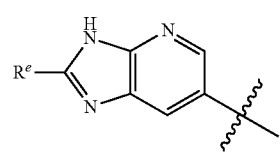

In another embodiment of the invention, A is

In another embodiment of the invention, A is

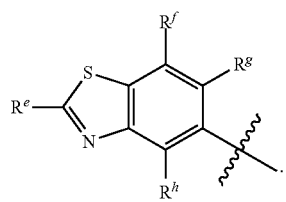

In another embodiment of the invention, A is

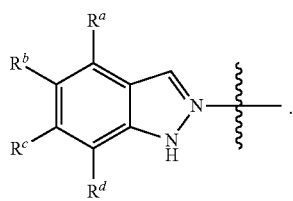

In another embodiment of the invention, A is

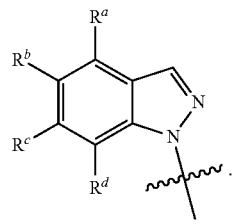

In another embodiment of the invention, A is

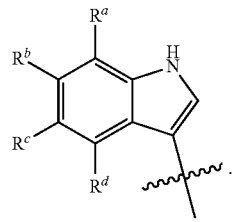

In another embodiment of the invention, A is

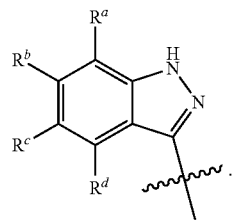

In another embodiment of the invention, A is

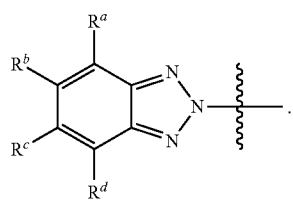

In another embodiment of the invention, A is

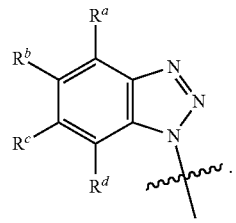

In another embodiment of the invention, A is

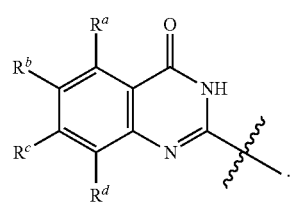

In another embodiment of the invention, A is

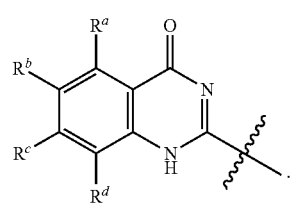

In another embodiment of the invention, A

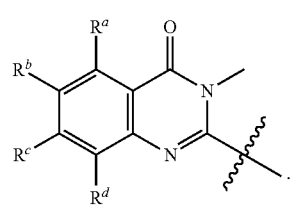

In another embodiment of the invention, A is

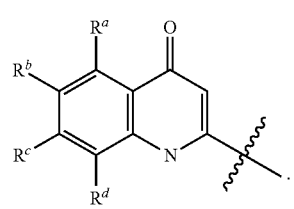

In another embodiment of the invention, A is

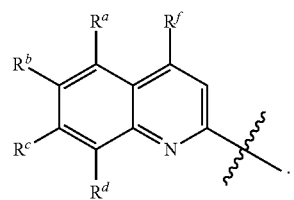

In another embodiment of the invention, A is

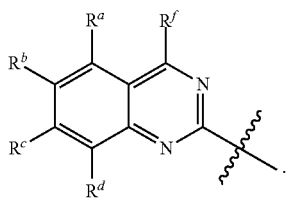

In another embodiment of the invention, A is

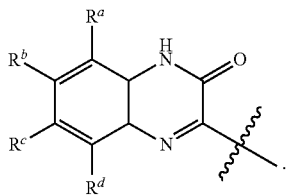

In an embodiment of the invention, $R^1$ is phenyl, which is optionally substituted with halo, $(C=O)OR^5$, $(C=O)NR^5R^6$ or $C_{1-3}$ alkyl$(C=O)OR^5$. In a class of the invention, $R^1$ is phenyl, which is optionally substituted with halo.

In an embodiment of the invention, $R^2$ is hydrogen. In another embodiment of the invention, $R^2$ is methyl.

In an embodiment of the invention, $R^3$ is 1,2,3-triazolyl, 1,2,4-triazolyl, imidazolyl, tetrazolyl, pyridyl, pyrimidinyl, pyrazolyl, pyridazinyl, quinolinyl, triazolopyridinyl, triazolonyl, pyridinyl or benzoimidazolyl, wherein said groups are optionally substituted with halo, oxo, cyclopropyl, $R^5$, $OR^5$, $(C=O)OR^5$ and $CH_2SO_2CH_3$. In a class of the invention, $R^3$ is 1,2,3-triazolyl, 1,2,4-triazolyl, triazolonyl, pyridonyl and benzoimidazolyl, wherein said groups are optionally substituted with halo, oxo, cyclopropyl, $R^5$, $OR^5$, $(C=O)OR^5$ and $CH_2SO_2CH_3$. In a subclass of the invention, $R^3$ is 1,2,3-triazolyl or 1,2,4-triazolyl, wherein said groups are optionally substituted with $R^5$.

In an embodiment of the invention, $R^4$ is Cl, F, $CH_3$, $CF_3$ or $OCH_3$.

In an embodiment of the invention, n is 0. In another embodiment of the invention, n is 1. In another embodiment of the invention, n is 2.

In an embodiment of the invention, $R^a$ is hydrogen, halo or $CH_3$.

In an embodiment of the invention, $R^b$ is hydrogen, halo, $CH_3$ or $OCH_3$.

In an embodiment of the invention, $R^c$ is hydrogen, halo, $CH_3$ or $OCH_3$.

In an embodiment of the invention, $R^d$ is hydrogen, halo or $CH_3$.

In an embodiment of the invention, $R^e$ is $CH_3$.

In an embodiment of the invention, $R^f$ is hydrogen, halo, $CH_3$ or $OCH_3$.

In an embodiment of the invention, $R^g$ is hydrogen.

In an embodiment of the invention, $R^h$ is hydrogen or halo.

Reference to the preferred classes and subclasses set forth above is meant to include all combinations of particular groups unless stated otherwise.

Specific embodiments of the present invention include, but are not limited to the compounds identified herein as Examples 1 to 116, or pharmaceutically acceptable salts thereof.

Also included within the scope of the present invention is a pharmaceutical composition which is comprised of a compound of Formula I or Formula Ia as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor IXa inhibitors and may have therapeutic value in, for example, preventing coronary artery disease.

It will be understood that, as used herein, references to the compounds of structural Formula I and Formula Ia are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I and Formula Ia. Unless a specific stereochemistry is indicated, the present invention is meant to comprehend all such isomeric forms of these compounds. Centers of asymmetry that are present in the compounds of Formula I and Formula Ia can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I and Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or Formula Ia or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I or Formula Ia simultaneously contain acidic and basic groups in the molecule the invention also includes, in addition to the salt forms mentioned, inner salts or betaines (zwitterions). Salts can be obtained from the compounds of Formula I and Formula Ia by customary methods which are known to the person skilled in the art, for example by combination with an organic or inorganic acid or base in a solvent or dispersant, or by anion exchange or cation exchange from other salts. The present invention also includes all salts of the compounds of Formula I and Formula Ia which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

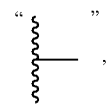

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_{1-4}C_4$ alkyl") for example, means linear or branched chain alkyl groups, including all isomers, having the specified number of carbon atoms. For example, the structures

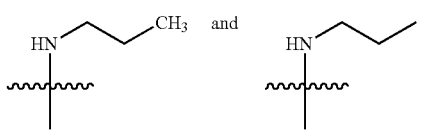

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic, and at least one ring contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzenyl, benzothiazolyl, benzothienyl, quinolinyl, isoquinolinyl, oxazoly, and tetra-hydroquinolinyl. Specific heteroaryl groups include 1,2,3-triazolyl, 1,2,4-triazolyl, imidazolyl, tetrazolyl, pyridyl, pyrimidinyl, pyrazolyl, pyridazinyl, quinolinyl, triazolopyridinyl, triazolonyl, pyridonyl and benzoimidazolyl. If the heteroaryl contains nitrogen atoms, it is understood that the corresponding N-oxides thereof are also encompassed by this definition.

"Celite®" (Fluka) diatomite is diatomaceous earth, and can be referred to as "celite".

Except where noted herein, structures containing substituent variables such as variable "R" below:

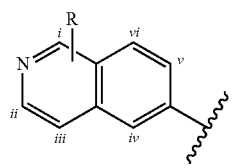

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I and Formula Ia, acting as prodrugs and solvates. Prodrugs, following administration to the patient, are converted in the body by normal metabolic or chemical processes, such as through hydrolysis in the blood, to the compound of Formula I or Formula Ia. Such prodrugs include those that demonstrate enhanced bioavailability, tissue specificity, and/or cellular delivery, to improve drug absorption of the compound of Formula I or Formula Ia. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I and Formula Ia capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I and Formula Ia form stable alkali metal, alkaline earth metal or optionally substituted ammonium salts. If the compounds of the Formula I and Formula Ia have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I or Formula Ia and/or of a pharmaceutically acceptable salt of the compound of the Formula I or Formula Ia and/or an optionally stereoisomeric form of the compound of the Formula I or Formula Ia or a pharmaceutically acceptable salt of the stereoisomeric form of the compound of Formula I or Formula Ia, together with a pharmaceutically suitable and pharmaceutically acceptable vehicle, additive and/or other active substances and auxiliaries.

The invention also relates to the use of a compound of the instant invention and/or of a pharmaceutically acceptable salt of the compound of the invention in the manufacture of a medicament for inhibiting thrombin, inhibiting thrombus formation, treating thrombus formation or preventing thrombus formation in a mammal.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor IXa inhibitors are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula I or Formula Ia into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably between 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I and Formula Ia can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor IXa inhibitors can also be co-administered with suitable anticoagulants, including, but not limited to, other Factor IXa inhibitors, thrombin inhibitors, thrombin receptor antagonists, factor VIIa inhibitors, factor Xa inhibitors, factor XIa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (coadministration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5 (S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

Scheme 1

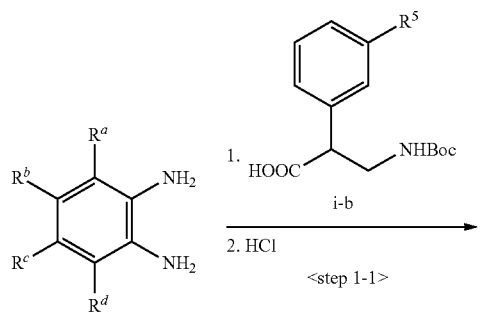

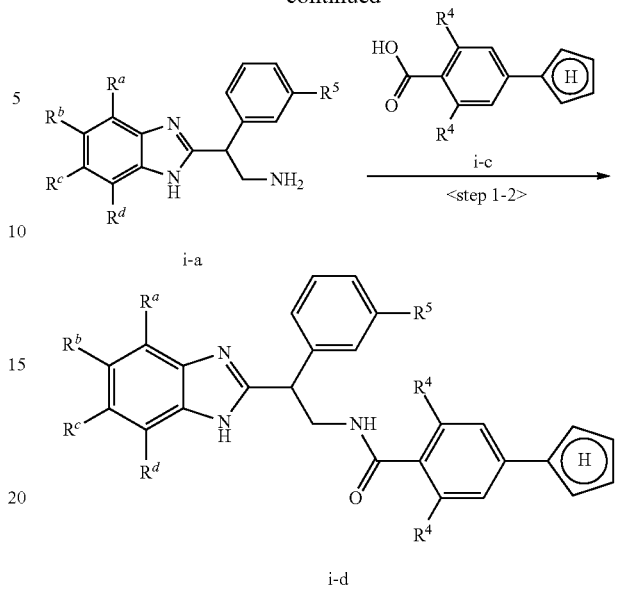

<Step 1-1> A compound represented by formula (i-a) can be produced by allowing a diaminophenyl compound to react with a carboxylic acid compound represented by (i-b) in the presence of HOBt, EDC in DMF at room temperature, followed by thermodehydration in the presence of AcOH and Boc deprotection in the presence of HCl in dioxane.

<Step 1-2> A compound represented by formula (i-d) can be produced from a compound represented by formula (i-a) and a key intermediate represented by formula (i-c) in the presence of HOBt, EDC in DMF at room temperature, followed by chiral resolution on chiral SFC columns.

Scheme 2

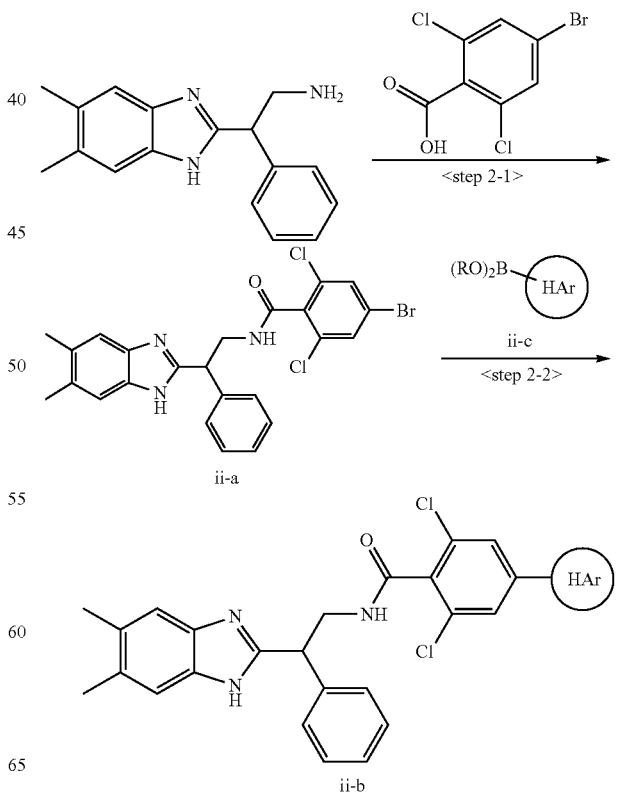

<Step 2-1> A compound represented by formula (ii-a) can be produced from 2-(5,6-dimethyl-1H-benzo[d]imidazol-2-yl)-2-phenylethanamine and 4-bromo-2,6-dichlorobenzoic acid in the presence of oxalyl chloride and DMF at room temperature.

<Step 2-2> A compound represented by formula (ii-b) can be produced from (ii-a) and (ii-b) in the presence of 2M sodium carbonate (aq) and $PdCl_2(dppf)$-$CH_2Cl_2$ adduct in DMF under $N_2$ at 80° C.

Scheme 3

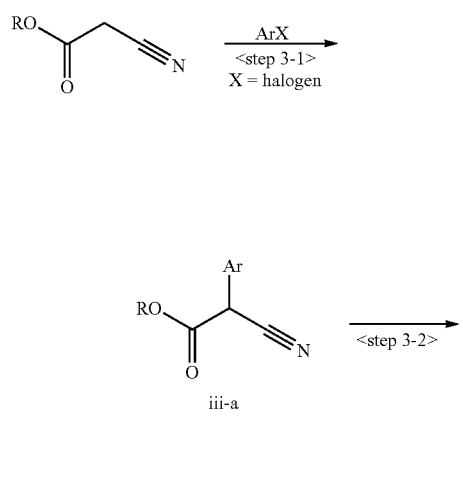

iii-a

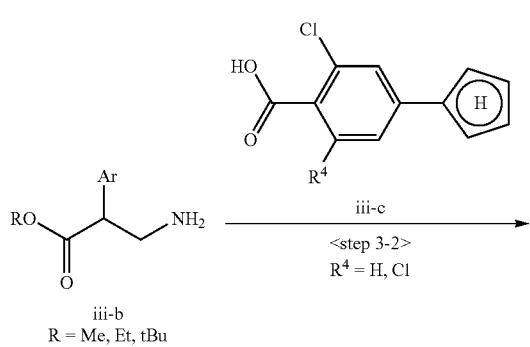

iii-b
R = Me, Et, tBu

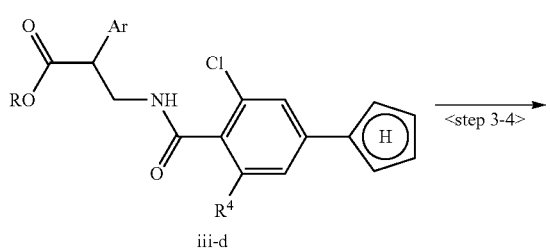

iii-d

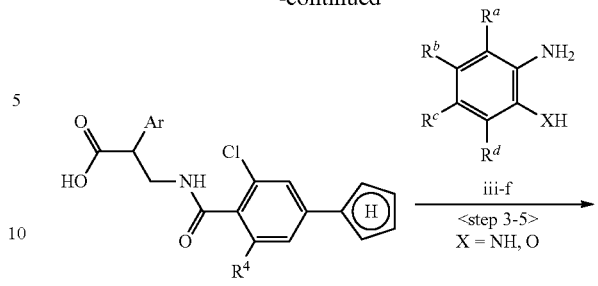

iii-e

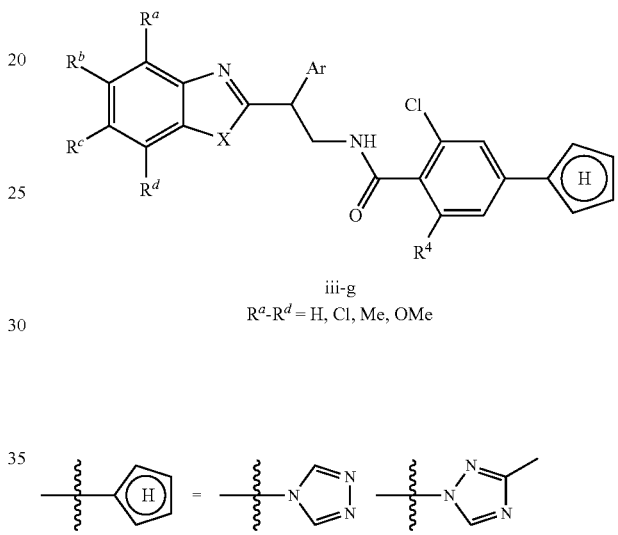

iii-g
$R^a$-$R^d$ = H, Cl, Me, OMe

<Step 3-1> A compound represented by formula (iii-a) can be produced by reacting alkyl cyanoacetate, aryl halide, a base such as potassium tert-butoxide, a palladium catalyst such as 1,1'-bis(diphenylphosphino)ferrocene-palladium(II) dichloride dichloromethane complex in a solvent such as 1,4-dioxane at elevated temperature.

<Step 3-2> A compound represented by formula (iii-b) can be produced by treating (iii-a) under reducing conditions such as hydrogenation under $H_2$ atmosphere with platinum (IV) oxide hydrate as catalyst and EtOH as solvent at room temperature.

<Step 3-3> A compound represented by formula (iii-d) can be produced by allowing key intermediate (iii-c) to react with (iii-b) under amide coupling conditions at room temperature, with HATU as catalyst, DMF as solvent and Hunig's base as base.

<Step 3-4> A compound represented by formula (iii-e) can be produced by treating intermediate (iii-d) with aqueous lithium hydroxide in 1,4-dioxane at room temperature.

<Step 3-5> A compound represented by formula (iii-g) can be produced from (iii-e) and (iii-f) in the presence of HATU in DMF at room temperature.

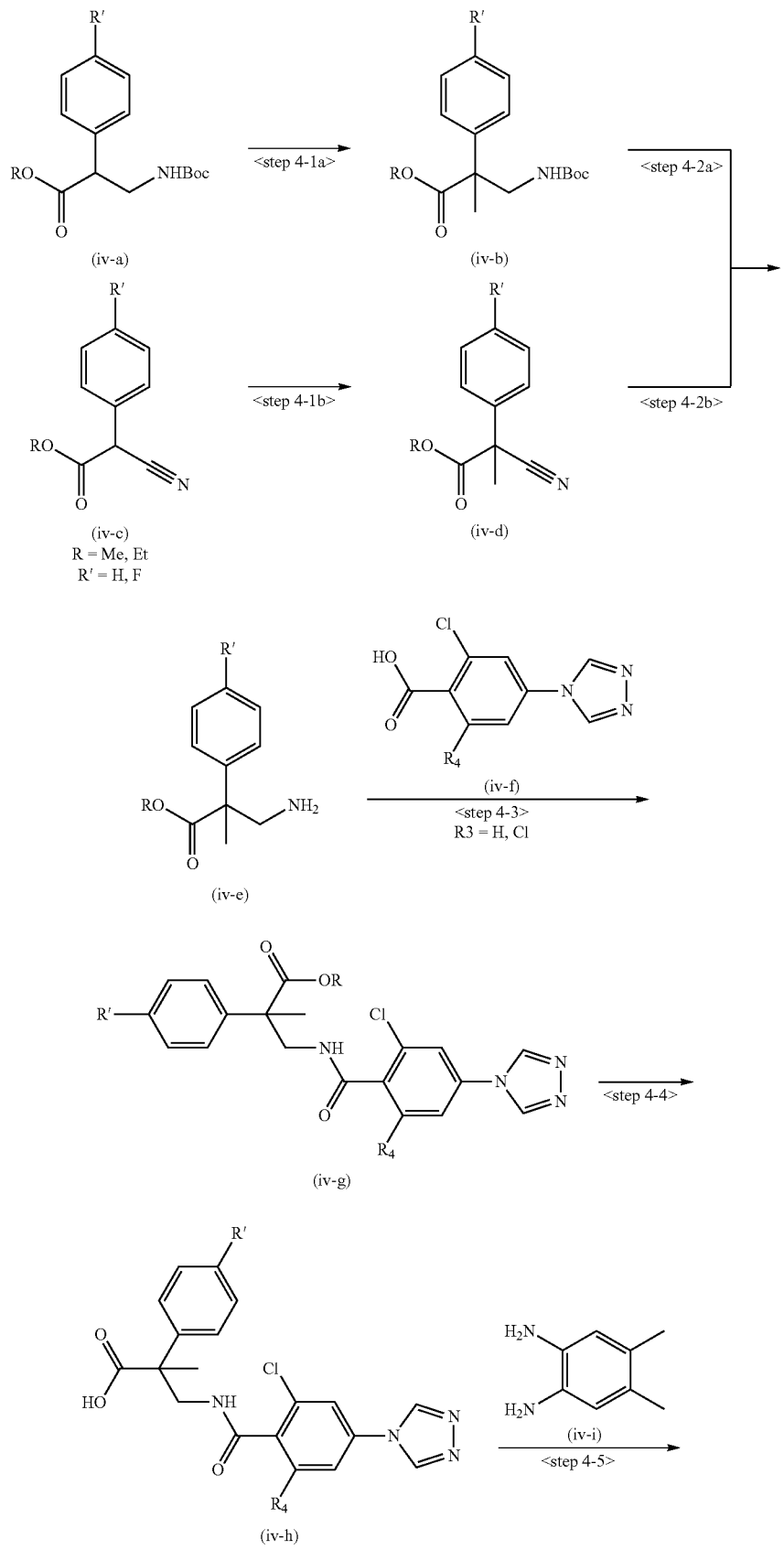

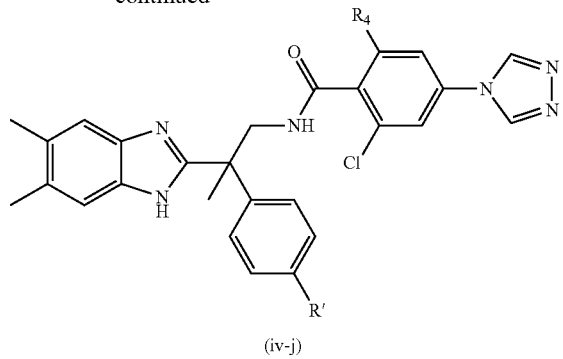

(iv-j)

<Step 4-1a> A compound represented by formula (iv-a) can be produced by methylating the corresponding carboxylic acid using trimethylsilyldiazomethane. A compound represented by formula (iv-b) can be produced by deprotonation of (iv-a) at −78° C. in THF with LDA, followed by alkylation with iodomethane.

<Step 4-2a> A compound represented by formula (iv-e) can be produced from (iv-b) by treatment with 4N HCl in dioxane at room temperature.

<Step 4-1b> A compound represented by formula (iv-c) can be produced by procedures described in <step 3-1>. A compound represented by formula (iv-d) can be produced by deprotonation of (iv-c) at 0° C. in THF with sodium hydride, followed by alkylation with iodomethane.

<Step 4-2b> A compound represented by formula (iv-e) can be produced by procedures described in <step 3-2>.

<Step 4-3> A compound represented by formula (iv-g) can be produced by similar procedures described in <step 3-3> with modifications.

<Step 4-4> A compound represented by formula (iv-h) can be produced by procedures described in <step 3-4>.

<Step 4-5> A compound represented by formula (iv-j) can be produced by similar procedures described in <step 3-5> with modifications.

Scheme 5

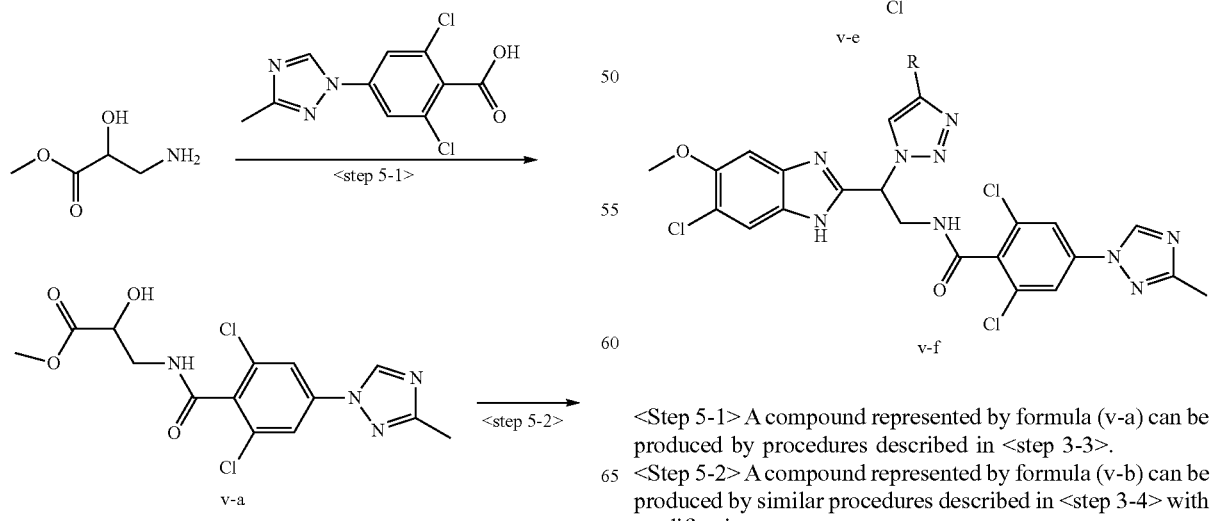

<Step 5-1> A compound represented by formula (v-a) can be produced by procedures described in <step 3-3>.

<Step 5-2> A compound represented by formula (v-b) can be produced by similar procedures described in <step 3-4> with modifications.

<Step 5-3> A compound represented by formula (v-c) can be produced by procedures described in <step 1-1>.
<Step 5-4> A compound represented by formula (v-d) can be produced by treating (v-c) with trifluoromethanesulfonic anhydride, DMAP and pyridine in DCE at room temperature.
<Step 5-5> A compound represented by formula (v-e) can be produced by treating (v-d) with 15-crown-5 and sodium azide in DMF at room temperature.
<Step 5-6> A compound represented by formula (v-f) can be produced by treating (v-e) with copper(I) iodide, sodium ascorbate, alkyne and DMF at 40° C.

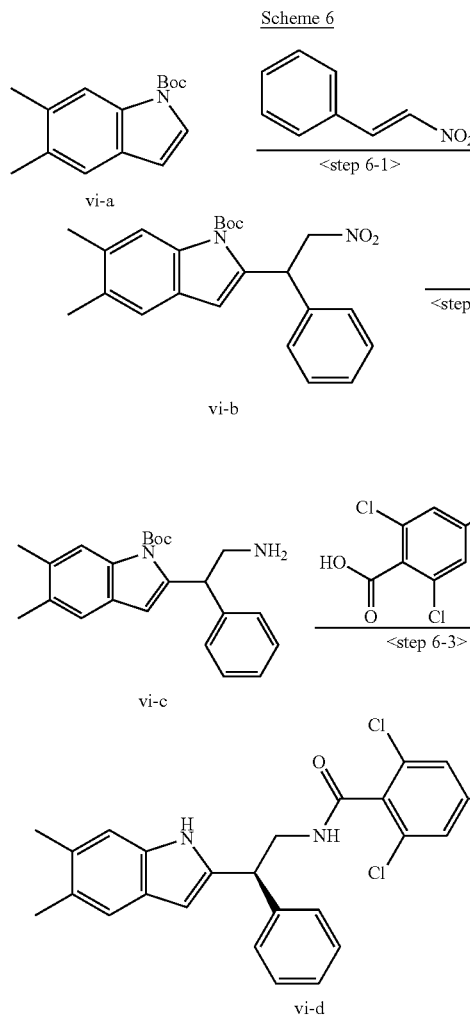

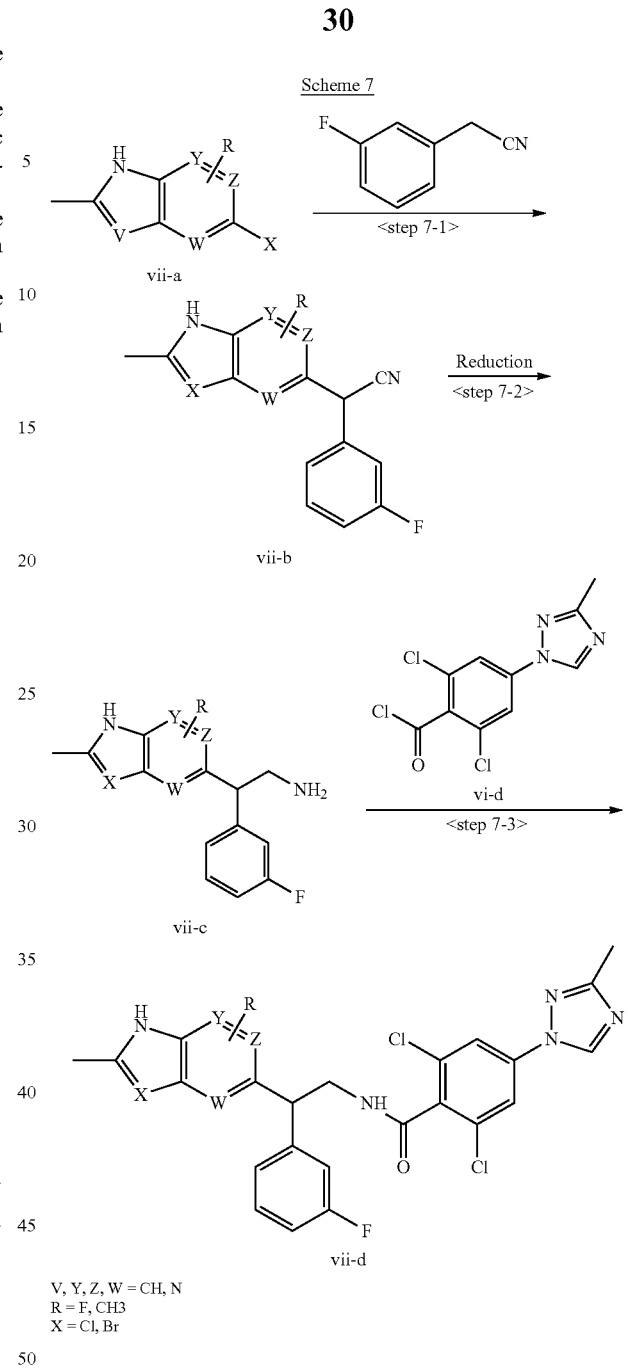

V, Y, Z, W = CH, N
R = F, CH3
X = Cl, Br

<Step 6-1> A compound represented by formula (vi-a) can be produced by treating 5,6-dimethyl-1H-indole with Boc-anhydride and DMAP in DCM at room temperature. A compound represented by formula (vi-b) can be produced by deprotonation of (vi-a) with tert-butyllithium at −78° C. in THF, followed by addition of trans-beta-nitrostyrene.
<Step 6-2> A compound represented by formula (vi-c) can be produced by heating (vi-b) with iron dust in AcOH and THF at 95° C.
<Step 6-3> A compound represented by formula (vi-d) can be produced by treating (vi-c), 2,6-dichloro-4-(4H-1,2,4-triazol-4-yl)benzoic acid, EDC (27.8 mg, 0.145 mmol) and 1-hydroxyl-7-azabenzotriazole in THF at 40° C. to RT.

<Step 7-1> A compound represented by formula (vii-b) can be produced by treating commercial or literature known heteroaryl halide (vii-a) (PCT Int. Appl., 2009137081, 12 Nov. 2009), 2-(3-fluorophenyl)acetonitrile in the presence of catalysts palladium(II) acetate and 2,8,9-triisobutyl-2,5,8,9-tetraaza-1-phosphabicyclo[3.3.3]undecane in solvents such as toluene or dioxane at 100° C. (*J. Org. Chem*, Vol. 68, No. 21, 2003, 8007).
<Step 7-2> A compound represented by formula (vii-c) can be produced by treating (vii-b) with NaBH$_4$ and anhydrous NiCl$_2$ in THF and EtOH at RT. (*Synth. Comm.* 32(8), 1265-69, 2002)
<Step 7-3> A compound represented by formula (vii-d) can be produced by in situ addition of the reaction mixture of <Step 7-2> to (vii-c) at RT.

Scheme 8

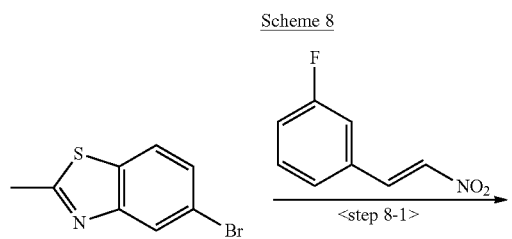

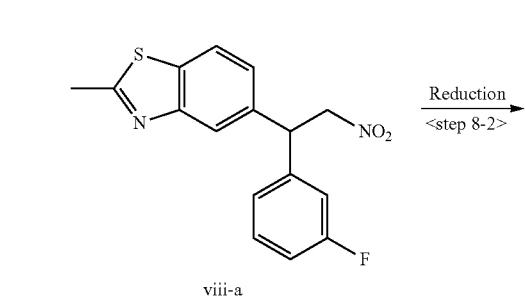

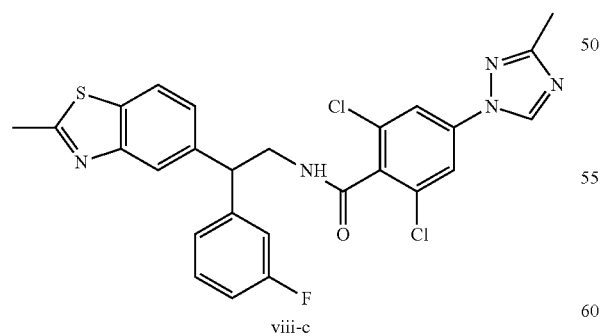

<Step 8-1> A compound represented by formula (viii-a) can be produced via Grignard reaction: 5-Bromo-2-methylbenzo[d]thiazole was treated with magnesium in ether followed by (E)-1-fluoro-3-(2-nitrovinyl)benzene at 40° C.-RT.

<Step 8-2> A compound represented by formula (viii-b) can be produced by using the same procedure described in step 6-2.

<Step 8-3> A compound represented by formula (viii-c) can be produced by using the same procedure described in step 6-3.

Scheme 9

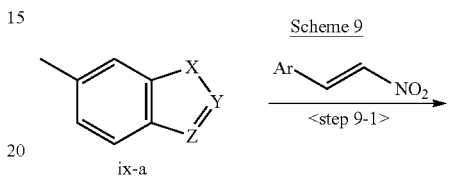

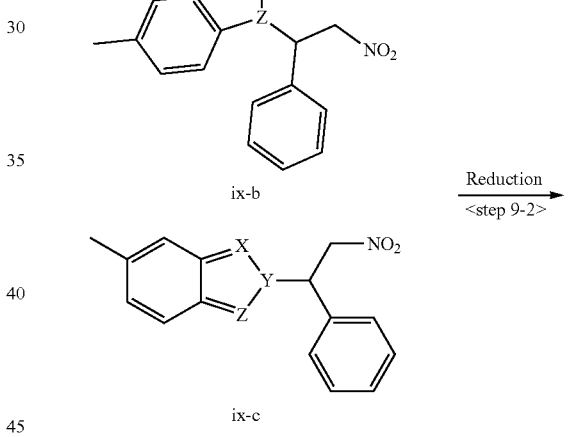

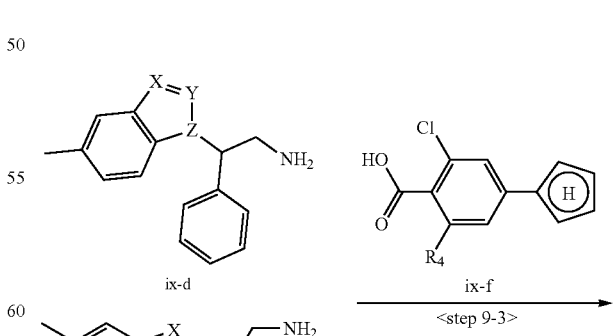

-continued

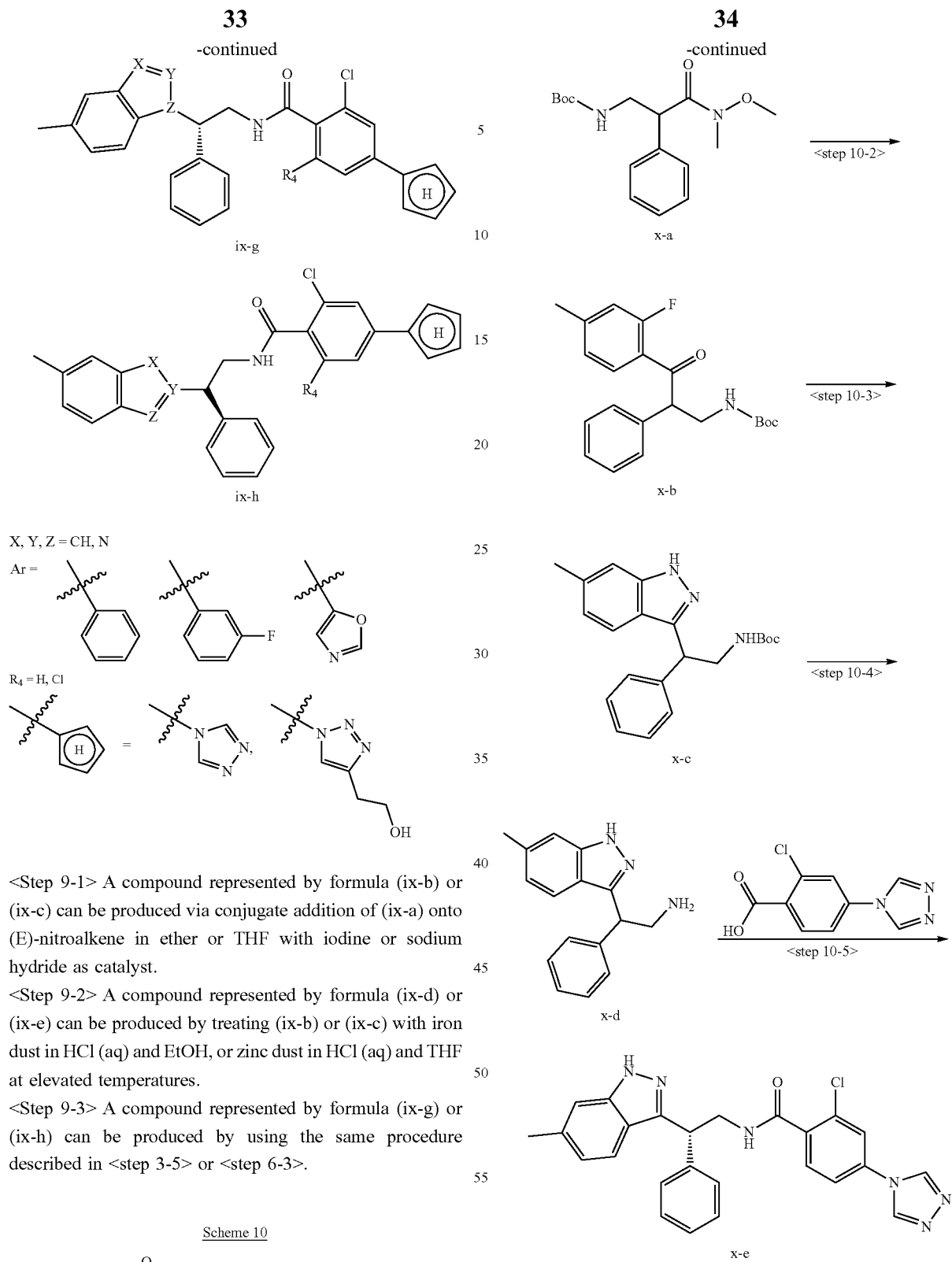

X, Y, Z = CH, N $R_4$ = H, Cl

<Step 9-1> A compound represented by formula (ix-b) or (ix-c) can be produced via conjugate addition of (ix-a) onto (E)-nitroalkene in ether or THF with iodine or sodium hydride as catalyst.

<Step 9-2> A compound represented by formula (ix-d) or (ix-e) can be produced by treating (ix-b) or (ix-c) with iron dust in HCl (aq) and EtOH, or zinc dust in HCl (aq) and THF at elevated temperatures.

<Step 9-3> A compound represented by formula (ix-g) or (ix-h) can be produced by using the same procedure described in <step 3-5> or <step 6-3>.

Scheme 10

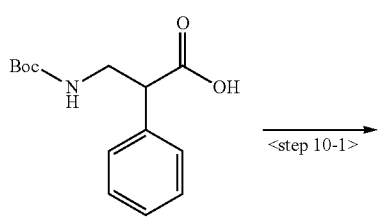

<Step 10-1> A compound represented by formula (x-a) can be produced from 3-((tert-butoxycarbonyl)amino)-2-phenylpropanoic acid (1 g) via amide coupling with N,O-dimethylhydroxylamine hydrochloride in the presence of Et$_3$N and HATU in DMF.

<Step 10-2> A compound represented by formula (x-b) can be produced by treating (x-a) with n-BuLi followed by tert-butyl (3-(methoxy(methyl)amino)-3-oxo-2-phenylpropyl)carbamate in THF at −78° C.-RT.

<Step 10-3> A compound represented by formula (x-c) can be produced by treating (x-b) with hydrazine hydrate in DMSO at 140° C.

<Step 10-4> A compound represented by formula (x-d) can be produced by treating (x-c) with TFA in DCM at RT.

<Step 10-5> A compound represented by formula (x-e) can be produced by treating (x-d) under the same procedures described in <step 1-2>.

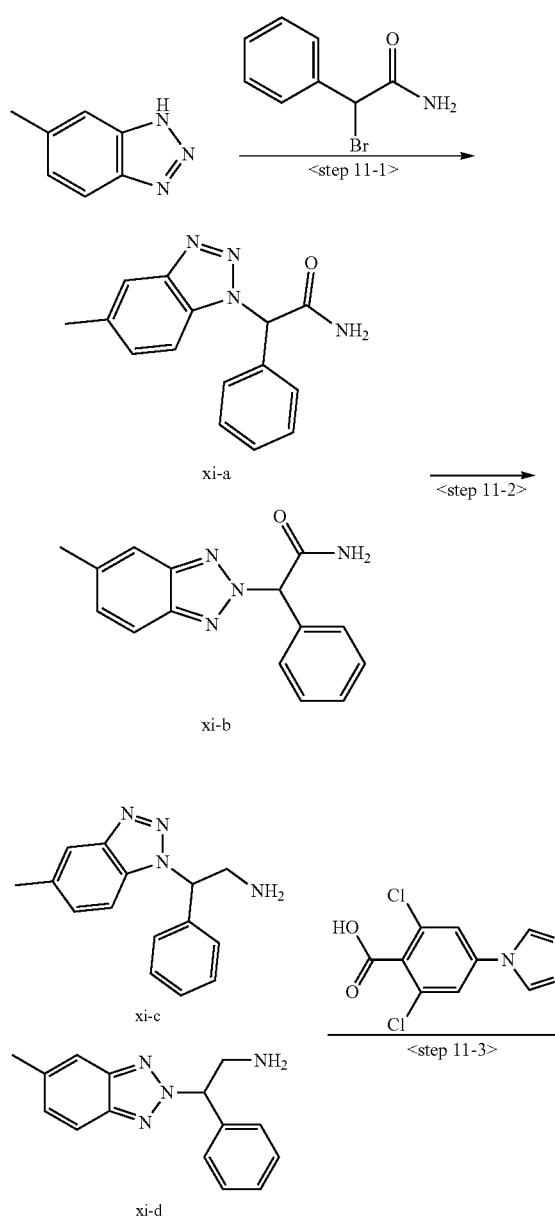

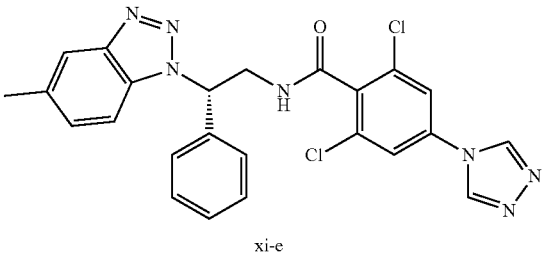

xi-e

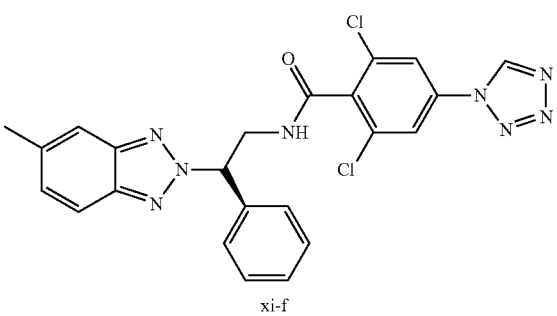

xi-f

<Step 11-1> A compound represented by formula (xi-a) or (xi-b) can be produced from 5-methyl-1H-benzo[d][1,2,3]triazole and 2-bromo-2-phenylacetamide in DMF at 0° C. to RT in the presence of sodium hydride.

<Step 11-2> A compound represented by formula (xi-c) or (xi-d) can be produced by treating (xi-a) or (xi-b) with DIBAL-H in THF at 85° C.

<Step 11-3> A compound represented by formula (xi-e) or (xi-f) can be produced by treating (xi-c) or (xi-d) under the same conditions as described in <step 10-5>.

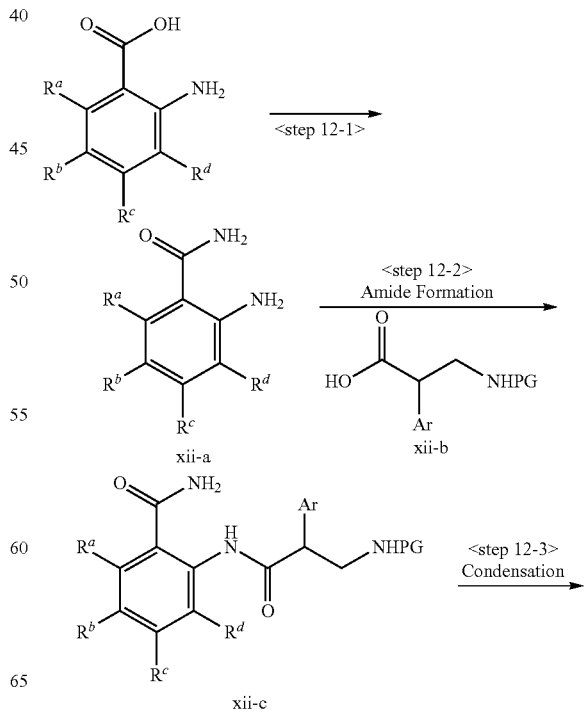

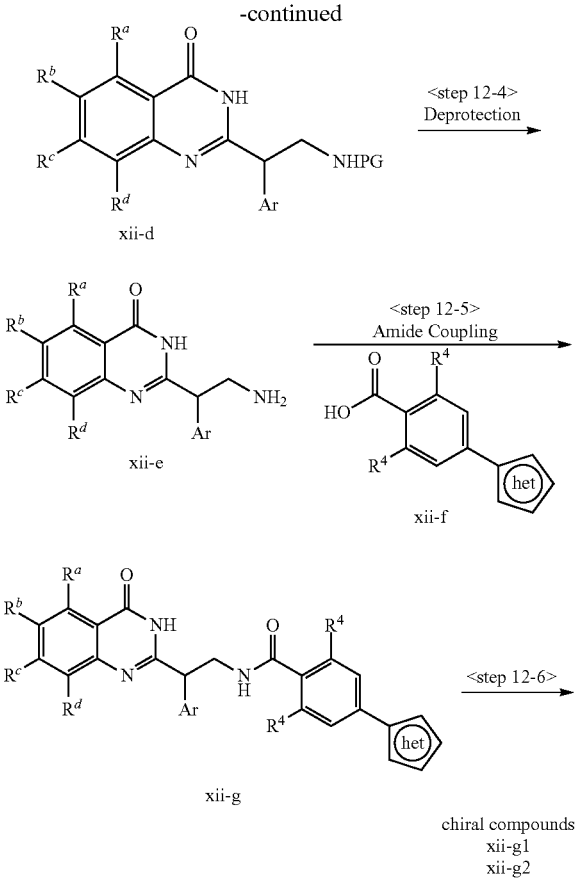

<Step 12-1> A compound represented by formula (xii-a) can be produced in two steps. The first step is allowing a commercial available substituted 2-amino benzoic acid to react with thionyl chloride at 40-60° C. to form an acid chloride. This can be done in neat thionyl chloride or in solvents that are inactive to the reaction, such as DCM. The acid chloride is obtained by evaporation without further purification. The second step involves the treatment with concentrated ammonia hydroxide in a solvent which is inactive to the reaction, such as DMA, at room temperature for a few hours or overnight.

<Step 12-2> A compound represented by formula (xii-c) can be produced by allowing a key intermediate compound represented by formula (xii-b) to react with a compound represented by formula (xii-a) through commonly used amide coupling conditions such as, HOAt and EDC, or HATU, or by a well-known process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature.

An alternative way for the amide formation is through an acid halide. When a compound represented by formula (xii-b) is converted to an acid chloride, a compound represented by formula (xii-c) can be similarly produced by reacting the acid chloride with a compound represented by formula (xii-a) in a inactive solvent, such as DMA, dichloroethane, or DCM, absence of base or in the presence of a base such as pyridine, at a temperature in a range of room temperature to the solvent-reflux temperature; or conducting a reaction by a process similar to that described in, for example, Organic synthesis IV, Acids, amino acids, and peptides, pp. 144-146, 1992, Maruzen Co., Ltd., in the presence of a base such as triethylamine, DIEA or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

<Step 12-3> A compound represented by formula (xii-d) can be produced from a compound represented by formula (xii-c) in the presence of base, such as potassium 2-methylpropan-2-olate, in a alcoholic solvent, such as methanol, ethanol, or 2-propanol, or in a mixed solvent such as methanol-tetrahydrofuran or methanol-N,N-dimethylformamide at room temperature or at an elevated temperature.

<Step 12-4> A compound represented by formula (xii-e) can be produced from a compound represented by formula (xii-d) through commonly used deprotection procedures for removing a Boc or a Cbz protecting group. When Boc is the protecting group, a compound represented by formula (xii-e) can be produced from treatment with 4N HCl in dioxane, or TFA in DCM, at room temperature. When Cbz is the protecting group, a compound represented by formula (xii-e) can be produced from Pd—C catalyzed hydrogenation in a solvent such as methanol or ethanol; or can be produced by treatment with TMSI in dichloromethane or acetonitrile at a temperature in the range of 0° C. to room temperature.

<Step 12-5> A compound represented by formula (xii-g) can be produced by allowing a key intermediate compound represented by formula (xii-f) to react with a compound represented by formula (xii-e) through commonly used amide coupling conditions such as, using HOAt and EDC, or HATU as coupling reagents, in a polar solvent such as DMF, DMA, or a process similar to that described in published documents, for example, Organic synthesis IV, Acids, amino acids, and peptides, pp. 191-309, 1992, Maruzen Co., Ltd.

<Step 12-6> A chiral compound represented by formula (xii-g1) or (xii-g2) can be produced from chiral resolution of a racemic compound represented by formula (xii-g) through SFC separation technique on a chiral column. The absolute stereochemistry can be determined by x-ray chromatography or presumed by comparing the FIXa inhibitory activity to the compound with known stereochemistry.

Scheme 13

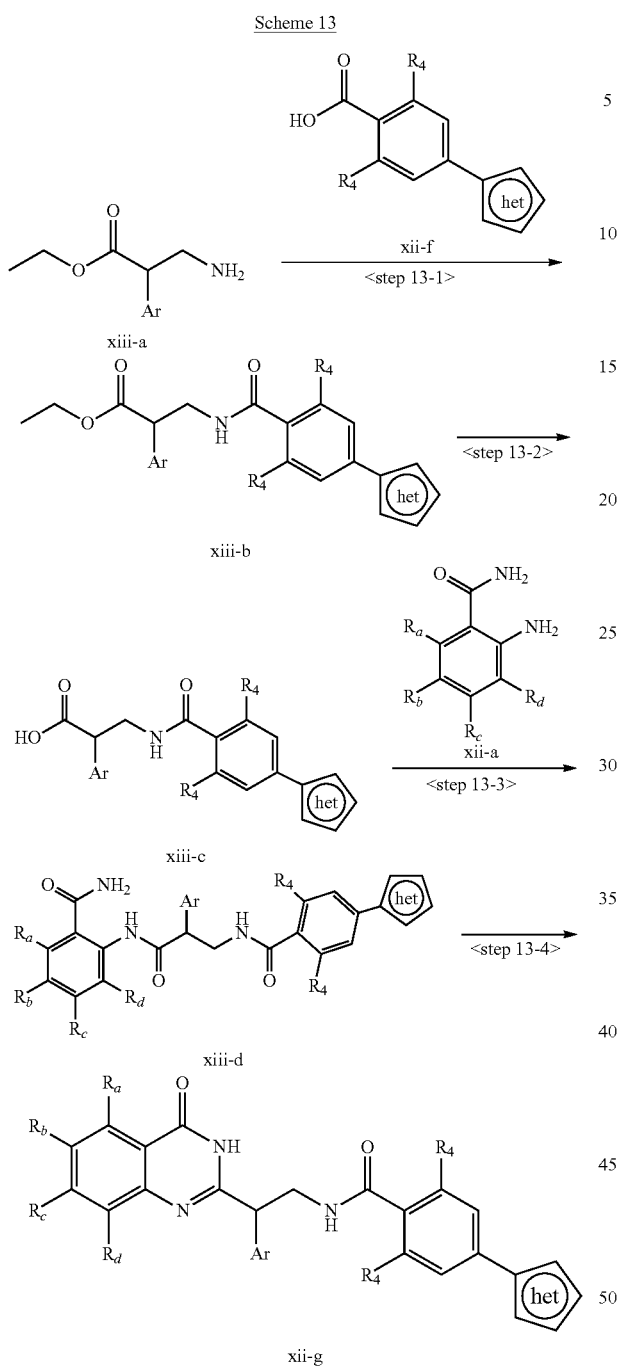

<Step 13-1> A compound represented by formula (xiii-b) can be produced by allowing a key intermediate compound represented by formula (xiii-a) to react with a compound represented by formula (xii-f) through commonly used amide coupling conditions, or converting a compound represented by formula (xii-f) to acid chloride, followed by reaction with a compound represented by formula (xiii-a), as described in Scheme 12 <Step 12-5>

<Step 13-2> A compound represented by formula (xiii-c) can be produced from a compound represented by formula (xiii-b) through commonly used ester hydrolysis conditions, such as using LiOH or NaOH as a base in a mixed solvent such dioxane-water or in alcoholic solvent-water at room temperature or at an elevated temperature.

<Step 13-3> A compound represented by formula (xiii-d) can be produced by allowing a compound represented by formula (xiii-c) to react with a compound represented by formula (xii-a) through a process as described in Scheme 12 <Step 12-2>.

<Step 13-4> A compound represented by formula (xii-g) can be produced by allowing a compound represented by formula (xiii-d) to condense through a process as described in Scheme 12 <Step 12-3>.

Scheme 14

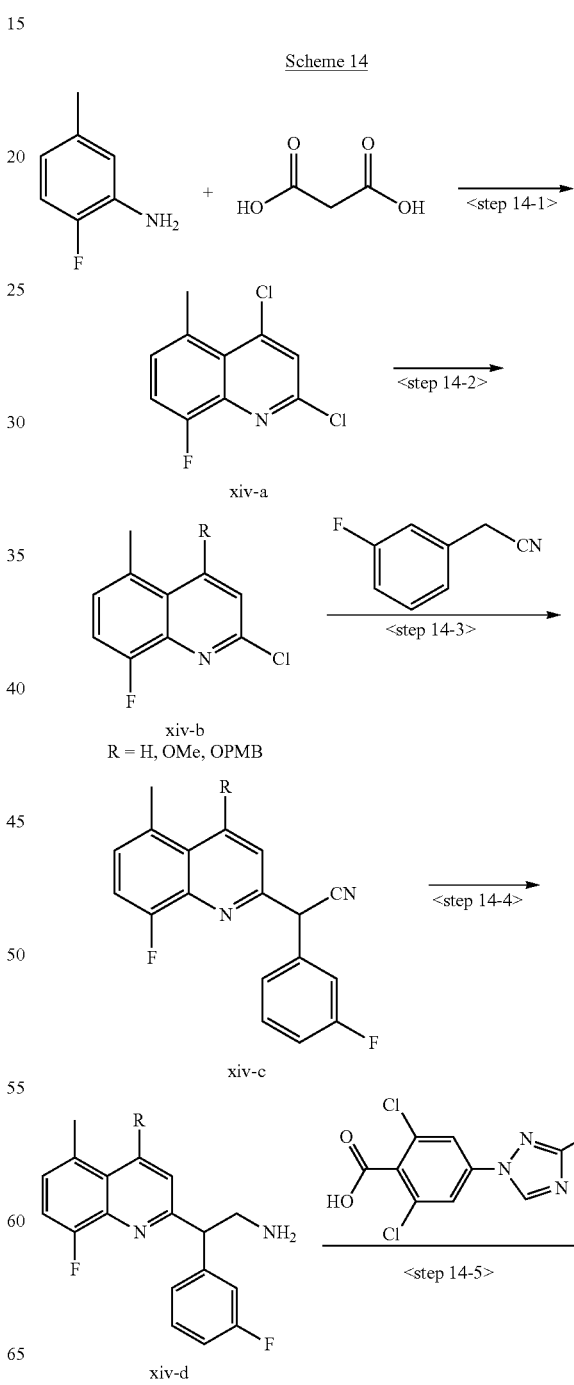

-continued

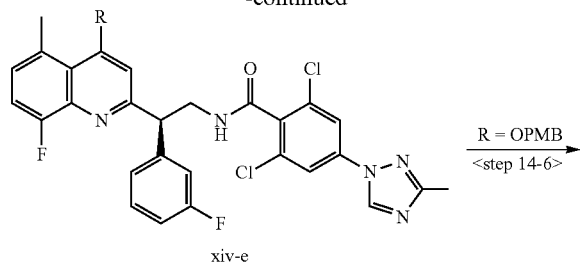
xiv-e

R = OPMB
<step 14-6>

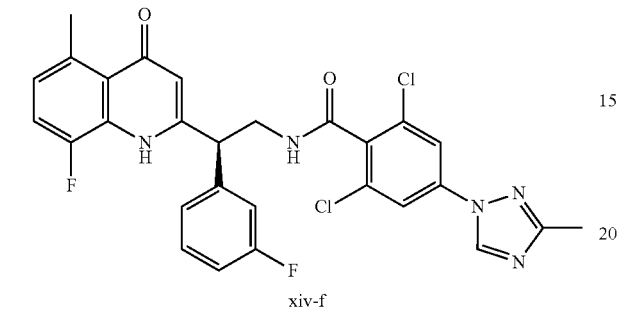
xiv-f

<Step 14-1> A compound represented by formula (xiv-a) can be produced from 2-fluoro-5-methylaniline and malonic acid refluxing in POCl₃ (PCT Int. Appl., 2011017389, 10 Feb. 2011).

<Step 14-2> A compound represented by formula (xiv-b) can be produced from (xiv-a) by reduction with Zn (R=H) or displacement with alcohols (methanol or anisyl alcohol) in the presence of sodium hydride.

<Step 14-3> A compound represented by formula (xiv-c) can be produced from (xiv-b) using procedures described in <step 7-1>.

<Step 14-4> A compound represented by formula (xiv-d) can be produced from (xiv-c) using procedures described in <step 7-2>.

<Step 14-5> A compound represented by formula (xiv-e) can be produced from (xv-d) using procedures described in <step 6-3>.

<Step 14-6> A compound represented by formula (xiv-f) can be produced by treating (xiv-e) with TFA in DCM at RT.

Scheme 15

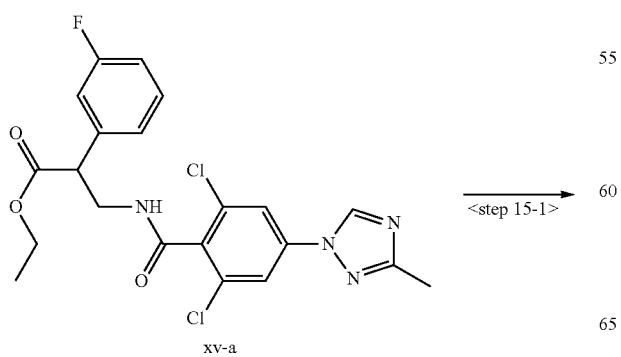
xv-a

-continued

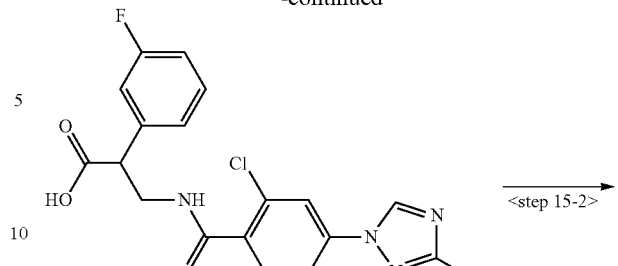
xv-b

<step 15-2>

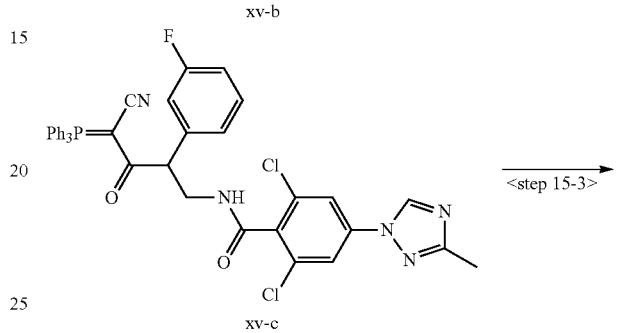
xv-c

<step 15-3>

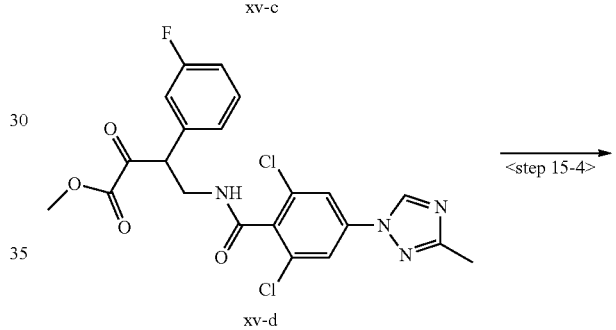
xv-d

<step 15-4>

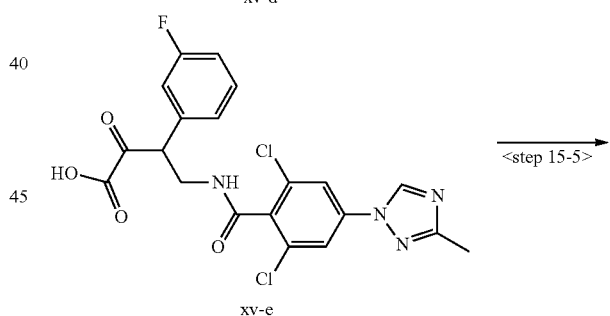
xv-e

<step 15-5>

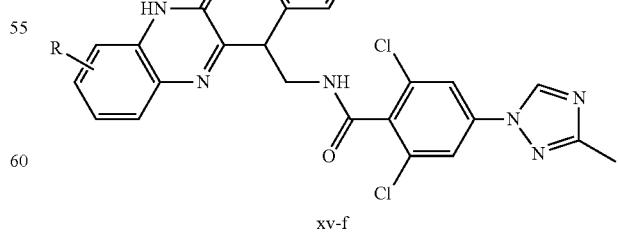
xv-f

<Step 15-1> A compound represented by formula (xv-a) can be produced from Ethyl 3-amino-2-(3-fluorophenyl)propanoate hydrochloride and 1-(4-carboxy-3,5-dichlorophenyl)-3-methyl-1H-1,2,4-triazol-4-ium chloride (INTERMEDIATE 12), 1-hydroxy-7-azabenzotriazole, EDC and Hunig's base in acetonitrile at room temperature. A compound represented by formula (xv-b) can be produced by treating (xv-a) with LiOH (aq) in dioxane at RT.
<Step 15-2> A compound represented by formula (xv-c) can be produced by treating (xv-b) with DMAP, (triphenylphosphoranylidene)acetonitrile and EDC in DCM (30 ml) at room temperature.
<Step 15-3> A compound represented by formula (xv-d) can be produced by ozonizing (xv-c) at −40° C. (JOC, 1994, 4364-4366).
<Step 15-4> A compound represented by formula (xv-e) can be produced by the same LiOH hydrolysis procedure as described in <step 15-1>.
<Step 15-5> A compound represented by formula (xv-f) can be produced by treating (xv-e) with substituted diaminobenzene in the presence of Hunig's base and HATU at RT in DMF; followed by heating in acetic acid at 100° C.

EXAMPLES

The present invention will now be described in more detail using examples, but the present invention is not limited to the examples.

Acronyms and abbreviations are as follows: aqueous solution (aq); tert-butyloxycarbonyl (Boc); acetic acid (AcOH); benzyloxycarbonyl (CBZ); 1,2-dichloroethane (DCE); dichloromethane (DCM); diisobutylaluminum hydride (DIBAL-H); N,N-diisopropyletyhlamine (DIEA); dimethylacetamide (DMA); 4-dimethylaminopyridine (DMAP); 1,2-dimethoxyethane (DME); dimethylsulfoxide (DMSO); dimethylformamide (DMF); 1,1'-bis(diphenylphsophino)ferrocene (dppf); 1-ethyl-3-(3-dimethylaminopropyl)carbodiimide (EDC); ethanol (EtOH); ethyl acetate (EtOAc); triethylamine ($Et_3N$); 1-[bis(dimethylamino)methylene]-1H-1,2,3-triazolo[4,5-b]pyridinium 3-oxid hexafluorophosphate (HATU); hexanes (Hex); 1-hydroxy-7-azabenzotriazole (HOAt); hydroxybenzotriazole (HOBt); N,N-diisopropylethylamine (Hunig's base); lithium diisopropylamide (LDA); acetonitrile (MeCN); methanol (MeOH); N-Bromosuccinimide (NBS); N-methylpyrrolidone (NMP); sodium bis(trimethylsilyl)amide (NaHMDS); phenyl (Ph); polyphorsphoric acid (PPA); saturated (sat); 2-(trimethylsilyl)ethoxymethyl (SEM); supercritical fluid chromatography (SFC); tetrabutylammonium fluoride (TBAF); tetrahydrofuran (THF); trifluoroacetic acid (TFA); trimethylsilyl iodide (TMSI); 15-crown-5 (1,4,7,10,13-Pentaoxacyclopentadecane); catalyst (cat.); anhydrous (anh.); aqueous solution (aq); concentrated (conc.); saturated (sat.); room temperature (RT).

The measurement of nuclear magnetic resonance (NMR) spectrum was performed using a JEOL JNM-ECX300 FT-NMR (manufactured by JEOL Ltd.), a JEOL JNM-ECX400 FT-NMR (manufactured by JEOL Ltd.), or a Varian Unity INOVAAS500 or AS600 FT-NMR (manufactured by Varian).

Liquid chromatography-mass spectrometry (LC-MS) was performed using a Waters FractionLynx MS system (manufactured by Waters Corporation) or a Waters Micromass ZQ Mass Spectromer/Agilent 1100 system. A Supelco Ascentis Express C18 Column™ (5 mm×30 cm, 5 micron) was used as an analytical column. 0.05% trifluoroacetic acid MeCN solution or 0.05% aqueous trifluoroacetic acid solution were used as the mobile phase. The analysis was performed under the following gradient conditions: 0.05% trifluoroacetic acid MeCN solution: 0.05% aqueous trifluoroacetic acid solution=1:9 (0 min), 99:1 (2 min or 5 min). Liquid chromatography-mass spectrometry (UPLC-MS) was also performed using an ACQUITY UPLC+MS system (manufactured by Waters Corporation). A BEH column (1.0 mm×5 cm, 1.7 micron) (manufactured Waters Corporation) was used as an analytical column. Aqueous trifluoroacetic acid solution (0.05%) and MeCN was used as the mobile phase, and the analysis was performed under a gradient of 10%-95% MeCN in 2 minutes. Purification was performed using a Waters mass-directed preparative system. For compounds purified under acidic conditions, a Sunfire column (19 mm×50 m, 5 micron, manufactured by Waters corporation) or a Sunfire column (19 mm×100 mm, 5 micron, manufactured by Waters corporation) was used. The gradient mobile phase varied but is generally described as 10-98% MeCN over 6 minutes with one of the following aqueous mixtures—0.1% trifluoroacetic acid or 0.1% formic acid. For compounds purified under basic conditions a BEH column (19 mm×50 mm, 5 micron, manufactured by Waters corporation) or a BEH column (19 mm×100 mm, 5 micron, manufactured by Waters corporation) was used. The gradient mobile phase varied but is generally described as 10-98% MeCN and 0.1% aqueous $NH_3$—$H_2O$ over 6 minutes. Liquid chromatography-mass spectrometry (UPLC-MS) was also performed using a ACQUITY UPLC+MS system (manufactured by Waters Corporation). A CAPCELL Pak® C18 MGIII-H (2.0 mm×5 cm, 3 micron) (manufactured by Shiseido Co., Ltd.) was used as an analytical column. Methanol and 0.05% aqueous trifluoroacetic acid solution were used as the mobile phase. The analysis was performed under the following gradient conditions: Methanol: 0.05% aqueous trifluoroacetic acid solution=5:95 (0 min), 95:5 (1 min), 95:5 (1.6 min), and 5:95 (2 min).

Intermediate 1

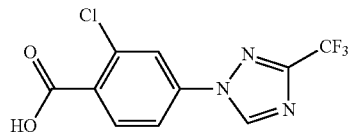 [SMILES: O=C(O)c1ccc(-n2cnc(C(F)(F)F)n2)cc1Cl]

2-Chloro-4-(3-(trifluoromethyl)-1H-1,2,4-triazol-1-yl)benzoic acid

Step A: Methyl 2-chloro-4-(3-(trifluoromethyl)-1H-1,2,4-triazol-1-yl)benzoate

To a solution of methyl 2-chloro-4-fluorobenzoate (1.0 g, 5.3 mmol) in DMF (40 mL) were added 3-(trifluoromethyl)-1H-1,2,4-triazole (0.73 g, 5.3 mmol) and potassium carbonate (0.73 g, 5.3 mmol) at room temperature. The reaction mixture was stirred at 100° C. for 12 h. After cooling to room temperature, it was diluted with $H_2O$ and extracted with EtOAc. The extract was washed with $H_2O$ and brine, dried over $Na_2SO_4$, filtered and concentrated in vacuo. The residue was purified by silica gel flash chromatography (eluent:Hexane:EtOAc=90:10~20:80) to give compound methyl 2-chloro-4-(3-(trifluoromethyl)-1H-1,2,4-triazol-1-yl)benzoate. LCMS calc.=306.02; found=306.10 (M+H)$^+$.
$^1$H NMR (500 MHz, DMSO-$d_6$): δ 9.73 (s, 1H); 8.22 (s, 1H); 8.21-8.01 (m, 2H); 3.89 (s, 3H).

Step B: 2-Chloro-4-(3-(trifluoromethyl)-1H-1,2,4-triazol-1-yl)benzoic acid

To a solution of methyl 2-chloro-4-(3-(trifluoromethyl)-1H-1,2,4-triazol-1-yl)benzoate (0.5 g, 1.64 mmol) in MeOH (30 mL) and THF (60 mL) was added 3N sodium hydroxide (aq) (1.1 mL, 3.27 mmol). The solution was stirred at room temperature for 3 h. The reaction solution was concentrated and the residue was dissolved in water, to which was added 5N HCl. The precipitate was filtered, washed with water and dried to give the product 2-chloro-4-(3-(trifluoromethyl)-1H-1,2,4-triazol-1-yl)benzoic acid. LCMS calc.=292.00; found=292.03 (M+H)$^+$. $^1$H NMR (500 MHz, CDCl$_3$): δ 8.85 (s, 1H); 8.10-8.08 (d, J=9 Hz, 1H); 7.92 (s, 1H); 7.72-7.70 (dd, J=8.5, 2 Hz, 1H).

Intermediate 2

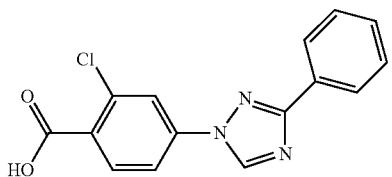 [SMILES: O=C(O)c1ccc(-n2cnc(-c3ccccc3)n2)cc1Cl]

2-Chloro-4-(3-phenyl-1H-1,2,4-triazol-1-yl)benzoic acid

In the same procedure as intermediate 1, 2-Chloro-4-(3-phenyl-1H-1,2,4-triazol-1-yl)benzoic acid was prepared. LCMS calc.=300.05; found=300.02 (M+H)$^+$. $^1$H NMR (500 MHz, DMSO-d$_6$): δ 9.53 (s, 1H); 8.19-8.18 (d, J=8.5 Hz, 1H); 8.11 (d, J=2 Hz); 8.02 (s, 1H); 7.52-7.46 (m, 5H).

Intermediate 3

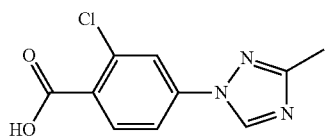

2-Chloro-4-(3-methyl-1H-1,2,4-triazol-1-yl)benzoic acid

Step A: Methyl 2-chloro-4-hydrazinylbenzoate hydrochloride

To a suspension of methyl 4-amino-2-chlorobenzoate (5 g, 26.9 mmol) in conc. HCl (75 mL) at 0° C. was added sodium nitrile (1.86 g, 26.9 mmol) solution in water (30 mL). The reaction mixture was stirred at 0° C. for 30 min, and continued to at RT for 90 min. Tin chloride (14.3 g, 75 mmol) in HCl (100 mL) was added to the mixture drop wise at 0° C. The reaction mixture was stirred at RT for 12 h. The reaction was filtered and the filter cake was washed with diethyl ether (3×100 mL) and DCM (2×100 mL) to give the product methyl 2-chloro-4-hydrazinylbenzoate hydrochloride. LCMS calc.=201.04; found=201.12 (M+H)$^+$. $^1$H NMR (500 MHz, DMSO-d$_6$): δ 9.27 (s, 1H); 7.79-7.77 (d, J=9.5 Hz, 1H); 7.14 (s, 1H); 6.98-6.96 (d, J=8 Hz, 1H); 4.31-4.03 (broad, 2H); 3.78 (s, 3H).

Step B: Methyl 2-chloro-4-(3-methyl-1H-1,2,4-triazol-1-yl)benzoate

To a suspension of ethyl acetamidate hydrochloride (2.95 g, 23.85 mmol) in DCM (50 mL) at −40° C. were added triethyl amine (3.07 mL, 22.02 mmol) and methyl 2-chloro-4-hydrazinylbenzoate hydrochloride (4.35 g, 18.35 mmol). The resulting slurry was allowed to warm to 0° C. over 15 min by replacing the dry ice bath with an ice bath. The mixture was allowed to stirred at 0° C. for 3 h. Triethyl orthoformate (54.4 g, 367 mmol) and pyridine (3 mL) were added to the mixture. The reaction was heated to 80° C. and stirred for 13 h. The reaction mixture was cooled to room temperature and then concentrated under reduced pressure. The resulting residue was added in a saturated aqueous solution of NaHCO$_3$, and the mixture was extracted with EtOAc (3×100 mL). The combined organic layers were washed with brine, dried over MgSO$_4$ and concentrated. The residue was purified by chromatography on silica (Eluant: Hexane:EtOAc=100:0-50:50) to afford the title compound methyl 2-chloro-4-(3-methyl-1H-1,2,4-triazol-1-yl)benzoate. LCMS calc.=252.05; found=252.07 (M+H)$^+$. $^1$H NMR (500 MHz, CD$_3$Cl): δ 8.62 (s, 1H); 8.4 (d, J=10 Hz, 1H); 7.87 (s, 1H); 7.66 (d, J=10 Hz, 1H); 3.99 (s, 3H); 2.54 (s, 3H).

Step C: 2-Chloro-4-(3-methyl-1H-1,2,4-triazol-1-yl)benzoic acid

In the same procedure as intermediate 1 (step B), 2-Chloro-4-(3-methyl-1H-1,2,4-triazol-1-yl)benzoic acid was prepared. LCMS calc.=238.08; found=238.04 (M+H)$^+$. $^1$H NMR (500 MHz, DMSO-d$_6$): δ 9.31 (s, 1H); 8.04 (s, 1H); 7.96 (d, J=9.0 Hz, 1H); 7.86 (d, J=9.0 Hz, 1H); 2.35 (s, 3H).

Intermediate 4

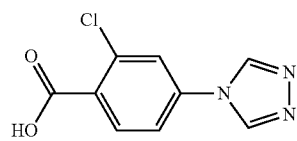 [SMILES: O=C(O)c1ccc(-n2cnnc2)cc1Cl]

2-Chloro-4-(4H-1,2,4-triazol-4-yl)benzoic acid

Step A: (E)-Ethyl 2-chloro-4-(((dimethylamino)methylene)amino)benzoate

A solution of 4-amino-2-chlorobenzoic acid (5 g, 29.1 mmol) in DMF-DEA (5.78 mL, 35.0 mmol) was stirred at 25° C. overnight. The solvent was removed in vacuo, and the residue was partitioned between EtOAc and saturated aq NaHCO$_3$. The aqueous layer was extracted with EtOAc (2×). The combined organic phase was washed with brine, dried over anhydrous MgSO$_4$, filtered and concentrated in vacuo to give the crude product (E)-methyl 2-chloro-4-(((dimethylamino)methylene)amino)benzoate. LCMS calc.=255.08; found=254.96 (M+H)$^+$.

Step B: Ethyl 2-chloro-4-(4H-1,2,4-triazol-4-yl)benzoate

To a solution of methyl 2-chloro-4-(((dimethylamino) methylene)amino)benzoate (7.41 g, 29.1 mmol) in MeOH (58 mL) were added formic acid hydrazine (2.10 g, 34.9 mmol) and acetic acid (3.33 mL, 58.2 mmol). The reaction mixture was stirred at 55° C. for overnight. After cooling to room temperature, the solvent was concentrated in vacuo. The residue was partitioned between EtOAc and saturated aq NaHCO$_3$. The aqueous layer was extracted with EtOAc (2×). The combined organic phase was washed with brine, dried over anhydrous MgSO$_4$, filtered and concentrated in vacuo. The crude product was dissolved in minimal amount of DCM and precipitated with hexane to give the product methyl 2-chloro-4-(4H-1,2,4-triazol-4-yl)benzoate.

Step C: 2-Chloro-4-(4H-1,2,4-triazol-4-yl)benzoic acid

In the same procedure as intermediate 1 Step B, 2-chloro-4-(4H-1,2,4-triazol-4-yl)benzoic acid was prepared. LCMS calc.=224.01; found=223.98 (M+H)$^+$. $^1$H NMR (500 MHz, CD$_3$OD): δ 9.11 (s, 2H); 8.05 (d, J=8.5H, 1H); 7.96 (d, J=2 Hz, 1H); 7.71-7.67 (dd, J=2.0, 8.0 Hz, 1H).

Intermediate 5

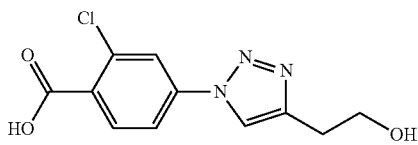 [SMILES: O=C(O)c1ccc(-n2cc(CCO)nn2)cc1Cl]

2-Chloro-4-(4-(2-hydroxyethyl)-1H-1,2,3-triazol-1-yl)benzoic acid

Step A: Methyl 4-azido-2-chlorobenzoate

To a solution of methyl 2-chloro-4-fluorobenzoate (3 g, 15.91 mmol) in DMF (15.91 mL) was added sodium azide (2.068 g, 31.8 mmol). The reaction mixture was stirred at 65° C. overnight. The reaction was quenched by the addition of water and extracted with EtOAc. The combined organic extracts were washed with water and brine, dried over MgSO$_4$, filtered and concentrated in vacuo. The crude mixture was purified by chromatography on silica (Eluant: Hexane:EtOAc=95:5) to afford the title compound methyl 4-azido-2-chlorobenzoate. LCMS calc.=212.01; found=212.00 (M+H)$^+$.

Step B: Methyl 2-chloro-4-(4-(2-hydroxyethyl)-1H-1,2,3-triazol-1-yl)benzoate To a solution of methyl 4-azido-2-chlorobenzoate (500 mg, 2.363 mmol) in DMF (5 mL) were added but-3-yn-1-ol (248 mg, 3.54 mmol), sodium ascorbate (189 mg, 0.945 mmol) and copper(I) iodide (90 mg, 0.473 mmol). The reaction mixture was stirred at 60° C. for 16 h. The reaction mixture was filtered through celite and washed with MeOH. The filtrate was partitioned between EtOAc (200 mL) and water (100 mL). The organic layer was washed with brine, dried over MgSO$_4$, filtered and concentrated in vacuo. The residue was purified by chromatography on silica (Eluant: Hexane:EtOAc=100:0-20:80) to afford the title compound methyl 2-chloro-4-(4-(2-hydroxyethyl)-1H-1,2,3-triazol-1-yl)benzoate. LCMS calc.=282.06; found=282.00 (M+H)$^+$.

Step C: 2-Chloro-4-(4-(2-hydroxyethyl)-1H-1,2,3-triazol-1-yl)benzoic acid

To a solution of methyl 2-chloro-4-(4-(2-hydroxyethyl)-1H-1,2,3-triazol-1-yl)benzoate (3.22 g, 11.43 mmol) in THF (16 mL)/Water (4.00 mL) was added lithium hydroxide hydrate (1.919 g, 45.7 mmol) and stirred at RT. The reaction was then concentrated in vacuo, and to the crude mixture was added water (3 mL). The mixture was then acidified with conc. hydrogen chloride (aq) (2.86 ml, 34.3 mmol) to pH=5, and filtered. The solid was washed with cold water and dried to provide the product 2-chloro-4-(4-(2-hydroxyethyl)-1H-1,2,3-triazol-1-yl)benzoic acid.

LCMS calc.=268.04; found=268.03 (M+H)$^+$. $^1$H NMR (500 MHz, CD$_3$OD): δ 8.46 (s, 1H); 8.16-8.04 (m, 2H); 7.92 (m, 1H); 3.85 (m, 2H); 3.01 (m, 2H).

Intermediate 6

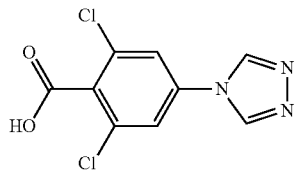 [SMILES: O=C(O)c1c(Cl)cc(-n2cnnc2)cc1Cl]

2,6-Dichloro-4-(4H-1,2,4-triazol-4-yl)benzoic acid

Step A: 4-Bromo-3,5-dichloroaniline

To a solution of 3,5-dichloroaniline (3.56 g, 21.97 mmol) in acetonitrile (60 mL) at 0° C. was added NBS (4.30 g, 24.17 mmol). The reaction was kept at 0° C. and stirred for 3 h. The solvent was concentrated under reduced pressure and the residue was partitioned between EtOAc (200 mL) and water (100 mL). The organic layer was washed with brine, dried over MgSO$_4$, filtered and concentrated in vacuo. The residue was purified by chromatography on silica (Eluant:Hexane:EtOAc=90:10) to afford the title compound 4-bromo-3,5-dichloroaniline. LCMS calc.=239.89; found=239.84/241.84 (M+H)$^+$. $^1$H NMR (500 MHz, CDCl$_3$): δ 7.71 (s, 2H); 3.80-3.75 (br, s, 2H).

Step B: tert-Butyl (4-bromo-3,5-dichlorophenyl)carbamate

To a solution of 4-bromo-3,5-dichloroaniline (480 mg, 1.99 mmol) in DCM (6 mL) were added di-tert-butyl dicarbonate (500 mg, 2.29 mmol), triethyl amine (0.84 mL, 5.98 mmol) and DMAP (24.3 mg, 0.20 mmol). The reaction was stirred at room temperature for 16 h. The reaction mixture was partitioned between EtOAc (100 mL) and water (50 mL). The organic layer was washed with brine, dried over MgSO$_4$, filtered and concentrated in vacuo. The residue was purified by chromatography on silica (Eluant:Hexane:EtOAc=100:0~90:10) to afford the title compound tert-butyl (4-bromo-3,5-dichlorophenyl)carbamate. LCMS calc.=339.94; found=339.85/341.85 (M+H)+. 1H NMR (500 MHz, CDCl3): δ 7.47 (s, 2H); 6.48-6.43 (br, s, 1H); 2.54 (s, 9H).

Step C: Methyl 4-((tert-butoxycarbonyl)amino)-2,6-dichlorobenzoate

To a solution of tert-butyl (4-bromo-3,5-dichlorophenyl) carbamate (200 mg, 0.59 mmol) in DMF (4 mL) and MeOH (2.14 mL) were added Hunig's base (0.51 mL, 2.93 mmol), palladium(II) acetate (28.7 mg, 0.13 mmol), and DPPF (142 mg, 0.26 mmol). The system was degassed and refilled with $N_2$, then degassed and refilled with CO twice. The reaction was stirred at 100° C. under 200 psi for 18 h. The reaction mixture was partitioned between EtOAc (50 mL) and water (20 mL). The organic layer was washed with brine, dried over $MgSO_4$, filtered and concentrated in vacuo. The residue was purified by chromatography on silica (Eluant:Hexane:EtOAc=100:0~90:10) to afford the title compound methyl 4-((tert-butoxycarbonyl)amino)-2,6-dichlorobenzoate. 1H NMR (500 MHz, $CD_3OD$): δ 7.40 (s, 1H); 6.81 (brs, 1H); 3.99 (s, 3H); 1.50 (s, 9H).

Step D: Methyl 4-amino-2,6-dichlorobenzoate

Methyl 4-((tert-butoxycarbonyl)amino)-2,6-dichlorobenzoate (45 mg, 0.14 mmol) was dissolved in $CH_2Cl_2$ (0.5 mL) and treated with TFA (0.5 mL). The reaction mixture was stirred at room temperature for 2 h and the solvents were removed and dried under high vacuum to afford methyl 4-amino-2,6-dichlorobenzoate TFA salt. This was used without further purification.
LCMS calc.=219.99; found=219.91 (M+H).

Step E: (E)-Methyl 2,6-dichloro-4-(((dimethylamino)methylene)amino)benzoate

To a sealed tube was added methyl 4-amino-2,6-dichlorobenzoate (0.10 g, 0.31 mmol) and DMF-DMA (0.42 mL, 3.12 mmol). The reaction mixture was stirred at 80° C. for 16 h. DMF-DMA was removed under reduced pressure, and the residue was partitioned between EtOAc (30 mL) and saturated aq $NaHCO_3$ (20 mL). The crude product (E)-methyl 2,6-dichloro-4-(((dimethylamino)methylene)amino) benzoate was directly used for next step without purification. LCMS calc.=275.03; found=275.01 (M+H)+.

Step F: Methyl 2,6-dichloro-4-(4H-1,2,4-triazol-4-yl)benzoate

To a sealed tube was added (E)-methyl 2,6-dichloro-4-(((dimethylamino)methylene)amino)benzoate (86 mg, 0.31 mmol), formohydrazide (37.5 mg, 0.62 mmol) and AcOH (2 mL). The mixture was flushed with $N_2$, sealed with cap, and then heated at 55° C. for 16 h. AcOH was removed under reduced pressure. The residue was partitioned between EtOAc and saturated aq $NaHCO_3$. The aqueous layer was extracted with EtOAc (2×). The combined organic phase was washed with brine, dried over anhydrous $MgSO_4$, filtered and concentrated in vacuo. The residue was purified by chromatography on silica (Eluant:Hexane:EtOAc=100:0-40:60) to afford the title compound methyl 2,6-dichloro-4-(4H-1,2,4-triazol-4-yl)benzoate. LCMS calc.=271.99; found=271.94 (M+H)+.

Step G: 2,6-Dichloro-4-(4H-1,2,4-triazol-4-yl)benzoic acid

To a solution of methyl 2,6-dichloro-4-(4H-1,2,4-triazol-4-yl)benzoate (146 mg, 0.54 mmol) in co-solvent of THF (1.6 mL), Water (0.4 mL) and MeOH (0.4 mL) was added lithium hydroxide hydrate (135 mg, 3.22 mmol). The reaction mixture was stirred at 60° C. for 16 h. The solvents were removed in vacuo, and the crude mixture was acidified to pH=5 with 2N HCl aq. The mixture was filtered, and the solid was washed with cold water and dried to provide the product 2,6-dichloro-4-(4H-1,2,4-triazol-4-yl)benzoic acid. LCMS calc.=257.98; found=257.91 (M+H)+. 1H NMR (500 MHz, $CD_3OD$): δ 9.45 (s, 2H); 7.88 (s, 2H).

Intermediate 7

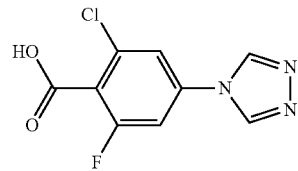 [SMILES: O=C(O)c1c(F)cc(-n2cnnc2)cc1Cl]

2-Chloro-6-fluoro-4-(4H-1,2,4-triazol-4-yl)benzoic acid

In the same procedure as intermediate 6, 2-chloro-6-fluoro-4-(4H-1,2,4-triazol-4-yl)benzoic acid was prepared. LCMS calc.=242.01; found=241.98 (M+H)+. 1H NMR (500 MHz, $CD_3OD$): δ 9.16 (s, 2H); 7.81 (s, 1H); 7.69 (d, 1H).

Intermediate 8

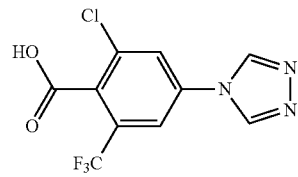 [SMILES: O=C(O)c1c(Cl)cc(-n2cnnc2)cc1C(F)(F)F]

2-Chloro-4-(4H-1,2,4-triazol-4-yl)-6-(trifluoromethyl)benzoic acid

In the same procedure as intermediate 6, 2-chloro-4-(4H-1,2,4-triazol-4-yl)-6-(trifluoromethyl)benzoic acid was prepared. LCMS calc.=292.00; found=292.06 (M+H)+. 1H NMR (500 MHz, DMSO-$d_6$): δ 9.31 (s, 2H); 8.40 (s, 1H); 8.24 (s, 1H).

Intermediate 9

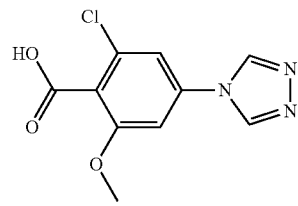 [SMILES: COc1cc(-n2cnnc2)cc(Cl)c1C(=O)O]

2-Chloro-6-methoxy-4-(4H-1,2,4-triazol-4-yl)benzoic acid

In the same procedure as intermediate 6, 2-chloro-6-methoxy-4-(4H-1,2,4-triazol-4-yl)benzoic acid was prepared. LCMS calc.=254.04; found=254.01 (M+H)$^+$. $^1$H NMR (500 MHz, CD$_3$OD): δ 9.82 (s, 2H); 7.59 (s, 1H); 7.56 (d, 1H); 4.01 (s, 3H).

Intermediate 10

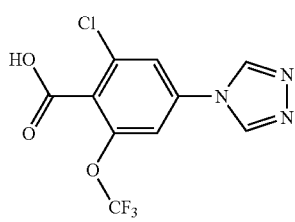 [SMILES: O=C(O)c1c(Cl)cc(-n2cnnc2)cc1OC(F)(F)F]

2-Chloro-4-(4H-1,2,4-triazol-4-yl)-6-(trifluoromethoxy)benzoic acid

In the same procedure as intermediate 6, 2-chloro-4-(4H-1,2,4-triazol-4-yl)-6-(trifluoromethoxy)benzoic acid was prepared. LCMS calc.=308.00; found=308.04 (M+H)$^+$. $^1$H NMR (500 MHz, CD$_3$OD): δ 9.18 (s, 2H); 7.97 (s, 1H); 7.88 (d, 1H).

Intermediate 11

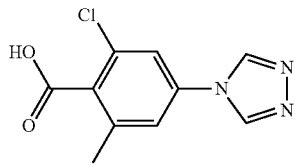 [SMILES: Cc1cc(-n2cnnc2)cc(Cl)c1C(=O)O]

2-Chloro-6-methyl-4-(4H-1,2,4-triazol-4-yl)benzoic acid

Step A: 3-Chloro-5-methylaniline

To a solution of 1-chloro-3-methyl-5-nitrobenzene (1.61 g, 9.38 mmol) in EtOH (30 ml) was added tin chloride (8.90 g, 46.9 mmol). The reaction was heated at 85° C. for 2 h and was then quenched with 1N NaOH (50 mL) and extracted with EtOAc (100 mL). The aqueous layer was extracted with EtOAc (2×). The combined organic phase was washed with brine, dried over anhydrous MgSO$_4$, filtered and concentrated in vacuo. The residue was purified by chromatography on silica (Eluant:Hexane:EtOAc=100:0-40:60) to afford the title compound 3-chloro-5-methylaniline. LCMS calc.=142.03; found=141.92 (M+H)$^+$. $^1$H NMR (500 MHz, CDCl$_3$): δ 6.56 (s, 1H); 6.49 (s, 1H); 6.37 (s, 1H); 3.65 (brs, 2H); 2.23 (s, 3H).

Step B: 2-Chloro-6-methyl-4-(4H-1,2,4-triazol-4-yl)benzoic acid

In the same procedure as intermediate 6, 2-chloro-6-methyl-4-(4H-1,2,4-triazol-4-yl)benzoic acid was prepared. LCMS calc.=238.03; found=237.99 (M+H)$^+$. $^1$H NMR (500 MHz, CD$_3$OD): δ 9.21 (s, 2H); 7.84 (s, 1H); 7.68 (d, 1H); 2.38 (s, 3H).

Intermediate 12

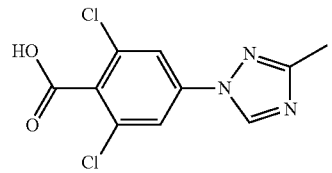 [SMILES: Cc1ncn(-c2cc(Cl)c(C(=O)O)c(Cl)c2)n1]

2,6-Dichloro-4-(3-methyl-1H-1,2,4-triazol-1-yl)benzoic acid

In the same procedure as intermediate 6 (step A-D), following procedures as intermediate 3 (step A-B), and intermediate 6 (step G), 2,6-dichloro-4-(3-methyl-1H-1,2,4-triazol-1-yl)benzoic acid.
LCMS calc.=271.99; found=271.95 (M+H)$^+$. $^1$H NMR (500 MHz, DMSO-d$_6$): δ 9.29 (s, 2H); 8.06 (s, 2H); 2.37 (s, 3H).

Intermediate 13

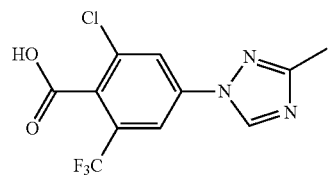 [SMILES: Cc1ncn(-c2cc(Cl)c(C(=O)O)c(C(F)(F)F)c2)n1]

2-Chloro-4-(3-methyl-1H-1,2,4-triazol-1-yl)-6-(trifluoromethyl)benzoic acid

In the same procedure as intermediate 12, 2-chloro-4-(3-methyl-1H-1,2,4-triazol-1-yl)-6-(trifluoromethyl)benzoic acid was prepared. LCMS calc.=306.02; found=306.11 (M+H)$^+$.

Intermediate 14

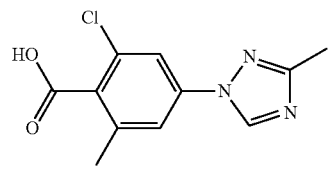 [SMILES: Cc1ncn(-c2cc(C)c(C(=O)O)c(Cl)c2)n1]

2-Chloro-6-methyl-4-(3-methyl-1H-1,2,4-triazol-1-yl)benzoic acid

In the same procedure as intermediate 11 (step A), following procedure as intermediate 12, 2-chloro-6-methyl-4-(3-methyl-1H-1,2,4-triazol-1-yl)benzoic acid was prepared. LCMS calc.=252.05; found=252.07 (M+H). $^1$H NMR (500 MHz, CD$_3$OD): δ 9.15 (s, 1H); 7.79 (s, 1H); 7.68 (s, 1H), 3.35 (s, 3H); 2.46 (s, 3H).

Intermediate 15

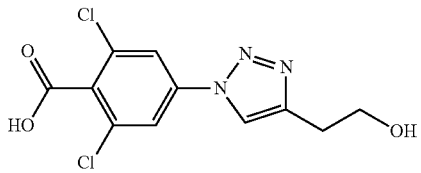

2,6-Dichloro-4-(4-(2-hydroxyethyl)-1H-1,2,3-triazol-1-yl)benzoic acid

In the same procedure as intermediate 6 (step C), following procedures as intermediate 5 (step A-B), and intermediate 6 (step G), 2,6-dichloro-4-(4-(2-hydroxyethyl)-1H-1,2,3-triazol-1-yl)benzoic acid was prepared. LCMS calc.=302.00; found=302.01 (M+H). $^1$H NMR (500 MHz, CD$_3$OD): δ 8.52 (s, 1H); 8.04 (s, 2H); 3.37 (m, 2H); 2.98 (m, 2H).

Intermediate 16

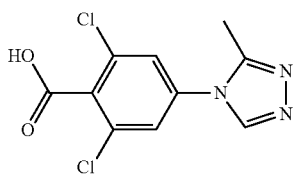 [SMILES: Cc1nncn1-c1cc(Cl)c(C(=O)O)c(Cl)c1]

2,6-Dichloro-4-(3-methyl-4H-1,2,4-triazol-4-yl)benzoic acid

Step A: Methyl 2,6-Dichloro-4-(3-methyl-4H-1,2,4-triazol-4-yl)benzoate

A solution of acethydrazide (0.37 g, 5.00 mmol) and N,N-dimethylformamide dimethyl acetal (1.08 g, 9.09 mmol) in MeCN (3.37 mL) was stirred for 0.5 h at 50° C. A solution of methyl 4-amino-2,6-dichlorobenzoate (1.00 g, 4.54 mmol) in MeCN (1.69 ml) and acetic acid (5.06 mL) was added and the resulting mixture was stirred at 120° C. overnight. The mixture was concentrated in vacuo to give the crude product. This was purified by flash chromatography on silica (Eluant:EtOAc:MeOH=100:0~90:10) to afford methyl 2,6-dichloro-4-(3-methyl-4H-1,2,4-triazol-4-yl)benzoate. LCMS calc.=286.01; found=286.06 (M+H)$^+$.

Step B: 2,6-Dichloro-4-(3-methyl-4H-1,2,4-triazol-4-yl)benzoic acid

To a solution of methyl 2,6-dichloro-4-(3-methyl-4H-1,2,4-triazol-4-yl)benzoate (0.42 g, 1.49 mmol) in 1,4-dioxane (7.42 mL) was added lithium hydroxide (1M solution, 2.97 mL, 2.97 mmol). The reaction mixture was stirred at 55° C. for 24 h. This mixture was neutralized with 1N aq. HCl (2.97 mL) and concentrated in vacuo. The resulting residue was suspended in water and the insoluble material was collected by filtration to afford the desired product 2,6-dichloro-4-(3-methyl-4H-1,2,4-triazol-4-yl)benzoic acid. LCMS calc.=271.99; found=272.06 (M+H)$^+$.

Intermediate 17

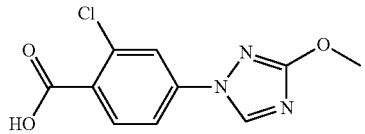

2-Chloro-4-(3-methoxy-1H-1,2,4-triazol-1-yl)benzoic acid

Step A: 2-Chloro-4-hydrazinylbenzoic acid hydrochloride

A suspension of methyl 4-amino-2-chlorobenzoate (4.50 g, 24.24 mmol) in 37% conc. HCl (67.6 mL) was cooled to 0° C. and a solution of sodium nitrite (1.67 g, 24.24 mmol) in Water (18.02 mL) was added dropwise over 30 min. The reaction mixture was warmed to room temperature and stirred for 90 min. A solution of Tin (II) chloride (15.32 g, 67.9 mmol) in 37% conc. HCl (90 mL) was added dropwise at 0° C. and stirred at room temperature for 2 h. The precipitate was collected by filtration and the solid was washed with cold water. The solid was dried in vacuo to afford the desired product 2-chloro-4-hydrazinylbenzoic acid hydrochloride. LCMS calc.=201.04; found=201.11 (M+H)$^+$. $^1$H NMR (500 MHz, DMSO-d$_6$): δ 10.91-10.32 (br, 3H); 7.78 (d, 1H); 7.16 (s, 1H); 6.92 (d, 1H); 3.81 (s, 3H).

Step B: Methyl 4-(2-carbamoylhydrazinyl)-2-chlorobenzoate

To a solution 2-chloro-4-hydrazinylbenzoic acid hydrochloride (0.66 g, 2.78 mmol) in water (27.8 mL) at 25° C. was added potassium cyanate (0.23 g, 2.78 mmol). A precipitate appeared immediately along with an exotherm. After 1 h the exotherm had dissipated so the precipitate was collected by filtration to afford the desired product methyl 4-(2-carbamoylhydrazinyl)-2-chlorobenzoate. LCMS calc.=244.04; found=244.05 (M+H)$^+$.

Step C: Methyl 2-chloro-4-(3-oxo-2,3-dihydro-1H-1,2,4-triazol-1-yl)benzoate

To a solution/suspension of methyl 4-(2-carbamoylhydrazinyl)-2-chlorobenzoate (0.68 g, 2.67 mmol) in triethyl orthoformate (6.59 mL, 39.6 mmol) was added p-toluenesulfonic acid monohydrate (5.02 mg, 0.026 mmol). The reaction mixture was heated at 100° C. overnight. The reaction mixture was cooled to room temperature and concentrated in vacuo to give the desired product methyl 2-chloro-4-(3-oxo-2,3-dihydro-1H-1,2,4-triazol-1-yl)benzoate. LCMS calc.=254.03; found=254.03 (M+H)$^+$. $^1$H NMR (500 MHz, DMSO-d$_6$): δ 11.72 (s, 1H); 9.07 (s, 1H); 7.93 (d, J=2.0 Hz, 2H); 7.81 (d, J=2.0 Hz, 1H); 3.86 (s, 3H).

Step D: Methyl 2-chloro-4-(3-methoxy-1H-1,2,4-triazol-1-yl)benzoate

To a solution of methyl 2-chloro-4-(3-oxo-2,3-dihydro-1H-1,2,4-triazol-1-yl)benzoate (0.48 g, 1.78 mmol) in dry DMF (5.28 mL) at 25° C. was added iodomethane (0.33 mL, 5.28 mmol) and potassium carbonate (1.10 g, 7.92 mmol). The reaction mixture was stirred at 25° C. for 4 h. The reaction mixture was diluted with saturated NH$_4$Cl solution and water, then extracted with EtOAc (3×). The combined extracts were dried over Na₂SO₄, filtered and concentrated in vacuo to give the crude product. This was purified by flash chromatography (Eluant: CH₂Cl₂:MeOH=100:0~90:10) to afford methyl 2-chloro-4-(3-methoxy-1H-1,2,4-triazol-1-yl)benzoate. LCMS calc.=268.04; found=268.06 (M+H)⁺. ¹H NMR (500 MHz, CD₃OD): δ 8.39 (s, 1H); 7.99 (d, J=8.5 Hz, 1H); 7.81 (s, 1H); 7.59 (dd, J=8.5, 2 Hz, 1H); 4.08 (st, 3H); 2.08 (s, 3H).

Step E: 2-Chloro-4-(3-methoxy-1H-1,2,4-triazol-1-yl)benzoic acid

To a solution of methyl 2-chloro-4-(3-methoxy-1H-1,2,4-triazol-1-yl)benzoate (0343285-0071-1) (0.48 g, 1.78 mmol) in 1,4-dioxane (12.54 mL) and water (2.51 mL) was added lithium hydroxide (3.55 mL, 3.55 mmol, 1M solution). The resulting mixture was stirred at 25° C. for 4 h. This mixture was neutralized with 1N aq. HCl (3.55 mL) and concentrated in vacuo to give the crude product. This was purified by flash chromatography (Eluant: containing 0.05% TFA in both water and MeCN, Water:MeCN=90:10~0:100) to afford 2-chloro-4-(3-methoxy-1H-1,2,4-triazol-1-yl)benzoic acid. LCMS calc.=254.03; found=254.08 (M+H)⁺.

Intermediate 18A

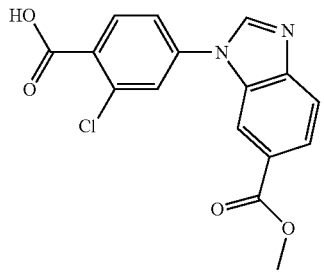 [SMILES: COC(=O)c1ccc2ncn(-c3ccc(C(=O)O)c(Cl)c3)c2c1]

2-chloro-4-(6-(methoxycarbonyl)-1H-benzo[d]imidazol-1-yl)benzoic acid

Intermediate 18B

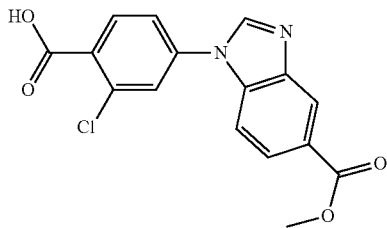 [SMILES: COC(=O)c1ccc2c(c1)ncn2-c1ccc(C(=O)O)c(Cl)c1]

2-chloro-4-(5-(methoxycarbonyl)-1H-benzo[d]imidazol-1-yl)benzoic acid

Step A 18A-a: Methyl 1-(4-(tert-butoxycarbonyl)-3-chlorophenyl)-1H-benzo[d]imidazole-6-carboxylate 18A-b: methyl 1-(4-(tert-butoxycarbonyl)-3-chlorophenyl)-1H-benzo[d]imidazole-5-carboxylate Tert-butyl-2-chloro-4-fluorobenzoate (200 mg, 0.867 mmol), methyl 1H-benzimidazole-5-carboxylate (214 mg, 1.214 mmol) and potassium carbonate (359 mg, 2.60 mmol) in dry acetonitrile (12 mL) was stirred at 85° C. for 6 h. The reaction mixture was cooled to RT and the solid was filtered and washed with EtOAc. The filtrate was concentrated and purified by flash chromatography (ISCO CombiFlash system, 80 g Silica gel column, 0-60% EtOAc in hexane as as eluting solvent) to afford the product as a mixture of two regioisomers. Further separation of this mixture of products by SFC technique on chiral AD-H column and using 55% MeOH/CO2 as mobile phase yielded compound 18A-a, methyl 1-(4-(tert-butoxycarbonyl)-3-chlorophenyl)-1H-benzo[d]imidazole-6-carboxylate, and compound 18A-b, methyl 1-(4-(tert-butoxycarbonyl)-3-chlorophenyl)-1H-benzo[d]imidazole-5-carboxylate.

For Compound 18A-a: methyl 1-(4-(tert-butoxycarbonyl)-3-chlorophenyl)-1H-benzo[d]imidazole-6-carboxylate (M+H) calc.=387.10; found=387.15. ¹H NMR (500 MHz, CD₃OD): δ 8.70 (s, br, 1H); 8.30 (s, br, 1H); 8.08 (dd, J=1.5 Hz, J=8.5 Hz, 1H); 8.01 (d, J=8.5 Hz, 1H); 7.89 (d, J=2.5 Hz, 1H); 7.86 (d, J=8.5 Hz, 1H); 7.74 (dd, J=2.0 Hz, J=8.5 Hz, 1H); 3.95 (s, 3H); 1.66 (s, 9H)

For Compound 18A-b: methyl 1-(4-(tert-butoxycarbonyl)-3-chlorophenyl)-1H-benzo[d]imidazole-5-carboxylate (M+H) calc.=387.10; found=387.15. ¹H NMR (500 MHz, CD₃OD): δ 8.56 (s, br, 1H); 8.47 (s, br, 1H); 8.12 (dd, J=1.5 Hz, J=8.5 Hz, 1H); 8.10 (d, J=8.5 Hz, 1H); 7.89 (d, J=2.0 Hz, 1H); 7.76 (d, J=8.5 Hz, 1H); 7.73 (dd, J=2.0 Hz, J=8.5 Hz, 1H); 3.97 (s, 3H); 1.65 (s, 9H) Additional NMR studies (NOE) confirmed the structure assignments of the two products.

Step B

18A: 2-chloro-4-(6-(methoxycarbonyl)-1H-benzo[d]imidazol-1-yl)benzoic acid

18B: 2-chloro-4-(5-(methoxycarbonyl)-1H-benzo[d]imidazol-1-yl)benzoic acid

The product 18A-a (94 mg, 0.243 mmol) from step A in TFA-DCM (2 ml-2 ml) was stirred at room temperature for 4 h. The volatile was evaporated, and the residue was redissolved in DCM (1 ml)-4N HCl in dioxane (0.304 mL), and stirred for 2 min, then evaporated to dryness, followed by lyophilization to give compound 18A, 2-chloro-4-(6-(methoxycarbonyl)-1H-benzo[d]imidazol-1-yl)benzoic acid.

Compound 18A-b (94 mg, 0.243 mmol) from step A in TFA-DCM (2 ml-2 ml) was stirred at room temperature for 4 h. The volatile was evaporated, and the residue was redissolved in DCM (1 mL)-4N HCl in dioxane (0.310 mL), and stirred for 2 min, then evaporated to dryness, followed by lyophilization to give the compound 18B, 2-chloro-4-(5-(methoxycarbonyl)-1H-benzo[d]imidazol-1-yl)benzoic acid.

For compound 18A:
LC-Mass: (M+H) calc.=331.04; found=331.05. ¹H NMR (500 MHz, CD₃OD): δ 8.85 (s, br, 1H); 8.34 (s, br, 1H); 8.18 (d, J=8.5 Hz, 1H); 8.13 (d, J=8.0 Hz, 1H); 7.94 (d, J=2.0 Hz, 1H); 7.90 (d, J=8.5 Hz, 1H); 7.78 (dd, J=2.0 Hz, J=8.5 Hz, 1H); 3.96 (s, 3H)

For compound 18B:
LC-Mass: (M+H) calc.=331.04; found=331.05. ¹H NMR (500 MHz, DMSO): δ 8.85 (s, br, 1H); 8.36 (d, J=1.5 Hz, 1H); 8.05 (d, J=8.5 Hz, 1H); 8.00 (d, J=2.0 Hz, 1H); 7.99 (d, J=1.5 Hz, 1H); 7.83-7.81 (m, 2H); 3.90 (s, 3H)

Intermediate 19

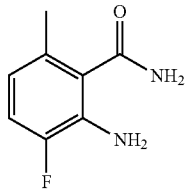

2-amino-3-fluoro-6-methylbenzamide 2-amino-3-fluoro-6-methylbenzoic acid (2 g, 11.82 mmol) was dissolved in thionyl chloride (26 mL) and the mixture was stirred at 40° C. for 1 h. The volatile was evaporated. To the residue was added dry DMA (40 mL), and then conc. NH₄OH (16.4 mL, 118 mmol) at 0° C. The mixture was stirred at RT for overnight, then partitioned between EtOAc and water. The aqueous was extracted with EtOAc for three times. Organic phases were combined, washed with water, dried over MgSO₄, filtered, concentrated, and purified by chromatography (ISCO CombiFlash system, 120 g silica gel column, 0-70% EtOAc in hexane as eluent) to afford 2-amino-3-fluoro-6-methylbenzamide. (M+H) calc.=169.07; found=169.01. ¹H NMR (500 MHz, CD₃OD): δ 6.89-6.84 (m, 1H); 6.50-6.48 (m, 1H); 2.28 (s, br, 3H).

Intermediate 20

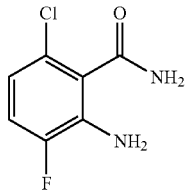 [SMILES: NC(=O)c1c(Cl)ccc(F)c1N]

2-amino-6-chloro-3-fluorobenzamide 2-amino-6-chloro-3-fluorobenzoic acid (1 g, 5.28 mmol) was dissolved in thionyl chloride (11.6 mL) and the mixture was stirred at 50° C. for 1 h. The volatile was evaporated. To the residue was added dry DMA (15 mL), and then conc. NH₄OH (7.34 mL, 52.8 mmol) at 0° C. The mixture was stirred at RT for overnight, then partitioned between EtOAc and water. The aqueous was extracted with EtOAc three times. Organic phases were combined, washed with water, dried over MgSO₄, filtered, concentrated, and purified by chromatography (ISCO CombiFlash system, 120 g silica gel column, 0-70% EtOAc in hexane as eluent) to afford 2-amino-3-fluoro-6-methylbenzamide. LC-Mass (M+H) calc.=189.02; found=188.95.

Intermediate 21

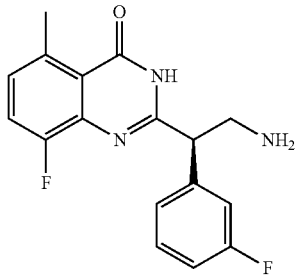 [SMILES: Cc1ccc(F)c2nc([C@@H](CN)c3cccc(F)c3)[nH]c(=O)c12]

(R)-2-(2-amino-1-(3-fluorophenyl)ethyl)-8-fluoro-5-methylquinazolin-4(3H)-one

Step A: ethyl 3-(((benzyloxy)carbonyl)amino)-2-(3-fluorophenyl)propanoate

To the stirred solution of ethyl 3-amino-2-(3-fluorophenyl)propanoate, HCl (3000 mg, 12.11 mmol) in dry DCM (50 ml) were added 4-methylmorpholine (2.695 g, 26.6 mmol), DMAP (148 mg, 1.211 mmol) and then CBZ-Cl (1.815 mL, 12.72 mmol) at 0° C. The mixture was stirred at room temperature overnight, then concentrated, and purified by ISCO CombiFlash system using 120 g ISCO RediSep silica gel column, and 0-50% EtOAc in hexane as eluenting solvent. The product was collected.

LC-Mass (M+H) calc.=346.14; found=346.15 (M+H); 368.17 (M+Na).

Step B: 3-(((benzyloxy)carbonyl)amino)-2-(3-fluorophenyl)propanoic acid

To the stirred solution of ethyl 3-(((benzyloxy)carbonyl)amino)-2-(3-fluorophenyl)propanoate (3.0 g, 8.69 mmol) in dioxane (20 ml)-water (20 mL) was added LiOH (0.832 g, 34.7 mmol). The mixture was stirred at room temperature overnight, then partitioned between EtOAc (50 mL) and 1N HCl in water (20 mL). The aqueous was extracted with EtOAc for additional three times. The organic phases were combined, washed with sat. NaCl, dried over Na₂SO₄, filtered and concentrated in vacuo to give the desired product.

LC-Mass (M+H) calc.=318.11; found=318.14 (M+H); 340.10 (M+Na).

Step C: benzyl (2-(8-fluoro-5-methyl-4-oxo-3,4-dihydroquinazolin-2-yl)-2-(3-fluorophenyl)ethyl) carbamate Step C1: benzyl (3-((2-carbamoyl-6-fluoro-3-methylphenyl)amino)-2-(3-fluorophenyl)-3-oxopropyl) carbamate The suspension of 3-(((benzyloxy)carbonyl)amino)-2-(3-fluorophenyl)propanoic acid (2.29 g, 7.22 mmol) in SOCl₂ (26.3 mL, 361 mmol) was stirred at 40° C. for 1 h. The volatile was evaporated, and the residue was redissolved in dry DMA (25 mL), followed by addition of 2-amino-3-fluoro-6-methylbenzamide (1.335 g, 7.94 mmol). The mixture was stirred at 40° C. for 30 min, then stirred at room temperature for 4 h. LC-Mass showed formation of the title compound. LCMS calc.=490.14; found=490.11 (M+Na)+.

Step C2: benzyl (2-(8-fluoro-5-methyl-4-oxo-3,4-dihydroquinazolin-2-yl)-2-(3-fluorophenyl)ethyl) carbamate To the crude mixture from step C1 was added MeOH (20 ml) and potassium 2-methylpropan-2-olate in t-BuOH (1 M, 24.6 mL, 24.6 mmol). The mixture was stirred at room temperature for 4 h, then was quenched with addition of acetic acid (1.24 mL, 21.6 mmol). The mixture was partitioned between EtOAc and sat. NaCl. The aqueous was extracted with EtOAc for three more times. Organic phases were combined, dried over $Na_2SO_4$, filtered and concentrated, and then purified by chromatography (ISCO CombiFlash Rf system, 120 g ISCO RediSep silica gel column, and 0-60% EtOAc in hexane as eluent) to give the title compound.

LC-Mass (M+H) calc.=450.16; found=450.11. $^1$H NMR (500 MHz, $CD_3OD$): δ 7.42 (t, J=4.5 Hz, 1H); 7.36-7.19 (m, 9H); 7.03-7.00 (m, 1H); 5.05 (dd, J=12.5 Hz, J=18.5 Hz, 2H); 4.23 (t, J=7.0 Hz, 1H); 3.95 (dd, J=8 Hz, J=14 Hz, 1H); 3.74 (dd, J=6.5 Hz, J=14.0 Hz, 1H); 2.74 (s, 3H).

Step D: (R)-benzyl (2-(8-fluoro-5-methyl-4-oxo-3,4-dihydroquinazolin-2-yl)-2-(3-fluorophenyl)ethyl) carbamate The racemic product from step C (2.44 g, 5.43 mmol) was then resolved by SFC separation (conditions listed below) to give peak-1 (enantiomer A, presumed as "R" enantiomer based on the FIXa activity of resulting final compounds, as the more potent enantiomer) and peak-2 (enantiomer B).

| Preparative Method: | Analytical Method: |
|---|---|
| AS-H (2 × 15 cm) | AS-H (25 × 0.46 cm) |
| 20% methanol/$CO_2$, 100 bar | 20% methanol(DEA)/$CO_2$, 100 bar |
| 70 mL/min, 220 nm | 3 mL/min, 220 and 254 nm |
| inj vol.: 0.8 mL, 20 mg/mL methanol | |

For Enantiomer A (the Titled Compound):
LC-Mass (M+H) calc.=450.16; found=450.13. $^1$H NMR (500 MHz, $CD_3OD$): same as the racemic product from step C.
For Enantiomer B:
LC-Mass (M+H) calc.=450.16; found=450.19. $^1$H NMR (500 MHz, $CD_3OD$): same as Enantiomer A and the racemic compound.

Step E: (R)-2-(2-amino-1-(3-fluorophenyl)ethyl)-8-fluoro-5-methylquinazolin-4(3H)-one To the 100-ml round bottom flask with (R)-benzyl (2-(8-fluoro-5-methyl-4-oxo-3,4-dihydroquinazolin-2-yl)-2-(3-fluorophenyl)ethyl)carbamate (1250 mg, 2.78 mmol) and Pd/C (10%, 444 mg, 0.417 mmol) was added EtOH (50 mL), then equipped with a $H_2$ balloon. The reaction flask was degassed and flushed with $H_2$ twice, then the mixture was stirred at room temperature in the presence of $H_2$ for 2 h. The catalyst was removed by filtration, and the filtrate was concentrated in vacuo to give the title compound.

LC-Mass (M+H) calc.=316.12; found=316.16. $^1$H NMR (500 MHz, $CD_3OD$): δ 7.44-7.34 (m, 2H); 7.22-7.14 (m, 3H); 7.04-7.00 (m, 1H); 4.04 (dd, J=5.5 Hz, J=8.5 Hz, 1H); 3.54 (dd, J=9.0 Hz, J=13.0 Hz, 1H); 3.13 (dd, J=5.5 Hz, J=13.0 Hz, 1H); 2.76 (s, 3H)

Intermediate 22

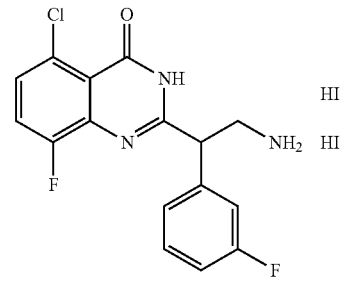

2-(2-amino-1-(3-fluorophenyl)ethyl)-5-chloro-8-fluoroquinazolin-4(3H)-one 2HI

Step A: benzyl (2-(5-chloro-8-fluoro-4-oxo-1,4-dihydroquinazolin-2-yl)-2-(3-fluorophenyl)ethyl) carbamate Step A1: benzyl (3-((2-carbamoyl-3-chloro-6-fluorophenyl)amino)-2-(3-fluorophenyl)-3-oxopropyl) carbamate The suspension of 3-(((benzyloxy)carbonyl)amino)-2-(3-fluorophenyl)propanoic acid (1.58 g, 4.98 mmol) in $SOCl_2$ (14.54 mL, 199 mmol) was stirred at 40° C. for 1 h. The volatile was evaporated, and the residue was redissolved in dry DMA (15 mL), followed by addition of 2-amino-6-chloro-3-fluorobenzamide (1.033 g, 5.48 mmol). The mixture was stirred at 40° C. for 60 min, then stirred at room temperature for 4 h. LC-Mass showed formation of the title compound.

LC-Mass (M+H) calc.=488.11; found=488.34.

Step A2: benzyl (2-(5-chloro-8-fluoro-4-oxo-1,4-dihydroquinazolin-2-yl)-2-(3-fluorophenyl)ethyl) carbamate To the crude mixture from step A1 was added MeOH (15 mL) and potassium 2-methylpropan-2-olate in t-BuOH (1 M, 19.92 mL, 19.92 mmol). The mixture was stirred at room temperature for 4 h, then was quenched with addition of acetic acid (1.71 ml, 29.9 mmol). The mixture was partitioned between EtOAc and sat. NaCl. The aqueous layer was extracted with EtOAc three more times. Organic phases were combined, dried over $Na_2SO_4$, filtered and concentrated, and then purified by chromatography (ISCO CombiFlash Rf system, 330 g ISCO RediSep silica gel column, and 0-60% EtOAc in hexane as eluent) to give the title compound.

LC-Mass (M+H) calc.=470.10; found=470.12. $^1$H NMR (500 MHz, $CD_3OD$): δ 7.52 (t, J=9.0 Hz, 1H); 7.46 (dd, J=4.5 Hz, J=8.5 Hz, 1H); 7.37-7.20 (m, 8H); 7.03 (t, J=8.5 Hz, 1H); 5.05 (dd, J=12.5 Hz, J=17.5 Hz, 2H); 4.24 (t, J=7.0 Hz, 1H); 3.95 (dd, J=8 Hz, J=1.5 Hz, 1H); 3.74 (dd, J=6.5 Hz, J=14.0 Hz, 1H).

Step B: 2-(2-amino-1-(3-fluorophenyl)ethyl)-5-chloro-8-fluoroquinazolin-4(3H)-one 2HI To the stirred solution of benzyl (2-(5-chloro-8-fluoro-4-oxo-1,4-dihydroquinazolin-2-yl)-2-(3-fluorophenyl)ethyl) carbamate (700 mg, 1.49 mmol) in dry DCM (8 ml) was added iodotrimethylsilane (1.70 mL, 11.92 mmol) at 0° C. and stirred at 0° C. for 60 min. The reaction was quenched by adding MeOH (~5 ml), then the mixture was evaporated to dryness to give the title compound.

LC-Mass (M+H) calc.=336.06; found=336.13. $^1$H NMR (500 MHz, CD3OD): δ 7.58 (t, J=9.0 Hz, 1H); 7.53 (dd, J=5.0 Hz, J=9.0 Hz, 1H); 7.48-7.38 (m, 1H); 7.29-7.12 (m, 3H); 4.41 (dd, J=5.0 Hz, J=9.0 Hz, 1H); 3.90 (dd, J=9.0 Hz, J=13.0 Hz, 1H); 3.49 (dd, J=5.0 Hz, J=13.0 Hz, 1H).

Intermediate 23

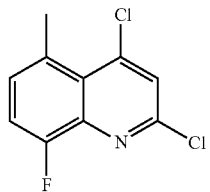

2,4-dichloro-8-fluoro-5-methylquinoline

WO2011017389, 10 Feb. 2011

A mixture of 2-fluoro-5-methylaniline (5 g, 40.0 mmol), malonic acid (6.24 g, 59.9 mmol), and POCl$_3$ (39.1 mL, 420 mmol) was refluxed overnight. The reaction mixture was slowly poured into ice-water and extracted with DCM. The organic layer was dried over MgSO$_4$, filtered, and concentrated under reduced pressure. The crude material was purified on silica gel flash chromatography using solid loading (eluent: 0-20% EtOAc in Hexanes). LCMS calc.=229.99, found=229.90 (M+H)$^+$. 1H NMR (499 MHz, Acetone-d6): δ 7.79 (s, 1H); 7.54 (d, J=7.8 Hz, 2H); 3.00 (s, 3H).

Intermediate 24

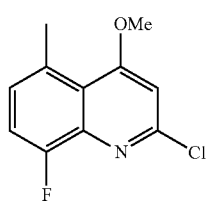

2-chloro-8-fluoro-4-methoxy-5-methylquinoline

Sodium hydride (0.104 g, 2.61 mmol) was added portionwise to a stirred solution of methanol (0.106 mL, 2.61 mmol) in anhydrous DMF (3 mL). The mixture was stirred at 25° C. for 1 h. INTERMEDIATE 23 (0.5 g, 2.173 mmol) was added as solids. The reaction mixture was stirred at 25° C. for 4 h, then poured into water, extracted with EtOAc, dried over MgSO$_4$, filtered, and concentrated under reduced pressure. The crude material was purified by column chromatography over silica gel (eluent: 0-20% EtOAc in Hexanes). LCMS calc.=226.04, found=225.97 (M+H)$^+$. $^1$H NMR (499 MHz, Acetone-d6): δ 7.41-7.35 (m, 1H); 7.31-7.25 (m, 1H); 7.04-6.99 (m, 1H); 4.14 (s, 3H); 2.77 (s, 3H).

Intermediate 25

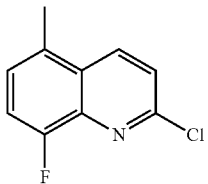

2-chloro-8-fluoro-5-methylquinoline

Journal of Medicinal Chemistry, 54(13), 4508-4522; 2011

A two-phased mixture of a solution of INTERMEDIATE 23 (920 mg, 4 mmol) in DCE (16 mL) and the same volume of saturated brine containing 9% NH$_4$OH (prepared by adding NaCl solid to 9-10% NH$_4$OH aq) is treated with zinc dust (785 mg, 12.00 mmol). The resultant mixture was refluxed at 70° C. for 4 h and then cooled and filtered. The organic layer of the filtrate was collected and diluted with EtOAc, washed with 1N HCl solution, dried and concentrated. The crude material was purified by column chromatography over silica gel (eluent: 0-20% EtOAc in Hexanes). LCMS calc.=196.03, found=195.96 (M+H)$^+$. 1H NMR (499 MHz, Acetone-d6): δ 8.56 (dd, J=8.8, 1.8 Hz, 1H); 7.66 (d, J=8.9 Hz, 1H); 7.49 (d, J=8.1 Hz, 2H); 2.71 (s, 3H).

Intermediate 26

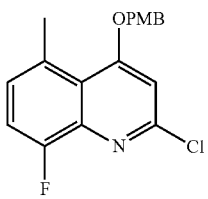

2-chloro-8-fluoro-4-((4-methoxybenzyl)oxy)-5-methylquinoline

WO2011017389, 10 Feb. 2011

Sodium hydride (83 mg, 2.086 mmol) was added portionwise to a stirred solution of 4-methoxybenzyl alcohol (288 mg, 2.086 mmol) and 15-Crown-5 (460 mg, 2.086 mmol) in anhydrous DMF (1 mL). The mixture was stirred at room temperature for 0.5 h. INTERMEDIATE 23 (400 mg, 1.739 mmol) in anhydrous DMF (2 mL) was then added and the reaction mixture was stirred at 25° C. for 16 h. The reaction mixture was then poured into water, extracted with EtOAc, dried over MgSO$_4$, filtered, and concentrated under reduced pressure. The crude material was purified by chromatography on silica gel (eluent: 0-30% EtOAc in Hexanes).

LCMS calc.=332.08, found=331.97 (M+H)$^+$. $^1$H NMR (499 MHz, Acetone-d6): δ 7.59 (d, J=8.3 Hz, 2H); 7.39 (dd, J=10.1, 8.1 Hz, 1H); 7.28 (t, J=6.5 Hz, 1H); 7.19 (s, 1H); 7.06-6.99 (m, 2H); 5.39 (s, 2H); 3.88-3.82 (m, 3H); 2.72 (s, 3H).

Example 1

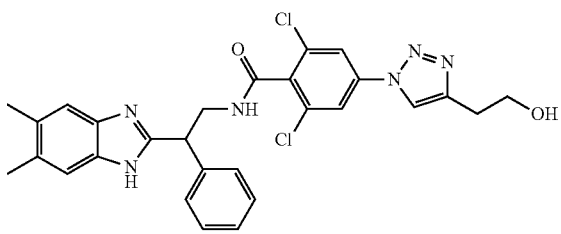 [SMILES: Cc1cc2nc(C(CNC(=O)c3c(Cl)cc(-n4cc(CCO)nn4)cc3Cl)c3ccccc3)[nH]c2cc1C]

(R)-2,6-Dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide FIXa IC50=10.4 nM

Step A: tert-Butyl (2-(5,6-dimethyl-1H-benzo[d]imidazol-2-yl)-2-phenylethyl)carbamate To a solution of 3-((tert-butoxycarbonyl)amino)-2-phenylpropanoic acid (1.8 g, 6.78 mmol) in DMF (10 mL) was added HOBt (1.14 g, 7.46 mmol), EDC (1.43 g, 7.46 mmol), and 4,5-dimethylbenzene-1,2-diamine (0.924 g, 6.78 mmol). The reaction mixture was stirred at room temperature for 16 h. Acetic acid (10 mL) was added to the reaction, and the resulting mixture heated to 90° C. for 2 h. The reaction was cooled to room temperature and acetic acid was removed in vacuo. To the resulting residue was added saturated aqueous solution of NaHCO$_3$, and the mixture was extracted with EtOAc (3×100 mL). The combined organic layers were washed with brine, dried over MgSO$_4$ and concentrated. The residue was purified by chromatography on silica (Eluent: Hexane:EtOAc=100:0~60:40) to afford the title compound tert-butyl (2-(5,6-dimethyl-1H-benzo[d]imidazol-2-yl)-2-phenylethyl)carbamate. LCMS calc.=366.21; found=366.13 (M+H)$^+$.

Step B: 2-(5,6-Dimethyl-1H-benzo[d]imidazol-2-yl)-2-phenylethanamine hydrochloride tert-Butyl (2-(5,6-dimethyl-1H-benzo[d]imidazol-2-yl)-2-phenylethyl)carbamate (1.35 g, 3.56 mmol) in 4N HCl in dioxane (8.90 mL, 17.8 mmol) was stirred at room temperature for 16 h. The solvents were removed and the residue was dried under high vacuum to afford 2-(5,6-dimethyl-1H-benzo[d]imidazol-2-yl)-2-phenylethanamine hydrochloride. LCMS calc.=266.16; found=266.10 (M+H)$^+$.

Step C: 2,6-Dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide To a solution of 2,6-dichloro-4-(4-(2-hydroxyethyl)-1H-1,2,3-triazol-1-yl)benzoic acid (29 mg, 0.096 mmol) in DMF (3 mL) was added HATU (40.13 mg, 0.105 mmol), HOAt (14.49 mg, 0.105 mmol), and 2-(5,6-dimethyl-1H-benzo[d]imidazol-2-yl)-2-phenylethanamine hydrochloride (59.1 mg, 0.20 mmol), followed by Hunig's base (63.33 µL, 0.354 mmol). The resulting mixture was stirred at room temperature for 16 h. The reaction mixture was diluted with DMSO and directly purified by reversed phase HPLC (Sunfire, C18, 10×100 mm, ~20 mL/min, gradient from 90% water in MeCN to 10% water in MeCN over 10 min, gradient to 100% MeCN over 2 min, both solvent containing 0.05% TFA, fractions containing desired product was combined and lyophilized) to afford 2,6-dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide. LCMS calc.=549.15; found=549.24 (M+H)$^+$.

Step D: (R)-2,6-Dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide Racemic 2,6-dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide (31 mg, 0.056 mmol) was resolved by chiral AD column (20×250 mm, ~50 mL/min, 100 bar, 230 nm, 35° C., eluted with 50% MeOH (containing 0.2% DEA)/CO$_2$) to obtain two enantiomers. The retention time for the first eluting enantiomer (presumed S enantiomer) is 4.39 min, The retention time for the second enantiomer (presumed R enantiomer, (R)-2,6-dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide) is 10.23 min. LCMS calc.=549.15, found=549.24 (M+H)$^+$. $^1$H NMR (500 MHz, CD$_3$OD): δ 8.40 (s, 1H); 7.91 (s, 2H); 7.46 (m, 2H); 7.34 (s, 2H); 7.31-7.23 (m, 3H); 4.79-4.75 (m, 1H); 4.32-4.31 (m, 1H); 4.18-4.09 (m, 1H); 3.86 (m, 2H); 2.95 (m, 2H); 2.35 (s, 6H).

Example 2

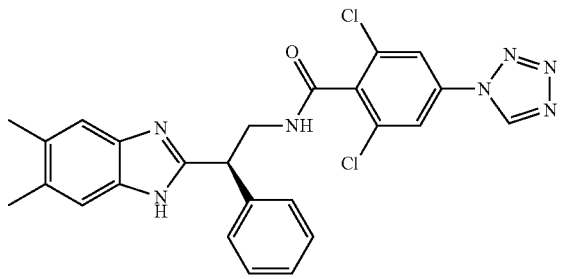 [SMILES: Cc1cc2nc([C@@H](CNC(=O)c3c(Cl)cc(-n4cnnn4)cc3Cl)c3ccccc3)[nH]c2cc1C]

(R)-2,6-dichloro-N-(2-(5,6-dimethyl-1H-benzo[d]imidazol-2-yl)-2-phenylethyl)-4-(1H-tetrazol-1-yl)benzamide FIXa IC50=26.4 nM

Step A: 4-Amino-2,6-dichlorobenzoic acid

To a solution of methyl 4-amino-2,6-dichlorobenzoate (150 mg, 0.682 mmol) in THF (1.2 mL), Water (0.300 mL), and MeOH (0.300 mL) was added lithium hydroxide hydrate (143 mg, 3.41 mmol). The reaction mixture was stirred at 65° C. for 2 days and concentrated in vacuo. The residue was acidified with 2N HCl to pH=3. The mixture was extracted with EtOAc (2×30 mL). The combined organic layers were dried over MgSO$_4$, filtered and concentrated in vacuo to afford the crude product 4-amino-2,6-dichlorobenzoic acid. LCMS calc.=205.97; found=205.90 (M+H)$^+$.

Step B: (R)-tert-butyl (2-(5,6-dimethyl-1H-benzo[d]imidazol-2-yl)-2-phenylethyl)carbamate According to Step A in the synthetic method for EXAMPLE 1, tert-Butyl (2-(5,6-benzo[d]imidazol-2-yl)-2- phenylethyl)carbamate (4.4 g, 12.04 mmol) was obtained and resolved by dimethyl-1H-chiral OJ column 4.6×250 mm, ~50 mL/min, 100 bar, 230 nm, 35° C., eluted with 20% MeOH:MeCN=2:1/$CO_2$) to obtain two enantiomers. The first eluting enantiomer (R)-tert-butyl (2-(5,6-dimethyl-1H-benzo[d]imidazol-2-yl)-2-phenylethyl)carbamate is the desired R enantiomer. LCMS calc.=366.21, found=366.23 $(M+H)^+$.

Step C: (R)-2-(5,6-Dimethyl-1H-benzo[d]imidazol-2-yl)-2-phenylethanamine hydrochloride In the same synthetic method as Step C for EXAMPLE 1, (R)-2-(5,6-dimethyl-1H-benzo[d]imidazol-2-yl)-2-phenylethanamine hydrochloride was prepared. LCMS calc.=266.16; found=266.15 $(M+H)^+$.

Step D: (R)-4-Amino-2,6-dichloro-N-(2-(5,6-dimethyl-1H-benzo[d]imidazol-2-yl)-2-phenylethyl)benzamide To a solution of ethyl (R)-2-(5,6-dimethyl-1H-benzo[d]imidazol-2-yl)-2-phenylethanamine hydrochloride (70 mg, 0.23 mmol) in DMF (1 mL) was added HATU (101 mg, 0.27 mmol), 4-amino-2,6-dichlorobenzoic acid (56.2 mg, 0.23 mmol), and Hunig's base (0.12 mL, 0.70 mmol). The reaction was stirred at 40° C. for 16 h. The resulting mixture was quenched with EtOAc (10 mL) and $H_2O$ (5 mL). The layers were separated. The organic layer was dried over $MgSO_4$ and concentrated in vacuo. The crude solid was purified by prep TLC (60% EtOAc in Hexane) to afford (R)-4-amino-2,6-dichloro-N-(2-(5,6-dimethyl-1H-benzo[d]imidazol-2-yl)-2-phenylethyl)benzamide. LCMS calc.=453.12, found=453.11 $(M+H)^+$.

Step E: (R)-2,6-Dichloro-N-(2-(5,6-dimethyl-1H-benzo[d]imidazol-2-yl)-2-phenylethyl)-4-(1H-tetrazol-1-yl)benzamide To a sealed tube was added (R)-4-amino-2,6-dichloro-N-(2-(5,6-dimethyl-1H-benzo[d]imidazol-2-yl)-2-phenylethyl)benzamide (82 mg, 0.18 mmol), triethoxymethane (0.12 mL, 0.72 mmol), sodium azide (35.3 mg, 0.54 mmol) and AcOH (1 mL). The tube was sealed and the mixture was stirred at 80° C. for 3 h. The reaction was cooled to room temperature, and neutralized with $NaHCO_3$ saturated solution till no bubble appeared. The mixture was extracted with EtOAc (2×20 mL). The organic layer was separated and dried over $MgSO_4$, filtered and concentrated in vacuo. The residue was purified by reversed phase HPLC (Sunfire, C18, 10×100 mm, ~20 mL/min, gradient from 95% water in MeCN to 25% water in MeCN over 10 min, gradient to 100% MeCN over 2 min, both solvent containing 0.05% TFA, fractions containing desired product combined, lyophilized) to afford (R)-2,6-dichloro-N-(2-(5,6-dimethyl-1H-benzo[d]imidazol-2-yl)-2-phenylethyl)-4-(1H-tetrazol-1-yl)benzamide. LCMS calc.=506.12; found=506.16 $(M+H)^+$. H NMR (500 MHz, $CD_3OD$): δ 9.73 (s, 1H); 7.94 (s, 2H); 7.51 (m, 4H); 7.49 (m, 2H); 7.43 (m, 1H); 5.02 (m, 1H); 4.50-4.48 (m, 1H); 4.14-4.08 (m, 1H); 2.36 (s, 6H).

The following compounds (Table 1) were synthesized using methods analogous to those described for EXAMPLES 1-2 from commercially available materials or intermediates whose syntheses are described above.

TABLE 1

| Example | Structure | Calc. $(M + H)^+$ | LCMS $(M + H)^+$ | hFIXa IC50 (nM) |
|---|---|---|---|---|
| 3 | 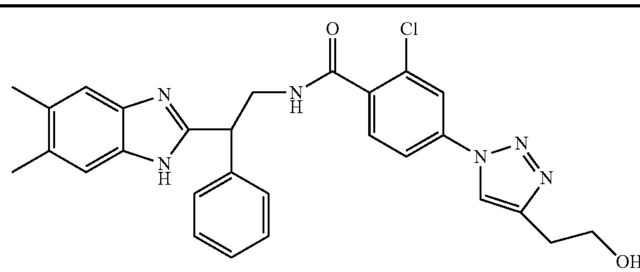 | 515.20 | 515.26 | 21.91 |
| 4 | 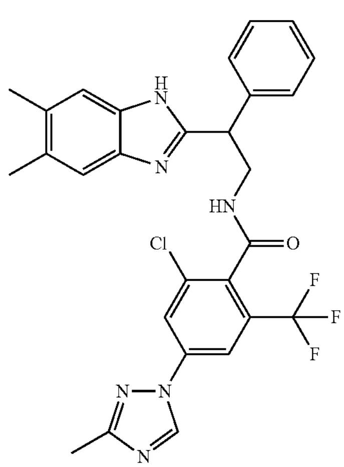 [SMILES: Cc1ncn(-c2cc(Cl)c(C(=O)NCC(c3ccccc3)c3nc4cc(C)c(C)cc4[nH]3)c(C(F)(F)F)c2)n1] | 553.17 | 553.39 | 63.1 |

TABLE 1-continued

| Example | Structure | Calc. (M + H)+ | LCMS (M + H)+ | hFIXa IC50 (nM) |
|---|---|---|---|---|
| 5 | 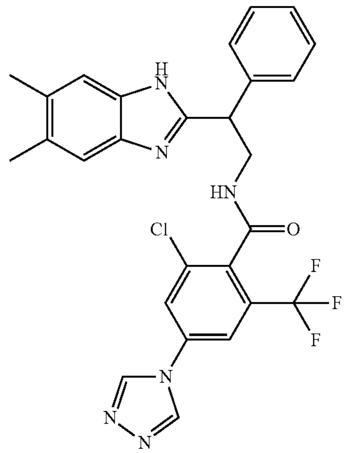 [SMILES: Cc1cc2nc(C(CNC(=O)c3c(Cl)cc(-n4cnnc4)cc3C(F)(F)F)c3ccccc3)[nH]c2cc1C] | 539.16 | 539.29 | 21.79 |
| 6 | 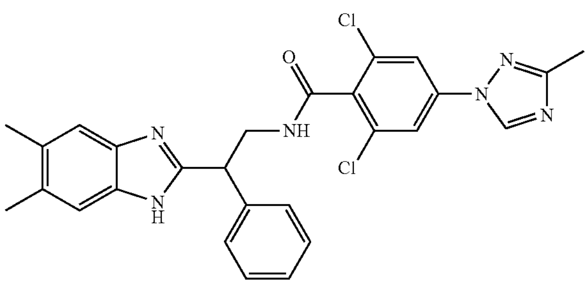 | 519.15 | 519.30 | 20.78 |
| 7 | 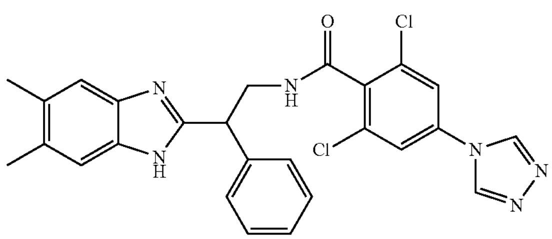 [SMILES: Cc1cc2nc(C(CNC(=O)c3c(Cl)cc(-n4cnnc4)cc3Cl)c3ccccc3)[nH]c2cc1C] | 505.13 | 505.15 | 3.64 |
| 8 | 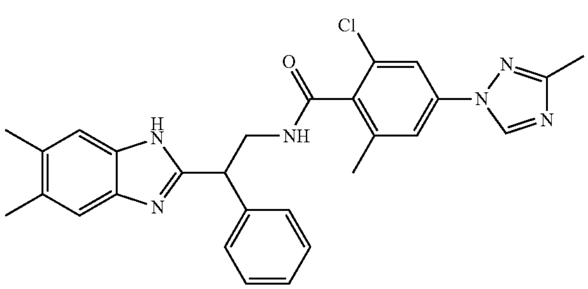 | 499.20 | 499.26 | 6.985 |
| 9 | 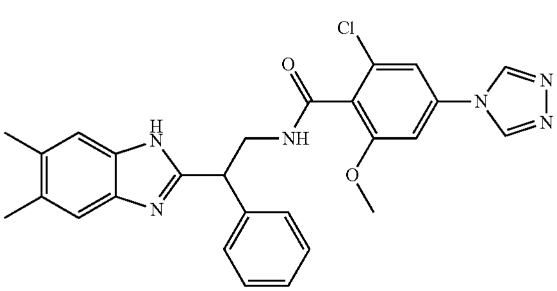 [SMILES: COc1cc(-n2cnnc2)cc(Cl)c1C(=O)NCC(c1ccccc1)c1nc2cc(C)c(C)cc2[nH]1] | 501.18 | 501.09 | 14.85 |

TABLE 1-continued

| Example | Structure | Calc. (M + H)+ | LCMS (M + H)+ | hFIXa IC50 (nM) |
|---|---|---|---|---|
| 10 | 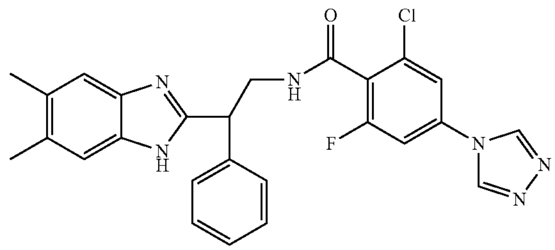 [SMILES: Cc1cc2nc(C(CNC(=O)c3c(F)cc(-n4cnnc4)cc3Cl)c3ccccc3)[nH]c2cc1C] | 489.16 | 489.07 | 15.17 |
| 11 | 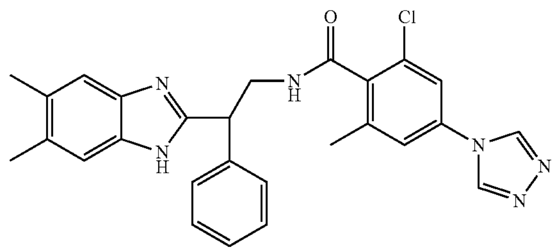 [SMILES: Cc1cc2nc(C(CNC(=O)c3c(C)cc(-n4cnnc4)cc3Cl)c3ccccc3)[nH]c2cc1C] | 485.19 | 485.31 | 8.047 |
| 12 | 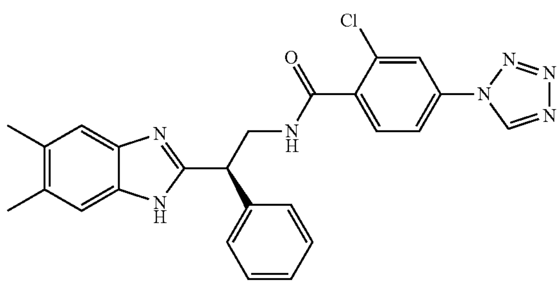 [SMILES: Cc1cc2nc([C@@H](CNC(=O)c3ccc(-n4cnnn4)cc3Cl)c3ccccc3)[nH]c2cc1C] | 472.17 | 472.27 | 78.28 |
| 13 | 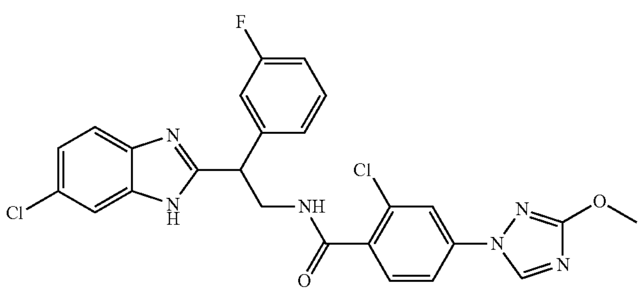 [SMILES: COc1ncn(-c2ccc(C(=O)NCC(c3cccc(F)c3)c3nc4ccc(Cl)cc4[nH]3)c(Cl)c2)n1] | 525.10 | 524.94 | 65.85 |
| 14 | 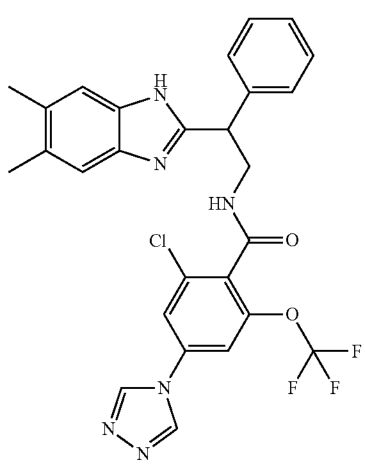 [SMILES: Cc1cc2nc(C(CNC(=O)c3c(Cl)cc(-n4cnnc4)cc3OC(F)(F)F)c3ccccc3)[nH]c2cc1C] | 555.15 | 555.32 | 39.97 |

TABLE 1-continued

| Example | Structure | Calc. (M + H)+ | LCMS (M + H)+ | hFIXa IC50 (nM) |
|---|---|---|---|---|
| 15 | 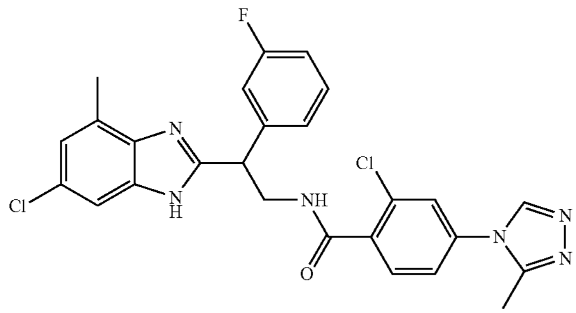 [SMILES: Cc1cc(Cl)cc2[nH]c(C(CNC(=O)c3ccc(-n4cnnc4C)cc3Cl)c3cccc(F)c3)nc12] | 523.12 | 523.04 | 4.9 |

Example 16

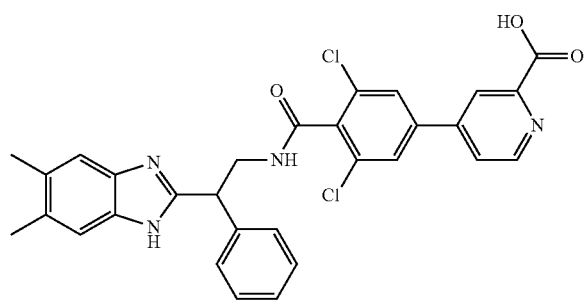 [SMILES: Cc1cc2nc(C(CNC(=O)c3c(Cl)cc(-c4ccnc(C(=O)O)c4)cc3Cl)c3ccccc3)[nH]c2cc1C]

4-(3,5-Dichloro-4-((2-(5,6-dimethyl-1H-benzo[d]imidazol-2-yl)-2-phenylethyl)carbamoyl)phenyl)picolinic acid FIXa IC50=73.6 nM

Step A: 4-Bromo-2,6-dichloro-N-(2-(5,6-dimethyl-1H-benzo[d]imidazol-2-yl)-2-phenylethyl)benzamide To a suspension of 4-bromo-2,6-dichlorobenzoic acid (300 mg, 1.11 mmol) in DCM (5 mL) was added oxalyl chloride (0.20 mL, 2.22 mmol), and several drops of DMF. The reaction was stirred at room temperature for 2 h. The solvent was removed by reduced pressure. The residue was chased with dry toluene twice, and then dry DCM (5 mL) was added to the resulting solid. This suspension was added to a mixture of 2-(5,6-dimethyl-1H-benzo[d]imidazol-2-yl)-2-phenylethanamine hydrochloride (295 mg, 1.11 mmol), and triethyl amine (0.78 mL, 5.55 mmol) in DCM (6 mL) at 0° C. drop wise. The reaction mixture was stirred at room temperature for 16 h before concentrated in vacuo, the solid was collected by filtration and was washed with cold water and a small volume of EtOAc. The solid was dried in vacuo to afford the desired product 4-bromo-2,6-dichloro-N-(2-(5,6-dimethyl-1H-benzo[d]imidazol-2-yl)-2-phenylethyl)benzamide. LCMS calc.=516.02; found=516.03 (M+H)+.

Step B: Ethyl 4-(3,5-dichloro-4-((2-(5,6-dimethyl-1H-benzo[d]imidazol-2-yl)-2-phenylethyl)carbamoyl)phenyl)picolinate A mixture of methyl 4-bromo-2,6-dichloro-N-(2-(5,6-dimethyl-1H-benzo[d]imidazol-2-yl)-2-phenylethyl)benzamide (121 mg, 0.24 mmol), ethyl 4-(4,4,5,5-tetramethyl-1,3,2-dioxaborolan-2-yl)picolinate (50 mg, 0.18 mmol), 2M sodium carbonate aq (0.23 mL, 0.45 mmol) and PdCl2(dppf)-CH2Cl2 adduct (42.7 mg, 0.058 mmol) in DMF (1 mL) was degassed by bubbling N2 for 10 min. The mixture was stirred at 80° C. for 12 h. The resulting mixture was quenched with EtOAc (10 mL) and H2O (5 mL). The layers were separated. The organics was dried over MgSO4 and concentrated in vacuo. The crude solid was purified by prepTLC (EtOAc) to afford ethyl 4-(3,5-dichloro-4-((2-(5,6-dimethyl-1H-benzo[d]imidazol-2-yl)-2-phenylethyl)carbamoyl)phenyl)picolinate. LCMS calc.=587.15, found=587.15 (M+H)+.

Step C: 4-(3,5-Dichloro-4-((2-(5,6-dimethyl-1H-benzo[d]imidazol-2-yl)-2-phenylethyl)carbamoyl)phenyl)picolinic acid To a solution of ethyl 4-(3,5-dichloro-4-((2-(5,6-dimethyl-1H-benzo[d]imidazol-2-yl)-2-phenylethyl)carbamoyl)phenyl)picolinate (30 mg, 0.051 mmol) in THF (4 mL) and water (1 mL) was added lithium hydroxide (2.14 mg, 0.051 mmol). The reaction mixture was stirred at room temperature for 16 h and was then concentrated in vacuo. The residue was purified by reversed phase HPLC (Sunfire, C18, 10×100 mm, ~20 mL/min, gradient from 90% water in MeCN to 10% water in MeCN over 10 min, gradient to 100% MeCN over 2 min, both solvent containing 0.05% TFA, fractions containing desired product combined, lyophilized) to afford 4-(3,5-dichloro-4-((2-(5,6-dimethyl-1H-benzo[d]imidazol-2-yl)-2-phenylethyl)carbamoyl)phenyl)picolinic acid. LCMS calc.=559.12; found=559.17 (M+H)+.

$^1$H NMR (500 MHz, CD3OD): δ 8.85 (brs, 1H); 8.21 (brs, 2H); 7.94 (brs, 2H); 7.55-7.35 (m, 7H); 5.10-5.00 (m, 1H); 4.41-4.35 (m, 1H); 4.18-4.10 (m, 1H); 2.40 (s, 6H).

The following compounds (Table 2) were synthesized using methods analogous to those described for EXAMPLE 16 from commercially available materials or intermediates whose syntheses are described above.

TABLE 2

| Example | Structure | Calc. (M + H)+ | LCMS (M + H)+ | hFIXa IC50 (nM) |
|---|---|---|---|---|
| 17 | 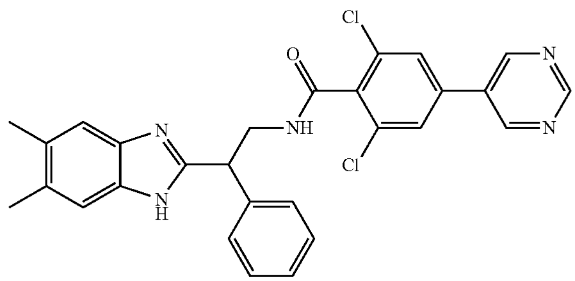 [SMILES: Cc1cc2nc(C(CNC(=O)c3c(Cl)cc(-c4cncnc4)cc3Cl)c3ccccc3)[nH]c2cc1C] | 516.14 | 516.12 | 18.12 |
| 18 | 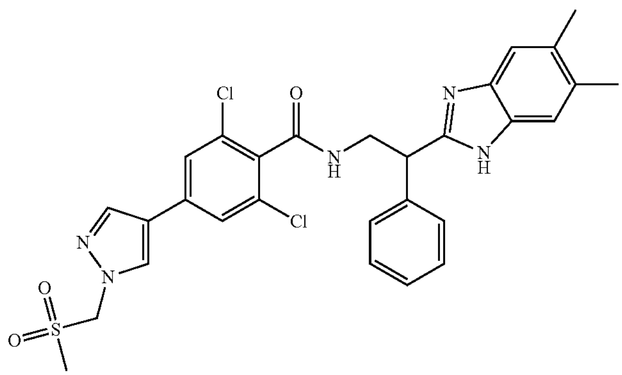 [SMILES: Cc1cc2nc(C(CNC(=O)c3c(Cl)cc(-c4cnn(CS(C)(=O)=O)c4)cc3Cl)c3ccccc3)[nH]c2cc1C] | 596.13 | 596.12 | 402.7 |
| 19 | 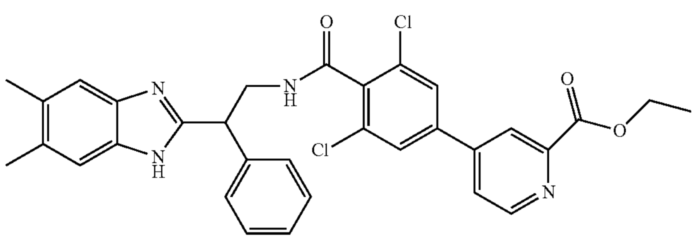 [SMILES: CCOC(=O)c1cc(-c2cc(Cl)c(C(=O)NCC(c3ccccc3)c3nc4cc(C)c(C)cc4[nH]3)c(Cl)c2)ccn1] | 587.16 | 587.15 | 343.1 |
| 20 | 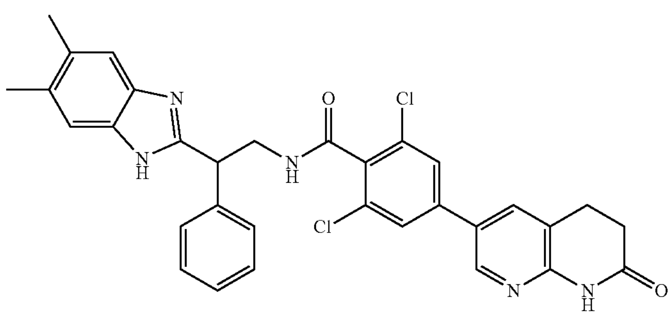 [SMILES: Cc1cc2nc(C(CNC(=O)c3c(Cl)cc(-c4cnc5c(c4)CCC(=O)N5)cc3Cl)c3ccccc3)[nH]c2cc1C] | 584.16 | 584.30 | 275.8 |
| 21 | 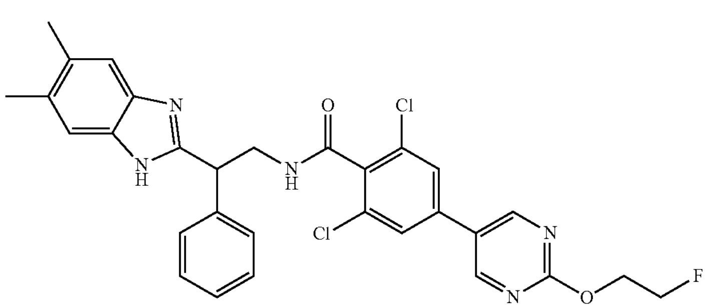 [SMILES: Cc1cc2nc(C(CNC(=O)c3c(Cl)cc(-c4cnc(OCCF)nc4)cc3Cl)c3ccccc3)[nH]c2cc1C] | 578.15 | 578.15 | 377.7 |

TABLE 2-continued

| Example | Structure | Calc. (M + H)+ | LCMS (M + H)+ | hFIXa IC50 (nM) |
| --- | --- | --- | --- | --- |
| 22 | 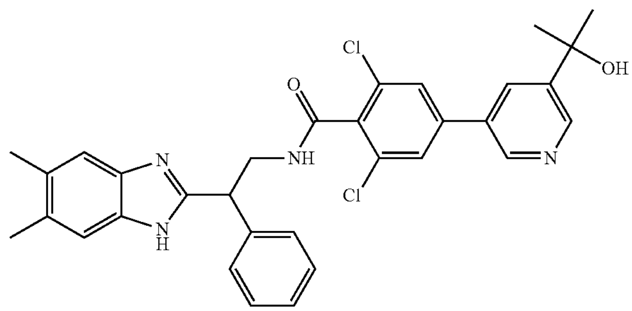 [SMILES: Cc1cc2nc(C(CNC(=O)c3c(Cl)cc(-c4cncc(C(C)(C)O)c4)cc3Cl)c3ccccc3)[nH]c2cc1C] | 573.18 | 573.10 | 44.66 |
| 23 | 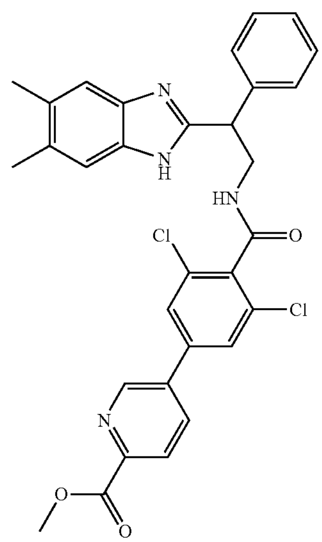 [SMILES: COC(=O)c1ccc(-c2cc(Cl)c(C(=O)NCC(c3ccccc3)c3nc4cc(C)c(C)cc4[nH]3)c(Cl)c2)cn1] | 573.15 | 573.09 | 544.1 |
| 24 | 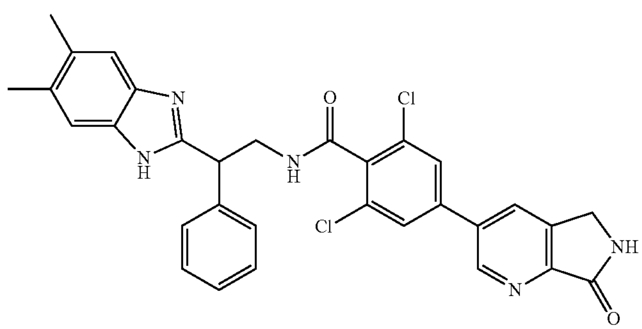 [SMILES: Cc1cc2nc(C(CNC(=O)c3c(Cl)cc(-c4cnc5c(c4)CNC5=O)cc3Cl)c3ccccc3)[nH]c2cc1C] | 570.15 | 570.14 | 141.3 |
| 25 | 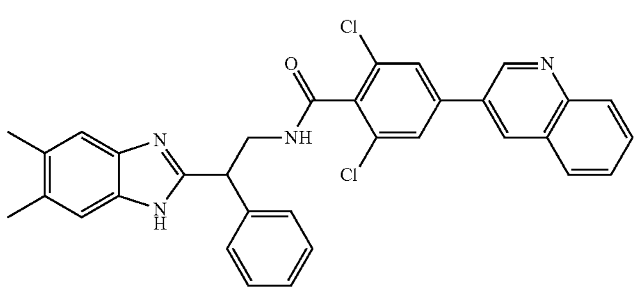 [SMILES: Cc1cc2nc(C(CNC(=O)c3c(Cl)cc(-c4cnc5ccccc5c4)cc3Cl)c3ccccc3)[nH]c2cc1C] | 565.16 | 565.08 | 463.6 |

TABLE 2-continued

| Example | Structure | Calc. (M + H)+ | LCMS (M + H)+ | hFIXa IC50 (nM) |
|---|---|---|---|---|
| 26 | 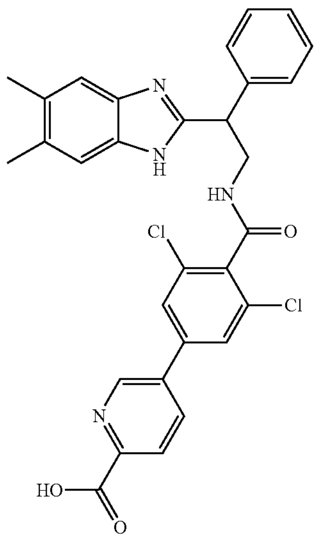 [SMILES: Cc1cc2nc(C(CNC(=O)c3c(Cl)cc(-c4ccc(C(=O)O)nc4)cc3Cl)c3ccccc3)[nH]c2cc1C] | 559.13 | 559.09 | 312.5 |
| 27 | 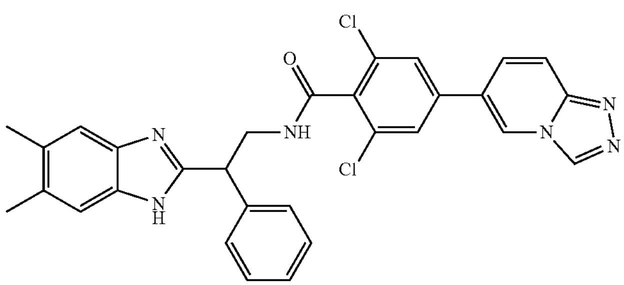 [SMILES: Cc1cc2nc(C(CNC(=O)c3c(Cl)cc(-c4ccc5nncn5c4)cc3Cl)c3ccccc3)[nH]c2cc1C] | 555.15 | 555.07 | 21 |
| 28 | 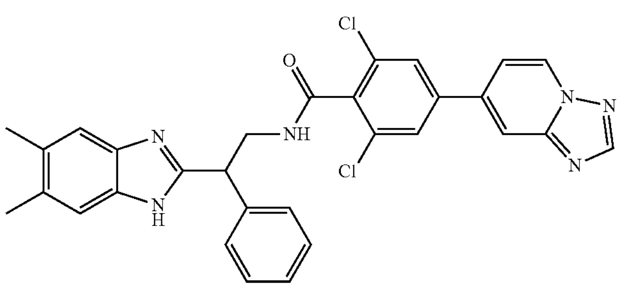 [SMILES: Cc1cc2nc(C(CNC(=O)c3c(Cl)cc(-c4ccn5ncnc5c4)cc3Cl)c3ccccc3)[nH]c2cc1C] | 555.15 | 555.14 | 64.76 |
| 29 | 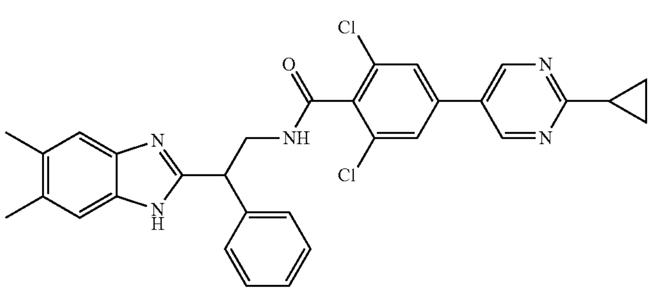 [SMILES: Cc1cc2nc(C(CNC(=O)c3c(Cl)cc(-c4cnc(C5CC5)nc4)cc3Cl)c3ccccc3)[nH]c2cc1C] | 556.17 | 556.09 | 653.5 |

TABLE 2-continued
| Example | Structure | Calc. (M + H)+ | LCMS (M + H)+ | hFIXa IC50 (nM) |
|---|---|---|---|---|
| 30 | 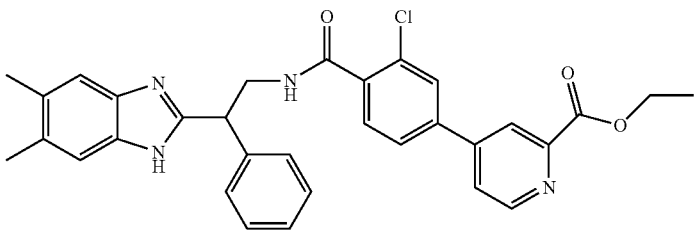 [SMILES: CCOC(=O)c1cc(-c2ccc(C(=O)NCC(c3ccccc3)c3nc4cc(C)c(C)cc4[nH]3)c(Cl)c2)ccn1] | 553.2 | 553.24 | 246.8 |
| 31 | 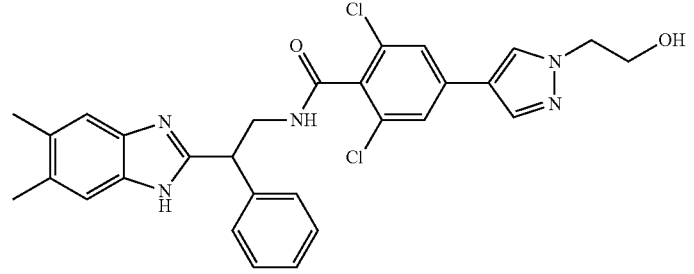 [SMILES: Cc1cc2nc(C(CNC(=O)c3c(Cl)cc(-c4cnn(CCO)c4)cc3Cl)c3ccccc3)[nH]c2cc1C] | 548.16 | 548.12 | 65.27 |
| 32 | 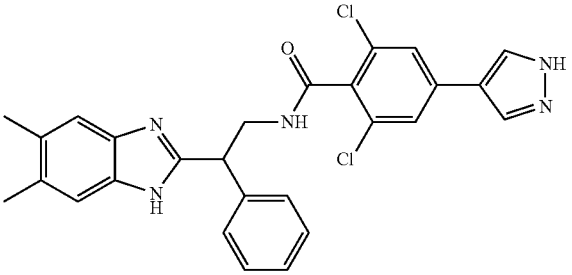 [SMILES: Cc1cc2nc(C(CNC(=O)c3c(Cl)cc(-c4cn[nH]c4)cc3Cl)c3ccccc3)[nH]c2cc1C] | 504.14 | 504.08 | 503.3 |
| 33 | 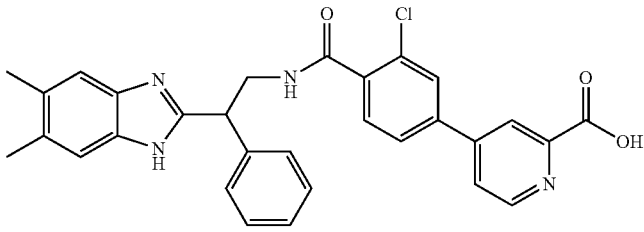 [SMILES: Cc1cc2nc(C(CNC(=O)c3ccc(-c4ccnc(C(=O)O)c4)cc3Cl)c3ccccc3)[nH]c2cc1C] | 525.17 | 525.11 | 537.9 |
| 34 | 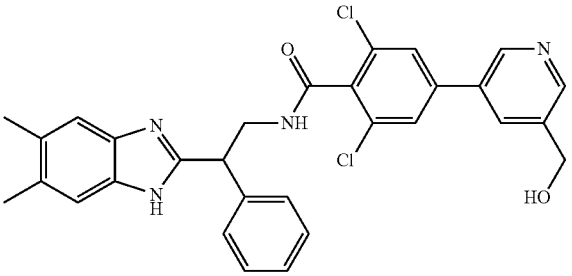 [SMILES: Cc1cc2nc(C(CNC(=O)c3c(Cl)cc(-c4cncc(CO)c4)cc3Cl)c3ccccc3)[nH]c2cc1C] | 545.15 | 545.08 | 10.32 |

TABLE 2-continued

| Example | Structure | Calc. (M + H)+ | LCMS (M + H)+ | hFIXa IC50 (nM) |
|---------|-----------|----------------|---------------|-----------------|
| 35 | 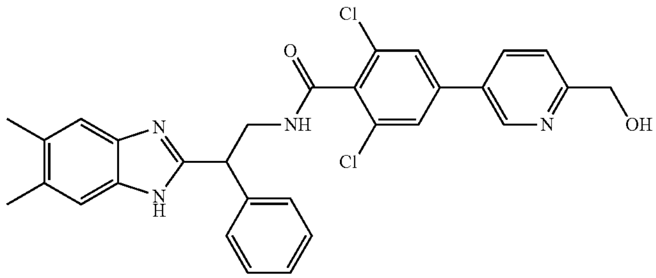 [SMILES: Cc1cc2nc(C(CNC(=O)c3c(Cl)cc(-c4ccc(CO)nc4)cc3Cl)c3ccccc3)[nH]c2cc1C] | 545.15 | 545.09 | 42.74 |
| 36 | 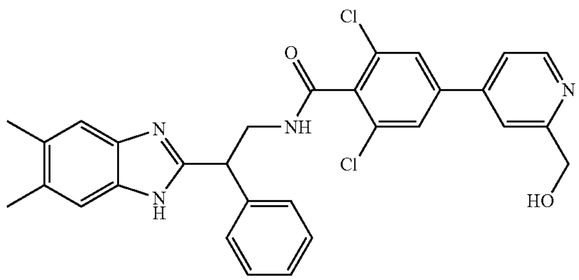 [SMILES: Cc1cc2nc(C(CNC(=O)c3c(Cl)cc(-c4ccnc(CO)c4)cc3Cl)c3ccccc3)[nH]c2cc1C] | 545.15 | 545.09 | 52.54 |

Example 37

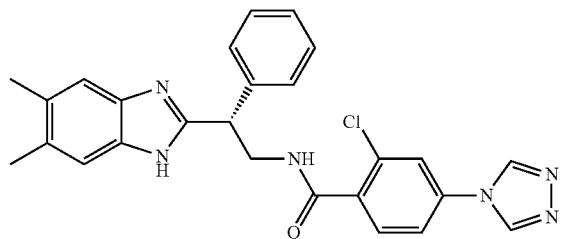 [SMILES: Cc1cc2nc([C@@H](CNC(=O)c3ccc(-n4cnnc4)cc3Cl)c3ccccc3)[nH]c2cc1C]

(R)-2-Chloro-N-(2-(5,6-dimethyl-1H-benzo[d]imidazol-2-yl)-2-phenylethyl)-4-(4H-1,2,4-triazol-4-yl)benzamide FIXa IC50=15.7 nM

Step A: Ethyl 3-(2-chloro-4-(4H-1,2,4-triazol-4-yl)benzamido)-2-phenylpropanoate 2-Chloro-4-(4H-1,2,4-triazol-4-yl)benzoic acid (INTERMEDIATE 4) (110 mg, 0.492 mmol), ethyl 3-amino-2-phenylpropanoate (95 mg, 0.492 mmol), 1-hydroxy-7-azabenzotriazole (87 mg, 0.639 mmol), 4-dimethylaminopyridine (3.00 mg, 0.025 mmol), 1-(3-dimethylaminopropyl)-3-ethylcarbodiimide hydrochloride (123 mg, 0.639 mmol) and pyridine (0.080 mL, 0.983 mmol) were stirred in DMF (3 mL) at room temperature overnight. The crude reaction was purified by preparative HPLC (reverse phase, YMC-Pack Pro C-18 100×20 mm) eluting with acetonitrile/water (10% to 80% organic in 10 min, then to 100% in 2 min, 20 mL/min). Related fractions were pooled and evaporated under reduced pressure to afford the title compound.

LCMS calc.=399.11; found=398.94 (M+H)+.

Step B: 3-(2-Chloro-4-(4H-1,2,4-triazol-4-yl)benzamido)-2-phenylpropanoic acid Ethyl 3-(2-chloro-4-(4H-1,2,4-triazol-4-yl)benzamido)-2-phenylpropanoate (146 mg, 0.366 mmol) and lithium hydroxide monohydrate (1.098 mL, 1.098 mmol) were stirred in 1,4-dioxane (4 mL)/water (2 mL) at room temperature overnight. The crude was acidified by HCl aq. (1N) and purified by preparative HPLC (reverse phase, YMC-Pack Pro C-18 100×20 mm) eluting with acetonitrile/water+ 0.1% formic acid (0% to 75% organic in 10 min, then to 100% in 2 min, 20 mL/min). Related fractions were pooled and evaporated under reduced pressure to afford the titled compound. LCMS calc.=371.08; found=370.92 (M+H)+.

Step C: (R)-2-Chloro-N-(2-(5,6-dimethyl-1H-benzo[d]imidazol-2-yl)-2-phenylethyl)-4-(4H-1,2,4-triazol-4-yl)benzamide HATU (41.0 mg, 0.108 mmol) was added to a stirred, cooled room temperature mixture of 3-(2-chloro-4-(4H-1,2,4-triazol-4-yl)benzamido)-2-phenylpropanoic acid (40 mg, 0.108 mmol), 4,5-dimethyl-1,2-phenylenediamine (14.69 mg, 0.108 mmol) and Hunig's base (0.028 mL, 0.162 mmol) in DMF (1 mL) and the mixture was stirred at room temperature for 50 min. Acetic acid (0.5 mL) was added to the reaction and heated to 80° C. for 3 h and then allowed to cool to ambient over the weekend. The reaction crude was purified by preparative HPLC (reverse phase, YMC-Pack ODS C-18 100×20 mm) eluting with acetonitrile/water+ 0.05% HCOOH (0% to 75% organic in 10 min, then to 100% in 2 min, 20 mL/min). Related fractions were pooled and evaporated under reduced pressure. This racemic mixture was resolved by SFC separation technique using the conditions as shown below to give both enationmers as white solid after concentration (peak-1 (enantiomer A) 13.6 mg; peak-2 (enantiomer B), 14.0 mg). The fast eluting enantionmer (1st peak) was presumed as "R" isomer based on its FIXa activity (more potent enantiomer). Preparation Method Info: OJ 20×250 mm, 25% MeOH (0.2% DEA)/C02, 50 ml/min, 100 bar, sample in MeOH, 220 nm, 35° C. LCMS calc.=471.16; found=470.90 (M+H)$^+$. $^1$H NMR (500 MHz, CD$_3$OD): δ 9.02 (s, 2H); 7.79 (d, J=2.1 Hz, 1H); 7.59 (dd, J=8.3, 2.1 Hz, 1H); 7.38-7.43 (m, 3H); 7.33-7.36 (m, 2H); 7.24-7.27 (m, 2H); 4.73 (dd, J=8.2, 7.7 Hz, 1H); 4.17-4.21 (m, 1H); 4.10-4.14 (m, 1H); 2.33 (s, 6H).

Example 38

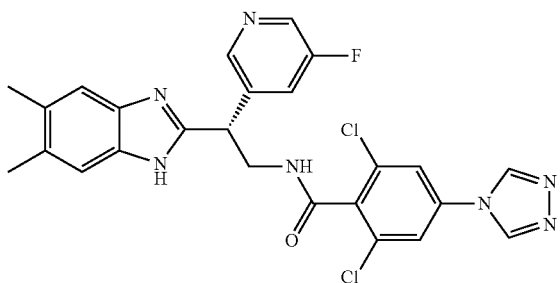 [SMILES: Cc1cc2nc([C@@H](CNC(=O)c3c(Cl)cc(-n4cnnc4)cc3Cl)c3cncc(F)c3)[nH]c2cc1C]

(R)-2,6-Dichloro-N-(2-(5,6-dimethyl-1H-benzo[d]imidazol-2-yl)-2-(5-fluoropyridin-3-yl)ethyl)-4-(4H-1,2,4-triazol-4-yl)benzamide FIXa IC50=14.8 nM Step A: Ethyl 2-cyano-2-(5-fluoropyridin-3-yl)acetate Ethyl cyanoacetate (0.472 ml, 4.42 mmol), 3-bromo-5-fluoropyridine (778 mg, 4.42 mmol), potassium tert-butoxide (1240 mg, 11.05 mmol), 1,1'-bis(diphenylphosphino)ferrocene-palladium(II)dichloride dichloromethane complex (361 mg, 0.442 mmol) and 1,4-dioxane (12 mL) were sealed in a reaction vessel and heated in a 70° C. oil bath for 3 h, then allowed to cool to ambient temperature overnight. The reaction was quenched with 5N acetic acid (1.768 mL, 8.84 mmol). The crude mixture was partioned between water and ethyl acetate. The combined organic layers were washed with brine, dried over Na$_2$SO$_4$, filtered and evaporated to dryness. The crude residue was purified by flash chromatography (SiO$_2$, Biotage SNAP Cartridge, silica gel, 80 g cartridge). The column was eluted by a EtOAc/hexanes mixture. Related fractions were pooled and evaporated in vacuo to afford the title compound. LCMS calc.=209.06; found=209.09 (M+H)$^+$.

Step B: Ethyl 3-amino-2-(5-fluoropyridin-3-yl)propanoate dihydrochloride

Ethyl 2-cyano-2-(5-fluoropyridin-3-yl)acetate (433.7 mg, 2.083 mmol), platinum(IV) oxide hydrate (63.0 mg, 0.208 mmol), HCl (4N in dioxane) (3.12 ml, 12.50 mmol) and EtOH (15 ml) were degassed and stirred under a H$_2$ balloon at room temperature overnight followed by filtration. Volatiles of the filtrate was evaporated under reduced pressure. The residual volatiles were chased by toluene (15 mL×2) to afford the titled compound. LCMS (free base) calc.=213.10; found=213.07. (M+H)$^+$.

Step C: Ethyl 3-(2,6-dichloro-4-(4H-1,2,4-triazol-4-yl)benzamido)-2-(5-fluoropyridin-3-yl)propanoate Ethyl 3-amino-2-(5-fluoropyridin-3-yl)propanoate dihydrochloride (266.3 mg, 0.934 mmol), 2,6-dichloro-4-(4H-1,2,4-triazol-4-yl)benzoic acid (INTERMEDIATE 6) (241 mg, 0.934 mmol), HATU (391 mg, 1.027 mmol), DMF (5 mL) and Hunig's Base (0.652 mL, 3.74 mmol) were stirred at room temperature for 2 h. The crude reaction was worked up with water/ethyl acetate. The extracts were dried over Na$_2$SO$_4$, filtered and evaporated in vacuo to afford a dark mixture. The residue was dissolved in DMSO and purified by preparative HPLC (reverse phase, YMC-Pack Pro C-18 100×20 mm) eluting with acetonitrile/water+0.1% TFA (0% to 50% organic in 10 min, then to 100% for 2 min, 20 mL/min). Related fractions were pooled and evaporated under reduced pressure to afford the title compound. LCMS calc.=452.06; found=452.01 (M+H)$^+$.

Step D: 3-(2,6-Dichloro-4-(4H-1,2,4-triazol-4-yl)benzamido)-2-(5-fluoropyridin-3-yl)propanoic acid Ethyl 3-(2,6-dichloro-4-(4H-1,2,4-triazol-4-yl)benzamido)-2-(5-fluoropyridin-3-yl)propanoate (269.7 mg, 0.596 mmol) and lithium hydroxide monohydrate (2.385 ml, 2.385 mmol) were stirred in 1,4-dioxane (5 mL)/water (3 ml) at room temperature overnight. The crude reaction was acidified by 1N HCl (aq). The resulting mixture was purified by preparative HPLC (reverse phase, YMC-Pack Pro C-18 100×20 mm) eluting with acetonitrile/water+0.1% TFA (10% to 60% organic in 10 min, then to 100% in 2 min, 20 mL/min). Related fractions were pooled and evaporated under reduced pressure to afford the title compound. LCMS calc.=424.03; found=423.89 (M+H)$^+$.

Step E: (R)-2,6-Dichloro-N-(2-(5,6-dimethyl-1H-benzo[d]imidazol-2-yl)-2-(5-fluoropyridin-3-yl)ethyl)-4-(4H-1,2,4-triazol-4-yl)benzamide HATU (53.8 mg, 0.141 mmol) was added to a stirred, room temperature mixture of 3-(2,6-dichloro-4-(4H-1,2,4-triazol-4-yl)benzamido)-2-(5-fluoropyridin-3-yl)propanoic acid (60 mg, 0.141 mmol), 4,5-dimethyl-1,2-phenylenediamine (19.26 mg, 0.141 mmol) and Hunig's base (0.049 mL, 0.283 mmol) in DMF (2 mL) and the mixture was stirred at room temperature overnight. Acetic acid (0.5 mL) was added to the reaction and it was heated to 100° C. for 6 h. LC-MS showed the desired product was formed. The crude reaction was purified by preparative HPLC (reverse phase, YMC-Pack ODS C-18 100×20 mm) eluting with acetonitrile/water (0% to 50% organic in 20 min, then to 100% in 5 min, 20 mL/min). Related fractions were pooled and evaporated under reduced pressure. This solid was submitted for chiral resolution; the 1st peak from OD-H column as the title compound and the 2nd peak as the other enantiomer. LCMS calc.=524.11; found=524.06 (M+H)$^+$. $^1$H NMR (500 MHz, CD$_3$OD): δ 9.04 (s, 2H); 8.52 (s, 1H); 8.40 (d, J=2.7 Hz, 1H); 7.81 (s, 2H); 7.77-7.79 (m, 1H); 7.31 (s, 2H); 4.86-4.88 (m, 1H); 4.22 (d, J=8.0 Hz, 2H); 2.34 (s, 6H).

| Chiral Preparative Method: | Analytical Method: |
|---|---|
| OD-H (3 × 15 cm) | OD-H (25 × 0.46 cm) |
| 30% ethanol/CO$_2$, 100 bar | 30% ethanol/CO$_2$, 100 bar |
| 60 mL/min, 220 nm | 3 mL/min, 220 and 254 nm |
| inj vol.: 0.75 mL, 6 mg/mL methanol | |

Example 39

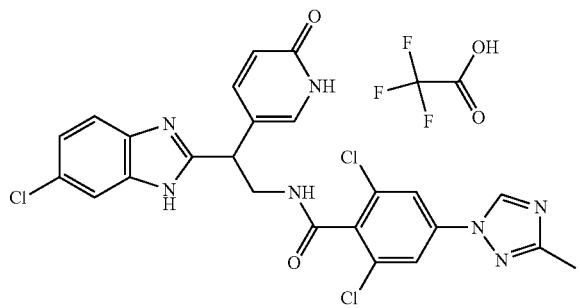 [SMILES: Cc1ncn(-c2cc(Cl)c(C(=O)NCC(c3ccc(=O)[nH]c3)c3nc4ccc(Cl)cc4[nH]3)c(Cl)c2)n1 ; O=C(O)C(F)(F)F]

2,6-Dichloro-N-(2-(6-chloro-1H-benzo[d]imidazol-2-yl)-2-(6-oxo-1,6-dihydropyridin-3-yl)ethyl)-4-(3-methyl-1H-1,2,4-triazol-1-yl)benzamide 2,2,2-trifluoroacetate FIXa IC50=2.4 nM

Step A: Ethyl 2-cyano-2-(6-methoxypyridin-3-yl)acetate

5-Bromo-2-methoxypyridine (1.144 mL, 8.84 mmol), 1,4-dioxane (40 ml), 1,1'-bis(diphenylphosphino)ferrocene-palladium(II)dichloride dichloromethane complex (0.505 g, 0.619 mmol), ethyl cyanoacetate (0.943 mL, 8.84 mmol) and potassium tert-butoxide (2.480 g, 22.10 mmol) were mixed in a reaction vessel and subjected to $N_2$ purging for 2 min. The reaction was heated in a 70° C. oil bath under a nitrogen atmosphere for 6 h then allowed to cool to ambient temperature overnight. The reaction was quenched with 5N acetic acid (4.42 mL, 22.10 mmol) and filtered through a pad of celite. The filtrate was partitioned between water and ethyl acetate. The combined organic layers were dried over $Na_2SO_4$, filtered and evaporated to dryness. The residue was purified by flash chromatography ($SiO_2$, 80 g cartridge). The column was eluted by a EtOAc/hexanes (0-75%) mixture. Related fractions were pooled and evaporated in vacuo to afford the title compound. LCMS calc.=221.08; found=221.21 $(M+H)^+$.

Step B: Ethyl 3-amino-2-(6-methoxypyridin-3-yl)propanoate 2,2,2-trifluoroacetate To a stirring solution of ethyl 2-cyano-2-(6-methoxypyridin-3-yl)acetate (200 mg, 0.908 mmol) in MeOH (15 mL) was added cobalt(II) chloride (707 mg, 5.45 mmol). The resulting purple solution was stirred at room temperature for 20 min. It was then cooled to −20° C. and $NaBH_4$ (309 mg, 8.17 mmol) was added in portions. The reaction was stirred at room temperature for 3 h and was then quenched by sat. $NaHCO_3$ (aq). The crude mixture was filtered through a pad of celite. The filter cake was washed with EtOAc. Volatiles were removed from the filtrate under reduced pressure. The resulting residue was purified by preparative HPLC (reverse phase, YMC-Pack Pro C-18 100×20 mm) eluting with acetonitrile/water+0.05% formic acid (10% to 60% organic in 10 min, then to 100% for 2 min, 20 mL/min). Related fractions were pooled and evaporated under reduced pressure to afford the title compound. LCMS (free base) calc.=225.12; found=225.17 $(M+H)^+$.

Step C: Ethyl 3-(2,6-dichloro-4-(3-methyl-1H-1,2,4-triazol-1-yl)benzamido)-2-(6-methoxypyridin-3-yl)propanoate Hunig's base (0.140 mL, 0.801 mmol) was added into a stirred mixture of 1-(4-carboxy-3,5-dichlorophenyl)-3-methyl-1H-1,2,4-triazol-4-ium chloride (INTERMEDIATE 12) (82 mg, 0.267 mmol), ethyl 3-amino-2-(6-methoxypyridin-3-yl)propanoate 2,2,2-trifluoroacetate (90.3 mg, 0.267 mmol) and HATU (112 mg, 0.294 mmol) in DMF (2 mL). The reaction mixture was stirred at room temperature overnight. The crude mixture was partitioned between water and ethyl acetate. The combined extracts were dried over $Na_2SO_4$, filtered and evaporated in vacuo. The resulting crude mixture was purified by flash chromatography ($SiO_2$, 80 g cartridge). The column was eluted by a $MeOH/CH_2Cl_2$ mixture (0% to 15%). Related fractions were pooled and evaporated in vacuo to afford the title compound. LCMS calc.=478.10; found=478.06 $(M+H)^+$.

Step D: 3-(2,6-Dichloro-4-(3-methyl-1H-1,2,4-triazol-1-yl)benzamido)-2-(6-methoxypyridin-3-yl)propanoic acid Ethyl 3-(2,6-dichloro-4-(3-methyl-1H-1,2,4-triazol-1-yl)benzamido)-2-(6-methoxypyridin-3-yl)propanoate (107 mg, 0.224 mmol) was stirred with 1,4-dioxane (5 mL) and lithium hydroxide monohydrate (0.224 ml, 0.224 mmol) at room temperature overnight. The reaction was neutralized by 1N HCl aq (0.224 ml, 0.224 mmol), and partitioned between brine and ethyl acetate. The combined extracts were dried over $Na_2SO_4$, filtered and evaporated in vacuo to afford \ the title compound. LCMS calc.=450.07; found=449.99 $(M+H)^+$.

Example 40

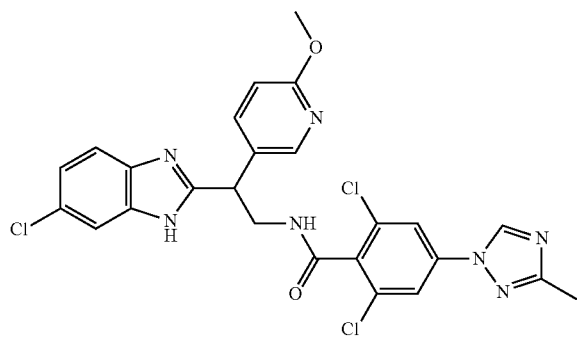 [SMILES: COc1ccc(C(CNC(=O)c2c(Cl)cc(-n3cnc(C)n3)cc2Cl)c2nc3ccc(Cl)cc3[nH]2)cn1]

Step A: (±)-2,6-Dichloro-N-(2-(6-chloro-1H-benzo[d]imidazol-2-yl)-2-(6-methoxypyridin-3-yl)ethyl)-4-(3-methyl-1H-1,2,4-triazol-1-yl)benzamide FIXa IC50=32.7 nM Hunig's Base (0.105 ml, 0.600 mmol) was added to a stirred, room temperature mixture of 3-(2,6-dichloro-4-(3-methyl-1H-1,2,4-triazol-1-yl)benzamido)-2-(6-methoxypyridin-3-yl)propanoic acid (108 mg, 0.240 mmol), 4-chloro-1,2-diaminobenzene (34.2 mg, 0.240 mmol) and HATU (91 mg, 0.240 mmol) in DMF (2 mL) and the mixture was stirred at room temperature overnight. Acetic acid (0.5 mL) was added to the reaction and the reaction was heated at 100° C. overnight. The crude reaction was partitioned between water and ethyl acetate. The combined extracts were dried over Na$_2$SO$_4$, filtered and evaporated in vacuo to afford a dark mixture. The resulting mixture was purified by flash chromatography (SiO$_2$, 80 g cartridge). The column was eluted by a MeOH/CH$_2$Cl$_2$ mixture (0% to 15%). Related fractions were pooled and evaporated in vacuo to afford the title compound. LCMS calc.=556.07; found=556 (M+H)$^+$ and 558.02. $^1$H NMR (400 MHz, CD$_3$OD): δ 9.00 (s, 1H); 8.18 (d, J=2.5 Hz, 1H); 7.84 (s, 2H); 7.74 (dd, J=8.7, 2.6 Hz, 1H); 7.57 (s, 1H); 7.40 (s, 1H); 7.17 (d, J=8.7 Hz, 1H); 6.77 (d, J=8.6 Hz, 1H); 4.70 (t, J=7.9 Hz, 1H); 4.20 (dd, J=13.5, 8.0 Hz, 1H); 4.05-4.11 (m, 1H); 3.85 (s, 3H); 2.38 (s, 3H).

Step B: (±)-2,6-Dichloro-N-(2-(6-chloro-1H-benzo[d]imidazol-2-yl)-2-(6-oxo-1,6-dihydropyridin-3-yl)ethyl)-4-(3-methyl-1H-1,2,4-triazol-1-yl)benzamide 2,2,2-trifluoroacetate 2,6-Dichloro-N-(2-(6-chloro-1H-benzo[d]imidazol-2-yl)-2-(6-methoxypyridin-3-yl)ethyl)-4-(3-methyl-1H-1,2,4-triazol-1-yl)benzamide (41.2 mg, 0.074 mmol) and HBr aq (0.5 mL, 4.42 mmol) were placed in a sealed vessel and subject to a 100° C. oil bath for 4 h then allowed to cool to ambient temperature overnight. The crude reaction was quenched with sat NaHCO$_3$ (aq), and extracted with ethyl acetate. The combined extracts were dried over Na$_2$SO$_4$, filtered and evaporated in vacuo. The residue was purified by preparative HPLC (reverse phase, YMC-Pack ODS C-18 100×20 mm) eluting with acetonitrile/water/0.05% TFA (10% to 65% organic in 10 min, then to 100% in 2 min, 20 mL/min). Related fractions were pooled and evaporated under reduced pressure to afford the title compound. LCMS calc.=542.06; found=542 (M+H)$^+$ and 543.86. $^1$H NMR (400 MHz, CD$_3$OD): δ 9.02 (s, 1H); 7.88 (s, 2H); 7.55-7.69 (m, 4H); 7.37 (dd, J=8.7, 1.9 Hz, 1H); 6.56 (d, J=9.5 Hz, 1H); 4.72 (t, J=7.9 Hz, 1H); 4.24 (dd, J=13.6, 7.3 Hz, 1H); 4.04-4.09 (m, 1H); 2.38 (s, 3H).

Example 41

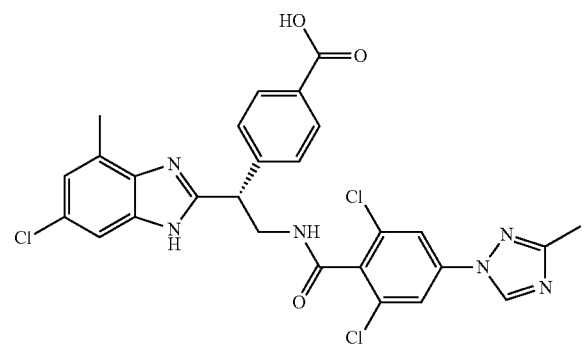 [SMILES: Cc1ncn(-c2cc(Cl)c(C(=O)NC[C@@H](c3ccc(C(=O)O)cc3)c3nc4c(C)cc(Cl)cc4[nH]3)c(Cl)c2)n1]

(R)-4-(1-(6-Chloro-4-methyl-1H-benzo[d]imidazol-2-yl)-2-(2,6-dichloro-4-(3-methyl-1H-1,2,4-triazol-1-yl)benzamido)ethyl)benzoic acid FIXa IC50=18.6 nM Step A: Ethyl 4-(2-(tert-butoxy)-1-cyano-2-oxoethyl)benzoate Ethyl 4-bromobenzoate (1.157 mL, 7.08 mmol), tert-butyl cyanoacetate (1.012 ml, 7.08 mmol), potassium tert-butoxide (1987 mg, 17.71 mmol), 1,1'-bis(diphenylphosphino)ferrocene-palladium(II)dichloride dichloromethane complex (578 mg, 0.708 mmol) and 1,4-dioxane (25 mL) were sealed in a reaction vessel and subject to N$_2$ purging for 2 min. The reaction was heated in a 70° C. oil bath for 6 h then allowed to cool to ambient temperature overnight. The reaction was quenched with 5N acetic acid (3.54 ml, 17.71 mmol) and partitioned between water and ethyl acetate. The combined organic layers were washed with brine, dried over Na$_2$SO$_4$, filtered and evaporated to dryness. The crude residue was purified by flash chromatography (SiO$_2$, 80 g cartridge). The column was eluted by a EtOAc/hexanes mixture. Related fractions were pooled and evaporated in vacuo to afford the title compound. LCMS calc.=290.13; found=234.10 (M+H-tBu)$^+$.

Step B: Ethyl 4-(3-amino-1-(tert-butoxy)-1-oxopropan-2-yl)benzoate

To a stirring solution of ethyl 4-(2-(tert-butoxy)-1-cyano-2-oxoethyl)benzoate (1 g, 3.46 mmol) in MeOH (40 mL) was added cobalt(II) chloride (2.69 g, 20.74 mmol). The resulting purple solution was stirred at RT for 20 min. The reaction was then cooled to −20° C. and NaBH$_4$ (1.177 g, 31.1 mmol) was added in portions. The reaction was stirred at room temperature for 1 h, and then quenched and filtered through a pad of celite. The filter cake was washed with EtOAc. Volatiles were removed under reduced pressure. The resulting residue was purified by flash chromatography (SiO$_2$, 80 g cartridge). The column was eluted by a MeOH/CH$_2$Cl$_2$ mixture (0% to 25%). Related fractions were pooled and evaporated in vacuo to afford the title compound.

LCMS calc.=294.16; found=238.16 (M+H-tBu)$^+$.

Step C: Ethyl 4-(1-(tert-butoxy)-3-(2,6-dichloro-4-(3-methyl-1H-1,2,4-triazol-1-yl)benzamido)-1-oxopropan-2-yl)benzoate Ethyl 4-(3-amino-1-(tert-butoxy)-1-oxopropan-2-yl)benzoate (300 mg, 1.023 mmol), 1-(4-carboxy-3,5-dichlorophenyl)-3-methyl-1H-1,2,4-triazol-4-ium chloride (INTERMEDIATE 12) (316 mg, 1.023 mmol), HATU (389 mg, 1.023 mmol), Hunig's base (0.536 mL, 3.07 mmol) and DMF (3 mL) were stirred at room temperature for 4 h. The crude reaction was purified by preparative HPLC (reverse phase, YMC-Pack Pro C-18 100×20 mm) eluting with acetonitrile/water (0% to 75% organic in 10 min, then to 100% for 2 min, 20 mL/min). Related fractions were pooled and evaporated under reduced pressure to afford title compound. LCMS calc.=547.14; found=547.13 (M+H)$^+$.

Step D: 3-(2,6-Dichloro-4-(3-methyl-1H-1,2,4-triazol-1-yl)benzamido)-2-(4-(ethoxycarbonyl)phenyl)propanoic acid Ethyl 4-(1-(tert-butoxy)-3-(2,6-dichloro-4-(3-methyl-1H-1,2,4-triazol-1-yl)benzamido)-1-oxopropan-2-yl)benzoate (143.4 mg, 0.262 mmol), 2,2,2-trifluoroacetic acid (0.101 mL, 1.310 mmol) and DCM (3 mL) were stirred at room temperature overnight. Volatiles were removed under reduced pressure to afford the title compound. LCMS calc.=491.08; found=491.09 (M+H)$^+$.

Example 42

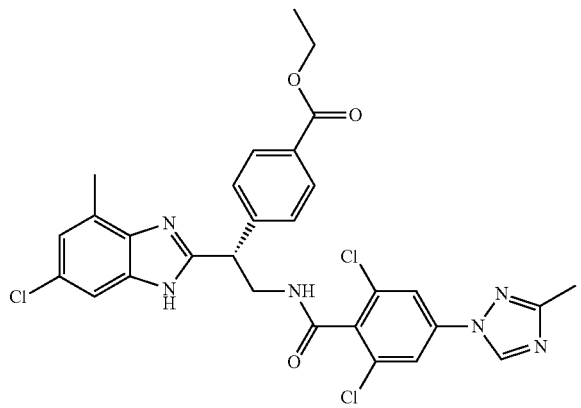 [SMILES: CCOC(=O)c1ccc([C@H](CNC(=O)c2c(Cl)cc(-n3cnc(C)n3)cc2Cl)c2nc3c(C)cc(Cl)cc3[nH]2)cc1]

Step A: (R)-Ethyl 4-(1-(6-chloro-4-methyl-1H-benzo[d]imidazol-2-yl)-2-(2,6-dichloro-4-(3-methyl-1H-1,2,4-triazol-1-yl)benzamido)ethyl)benzoate FIXa IC50=39.1 nM HATU (100 mg, 0.263 mmol) was added to a stirred, room temperature mixture of 3-(2,6-dichloro-4-(3-methyl-1H-1,2,4-triazol-1-yl)benzamido)-2-(4-(ethoxycarbonyl) phenyl)propanoic acid (129 mg, 0.263 mmol), 5-chloro-3-methylbenzene-1,2-diamine hydrochloride (50.7 mg, 0.263 mmol) and Hunig's base (0.183 ml, 1.050 mmol) in DMF (1.5 mL) was stirred at room temperature for 2 h. Acetic acid (0.5 ml) was added to the reaction and heated to 90° C. for 6 hrs. The reaction was purified by preparative HPLC (reverse phase, YMC-Pack ODS C-18 100×20 mm) eluting with acetonitrile/water/0.1% TFA (10% to 65% organic in 10 min, then to 100% in 2 min, 20 mL/min). Related fractions were pooled and evaporated under reduced pressure. This solid was submitted for chiral resolution. The 1st peak from OD-H column as the S enantiomer and the 2nd peak as the title compound. LCMS calc.=611.11; found=611 (M+H)$^+$ and 613.20. $^1$H NMR (500 MHz, CD$_3$OD): δ 9.02 (s, 1H); 8.00 (d, J=7.9 Hz, 2H); 7.86 (s, 2H); 7.59 (d, J=7.9 Hz, 2H); 7.37 (d, J=4.3 Hz, 1H); 7.02 (s, 1H); 4.89 (d, J=8.6 Hz, 1H); 4.32-4.35 (m, 1H); 4.27 (s, 3H); 4.16 (d, J=12.5 Hz, 1H); 2.52 (s, 3H); 2.40 (s, 3H).

| Preparative Method: | Analytical Method: |
|---|---|
| OD-H (3 × 15 cm) | OD-H (25 × 0.46 cm) |
| 30% methanol(0.1% DEA)/CO$_2$, 100 bar | 35% methanol(DEA)/CO$_2$, 100 bar |
| 75 mL/min, 220 nm | 3.0 mL/min, 220 and 254 nm |
| inj vol.: 0.5 mL, 14.7 mg/mL methanol | |

Step B: (R)-4-(1-(6-Chloro-4-methyl-1H-benzo[d]imidazol-2-yl)-2-(2,6-dichloro-4-(3-methyl-1H-1,2,4-triazol-1-yl)benzamido)ethyl)benzoic acid (R)-Ethyl 4-(1-(6-chloro-4-methyl-1H-benzo[d]imidazol-2-yl)-2-(2,6-dichloro-4-(3-methyl-1H-1,2,4-triazol-1-yl)benzamido)ethyl)benzoate (36.7 mg, 0.060 mmol) was stirred with 1,4-dioxane (1 mL) and lithium hydroxide monohydrate (0.240 mL, 0.240 mmol) at room temperature overnight. The crude mixture was acidified by 1N HCl (0.240 mL, 0.240 mmol). The resulting clear solution was diluted in DMSO and purified by preparative HPLC (reverse phase, YMC-Pack Pro C-18 100×20 mm) eluting with acetonitrile/water+0.1% TFA (10% to 80% organic in 10 min, then to 100% for 2 min, 20 mL/min). Related fractions were pooled and concentrated under reduced pressure to afford the title compound. LCMS calc.=583.07; found=583/585.09 (M+H)$^+$. $^1$H NMR (500 MHz, CD$_3$OD): δ 9.11 (s, 1H); 8.08 (d, J=8.0 Hz, 2H); 7.90 (s, 2H); 7.62 (d, J=8.0 Hz, 2H); 7.57 (s, 1H); 7.33 (s, 1H); 5.10 (s, 1H); 4.47 (br s, 1H); 4.22 (br s, 1H); 2.61 (s, 3H); 2.40 (s, 3H).

Example 43

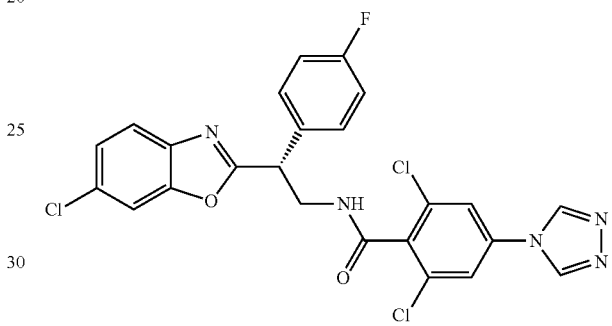

(R)-2,6-Dichloro-N-(2-(6-chlorobenzo[d]oxazol-2-yl)-2-(4-fluorophenyl)ethyl)-4-(4H-1,2,4-triazol-4-yl)benzamide FIXa IC50=96.2 nM

Step A: Ethyl 3-(2,6-dichloro-4-(4H-1,2,4-triazol-4-yl)benzamido)-2-(4-fluorophenyl)propanoate Ethyl 3-amino-2-(4-fluorophenyl)propanoate hydrochloride (2000 mg, 8.07 mmol), 2,6-dichloro-4-(4H-1,2,4-triazol-4-yl)benzoic acid (INTERMEDIATE 6) (2084 mg, 8.07 mmol), DMF (48 mL) and Hunig's base (3.53 mL, 20.19 mmol) were stirred at room temperature for 2 h. The reaction mixture was partitioned between water and ethyl acetate. The combined extracts were dried over Na$_2$SO$_4$, filtered and evaporated in vacuo. The resulting crude mixture was purified by flash chromatography (SiO$_2$, Silica 80 g cartridge). The column was eluted by a MeOH/CH$_2$Cl$_2$ mixture (0% to 25%). Related fractions were pooled and evaporated in vacuo to afford the title compound. LCMS calc.=451.07; found=451.00 (M+H)$^+$.

Step B: 3-(2,6-Dichloro-4-(4H-1,2,4-triazol-4-yl)benzamido)-2-(4-fluorophenyl)propanoic acid Ethyl 3-(2,6-dichloro-4-(4H-1,2,4-triazol-4-yl)benzamido)-2-(4-fluorophenyl)propanoate (2.68 g, 5.95 mmol) was stirred with 1,4-dioxane (24 mL) and lithium hydroxide monohydrate (24 mL, 24.00 mmol) at room temperature overnight. The crude mixture was acidified by 1N HCl (24 mL, 24.00 mmol), and partitioned between water and ethyl acetate. The combined extracts were dried over $Na_2SO_4$, filtered and evaporated in vacuo to afford the title compound. LCMS calc.=423.03; found=423.05 (M+H)+.

Step C: (R)-2,6-Dichloro-N-(2-(6-chlorobenzo[d]oxazol-2-yl)-2-(4-fluorophenyl)ethyl)-4-(4H-1,2,4-triazol-4-yl)benzamide Hunig's base (0.050 mL, 0.284 mmol) was added to a stirred, room temperature mixture of 3-(2,6-dichloro-4-(4H-1,2,4-triazol-4-yl)benzamido)-2-(4-fluorophenyl)propanoic acid (60 mg, 0.142 mmol), 2-amino-4-chlorophenol (20.35 mg, 0.142 mmol) and HATU (53.9 mg, 0.142 mmol) in NMP (3 mL) and the mixture was stirred at room temperature for 2 h. The reaction mixture and acetic acid (0.014 mL, 0.236 mmol) was subject to microwave irradiation at 200° C. for a total of 18 h. The resulting mixture was purified by preparative HPLC (reverse phase, YMC-Pack Pro C-18 100×20 mm) eluting with acetonitrile/water+0.1% TFA (10% to 80% organic in 10 min, then to 100% for 2 min, 20 mL/min). Related fractions were pooled and evaporated under reduced pressure to afford a brown glass of 14.2 mg. This solid was submitted for chiral resolution. The 1st peak from AD column as the S enantiomer and the 2nd peak as the title compound. Chiral Resolution Method Info: AD 20×250 mm, 40% MeOH (0.1% DEA)/C02, 50 ml/min, 100 bar, 230 nm, 35 C, sample in MeOH/DCM.

LCMS calc.=530.03; found=530 (M+H)+ and 532.01. $^1$H NMR (400 MHz, $CD_3OD$): δ 9.02 (s, 2H); 7.78 (s, 2H); 7.68 (d, J=2.1 Hz, 1H); 7.52-7.54 (m, 1H); 7.45-7.48 (m, 2H); 7.34 (dd, J=8.7, 2.1 Hz, 1H); 7.09 (t, J=8.6 Hz, 2H); 4.80-4.83 (m, 1H); 4.20 (dd, J=13.5, 9.1 Hz, 1H); 4.04 (dd, J=13.5, 6.8 Hz, 1H).

The following compounds (Table 3) were synthesized using methods analogous to those described for EXAMPLES 37-43 from commercially available materials or intermediates whose syntheses are described above.

TABLE 3

| Example | Structure | Calc. (M + H)+ | LCMS (M + H)+ | hFIXa IC50 (nM) |
|---|---|---|---|---|
| 44 | 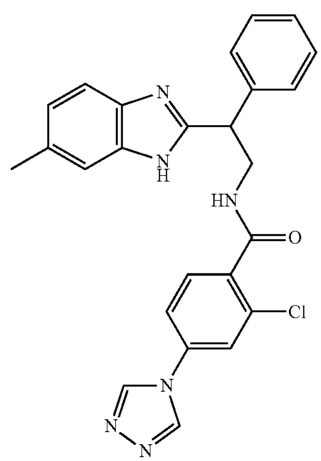 [SMILES: Cc1ccc2nc(C(CNC(=O)c3ccc(-n4cnnc4)cc3Cl)c3ccccc3)[nH]c2c1] | 457.15 | 457.14 | 53.53 |
| 45 | 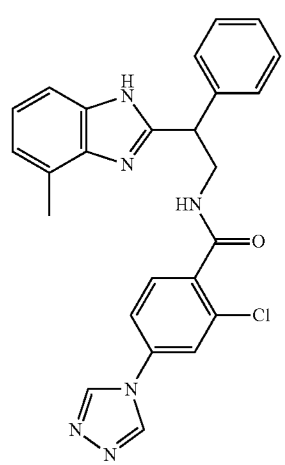 [SMILES: Cc1cccc2[nH]c(C(CNC(=O)c3ccc(-n4cnnc4)cc3Cl)c3ccccc3)nc12] | 457.15 | 457.17 | 621.5 |

TABLE 3-continued

| Example | Structure | Calc. (M + H)+ | LCMS (M + H)+ | hFIXa IC50 (nM) |
|---|---|---|---|---|
| 46 | 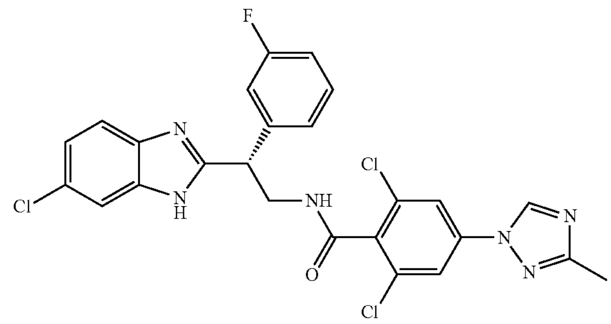 [SMILES: Cc1ncn(-c2cc(Cl)c(C(=O)NC[C@@H](c3cccc(F)c3)c3nc4ccc(Cl)cc4[nH]3)c(Cl)c2)n1] | 543.07 | 542.99 | 9.781 |
| 47 | 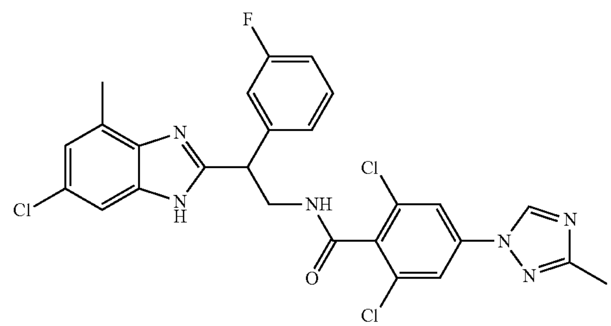 [SMILES: Cc1ncn(-c2cc(Cl)c(C(=O)NCC(c3cccc(F)c3)c3nc4c(C)cc(Cl)cc4[nH]3)c(Cl)c2)n1] | 557.08 | 557.05 | 6.176 |
| 48 | 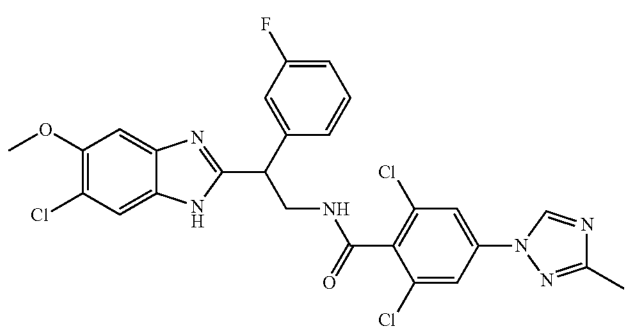 | 573.08 | 572.94 | 2.857 |
| 49 | 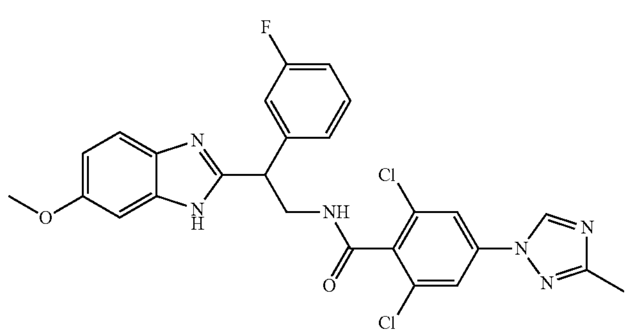 | 539.12 | 539.02 | 49.08 |

TABLE 3-continued

| Example | Structure | Calc. (M + H)+ | LCMS (M + H)+ | hFIXa IC50 (nM) |
|---|---|---|---|---|
| 50 | 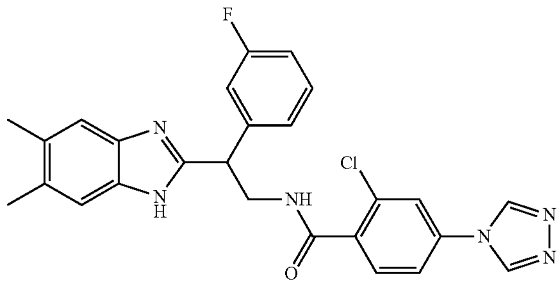 [SMILES: Cc1cc2nc(C(CNC(=O)c3ccc(-n4cnnc4)cc3Cl)c3cccc(F)c3)[nH]c2cc1C] | 489.16 | 489.05 | 5.692 |
| 51 | 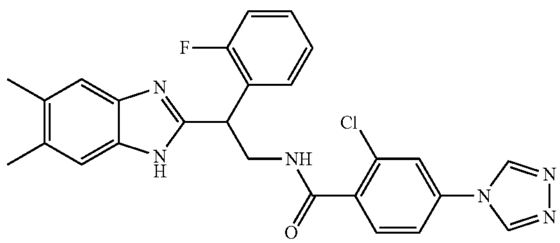 [SMILES: Cc1cc2nc(C(CNC(=O)c3ccc(-n4cnnc4)cc3Cl)c3ccccc3F)[nH]c2cc1C] | 489.16 | 489.16 | 19.29 |
| 52 | 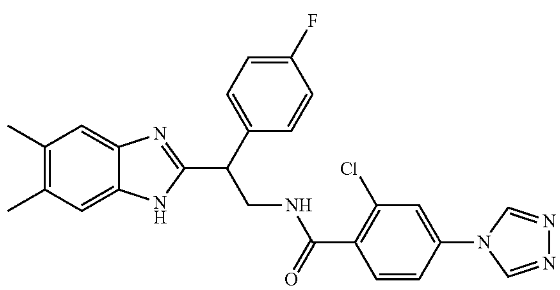 [SMILES: Cc1cc2nc(C(CNC(=O)c3ccc(-n4cnnc4)cc3Cl)c3ccc(F)cc3)[nH]c2cc1C] | 489.16 | 489.05 | 8.416 |
| 53 | 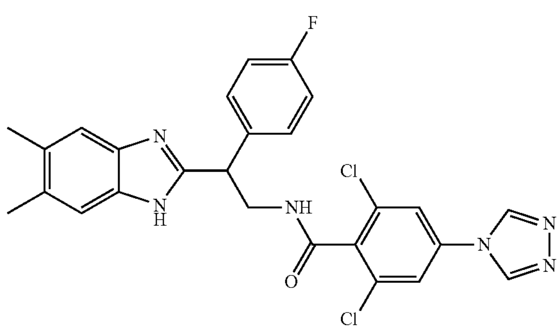 [SMILES: Cc1cc2nc(C(CNC(=O)c3c(Cl)cc(-n4cnnc4)cc3Cl)c3ccc(F)cc3)[nH]c2cc1C] | 523.12 | 523.08 | 2.823 |
| 54 | 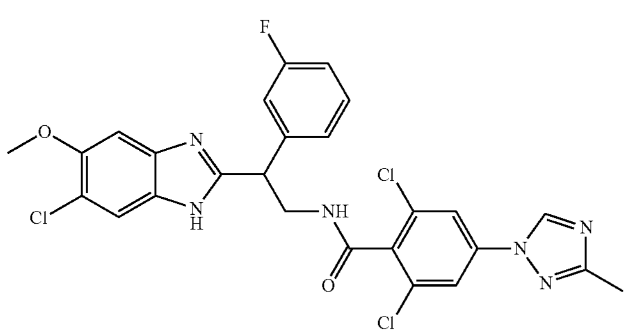 | 573.08 | 572.94 | 2.857 |

TABLE 3-continued
| Example | Structure | Calc. (M + H)+ | LCMS (M + H)+ | hFIXa IC50 (nM) |
|---|---|---|---|---|
| 55 | 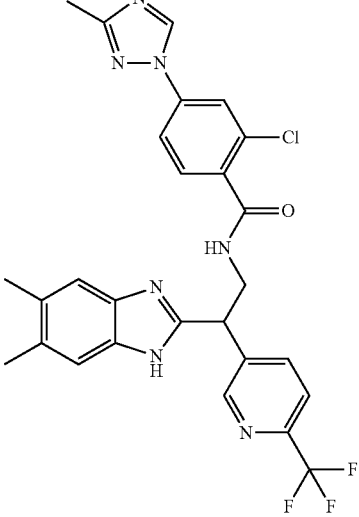 | 554.17 | 554.08 | 427.3 |
| 56 | 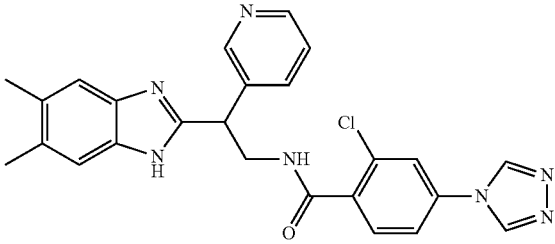 [SMILES: Cc1cc2nc(C(CNC(=O)c3ccc(-n4cnnc4)cc3Cl)c3cccnc3)[nH]c2cc1C] | 472.17 | 471.98 | 15.35 |
| 57 | 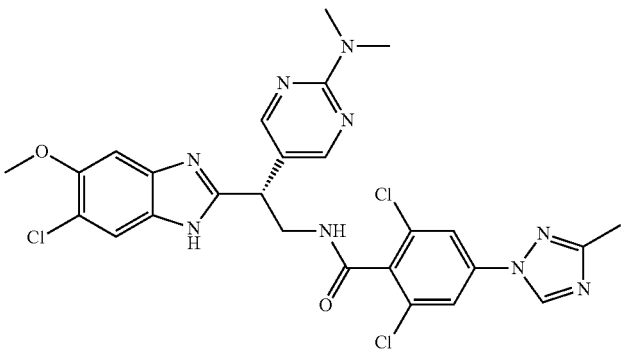 | 600.12 | 600.10 | 8.761 |
| 58 | 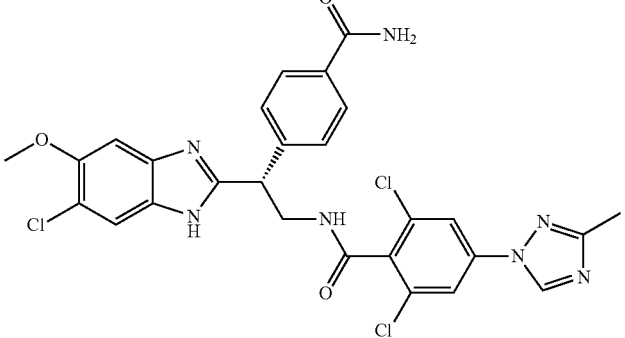 | 598.09 | 598.10 | 2.363 |

TABLE 3-continued
| Example | Structure | Calc. (M + H)+ | LCMS (M + H)+ | hFIXa IC50 (nM) |
|---|---|---|---|---|
| 59 | 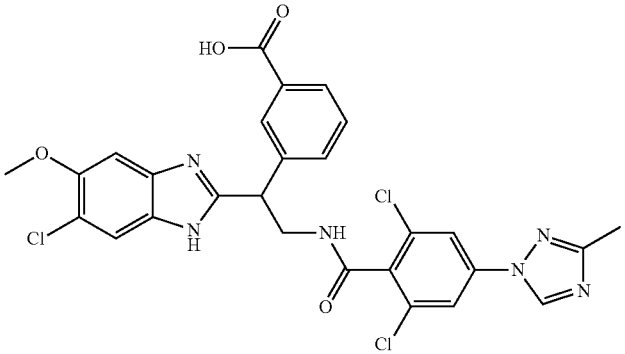 | 599.08 | 599.04 | 1.5 |
| 60 | 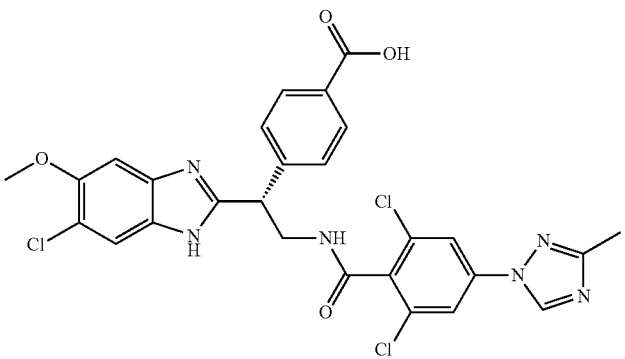 | 599.08 | 599.13 | 4.793 |
| 61 | 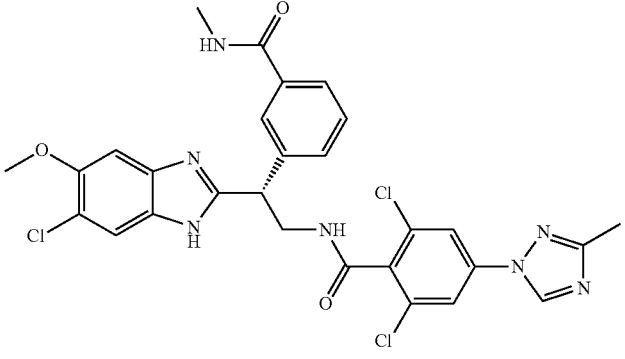 | 612.11 | 612.14 | 4.779 |
| 62 | 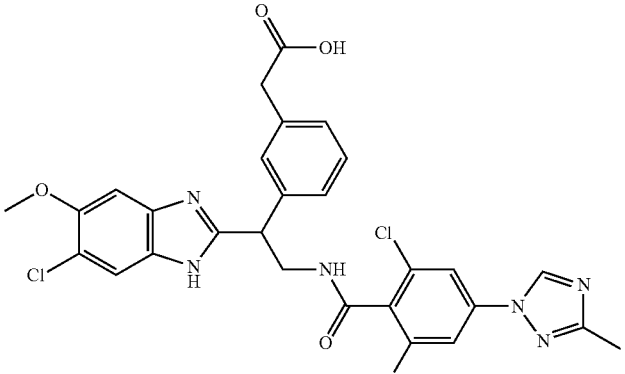 | 613.09 | 613.02 | 1.748 |

TABLE 3-continued

| Example | Structure | Calc. (M + H)+ | LCMS (M + H)+ | hFIXa IC50 (nM) |
|---|---|---|---|---|
| 63 | 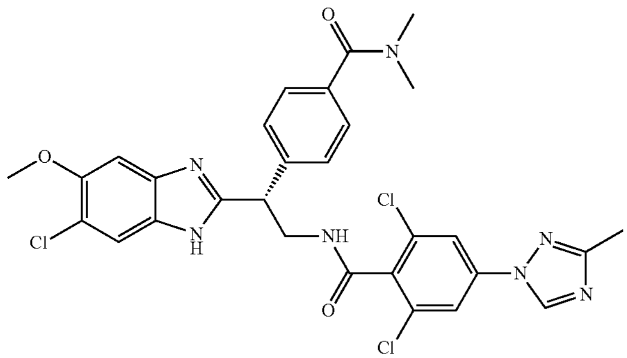 | 626.12 | 626.23 | 27.71 |
| 64 | 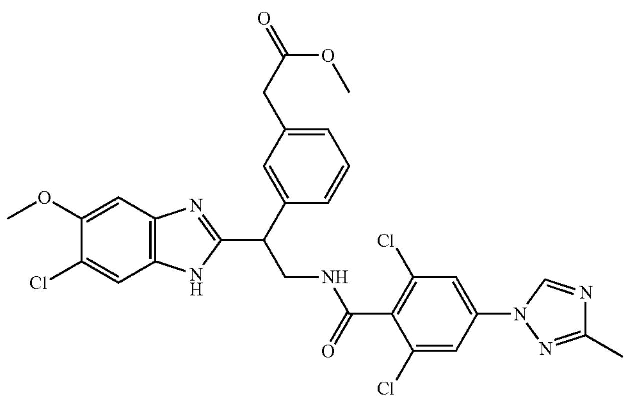 | 627.11 | 627.06 | 6.1 |
| 65 | 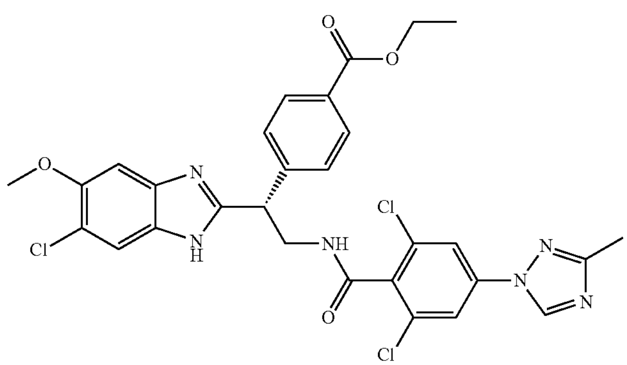 | 627.11 | 627.16 | 5.598 |
| 66 | 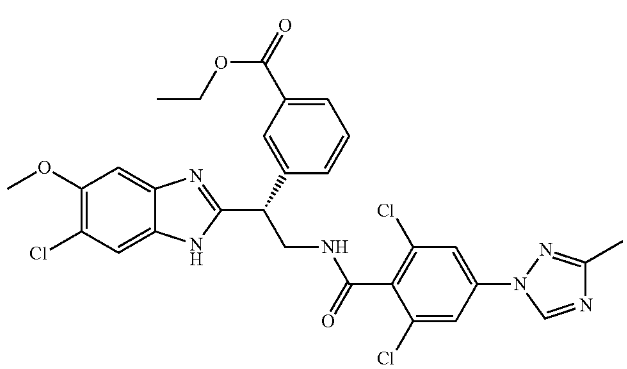 | 627.11 | 627.10 | 16.8 |

TABLE 3-continued

| Example | Structure | Calc. (M + H)+ | LCMS (M + H)+ | hFIXa IC50 (nM) |
|---|---|---|---|---|
| 67 | 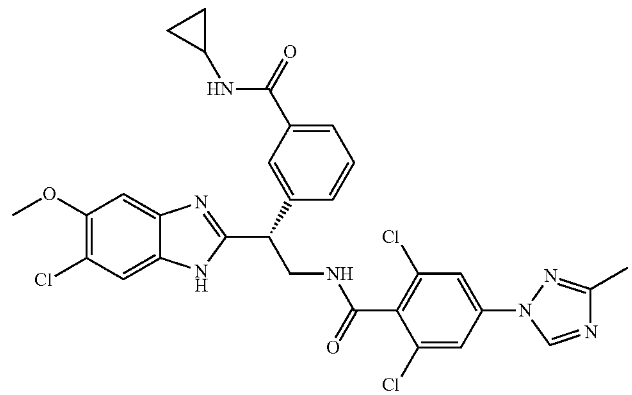 | 638.12 | 638.09 | 2.898 |
| 68 | 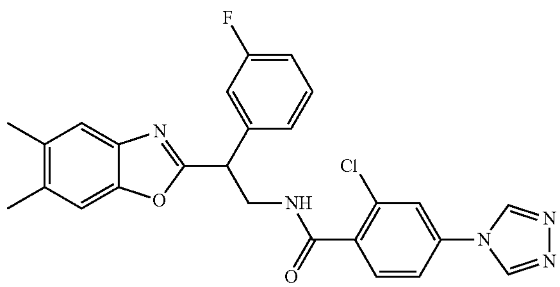 [SMILES: Cc1cc2nc(C(CNC(=O)c3ccc(-n4cnnc4)cc3Cl)c3cccc(F)c3)oc2cc1C] | 490.14 | 490.21 | 71.94 |

Example 69

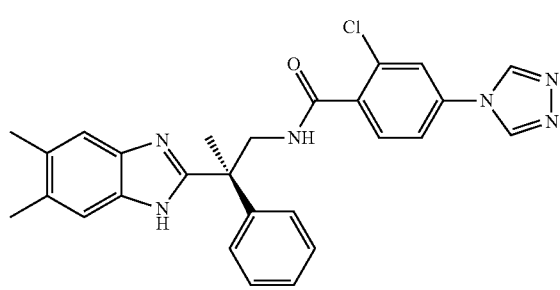

(R)-2-chloro-N-(2-(5,6-dimethyl-1H-benzo[d]imidazol-2-yl)-2-phenylpropyl)-4-(4H-1,2,4-triazol-4-yl)benzamide FIXa IC50=55.2 nM

Step A: methyl 3-((tert-butoxycarbonyl)amino)-2-phenylpropanoate

To a stirred solution of 3-tert-butoxycarbonyl}amino-2-phenyl-propionic acid (1.5 g, 5.65 mmol) in DCM-MeOH (15 mL-15-mL) was added trimethylsilyldiazomethane in hexane (2.0 M, 5.65 mL, 11.31 mmol). The mixture was stirred at RT for 3 h, and then evaporated to dryness to afford the desired product.

(M+H) calc.=280.15; found=302.11 (M+Na).

Step B: methyl 3-((tert-butoxycarbonyl)amino)-2-methyl-2-phenylpropanoate

To a stirred solution of methyl 3-((tert-butoxycarbonyl)amino)-2-phenylpropanoate (150 mg, 0.537 mmol) in dry THF (4 ml) was added LDA (2.0M, 0.35 ml, 0.698 mmol) at −78° C. The mixture was stirred at −78° C. for 30 min, then to it was added MeI (0.047 ml, 0.752 mmol). The mixture was slowly warmed up to room temperature and stirred at room temperature overnight. The mixture was partitioned between EtOAc and sat. NH$_4$Cl aq. The aqueous layer was extracted with EtOAc three times. The organic phases were combined, dried over MgSO$_4$, filtered, concentrated, and purified by flash chromatography (Isco Combi-Flash system, 40 g Isco silica gel gold column and 0-20% EtOAc in hexane as eluent) to afford the title compound. LCMS calc.=294.16; found=294.08 (M+H)+.

Step C: methyl 3-amino-2-methyl-2-phenylpropanoate, HCl

Methyl 3-((tert-butoxycarbonyl)amino)-2-methyl-2-phenylpropanoate (73 mg, 0.249 mmol) in 4N HCl in dioxane (1.24 mL) was stirred at room temperature for 60 min, and then evaporated to dryness to give the desired product. LCMS, calc.=194.11; found=194.16 (M+H)+.

Step D: methyl 3-(2-chloro-4-(4H-1,2,4-triazol-4-yl)benzamido)-2-methyl-2-phenylpropanoate To the stirred solution of 2-chloro-4-(4H-1,2,4-triazol-4-yl)benzoic acid (61.2 mg, 0.274 mmol), methyl 3-amino-2-methyl-2-phenylpropanoate, HCl (57.2 mg, 0.249 mmol) in DMA (1 ml) was added Hunig's base (0.087 mL, 0.498 mmol), HOAt (37.3 mg, 0.274 mmol), then EDC (62.1 mg, 0.324 mmol). The mixture was stirred at room temperature for 4 h, then diluted with DCM (1 mL) and purified by flash chromatography (ISCO CombiFlash Rf system, 24 g ISCO gold silica gel column, 0-10% MeOH in DCM as eluent) to afford the title compound.
LCMS, calc.=399.11; found=399.14 (M+H)$^+$.

Step E: 3-(2-chloro-4-(4H-1,2,4-triazol-4-yl)benzamido)-2-methyl-2-phenylpropanoic acid To the stirred solution of methyl 3-(2-chloro-4-(4H-1,2,4-triazol-4-yl)benzamido)-2-methyl-2-phenylpropanoate (84 mg, 0.211 mmol) in THF-water (1 mL:1 mL) was added LiOH (10.1 mg, 0.421 mmol). The mixture was stirred at 40° C. overnight, then cooled to room temperature and acidified with addition of HCl (4N in dioxane, 0.105 mL, 0.421 mmol). The mixture was evaporated to dryness to give the desired product (mixed with 0.421 mmol LiCl). LCMS, calc.=385.10; found=385.12 (M+H)$^+$.

Step F: 2-chloro-N-(2-(5,6-dimethyl-1H-benzo[d]imidazol-2-yl)-2-phenylpropyl)-4-(4H-1,2,4-triazol-4-yl)benzamide The crude product from last step E (40 mg, 0.085 mmol) in thionyl chloride (0.379 mL, 5.20 mmol) was stirred at 50° C. for 2 h, cooled to room temperature and evaporated to dryness. To the residue were added DMA (1 mL), 4,5-dimethyl-1,2-phenylenediamine (15.6 mg, 0.114 mmol), and pyridine (0.017 mL, 0.21 mmol). The mixture was stirred at room temperature overnight, followed by addition of acetic acid (1.5 mL), then warmed up to 90° C. and stirred at 90° C. overnight. Reversed HPLC purification (Gilson system, column: Waters Sunfire 19×100 mm, 5 um, 5-75% acetonitrile in water (with 0.1% TFA) as eluenting solvent) afforded the title compound. LCMS, calc.=485.18; found=485.17 (M+H)$^+$.

Step G: (R)-2-chloro-N-(2-(5,6-dimethyl-1H-benzo[d]imidazol-2-yl)-2-phenylpropyl)-4-(4H-1,2,4-triazol-4-yl)benzamide The racemic compound from step F (45 mg, 0.093 mmol) was resolved by SFC separation technique using the conditions as shown below to give both enationmers after concentration (7 mg, peak-1 (enantiomer A) ee>99%; peak-2 (enantiomer B), 6.5 mg, ee>99%). The fast eluting enantiomer (1$^{st}$ peak) was presumed as "R" isomer based on its FIXa activity (more potent enantiomer).

| Preparative Method: | Analytical Method: |
|---|---|
| OJ (2 × 25 cm) | OJ (25 × 0.46 cm) |
| 20% methanol/CO$_2$, 100 bar | 30% methanol/CO$_2$, 100 bar |
| 70 mL/min, 220 nm | 3 mL/min, 220 and 254 nm |
| inj vol.: 1 mL, 4.5 mg/mL methanol | |

For enantiomer A:
LC-Mass (M+H) calc.=485.18; found=485.23. $^1$H NMR (500 MHz, CD$_3$OD): δ 9.05 (s, 2H); 7.83-7.82 (m, 1H); 7.63-7.61 (m, 1H); 7.48-7.41 (m, 1H); 7.38-7.33 (m, 2H); 7.28-7.21 (m, 5H); 4.28 (s, br, 2H); 2.35 (s, br, 6H); 1.96 (s, 3H).

For enantiomer B:
LC-Mass (M+H) calc.=485.18; found=485.23. $^1$H NMR (500 MHz, CD$_3$OD): same as enantiomer A.

Example 70

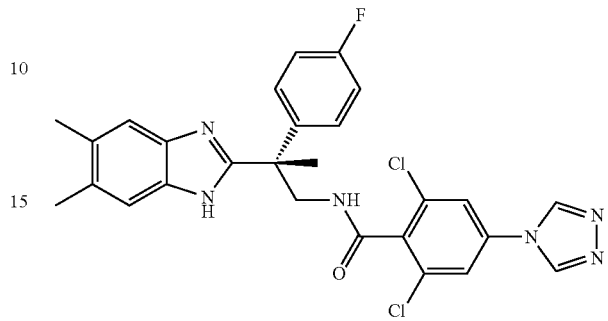

((R)-2,6-Dichloro-N-(2-(5,6-dimethyl-1H-benzo[d]imidazol-2-yl)-2-(4-fluorophenyl)propyl)-4-(4H-1,2,4-triazol-4-yl)benzamide FIXa IC50=5.6 nM Step A: Ethyl 2-cyano-2-(4-fluorophenyl)acetate Ethyl cyanoacetate (4.72 mL, 44.2 mmol), 4-bromofluorobenzene (4.86 ml, 44.2 mmol), potassium tert-butoxide (12.40 g, 111 mmol), 1,1'-bis(diphenylphosphino)ferrocenepalladium(II)dichloride dichloromethane complex (2.53 g, 3.09 mmol) and 1,4-dioxane (200 ml) were sealed in a reaction vessel and subjected to N$_2$ purging for 2 min. The reaction was heated in a 70° C. oil bath for 6 h then allowed to cool to ambient temperature overnight. The reaction was quenched with 5N acetic acid (22.10 mL, 111 mmol) and filtered through a pad of celite. The filtrate was partitioned between water and ethyl acetate. The combined organic layers were dried over Na$_2$SO$_4$, filtered and evaporated to dryness. The residue was purified by flash chromatography (SiO$_2$, 120 g cartridge). The column was eluted by a EtOAc/hexanes mixture. Related fractions were pooled and evaporated in vacuo to afford the title compound. LCMS calc.=208.07; found=208 (M+H)$^+$.

Step B: Ethyl 2-cyano-2-(4-fluorophenyl)propanoate

To solution of ethyl 2-cyano-2-(4-fluorophenyl)acetate (4.5 g, 21.72 mmol) in THF (181 mL) (ice bath) was added sodium hydride (1.042 g, 26.1 mmol). The mixture turned dark red immediately, and was stirred for 15 min. Iodomethane (5.43 mL, 87 mmol) was added into the resulting mixture. The reaction mixture was stirred at room temperature overnight then quenched with water and extracted with EtOAc. The organic layers were dried (Na$_2$SO$_4$), filtered and concentrated in vacuo. The resulting residue was purified by flash chromatography (SiO$_2$, 120 g cartridge). The column was eluted by a EtOAc/hexanes mixture. Related fractions were pooled and evaporated in vacuo to afford the title compound. LCMS calc.=222.09; found=222 (M+H)$^+$.

Step C: Ethyl 3-amino-2-(4-fluorophenyl)-2-methylpropanoate hydrochloride

Ethyl 2-cyano-2-(4-fluorophenyl)propanoate (3.3874 g, 15.31 mmol), platinum(IV) oxide hydrate (0.463 g, 1.531 mmol), HCl (4M in dioxane) (22.97 ml, 92 mmol) and EtOH (225 ml) were degassed and stirred under a $H_2$ balloon at room temperature overnight. The crude reaction was filtered through a bed of celite. The filtrate was evaporated under reduced pressure. The residual volatiles were chased by toluene (50 mL×2) to afford the title compound. LCMS (free base) calc.=226.12; found=226.14 $(M+H)^+$.

Step D: Ethyl 3-(2,6-dichloro-4-(4H-1,2,4-triazol-4-yl)benzamido)-2-(4-fluorophenyl)-2-methylpropanoate Ethyl 3-amino-2-(4-fluorophenyl)-2-methylpropanoate hydrochloride (2.228 g, 8.51 mmol), 2,6-dichloro-4-(4H-1,2,4-triazol-4-yl)benzoic acid (INTERMEDIATE 6) (2.1973 g, 8.51 mmol), HATU (3.24 g, 8.51 mmol), Hunig's Base (3.72 mL, 21.29 mmol) and DMF (53.2 mL) were stirred at room temperature for 2 h. The crude reaction was partitioned between water and ethyl acetate. The combined extracts were dried over $Na_2SO_4$, filtered and evaporated in vacuo. The resulting crude mixture was purified by flash chromatography ($SiO_2$, Silica 80 g cartridge). The column was eluted by a $MeOH/CH_2Cl_2$ mixture (0% to 25%). Related fractions were pooled and evaporated in vacuo to afford the titled compound. LCMS calc.=465.08; found=465.04 $(M+H)^+$.

Step E: 3-(2,6-Dichloro-4-(4H-1,2,4-triazol-4-yl)benzamido)-2-(4-fluorophenyl)-2-methylpropanoic acid Ethyl 3-(2,6-dichloro-4-(4H-1,2,4-triazol-4-yl)benzamido)-2-(4-fluorophenyl)-2-methylpropanoate (2.9862 g, 6.42 mmol) was stirred with 1,4-dioxane (26 mL) and lithium hydroxide monohydrate (26 mL, 26.0 mmol) at room temperature overnight. The crude mixture was acidified by HCl (26 mL, 26.0 mmol), and partitioned between water and ethyl acetate. The combined extracts were dried over $Na_2SO_4$, filtered and evaporated in vacuo to afford the title compound. LCMS calc.=437.05; found=437.11 $(M+H)^+$.

Step F: (R)-2,6-Dichloro-N-(2-(5,6-dimethyl-1H-benzo[d]imidazol-2-yl)-2-(4-fluorophenyl)propyl)-4-(4H-1,2,4-triazol-4-yl)benzamide Hunig's Base (0.240 mL, 1.372 mmol) was added to a stirred, room temperature mixture of 3-(2,6-dichloro-4-(4H-1,2,4-triazol-4-yl)benzamido)-2-(4-fluorophenyl)-2-methylpropanoic acid (300 mg, 0.686 mmol), 4,5-dimethyl-1,2-phenylenediamine (93 mg, 0.686 mmol) and HATU (261 mg, 0.686 mmol) in DMF (2 mL) and the mixture was stirred at room temperature for 3 h. Acetic acid (0.5 ml) was added to the reaction and it was heated to 100° C. for 8 h and then allowed to cooled to ambient temperature overnight. The crude reaction was purified by preparative HPLC (reverse phase, YMC-Pack ODS C-18 100×20 mm) eluting with acetonitrile/water/0.1% TFA (10% to 80% organic in 10 min, then to 100% in 2 min, 20 mL/min). Volatiles were removed under reduced pressure. The resulting aqueous mixture was partitioned between aqueous sodium hydrogen carbonate and ethyl acetate. The combined organic extracts were washed with water, separated, dried over $Na_2SO_4$, filtered and evaporated in vacuo. This solid was submitted for chiral resolution, The 2nd peak from AD column as the title compound. LCMS calc.=537.13; found=537.11 $(M+H)^+$. $^1$H NMR (500 MHz, $CD_3OD$): δ 9.04 (s, 2H); 7.80 (s, 2H); 7.27-7.30 (m, 4H); 7.04 (t, J=8.7 Hz, 2H); 4.35 (d, J=13.6 Hz, 1H); 4.26 (d, J=13.5 Hz, 1H); 2.34 (s, 6H); 1.98 (s, 3H).

| Preparative Method: | Analytical Method: |
|---|---|
| AD-H(2 × 25 cm) | AD-H (25 × 0.46 cm) |
| 30% methanol(0.1% DEA)/$CO_2$, 100 bar | 40% methanol/$CO_2$, 100 bar |
| 60 mL/min, 220 nm | 3 mL/min, 220 and 254 nm |

Example 71

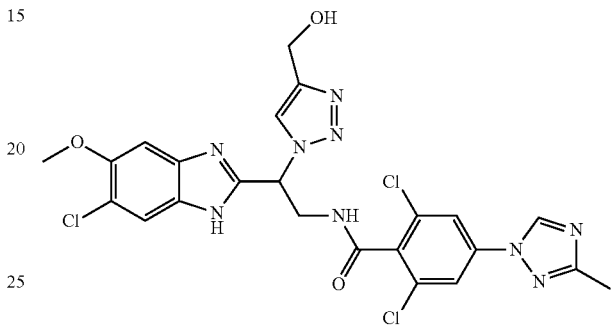

(±)-2,6-Dichloro-N-(2-(6-chloro-5-methoxy-1H-benzo[d]imidazol-2-yl)-2-(4-(hydroxymethyl)-1H-1,2,3-triazol-1-yl)ethyl)-4-(3-methyl-1H-1,2,4-triazol-1-yl)benzamide FIXa IC50=20.5 nM Step A: Methyl 3-(2,6-dichloro-4-(3-methyl-1H-1,2,4-triazol-1-yl)benzamido)-2-hydroxypropanoate Methyl 3-amino-2-hydroxypropanoate hydrochloride (400 mg, 2.57 mmol), 1-(4-carboxy-3,5-dichlorophenyl)-3-methyl-1H-1,2,4-triazol-4-ium chloride (INTERMEDIATE 12) (793 mg, 2.57 mmol), EDC (493 mg, 2.57 mmol), 1-hydroxy-7-azabenzotriazole (350 mg, 2.57 mmol), acetonitrile (17.100 mL) and Hunig's base (1.347 ml, 7.71 mmol) were stirred at room temperature overnight. Volatiles were removed under reduced pressure. The residue was partitioned between water and ethyl acetate. The combined extracts were dried over $Na_2SO_4$, filtered and evaporated in vacuo. The resulting oil was purified by flash chromatography ($SiO_2$, 80 g cartridge). The column was eluted by a $MeOH/CH_2Cl_2$ mixture (0% to 25%). Related fractions were pooled and evaporated in vacuo to afford the title compound. LCMS calc.=373.04; found=373.02 $(M+H)^+$.

Step B: 3-(2,6-dichloro-4-(3-methyl-1H-1,2,4-triazol-1-yl)benzamido)-2-hydroxypropanoic acid Methyl 3-(2,6-dichloro-4-(3-methyl-1H-1,2,4-triazol-1-yl)benzamido)-2-hydroxypropanoate (225.7 mg, 0.605 mmol) was stirred with 1,4-dioxane (2 mL) and lithium hydroxide monohydrate (1 mL, 1.000 mmol) at RT overnight. The crude mixture was acidified by HCl (1.814 mL, 1.814 mmol) and partitioned between water and ethyl acetate. The combined extracts were dried over $Na_2SO_4$, filtered and evaporated in vacuo to afford the title compound. LCMS calc.=359.02; found=358.99 $(M+H)^+$.

Step C: 2,6-Dichloro-N-(2-(6-chloro-5-methoxy-1H-benzo[d]imidazol-2-yl)-2-hydroxyethyl)-4-(3-methyl-1H-1,2,4-triazol-1-yl)benzamide Hunig's Base (0.317 mL, 1.813 mmol) was added to a stirred, room temperature mixture of 3-(2,6-dichloro-4-(3-methyl-1H-1,2,4-triazol-1-yl)benzamido)-2-hydroxypropanoic acid (217 mg, 0.604 mmol), 4-chloro-5-methoxybenzene-1,2-diamine (104 mg, 0.604 mmol), EDC (116 mg, 0.604 mmol) and HOBT (93 mg, 0.604 mmol) in DMF (7.55 mL) and the mixture was stirred at room temperature for two overnights. LC-MS indicated formation of the intermediate and complete consumption of the starting acid. Acetic acid (0.5 mL) was added to the reaction and heated to 100° C. overnight. The resulting crude mixture was partitioned between water and ethyl acetate. The combined extracts were dried over $Na_2SO_4$, filtered and evaporated in vacuo. The pot residue was purified by flash chromatography ($SiO_2$, 80 g cartridge). The column was eluted by a $MeOH/CH_2Cl_2$ mixture (0% to 15%). Related fractions were pooled and evaporated in vacuo. It was further purified by preparative HPLC (reverse phase, YMC-Pack ODS C-18 100×20 mm) eluting with acetonitrile/water (0% to 100% organic in 12 min, then to 100% in 2 min, 20 mL/min). Related fractions were pooled and evaporated under reduced pressure. LCMS calc.=495.04; found=494, 496.98. $^1H$ NMR (500 MHz, $CD_3OD$): δ 9.04 (s, 1H); 7.89 (s, 2H); 7.55 (s, 1H); 7.18 (s, 1H); 5.15 (br s, 1H); 3.99 (br s, 1H); 3.90 (s, 3H); 3.85 (br s, 1H); 2.42 (s, 3H).

Step D: 1-(6-Chloro-5-methoxy-1H-benzo[d]imidazol-2-yl)-2-(2,6-dichloro-4-(3-methyl-1H-1,2,4-triazol-1-yl)benzamido)ethyl trifluoromethanesulfonate To the mixture of step C product (50 mg, 0.101 mmol) and DMAP (12.32 mg, 0.101 mmol) was added DCE (2 mL) and then pyridine (0.041 mL, 0.504 mmol). To this mixture was added trifluoromethanesulfonic anhydride (0.085 mL, 0.504 mmol) and it was stirred at room temperature for 20 min. TLC (10% MeOH/DCM) of the aliquot indicated complete consumption of the starting material and a major spot of a less polar substance. Partitioned the crude reaction between water and EtOAc. The separated organic phase was dried ($Na_2SO_4$), filtered and the solvent was evaporated under reduced pressure, which was purified by flash chromatography ($SiO_2$, Silica 40 g cartridge). The column was eluted by a $MeOH/CH_2Cl_2$ mixture (0% to 15%). Related fractions were pooled and evaporated in vacuo to afford the title compound. LCMS calc.=626.99; found=626.93 (M+H)⁺.

Step E: N-(2-Azido-2-(6-chloro-5-methoxy-1H-benzo[d]imidazol-2-yl)ethyl)-2,6-dichloro-4-(3-methyl-1H-1,2,4-triazol-1-yl)benzamide To the mixture of 1-(6-chloro-5-methoxy-1H-benzo[d]imidazol-2-yl)-2-(2,6-dichloro-4-(3-methyl-1H-1,2,4-triazol-1-yl)benzamido)ethyl trifluoromethanesulfonate (12 mg, 0.019 mmol), 15-crown-5 (1.135 µL, 5.73 µmol) and DMF (0.5 ml) was added sodium azide (1.491 mg, 0.023 mmol) and the reaction was stirred at room temperature overnight. The reaction was partitioned between water and EtOAc. The combined extracts were dried over $Na_2SO_4$, filtered and evaporated. The resulting crude mixture was purified by preparative HPLC (reverse phase, YMC-Pack ODS C-18 100×20 mm) eluting with acetonitrile/water (0% to 50% organic in 12 min, then to 100% in 2 min, 20 mL/min). Related fractions were pooled and evaporated under reduced pressure to afford the title compound. LCMS calc.=520.05; found=520.00 (M+H)⁺.

Step F: (±)-2,6-Dichloro-N-(2-(6-chloro-5-methoxy-1H-benzo[d]imidazol-2-yl)-2-(4-(hydroxymethyl)-1H-1,2,3-triazol-1-yl)ethyl)-4-(3-methyl-1H-1,2,4-triazol-1-yl)benzamide To the mixture of N-(2-azido-2-(6-chloro-5-methoxy-1H-benzo[d]imidazol-2-yl)ethyl)-2,6-dichloro-4-(3-methyl-1H-1,2,4-triazol-1-yl)benzamide (3.6 mg, 6.91 µmol), sodium ascorbate (0.548 mg, 2.77 µmol) and DMF (0.2 mL) was added copper(I) iodide (0.263 mg, 1.383 µmol) and propargyl alcohol (1.979 µL, 0.035 mmol) and stirred at 40° C. for 2 h. The crude mixture was purified by preparative HPLC (reverse phase, YMC-Pack ODS C-18 100×20 mm) eluting with acetonitrile/water/0.05% TFA (0% to 40% organic in 25 min, then to 100% in 5 min, 20 mL/min). Related fractions were pooled and evaporated under reduced pressure to afford the title compound. LCMS calc.=576.08; found=576.00 (M+H)⁺. $^1H$ NMR (500 MHz, $CD_3OD$): δ 9.07 (s, 1H); 8.18 (s, 1H); 7.91 (s, 2H); 7.64 (br s, 1H); 7.20 (s, 1H); 6.46 (br s, 1H); 4.90 (d, J=0.3 Hz, 1H); 4.71 (d, J=7.1 Hz, 2H); 4.50 (br s, 2H); 3.92 (s, 3H); 2.42 (s, 3H).

The following compounds (Table 4) were synthesized using methods analogous to those described for EXAMPLES 71 from commercially available materials or intermediates whose syntheses are described above.

TABLE 4

| Example | Structure | Calc. (M + H)⁺ | LCMS (M + H)⁺ | hFIXa IC50 (nM) |
|---|---|---|---|---|
| 72 | 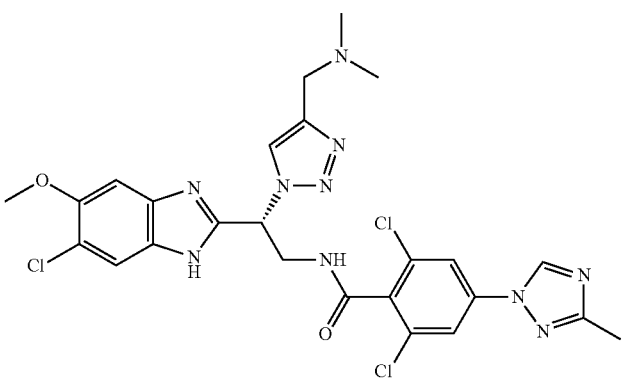 | 603.13 | 603.02 | 67.16 |

TABLE 4-continued

| Example | Structure | Calc. (M + H)+ | LCMS (M + H)+ | hFIXa IC50 (nM) |
|---|---|---|---|---|
| 73 | 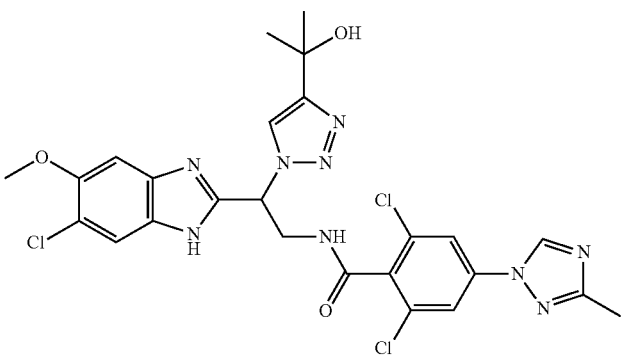 | 604.11 | 604.03 | 34.43 |

Example 74

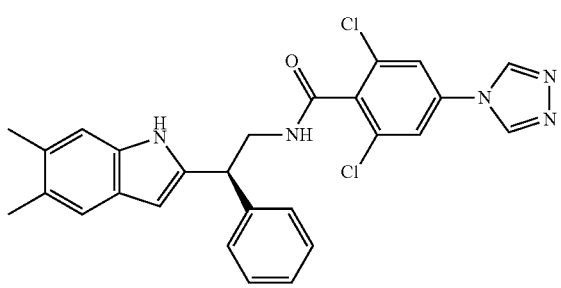 [SMILES: Cc1cc2cc([C@@H](CNC(=O)c3c(Cl)cc(-n4cnnc4)cc3Cl)c3ccccc3)[nH]c2cc1C]

Presumed (R)-2,6-dichloro-N-(2-(5,6-dimethyl-1H-indol-2-yl)-2-phenylethyl)-4-(4H-1,2,4-triazol-4-yl)benzamide FIXa IC50=29.1 nM Step A: tert-butyl 5,6-dimethyl-1H-indole-1-carboxylate To a solution of 5,6-dimethyl-1H-indole (500 mg, 3.44 mmol) and Boc-anhydride (959 μL, 4.13 mmol) in DCM (3.4 mL) was added DMAP (42.1 mg, 0.344 mmol) at 25° C., and stirred at 25° C. for 1 h. The crude mixture was purified by chromatography on silica gel (eluent: 0-10% EtOAc in Hexanes). LCMS calc.=246.14, found=246.23 (M+H). ¹H NMR (499 MHz, Acetone-d6): δ 7.98 (s, 1H); 7.54 (d, J=3.7 Hz, 1H); 7.36 (s, 1H); 6.54 (d, J=3.7 Hz, 1H); 2.39 (s, 3H); 2.34 (s, 3H); 1.70 (m, 9H).

Step B: (±)-tert-butyl 5,6-dimethyl-2-(2-nitro-1-phenylethyl)-1H-indole-1-carboxylate In an oven-dried vial, to a solution of tert-butyl 5,6-dimethyl-1H-indole-1-carboxylate (123 mg, 0.503 mmol) in THF (1.7 mL) at −78° C. was added tert-butyllithium (296 μL, 0.503 mmol) in pentane. The mixture was stirred for 3 h at −78° C. Trans-beta-nitrostyrene (50 mg, 0.335 mmol) in 200 μL THF was added dropwise at −78° C. and the reaction was stirred at −78° C. for 1 h. It was then quenched with sat. NH₄Cl (aq), and extracted with EtOAc. The organic phase was dried (MgSO₄), filtered and concentrated. The residue was purified by preparative TLC using 5% EtOAc in Hexanes as developing solvent. ¹H NMR (499 MHz, Acetone-d6): δ 7.86 (s, 1H); 7.36-7.25 (m, 6H); 6.72 (s, 1H); 5.95 (t, J=8.0 Hz, 1H); 5.32 (ddd, J=13.7, 8.5, 2.3 Hz, 1H); 5.15 (ddd, J=13.7, 7.5, 2.3 Hz, 1H); 2.37 (s, 3H); 2.33 (s, 3H); 1.60 (d, J=2.3 Hz, 9H).

Step C: (±)-tert-butyl 2-(2-amino-1-phenylethyl)-5,6-dimethyl-1H-indole-1-carboxylate Iron (102 mg, 1.825 mmol) was added to a solution of (±)-tert-butyl 5,6-dimethyl-2-(2-nitro-1-phenylethyl)-1H-indole-1-carboxylate (72 mg, 0.183 mmol), AcOH (608 μL) and THF (608 μL). The reaction mixture was stirred at 95° C. for 1 h. After cooled to room temperature, the reaction mixture was filtered through a celite bed, and the filter cake was rinsed with EtOAc. The filtrate was basified with 30% sodium hydroxide (10N) aq (3.6 mL). This basified solution was extracted with EtOAc (3×), dried over MgSO₄, filtered, and concentrated. The crude material was purified by chromatography on silica gel (eluent: 0-100% A in B. A: 10% MeOH in DCM; B: DCM.). LCMS calc.=365.22, found=365.21 (M+H)+.

Step D: Presumed (R)-2,6-dichloro-N-(2-(5,6-dimethyl-1H-indol-2-yl)-2-phenylethyl)-4-(4H-1,2,4-triazol-4-yl)benzamide To 2,6-dichloro-4-(4H-1,2,4-triazol-4-yl)benzoic acid (31.2 mg, 0.121 mmol), EDC (27.8 mg, 0.145 mmol) and 1-hydroxyl-7-azabenzotriazole (19.72 mg, 0.145 mmol) were added THF (1207 μl), and the mixture was stirred at 40° C. for 10 min. Amine was added (in THF 200 uL) and the reaction was stirred at RT overnight. The product was purified using preparative TLC with 10% MeOH in DCM as eluent to give Boc-indole product. LCMS calc.=604.18, found=604.16 (M+H)+. This product (50 mg) was then dissolved in 1:1 THF: TFA=1.2 mL, and stirred at 25° C. for 1 h. The reaction was diluted with EtOAc, washed with saturated NaHCO₃ (aq), dried (MgSO₄), and concentrated. The residue was purified by preparative TLC using 10% MeOH in DCM as developing solvent. LCMS calc.=504.13, found=504.05 (M+H)+. 1H NMR (499 MHz, Acetone-d6): δ 9.90 (s, 1H); 8.96 (s, 2H); 8.02 (s, 1H); 7.81 (s, 2H); 7.43 (d, J=7.6 Hz, 2H); 7.34 (t, J=7.5 Hz, 2H); 7.23-7.26 (m, 2H); 7.09 (s, 1H); 6.37 (s, 1H); 4.63 (t, J=7.8 Hz, 1H); 4.10-4.21 (m, 2H); 2.30 (s, 6H).

Chiral separation: AD column (30×250 mm), 45% 2:1 MeOH:MeCN/CO$_2$, 70 mL/min, 100 bar, 220 nm, 35 C, 7 mg/mL in MeOH/MeCN. Fast eluent, enantiomer A, 4.6 mg; Slow eluent, 5.9 mg, enantiomer B. The title compound is enantiomer A.

Example 75

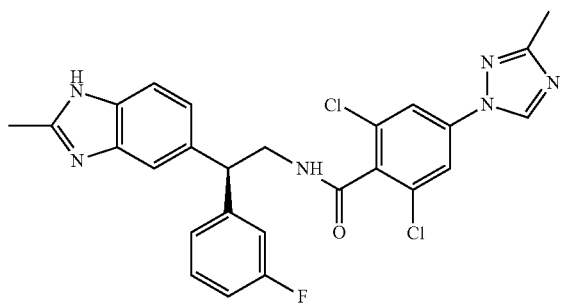 [SMILES: Cc1ncn(-c2cc(Cl)c(C(=O)NC[C@@H](c3cccc(F)c3)c3ccc4[nH]c(C)nc4c3)c(Cl)c2)n1]

Presumed (R)-2,6-dichloro-N-(2-(3-fluorophenyl)-2-(2-methyl-1H-benzo[d]imidazol-5-yl)ethyl)-4-(3-methyl-1H-1,2,4-triazol-1-yl)benzamide FIXa IC50=9.1 nM Step A: (±)-2-(3-fluorophenyl)-2-(2-methyl-1H-benzo[d]imidazol-5-yl)acetonitrile

*J. Org. Chem*, Vol. 68, No. 21, 2003 8007

The reactor was charged with palladium(II) acetate (0.160 g, 0.711 mmol), 2,8,9-triisobutyl-2,5,8,9-tetraaza-1-phosphabicyclo[3.3.3]undecane (0.507 mL, 1.421 mmol), and 5-bromo-2-methyl-1H-benzo[d]imidazole (1.5 g, 7.11 mmol). The vessel was evacuated and refilled with N$_2$ for 3 cycles and degassed dioxane (14.21 mL) was added, followed by NaHMDS (28.4 mL, 28.4 mmol). The reaction was stirred at 25° C. for 20 min before 2-(3-fluorophenyl)acetonitrile (73.3 mg, 0.543 mmol) was added. The reaction was then capped and heated at 100° C. for 3 h. More NaHMDS (6 mL) was added and the reaction was stirred for another 1 h; More NaHMDS (4 mL) was added and the reaction was stirred for another 1 h before it was cooled to room temperature, and quenched with water. The aqueous layer was extracted with EtOAc (3×), washed with brine, dried over MgSO$_4$, filtered, and the filtrate was concentrated in vacuo. The crude material was purified by chromatography on silica gel (eluent: 0-100% A in B. A: 10% MeOH in DCM; B: DCM.). LCMS calc.=266.10, found=266.04 (M+H)$^+$.

Step B: 2,6-dichloro-4-(3-methyl-1H-1,2,4-triazol-1-yl)benzoyl chloride

At 0° C., in a pre-weighed flask containing INTERMEDIATE 12 (2.28 g, 8.38 mmol) in 3 mL DCM, was added oxalyl chloride (1.467 mL, 16.76 mmol), followed by 1 drop of DMF. After 0.5 h, the reaction was warmed to 25° C. and stirred for 2 h. The reaction mixture was concentrated and the excess oxalyl chloride was azeotropically removed with toluene. LCMS calc.=289.96, found=289.88 (M+H)$^+$.

Step C: (±)-2-(3-fluorophenyl)-2-(2-methyl-1H-benzo[d]imidazol-5-yl)ethanamine

*Synth. Comm.* 32(8), 1265-69 (2002)

Under N$_2$, to step A product (1.62 g, 6.11 mmol), anhydrous nickel(II) chloride (0.791 g, 6.11 mmol) in anhydrous ethanol (15.27 mL) and THF (15.27 mL) was added sodium borohydride (1.386 g, 36.6 mmol). The reaction was stirred at 25° C. overnight. LCMS, calc.=270.13, found=270.12 (M+H)$^+$.

Step D: presumed(R)-2,6-dichloro-N-(2-(3-fluorophenyl)-2-(2-methyl-1H-benzo[d]imidazol-5-yl)ethyl)-4-(3-methyl-1H-1,2,4-triazol-1-yl)benzamide The reaction mixture of step C was added to step B product (2.66 g, 9.16 mmol). The vial containing the step C reaction was rinsed with a total of 5 mL THF and also added to the step B product. The mixture was stirred at 25° C. for 1 h. The reaction was then quenched with saturated NaHCO$_3$ aqueous solution (200 mL), diluted with 300 mL EtOAc, agitated, and filtered. The filtrated was collected, and phases were separated. The aqueous phase was extracted with EtOAc (300 mL×3). The combined aqueous layers were washed with brine, dried over MgSO$_4$, filtered and concentrated in vacuo. The crude material was purified by chromatography on silica gel (eluent: 0-100% A in B. A: 10% MeOH in DCM; B: DCM.) to yield 0.88 g racemic product. LCMS calc.=523.11, found=523.04 (M+H)$^+$. $^1$H NMR (500 MHz, CD$_3$OD): δ 8.97 (s, 1H); 7.79 (s, 2H); 7.46 (s, 1H); 7.39 (t, J=8.3 Hz, 1H); 7.33-7.25 (m, 1H); 7.22-7.09 (m, 3H); 6.91 (td, J=8.5, 2.4 Hz, 1H); 4.55 (t, J=8.1 Hz, 1H); 4.16-4.00 (m, 2H); 2.53 (s, 3H); 2.39 (s, 3H).

Chiral separation: IC column (2×15 cm), 35% ethanol (0.1% DEA)/CO$_2$, 50 mL/min, 100 bar, 220 nm, inj vol.: 1 mL; 9 mg/mL methanol. Fast eluent, enantiomer A; Slow eluent, enantiomer B. The title compound is enantiomer B.

Example 76

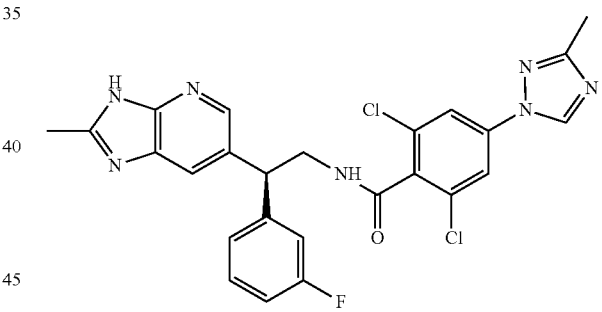

Presumed (S)-2,6-dichloro-N-(2-(3-fluorophenyl)-2-(2-methyl-3H-imidazo[4,5-b]pyridin-6-yl)ethyl)-4-(3-methyl-1H-1,2,4-triazol-1-yl)benzamide FIXa IC50=80.6 nM Step A: 6-bromo-2-methyl-3H-imidazo[4,5-b]pyridine WO2009137081, 12 Nov. 2009

A solution of 5-bromopyridine-2,3-diamine (5.79 g, 30.8 mmol), acetic acid (17.61 ml, 308 mmol) in PPA (30.8 ml) was heated to 135-140° C. for 7 h under N$_2$. To the reaction was added 150 mL ice-water (150 mL). Charcoal (6 g) was added and the mixture was filtered over a celite bed and the filter cake was rinsed with water. The filtrate was basified with 28-30% ammonia (aq) to pH~10-12, and precipitation appeared. The mixture was extracted with EtOAc (300 ml×6), and the combined organic layers were dried with MgSO$_4$ and concentrated. To the residue was added hexane

Step B: (±)-2-(3-fluorophenyl)-2-(2-methyl-3H-imidazo[4,5-b]pyridin-6-yl)acetonitrile The product was produced using the same procedure in Example 75, step A. LCMS calc.=267.10, found=267.11 (M+H)⁺. ¹H NMR (499 MHz, Acetone-d6): δ 8.44 (s, 1H); 8.04 (s, 1H); 7.51-7.44 (m, 1H); 7.38 (t, J=7.9 Hz, 1H); 7.29 (d, J=9.8 Hz, 1H); 7.16-7.09 (m, 1H); 5.90 (s, 1H); 2.65 (s, 3H).

Step C: (±)-2-(3-fluorophenyl)-2-(2-methyl-3-((2-(trimethylsilyl)ethoxy)methyl)-3H-imidazo[4,5-b]pyridin-6-yl)acetonitrile Step B product (300 mg, 1.127 mmol) was dissolved in THF (9.0 mL). To this solution was added triethylamine (314 μL, 2.253 mmol) and SEM-Cl (300 μL, 1.690 mmol). The reaction was stirred at 25° C. for 1 h. Another 100 uL of Et₃N and 100 uL of SES-Cl was added, and the reaction was stirred for another 1 h. The volatiles were removed, and the residue was taken up in EtOAc, and washed with saturated. NaHCO₃. The aqueous wash was extracted with EtOAc (×3), and combined organic layers were dried over MgSO₄ and condensed. The crude material was purified by chromatography on silica gel (eluent: 0-50%-100% EtOAc in Hexanes.). LCMS calc.=397.18, found=397.13 (M+H)⁺. ¹H NMR (499 MHz, Acetone-d6): δ 8.47 (s, 1H); 8.03 (s, 1H); 7.52 (q, J=7.3 Hz, 1H); 7.42 (d, J=7.8 Hz, 1H); 7.34 (t, J=10.0 Hz, 1H); 7.17 (t, J=8.7 Hz, 1H); 5.90 (s, 1H); 5.73 (s, 2H); 3.77-3.60 (m, 2H); 2.69 (s, 3H); 0.94 (dt, J=24.8, 8.0 Hz, 2H), −0.06 (s, 9H).

Step D: (±)-2,6-dichloro-N-(2-(3-fluorophenyl)-2-(2-methyl-3-((2-(trimethylsilyl)ethoxy)methyl)-3H-imidazo[4,5-b]pyridin-6-yl)ethyl)-4-(3-methyl-1H-1,2,4-triazol-1-yl)benzamide The product was produced using the same procedure in Example 75, step C-D. LCMS calc.=654.19, found=654.07 (M+H)⁺. ¹H NMR (499 MHz, Acetone): δ 9.01 (s, 1H); 8.39 (s, 1H); 8.28 (s, 1H); 8.01 (t, J=15.2 Hz, 1H); 7.95-7.81 (m, 2H); 7.43-7.27 (m, 3H); 7.01 (t, J=8.7 Hz, 1H); 5.68 (s, 2H); 4.81-4.67 (m, 1H); 4.33-4.19 (m, 2H); 3.62 (t, J=8.0 Hz, 2H); 2.64 (s, 3H); 2.37 (s, 3H); 0.98-0.87 (m, 2H); −0.06 (s, 9H).

Step E: Presumed (S)-2,6-dichloro-N-(2-(3-fluorophenyl)-2-(2-methyl-3H-imidazo[4,5-b]pyridin-6-yl)ethyl)-4-(3-methyl-1H-1,2,4-triazol-1-yl)benzamide To the product from step D (104 mg, 0.159 mmol) was added 5N HCl (aq) (1.6 mL) and dioxane (1.6 mL), and the solution was heated at 90° C. for 1.5 h. The reaction mixture was basified with 10N NaOH (aq), extract with EtOAc, dried over MgSO₄, filtered and concentrated. The crude product was purified by chromatography on silica gel (eluent: 0-50%-100% A in B. A: 10% MeOH in DCM; B: DCM.) to yield racemic product. LCMS calc.=524.11, found=524.08 (M+H)⁺. ¹H NMR (499 MHz, Acetone-d6): δ 8.99 (s, 1H); 8.50 (d, J=6.1 Hz, 1H); 8.33 (s, 1H); 7.92 (t, J=16.9 Hz, 1H); 8.02-7.61 (m, 2H); 7.42-7.26 (m, 3H); 7.03-6.97 (m, 1H); 5.65 (s, 1H); 4.73-4.62 (m, 1H); 4.31 (s, 1H); 4.25-4.17 (m, 1H); 2.56 (s, 3H); 2.38 (m, 3H); Chiral separation: AS column (2×25 cm), 35% 1:1 heptane:isopropanol (0.15% DEA)/CO₂, 60 mL/min, 100 bar, 220 nm, inj vol.: 0.5 mL; 6 mg/mL methanol. Fast eluent, enantiomer A; Slow eluent, enantiomer B. The title compound is enantiomer B.

The following compounds (Table 5) were synthesized using methods analogous to those described for EXAMPLES 75 and 76 from commercially available materials or intermediates whose syntheses are described above.

TABLE 5

| Example | Structure | Calc. (M + H)⁺ | LCMS (M + H)⁺ | hFIXa IC50 (nM) |
|---|---|---|---|---|
| 77 | 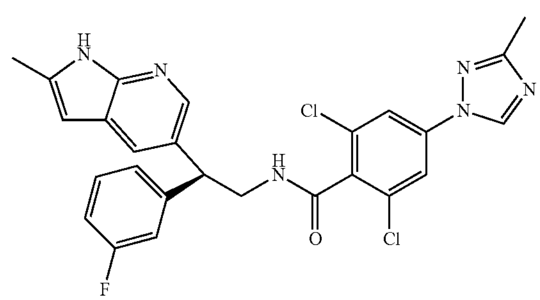 [SMILES: Cc1ncn(-c2cc(Cl)c(C(=O)NC[C@@H](c3cccc(F)c3)c3cnc4[nH]c(C)cc4c3)c(Cl)c2)n1] | 523.12 | 524.08 | 3.697 |
| 78 | 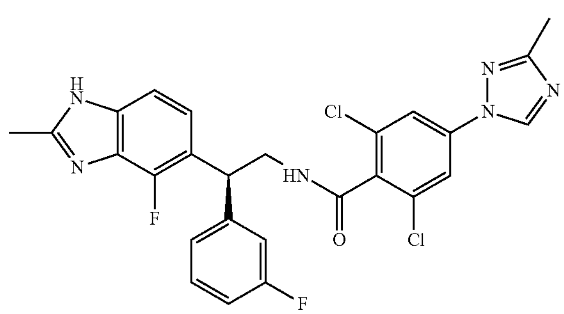 [SMILES: Cc1ncn(-c2cc(Cl)c(C(=O)NC[C@@H](c3cccc(F)c3)c3ccc4[nH]c(C)nc4c3F)c(Cl)c2)n1] | 541.11 | 541.05 | 1.929 |

TABLE 5-continued

| Example | Structure | Calc. (M + H)+ | LCMS (M + H)+ | hFIXa IC50 (nM) |
|---|---|---|---|---|
| 79 | 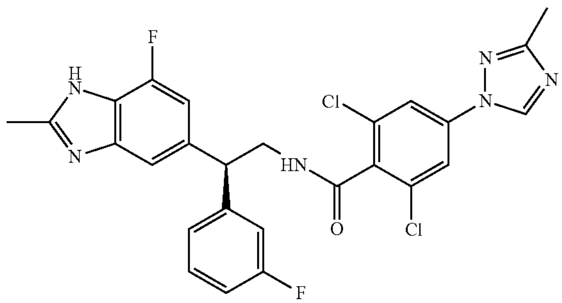 [SMILES: Cc1ncn(-c2cc(Cl)c(C(=O)NC[C@@H](c3cccc(F)c3)c3cc(F)c4[nH]c(C)nc4c3)c(Cl)c2)n1] | 541.11 | 541.10 | 6.421 |
| 80 | 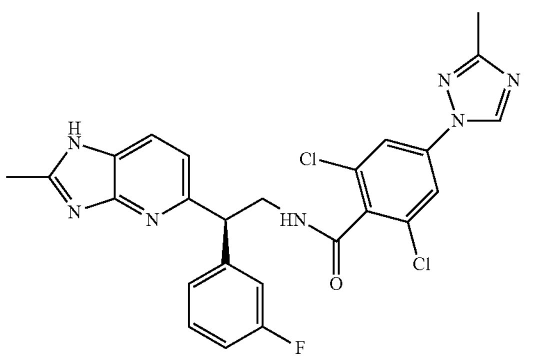 [SMILES: Cc1ncn(-c2cc(Cl)c(C(=O)NC[C@@H](c3cccc(F)c3)c3ccc4[nH]c(C)nc4n3)c(Cl)c2)n1] | 524.12 | 524.04 | 16.95 |
| 81 | 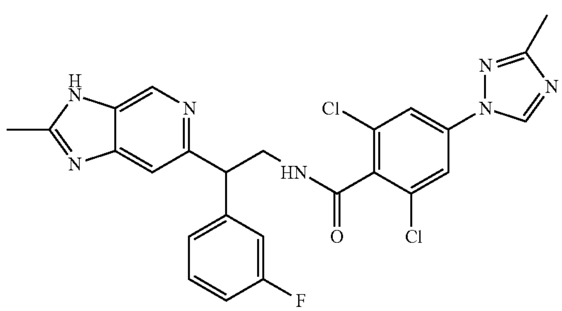 [SMILES: Cc1ncn(-c2cc(Cl)c(C(=O)NCC(c3cccc(F)c3)c3cc4nc(C)[nH]c4cn3)c(Cl)c2)n1] | 524.12 | 524.15 | 125.7 |
| 82 | 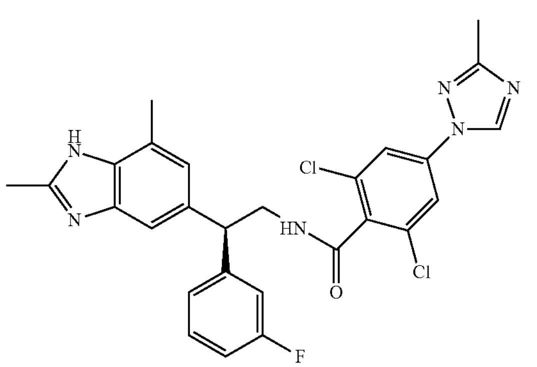 [SMILES: Cc1ncn(-c2cc(Cl)c(C(=O)NC[C@@H](c3cccc(F)c3)c3cc(C)c4[nH]c(C)nc4c3)c(Cl)c2)n1] | 537.14 | 537.08 | 75.22 |

Example 83

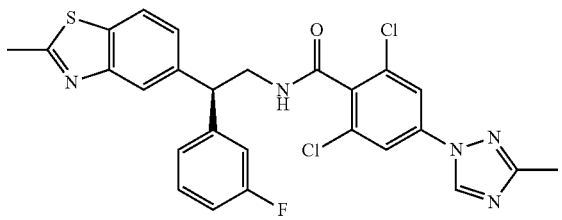

Presumed (R)-2,6-dichloro-N-(2-(3-fluorophenyl)-2-(2-methylbenzo[d]thiazol-5-yl)ethyl)-4-(3-methyl-1H-1,2,4-triazol-1-yl)benzamide FIXa IC50=59.5 nM

Step A: (±)-5-(1-(3-fluorophenyl)-2-nitroethyl)-2-methylbenzo[d]thiazole

WO2004067529, 12 Aug. 2004

To a pre-dried flask equipped with a reflux condenser was added magnesium (425 mg, 17.49 mmol) and $Et_2O$ (5 mL). To this mixture was added ~1/10 of a solution of iodomethane (0.683 mL, 10.92 mmol) and 5-bromo-2-methylbenzo[d]thiazole (500 mg, 2.192 mmol) in $Et_2O$ (10 mL). After addition of 2-3 crystals of iodine, the reaction mixture was heated to reflux using an oil bath. After a few minutes the iodine coloration faded and another portion (~0.5 mL) of the iodomethane/5-bromo-2-methyl-benzothiazole solution was added. The oil bath was removed and further additions (~0.5 mL) were added such that reflux was sustained. After completion of the addition, reflux was maintained for 30 min using an oil bath. The reaction was then cooled to 0° C. in an ice bath, and a solution of (E)-1-fluoro-3-(2-nitrovinyl)benzene (330 mg, 1.974 mmol) in dry $Et_2O$ was added dropwise while maintaining temperature between 0-10° C., After 15 min, the ice was removed and the reaction mixture was stirred for 1 h at 25° C. The reaction was then quenched with 1N HCl (aq) (25 mL), diluted with EtOAc (150 mL), and the organic layer was washed with saturated $NaHCO_3$ (aq) (25 mL). The organic layer was dried ($MgSO_4$), filtered and concentrated. The crude material was purified by chromatography on silica gel (eluent: 0-30% EtOAc in Hexanes). LCMS calc.=317.07, found=316.99 (M+H)$^+$. $^1$H NMR (499 MHz, Acetone-d6): δ 8.04 (s, 1H); 8.01-7.94 (m, 1H); 7.61-7.31 (m, 4H); 7.02 (m, 1H); 5.46 (d, J=8.2 Hz, 2H); 5.22-5.11 (m, 1H); 2.85 (s, 3H).

Step B: (±)-2-(3-fluorophenyl)-2-(2-methylbenzo[d]thiazol-5-yl)ethanamine

Synthetic Communications, 40: 1588-1594, 2010

Iron (265 mg, 4.74 mmol) was added to a solution of step A product (150 mg, 0.474 mmol), AcOH (1.6 mL) and THF (1.6 mL). The reaction mixture was stirred at 95° C. for 1 h. After cooled to room temperature, the reaction mixture was filtered through a celite bed, and the filter cake was rinsed with EtOAc. The filtrate was basified with 30% sodium hydroxide (10N) aqueous solution (5 mL). This basified solution was extracted with EtOAc (3×), dried over $MgSO_4$, filtered, and concentrated. The crude material was purified by chromatography on silica gel (eluent: 0-50% then 50% A in B. A: 10% MeOH in DCM; B: DCM). LCMS calc.=287.09, found=287.13 (M+H)$^+$. $^1$H NMR (499 MHz, Acetone): δ 7.92-7.85 (m, 2H); 7.40-7.31 (m, 2H); 7.24-7.15 (m, 2H); 7.00-6.94 (m, 1H); 4.56 (t, J=7.3 Hz, 1H); 3.96 (d, J=7.3 Hz, 2H); 2.89 (brs, 2H), 2.80 (s, 3H).

Step C: Presumed (R)-2,6-dichloro-N-(2-(3-fluorophenyl)-2-(2-methylbenzo[d]thiazol-5-yl)ethyl)-4-(3-methyl-1H-1,2,4-triazol-1-yl)benzamide To (INTERMEDIATE 12) (19.00 mg, 0.070 mmol), EDC (16.07 mg, 0.084 mmol) and 1-hydroxyl-7-azabenzotriazole (11.41 mg, 0.084 mmol) were added THF (698 μL), and the mixture was stirred at 40° C. for 10 min. To the reaction was added step B product (20 mg, 0.070 mmol, in 200 μL THF), and the resulting mixture was stirred at 25° C. overnight. The reaction was concentrated in vacuo and the crude residue was purified by chromatography on silica gel (eluent: 0-100% EtOAc in Hexanes) to yield the racemic product. LCMS calc.=540.07, found=539.97 (M+H)$^+$. $^1$H NMR (499 MHz, Acetone-d6): δ 9.02 (s, 1H); 8.05 (s, 1H); 7.99 (s, 1H); 7.93 (d, J=8.3 Hz, 1H); 7.85 (s, 2H); 7.48 (d, J=8.3 Hz, 1H); 7.44-7.23 (m, 3H); 7.03-6.98 (m, 1H); 4.71 (t, J=8.0 Hz, 1H); 4.31-4.17 (m, 2H); 2.80 (s, 3H); 2.38 (s, 3H).

Chiral separation: OD column (20×250 mm), 40% MeOH/$CO_2$, 50 mL/min, 100 bar, 220 nm, 40° C., sample in MeOH. Fast eluent, enantiomer A; Slow eluent, enantiomer B. The title compound is enantiomer B.

Example 84

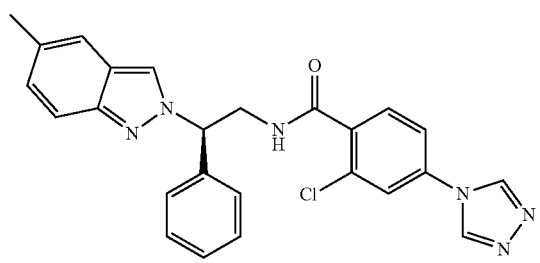 [SMILES: Cc1ccc2nn([C@@H](CNC(=O)c3ccc(-n4cnnc4)cc3Cl)c3ccccc3)cc2c1]

(R)-2-chloro-N-(2-(5-methyl-2H-indazol-2-yl)-2-phenylethyl)-4-(4H-1,2,4-triazol-4-yl)benzamide FIXa IC50=240.4 nM

Step A: (±)-5-methyl-1-(2-nitro-1-phenylethyl)-1H-indazole

To a stirred suspension of (E)-(2-nitrovinyl)benzene (350 mg, 2.347 mmol) in $Et_2O$ (2 mL) was added 5-methyl-1H-indazole (700 mg, 5.30 mmol) and iodine (596 mg, 2.347 mmol). The reaction mixture was stirred at room temperature for 5 days. LCMS showed the product. The reaction was heated at 50° C. for 16 h. The mixture was quenched with water, washed with a mix of saturated sodium thiosulfate/$NaHCO_3$ (aq) (4/1) solution, extracted with DCM (100 mL×2). The organic layer was washed with brine, dried over $Na_2SO_4$, filtered and concentrated. The residue was purified by column chromatography on silica gel Biotage 25M, eluting with 0, 2, 5, 10 and 15% EtOAc in Hexanes to give regioisomer A (5-methyl-1-(2-nitro-1-phenylethyl)-1H-indazole) and regioisomer B (5-methyl-2-(2-nitro-1-phenylethyl)-2H-indazole).

Step A, regioisomer A, LCMS calc.=282.12, found=282.05 (M+H)⁺. Step A, regioisomer B, LCMS calc.=282.12, found=282.04 (M+H)⁺.

Step B: (±)-2-(5-methyl-2H-indazol-2-yl)-2-phenylethanamine

To a stirred solution of Step A, regioisomer A (5-methyl-2-(2-nitro-1-phenylethyl)-2H-indazole) (160 mg, 0.569 mmol) in EtOH (3 mL) was added iron (476 mg, 8.53 mmol) and hydrochloric acid (0.853 mL, 0.085 mmol). The reaction mixture was heated at 90° C. overnight. The reaction was filtered, washed with MeOH and concentrated. The residue was purified by column chromatography on silica gel Biotage 25M, eluting with 0, 1, 2, 3 and 4% MeOH (containing 1/10 NH$_4$OH) in DCM to give the product. LCMS calc.=252.14, found=252.19 (M+H)⁺. ¹H NMR (499 MHz, CDCl$_3$): 7.91 (s, 1H); 7.74-7.64 (m, 1H); 7.41-7.30 (m, 6H), 7.21-7.15 (m, 1H); 5.59 (dd, J=9.0, 4.9 Hz, 1H); 3.91 (dd, J=13.5, 9.1 Hz, 1H); 3.52-3.43 (m, 1H); 2.45 (s, 3H), 1.61 (brs, 2H).

Step C: (R)-2-chloro-N-(2-(5-methyl-2H-indazol-2-yl)-2-phenylethyl)-4-(4H-1,2,4-triazol-4-yl)benzamide The mixture of 2-chloro-4-(4H-1,2,4-triazol-4-yl)benzoic acid (INTERMEDIATE 4) (16.02 mg, 0.072 mmol), Hunig's base (0.042 mL, 0.239 mmol), HATU (34.0 mg, 0.090 mmol) and step B product (2-(5-methyl-2H-indazol-2-yl)-2-phenylethanamine) (15 mg, 0.060 mmol) in DMF (1 mL) was heated at 55° C. overnight. The reaction was filtered and the filtrate was purified by preparative HPLC Reverse phase (C-18), eluting with 5 to 80% Acetonitrile/Water+0.1% TFA, to give the title compound.

Chiral separation: OJ column (20×250 mm), 35% MeOH (0.1% NH$_4$OH)/CO$_2$, 50 mL/min, 100 bar, 220 nm, 35 C, sample in MeOH. Fast eluent, enantiomer A; Slow eluent, enantiomer B. The title compound is enantiomer A.

LCMS calc.=457.15, found=457.43 (M+H)⁺. ¹H NMR (499 MHz, CD$_3$OD): δ 9.04 (s, 2H); 8.31 (s, 1H); 7.81 (d, J=2.2 Hz, 1H); 7.63-7.55 (m, 2H); 7.47 (t, J=8.5 Hz, 3H); 7.43-7.33 (m, 4H); 7.17 (dd, J=8.9, 1.6 Hz, 1H); 6.11 (dd, J=9.8, 5.3 Hz, 1H); 4.44 (dd, J=13.9, 9.8 Hz, 1H); 4.30 (dd, J=13.9, 5.3 Hz, 1H); 2.41 (s, 3H).

Example 85

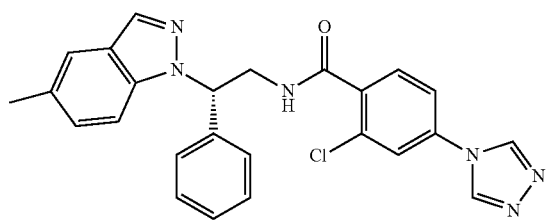 [SMILES: Cc1ccc2c(cnn2[C@H](CNC(=O)c2ccc(-n3cnnc3)cc2Cl)c2ccccc2)c1]

(S)-2-chloro-N-(2-(5-methyl-1H-indazol-1-yl)-2-phenylethyl)-4-(4H-1,2,4-triazol-4-yl)benzamide FIXa IC50=38.0 nM The regioisomer B from EXAMPLE 84, step A was carried through the same reduction and amide coupling sequence as described in EXAMPLE 84, step B and C to give the title product.

Chiral separation: AD column (2×25 cm), 35% MeOH (0.1% DEA)/CO$_2$, 60 mL/min, 100 bar, 220 nm, inj vol=0.5 mL, 3.5 mg/mL MeOH. Fast eluent, enantiomer A; Slow eluent, enantiomer B. The title compound is enantiomer A.

LCMS calc.=457.15, found=457.27 (M+H)⁺. ¹H NMR (499 MHz, CD$_3$OD): δ 9.03 (s, 2H); 8.06 (s, 1H); 7.78 (d, J=2.1 Hz, 1H); 7.59-7.54 (m, 2H); 7.43 (t, J=7.4 Hz, 3H); 7.38-7.21 (m, 5H); 6.19 (dd, J=9.6, 5.2 Hz, 1H); 4.40 (dd, J=13.6, 9.6 Hz, 1H); 4.32 (dd, J=13.6, 5.2 Hz, 1H); 2.44 (s, 3H).

Example 86

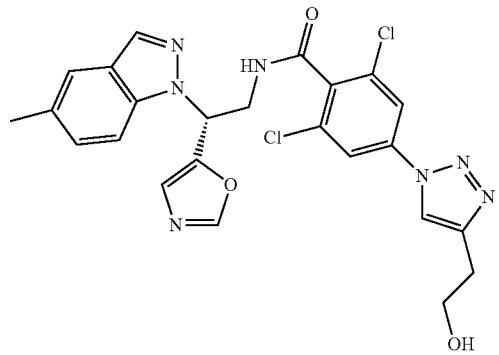 [SMILES: Cc1ccc2c(cnn2[C@H](CNC(=O)c2c(Cl)cc(-n3cc(CCO)nn3)cc2Cl)c2cnco2)c1]

Presumed (R)-2,6-dichloro-4-(4-(2-hydroxyethyl)-1H-1,2,3-triazol-1-yl)-N-(2-(5-methyl-1H-indazol-1-yl)-2-(oxazol-5-yl)ethyl)benzamide FIXa IC50=7.0 nM Step A: (E)-5-(2-nitrovinyl)oxazole To a solution of oxazole-5-carbaldehyde (2 g, 20.60 mmol) and nitromethane (3.33 mL, 61.8 mmol) in DCM (4 mL) was added 1,1,3,3-tetramethylguanidine (0.258 mL, 2.060 mmol) at 25° C., and stirred for 10 min. The reaction was then cooled to 0° C., and methanesulfonyl chloride (3.21 mL, 41.2 mmol) was added to the reaction mixture. The reaction was stirred at 0° C. for 10 min and then at 25° C. for 20 min. At 0° C., triethylamine (5.74 mL, 41.2 mmol) was added and the mixture was stirred at 25° C. for 1.5 h. The reaction was quenched with saturated NaHCO$_3$ (aq), layers were separated and the aqueous layer was extracted with DCM 100 mL (×2). The combined organic layers were washed with brine, dried over MgSO$_4$, filtered and concentrated. The residue was triturated with DCM:heptane 1:9, and filtered. ¹H NMR (499 MHz, Acetone): δ 8.47 (s, 1H); 8.12 (d, J=13.4 Hz, 1H); 7.84 (s, 1H); 7.76 (d, J=13.4 Hz, 1H).

Step B: (±)-5-(1-(5-methyl-1H-indazol-1-yl)-2-nitroethyl)oxazole

To a solution of 5-methyl-1H-indazole (1.038 g, 7.85 mmol) in THF (24 mL) was added sodium hydride (0.428 g, 60% in mineral oil, 10.71 mmol) at 0° C. The reaction mixture was stirred at 0° C. for 10 min. To the reaction mixture was added (E)-5-(2-nitrovinyl)oxazole from step A (1 g, 7.14 mmol) in THF (6 mL) at 0° C. The reaction mixture was stirred at 0° C. for 20 min. It was then quenched with saturated NH₄Cl (aq) and extracted with EtOAc. The organic layer was dried over MgSO₄, filtered and concentrated. The crude material was purified by chromatography on silica gel (eluent: 0-50% EtOAc in Hexanes). LCMS calc.=273.09, found=273.20 (M+H)⁺.

Step C: (±)-2-(5-methyl-1H-indazol-1-yl)-2-(oxazol-5-yl)ethanamine

To a solution of the product from step B (0.85 g, 3.12 mmol) in THF (15.61 mL) was added zinc (1.021 g, 15.61 mmol) and 1N HCl (aq) (15.61 ml, 15.61 mmol) at 25° C. The reaction was stirred at 80° C. for 1 h under N₂. It was then cooled and quenched with 3N NaOH (20 mL), and filtered through celite. The filtrate was extracted with EtOAc (×2). The combined organic layer was washed with brine, dried over MgSO₄, filtered and concentrated to give crude product, which was used without further purification. LCMS calc.=243.12, found=243.05 (M+H)⁺.

Step D: Presumed (R)-2,6-dichloro-4-(4-(2-hydroxyethyl)-1H-1,2,3-triazol-1-yl)-N-(2-(5-methyl-1H-indazol-1-yl)-2-(oxazol-5-yl)ethyl)benzamide To INTERMEDIATE 15 (1.037 g, 3.43 mmol), EDC (0.718 g, 3.74 mmol) and 1-hydroxy-7-azabenzotriazole (0.510 g, 3.74 mmol) were added THF (10 mL) and the mixture was stirred at 40° C. for 10 min. At 25° C., product from step C (0.756 g, 3.12 mmol) in THF (11 mL total) was added and the reaction was stirred at 25° C. overnight. The top clear solution was decanted and the bottom gue was rinsed with EtOAc. The combined organic solution was concentrated in vacuo. The crude material was purified by chromatography on silica gel (eluent: 0-30%-50% A in B. A: 10% MeOH in DCM, B: DCM). LCMS calc.=526.11, found=525.85 (M+H)⁺. ¹H NMR (500 MHz, Acetone): δ 8.45 (s, 1H); 8.22 (s, 1H); 8.09 (s, 1H); 7.99 (s, 1H); 7.91 (s, 1H); 7.69 (d, J=8.6 Hz, 1H); 7.55 (s, 1H); 7.30 (d, J=8.6 Hz, 1H); 7.24 (s, 1H); 6.40 (dd, J=8.9, 5.7 Hz, 1H); 4.56-4.49 (m, 2H); 4.48-4.41 (m, 2H); 3.84 (t, J=6.6 Hz, 2H); 2.44 (s, 3H).

Chiral separation: OJ column (2×25 cm), 20% methanol/CO₂, 60 mL/min, 100 bar, 220 nm, inj vol.: 1 mL; 12 mg/mL methanol. Fast eluent, enantiomer A; Slow eluent, enantiomer B. The title compound is enantiomer B.

The following compound (Table 6) was synthesized using methods analogous to those described for EXAMPLES 84-86 from commercially available materials or intermediates whose syntheses are described above.

Example 88

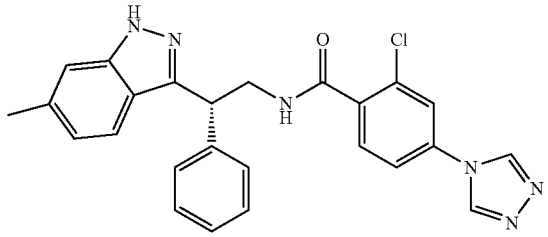

Presumed (S)-2-chloro-N-(2-(6-methyl-1H-indazol-3-yl)-2-phenylethyl)-4-(4H-1,2,4-triazol-4-yl)benzamide FIXa IC50=68.8 nM Step A: (±)-tert-butyl (3-(methoxy(methyl)amino)-3-oxo-2-phenylpropyl)carbamate To a stirred solution of 3-((tert-butoxycarbonyl)amino)-2-phenylpropanoic acid (1 g, 3.77 mmol), Et₃N (2.63 mL, 18.85 mmol) and HATU (2.150 g, 5.65 mmol) in DMF (10 mL) was added N,O-dimethylhydroxylamine hydrochloride (0.735 g, 7.54 mmol). The reaction mixture was stirred at 25° C. overnight. The reaction mixture was diluted with EtOAc (200 mL), washed with water (2×), brine, dried over Na₂SO₄, filtered and concentrated. The residue was purified by column chromatography on silica gel Biotage 40M, eluting with 0, 5, 10, 15 and 20% EtOAc in Hex to give tert-butyl (3-(methoxy(methyl)amino)-3-oxo-2-phenylpropyl)carbamate. LCMS calc.=309.17, found=309.21 (M+H).

Step B: (±)-tert-butyl (3-(2-fluoro-4-methylphenyl)-3-oxo-2-phenylpropyl)carbamate To a stirred solution of 1-bromo-2-fluoro-4-methylbenzene (0.882 mL, 6.97 mmol) in THF (10 mL) at −78° C. under nitrogen was added n-BuLi (4.36 mL, 6.97 mmol) dropwise. After it was stirred for 30 min, a solution of tert-butyl (3-(methoxy(methyl)amino)-3-oxo-2-phenylpropyl)carbamate (215 mg, 0.697 mmol) in THF (3 mL) was added. The reaction mixture was slowly warmed up to 25° C. and stirred overnight. The reaction was quenched with saturated NH₄Cl(aq), extracted with EtOAc (200 mL). The organic layer was washed with brine, dried over Na₂SO₄, filtered and concentrated. The residue was purified by column chromatography on silica gel Biotage 40S, eluting with 0, 5 and 10% EtOAC in Hex, to give tert-butyl (3-(2-fluoro-4-methylphenyl)-3-oxo-2-phenylpropyl)carbamate. LCMS calc.=358.17, found=358.1 (M+H).

TABLE 6

| Example | Structure | Calc. (M + H)⁺ | LCMS (M + H)⁺ | hFIXa IC50 (nM) |
|---|---|---|---|---|
| 87 | 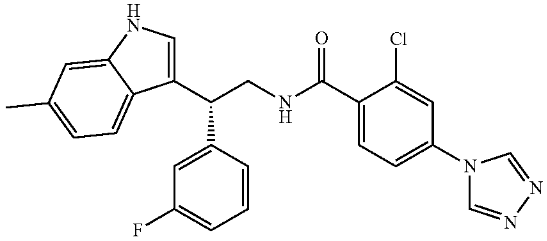 [SMILES: Cc1ccc2c([C@H](CNC(=O)c3ccc(-n4cnnc4)cc3Cl)c3cccc(F)c3)c[nH]c2c1] | 474.15 | 474.07 | 31.09 |

Step C: (±)-tert-butyl (2-(6-methyl-1H-indazol-3-yl)-2-phenylethyl)carbamate

To a stirred solution of tert-butyl (3-(2-fluoro-4-methylphenyl)-3-oxo-2-phenylpropyl)carbamate (165 mg, 0.462 mmol) in DMSO (4 mL) was added hydrazine hydrate (0.113 mL, 2.308 mmol) in a microwave tube. The reaction mixture was heated in a microwave at 140° C. for 1.2 h. The residue was purified by column chromatography on silica gel Biotage 25M, eluting with 10, 20, 30 and 40% EtOAc in hexanes, to give the tert-butyl (2-(6-methyl-1H-indazol-3-yl)-2-phenylethyl)carbamate. LCMS calc.=352.19, found=352.33 (M+H).

Step D: (±)-2-(6-methyl-1H-indazol-3-yl)-2-phenylethanamine

A solution of tert-butyl (2-(6-methyl-1H-indazol-3-yl)-2-phenylethyl)carbamate (182 mg, 0.518 mmol) in DCM (2 mL) was added TFA (2 mL). The reaction was stirred at 25° C. for 1 h, and concentrated in vacuo. The residue was purified by column chromatography on silica gel Biotage 25M, eluting with 0, 2, 3 and 4% MeOH (containing 1/10 NH4OH) in DCM to give the TFA salt of 2-(6-methyl-1H-indazol-3-yl)-2-phenylethanamine, TFA. LCMS calc.=252.14, found=252.17 (M+H)$^+$.

Presumed (S)-2-chloro-N-(2-(6-methyl-1H-indazol-3-yl)-2-phenylethyl)-4-(4H-1,2,4-triazol-4-yl)benzamide Step D product was subjected to the same reaction conditions as described in EXAMPLE 84, step C to give the title compound. LCMS calc.=457.15, found=457.30 (M+H)$^+$. $^1$H NMR (499 MHz, CD$_3$OD): 9.00 (s, 2H); 7.77 (d, J=2.2 Hz, 1H); 7.56 (dd, J=8.3, 2.2 Hz, 1H); 7.28-7.42 (m, 6H); 7.21 (dd, J=14.5, 7.1 Hz, 2H); 6.85 (d, J=8.4 Hz, 1H); 4.16-4.24 (m, 2H); 3.31 (m, 1H), 2.41 (s, 3H).

Chiral separation: AS column (30×250 mm), 40% MeOH (0.2% NH$_4$OH)/CO$_2$, 70 mL/min, 120 bar, 254 nm, inj vol=0.5 mL, 10 mg/mL in MeOH/DCM. Fast eluent, enantiomer A; Slow eluent, enantiomer B. The title compound is enantiomer B.

Example 89

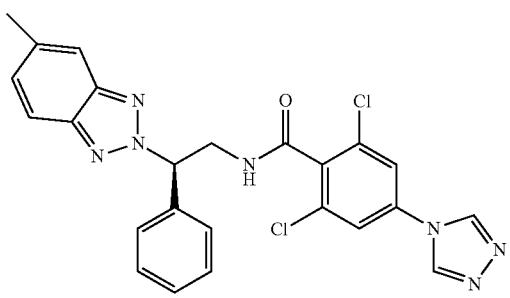 [SMILES: Cc1ccc2nn([C@@H](CNC(=O)c3c(Cl)cc(-n4cnnc4)cc3Cl)c3ccccc3)nc2c1]

Presumed (R)-2,6-dichloro-N-(2-(5-methyl-2H-benzo[d][1,2,3]triazol-2-yl)-2-phenylethyl)-4-(4H-1,2,4-triazol-4-yl)benzamide FIXa IC50=20.9 nM Step A A: (±)-2-(5-methyl-2H-benzo[d][1,2,3]triazol-2-yl)-2-phenylacetamide B: (±)-2-(5-methyl-H-benzo[d][1,2,3]triazol-1-yl)-2-phenylacetamide C: (±)-2-(6-methyl-1H-benzo[d][1,2,3]triazol-1-yl)-2-phenylacetamide To a stirred mixture of sodium hydride (83 mg, 2.065 mmol) in DMF (1 mL) was added 5-methyl-1H-benzo[d][1,2,3]triazole (250 mg, 1.878 mmol) at 0° C. After it was stirred for 10 min at 0° C., 2-bromo-2-phenylacetamide (482 mg, 2.253 mmol) was added. The reaction mixture was warmed up and stirred at room 25° C. overnight. Another batch was set up with 2 eq. of sodium hydride (150 mg, 3.76 mmol). LCMS showed two peaks of the compounds. Both reactions were quenched saturated NH$_4$Cl (aq), extracted with DCM. The organic layer was washed with brine, dried over Na$_2$SO$_4$, filtered and concentrated. The residue was combined and purified by column chromatography on silica gel Biotage 40S, eluting with 0, 20, 25, 30, 40, 50 and 60% EtOAc in Hex to give the product A and a mix of B and C. LCMS calc.=267.12, found=267.19 (M+H)$^+$.

Step B

A1: (±)-2-(5-methyl-2H-benzo[d][1,2,3]triazol-2-yl)-2-phenylethanamine

B1: (±)-2-(5-methyl-1H-benzo[d][1,2,3]triazol-1-yl)-2-phenylethanamine

C1: (±)-2-(6-methyl-1H-benzo[d][1,2,3]triazol-1-yl)-2-phenylethanamine

To a stirred solution of step A, product A (2-(5-methyl-2H-benzo[d][1,2,3]triazol-2-yl)-2-phenylacetamide) (80 mg, 0.300 mmol) in THF (5 mL) was added a solution of DIBAL-H (4.51 mL, 4.51 mmol). The reaction mixture was heated at 85° C. for 18 h. The reaction was cooled and quenched with saturated Na$_2$SO$_4$ (aq) with an ice-bath until no bubbles evolved. Then it was diluted with EtOAc (100 mL). Solid Na$_2$SO$_4$ was added, and the mixture was stirred for 15 min and filtered. The solid was stirred with EtOAc (50 mL) one more time. The combined organic layers were concentrated. The residue was purified by column chromatography on silica gel Biotage 25M, eluting with 0, 2, 3 and 4% MeOH (containing 1/10 NH$_4$OH) in CH$_2$Cl$_2$, to give product A1 (2-(5-methyl-2H-benzo[d][1,2,3]triazol-2-yl)-2-phenylethanamine). LCMS calc.=253.14, found=253.26 (M+H)$^+$. The regioisomeric mixture B and C was carried through the same reduction and amide coupling sequence to give title products as an inseparable mixture.
LCMS calc.=253.14, found=253.11 (M+H)+.

Step C: Presumed (R)-2,6-dichloro-N-(2-(5-methyl-2H-benzo[d][1,2,3]triazol-2-yl)-2-phenylethyl)-4-(4H-1,2,4-triazol-4-yl)benzamide The same amide coupling procedure as EXAMPLE 88 was used to give title product.
Chiral separation: AD column (2×15 cm), 20% MeOH/CO$_2$, 60 mL/min, 100 bar, 220 nm, inj vol=0.75 mL, 1.5 mg/mL 1:1 DCM: MeOH. Fast eluent, enantiomer A; Slow eluent, enantiomer B. The title compound is enantiomer B.
LCMS calc.=492.10, found=491.95 (M+H)+. $^1$H NMR (499 MHz, CD$_3$OD): δ 9.04 (s, 2H); 7.79-7.74 (m, 3H); 7.64

(s, 1H); 7.51 (d, J=7.5 Hz, 2H); 7.43-7.33 (m, 3H); 7.29 (d, J=8.8 Hz, 1H); 6.45 (dd, J=10.4, 4.7 Hz, 1H); 4.59 (dd, J=14.0, 10.4 Hz, 1H); 4.33 (dd, J=13.9, 4.8 Hz, 1H); 2.49 (s, 3H).

Example 90

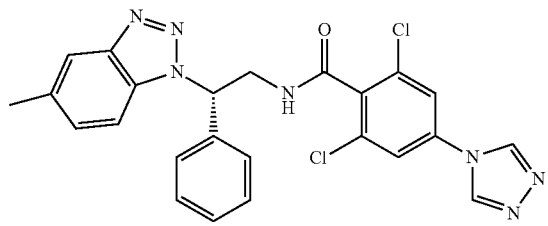 [SMILES: Cc1ccc2c(c1)nnn2[C@H](CNC(=O)c1c(Cl)cc(-n2cnnc2)cc1Cl)c1ccccc1]

Presumed (S)-2,6-dichloro-N-(2-(5-methyl-1H-benzo[d][1,2,3]triazol-1-yl)-2-phenylethyl)-4-(4H-1,2,4-triazol-4-yl)benzamide FIXa IC50=38.0 nM Mixture B1 and C1 from EXAMPLE 89, step B was carried to amide coupling step. The same amide coupling procedure as in EXAMPLE 89, step C was used. The products were separated using chiral SFC.

First separation: AD column (30×250 cm), 45% MeOH (0.2% NH₄OH)/CO₂, 70 mL/min, 100 bar, 220 nm, inj vol=1.5 mL, 12 mg/mL in MeOH. Fast eluent, product from C1; Slow eluent, product from B1.

Second separation: The second peak from AD column separation was subjected to OJ column to separate enantiomers. Analytical conditions: OJ column (4.6×250 mm), 5% to 50% MeOH/CO₂, 2.5 mL/min, 100 bar, 35 C, 220 nm. Fast eluent, enantiomer A; Slow eluent, enantiomer B. The title compound is enantiomer A.

LCMS calc.=492.10, found=491.85 (M+H)+. ¹H NMR (499 MHz, CD₃OD): δ 9.04 (s, 1H); 7.77 (m, 3H); 7.62 (d, J=8.6 Hz, 1H); 7.50 (d, J=7.4 Hz, 2H); 7.37-7.43 (m, 4H); 6.46 (dd, J=10.3, 4.8 Hz, 1H); 4.61-4.67 (m, 2H); 4.42 (dd, J=14.0, 4.8 Hz, 1H); 2.51 (s, 3H).

Example 91

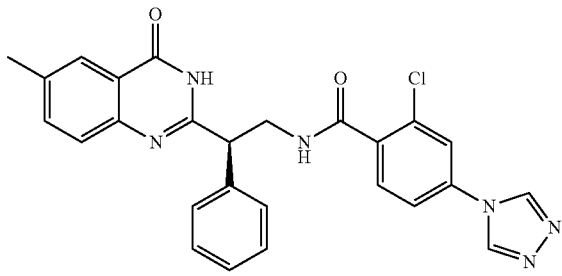 [SMILES: Cc1ccc2nc([C@@H](CNC(=O)c3ccc(-n4cnnc4)cc3Cl)c3ccccc3)[nH]c(=O)c2c1]

(R)-2-Chloro-N-(2-(6-methyl-4-oxo-3,4-dihydroquinazolin-2-yl)-2-phenylethyl)-4-(4H-1,2,4-triazol-4-yl)benzamide FIXa IC50=189.2 nM Step A: tert-butyl (3-((2-carbamoyl-4-methylphenyl)amino)-3-oxo-2-phenylpropyl)carbamate To a stirred solution of 3-tert-butoxycarbonylamino-2-phenyl-propionic acid (100 mg, 0.377 mmol) and 2-amino-5-methylbenzamide (56.6 mg, 0.377 mmol) in DMA (1 mL) was added HOAt (56.4 mg, 0.415 mmol) and EDC (94 mg, 0.49 mmol). The mixture was stirred at RT overnight. The mixture was diluted with DCM, then loaded to a 40 g ISCO silica gel column and purified by ISCO CombiFlash Rf system using 0-100% EtOAc in hexane as eluent to afford tert-butyl (3-((2-carbamoyl-4-methylphenyl)amino)-3-oxo-2-phenylpropyl)carbamate. LC-Mass (M+H) calc.=398.20; found=420.18 (M+Na).

Step B: tert-butyl (2-(6-methyl-4-oxo-3,4-dihydroquinazolin-2-yl)-2-phenylethyl)carbamate To a stirred solution of the product from step A (49.7 mg, 0.125 mmol) in MeOH (0.5 ml) was added potassium tert-butoxide (1.0 M in tBuOH, 0.25 ml, 0.25 mmol). The mixture was stirred at room temperature for 1 h. LC-Mass showed the reaction was completed. The reaction was quenched by addition of HCl (4M in dioxane, 0.062 mL, 0.25 mmol). Evaporation to dryness afforded the desired product, tert-butyl (2-(6-methyl-4-oxo-3,4-dihydroquinazolin-2-yl)-2-phenylethyl)carbamate.

LC-Mass (M+H) calc.=380.19; found=380.17.

Step C: 2-(2-amino-1-phenylethyl)-6-methylquinazolin-4(3H)-one dihydrochloride

The product from step B (tert-butyl (2-(6-methyl-4-oxo-3,4-dihydroquinazolin-2-yl)-2-phenylethyl)carbamate, 0.125 mmol) was dissolved in 4N HCl in dioxane (~3 mL). The mixture was stirred at room temperature for 60 min. Evaporation to dryness afforded the desired product, 2-(2-amino-1-phenylethyl)-6-methylquinazolin-4(1H)-one dihydrochloride. LC-Mass: (M+H) calc.=280.14; found=280.11.

Step D: 2-chloro-N-(2-(6-methyl-4-oxo-3,4-dihydroquinazolin-2-yl)-2-phenylethyl)-4-(4H-1,2,4-triazol-4-yl)benzamide To the stirred solution of 2-chloro-4-(4H-1,2,4-triazol-4-yl)benzoic acid (28 mg, 0.125 mmol) and 2-(2-amino-1-phenylethyl)-6-methylquinazolin-4(1H)-one dihydrochloride (40 mg, 0.12 mmol) in DMA (0.8 mL) was added Hunig's base (0.055 mL, 0.313 mmol) and HATU (57 mg, 0.150 mmol). The mixture was stirred at RT for overnight. The mixture was diluted with DCM, then loaded to a 40 g ISCO silica gel gold column and purified by ISCO CombiFlash Rf system using 0-10% MeOH in DCM to afford the title compound. A less pure portion of the product was further purified on the reversed HPLC (Gilson system on column: Waters Sunfire 19×100 mm, 5 um. 5-75% acetonitrile (with 0.1% TFA) in water (with 0.1% TFA). The title compound was collected.

LC-Mass: (M+H) calc.=485.14; found=485.13. ¹H NMR (500 MHz, CD₃OD): δ 9.23-9.20 (m, 2H); 7.97 (s, br, 1H); 7.85-7.83 (m, 1H); 7.73-7.63 (m, 3H); 7.53-7.49 (m, 3H); 7.42-7.31 (m, 3H); 4.53-4.51 (m, 1H); 4.26-4.21 (m, 1H); 4.08-4.05 (m, 1H); 2.49 (s, br, 3H)

Step E: (R)-2-chloro-N-(2-(6-methyl-4-oxo-3,4-dihydroquinazolin-2-yl)-2-phenylethyl)-4-(4H-1,2,4-triazol-4-yl)benzamide The racemic compound from step D (30 mg, 0.062 mmol) was resolved by SFC separation technique (using the following conditions: Column IA (2×25 cm), 35% methanol (0.1% DEA)/CO₂ as mobile phase, 100 bar; 70 ml/min, 220 nm, inj vol: 1 ml, 10 mg/ml methanol) to give both enantiomers as white solid after concentration and lyophilization. The slow eluting enantiomer (2$^{nd}$ peak) was the more potent FIXa inhibitor, and X-ray crystagraphy showed its stereo configuration is "R".

LC-Mass: (M+H) calc.=485.14; found=485.12 for enantiomer A; found=485.09 for enantiomer B. $^1$H NMR (500 MHz, CD$_3$OD): both enantiomers are same as in step D.

Example 92

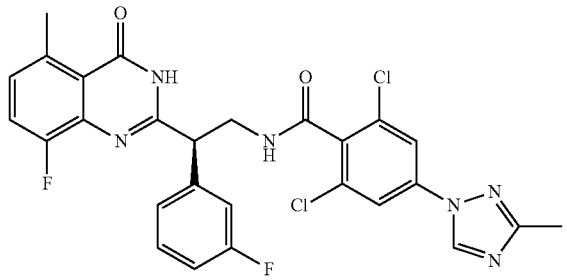

(R)-2,6-dichloro-N-(2-(8-fluoro-5-methyl-4-oxo-3,4-dihydroquinazolin-2-yl)-2-(3-fluorophenyl)ethyl)-4-(3-methyl-1H-1,2,4-triazol-1-yl)benzamide FIXa IC50=1.0 nM To the stirred solution of 2,6-dichloro-4-(3-methyl-1H-1,2,4-triazol-1-yl)benzoic acid, HCl (68 mg, 0.250 mmol) in DMA (1 mL) were added HOAt (38.8 mg, 0.285 mmol), EDC (59.3 mmol, 0.309 mmol), and Hunig's base (0.042 mL, 0.238 mmol). The mixture was stirred at room temperature for 10 min, then was added (R)-2-(2-amino-1-(3-fluorophenyl)ethyl)-8-fluoro-5-methylquinazolin-4(1H)-one (75 mg, 0.238 mmol). The mixture was stirred at room temperature for additional 4 h, quenched by adding water (0.2 mL) and TFA (0.018 ml, 0.238 mmol), then purified by reversed HPLC (Gilson system, using column: Waters Sunfire prep C18, 19×100 mm, 5 um and 10-95% acetonitrile (0.05% TFA)-water (0.05% TFA) as eluting solvent) to afford the title compound after lyophilization. LC-Mass: (M+H) calc.=569.10; found=569.16. $^1$H NMR (500 MHz, CD$_3$OD): δ 9.06 (s, 1H); 7.90 (s, 2H); 7.44-7.31 (m, 4H); 7.21 (dd, J=5.0 Hz, J=8.5 Hz, 1H); 7.06-7.03 (m, 1H); 4.52 (dd, J=6.0 Hz, J=9.5 Hz, 1H); 4.27-4.21 (m, 1H); 4.05-4.00 (m, 1H); 2.76 (s, 3H); 2.43 (s, 3H).

Example 93

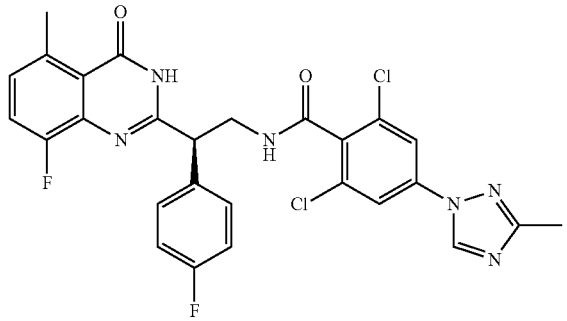 [SMILES: Cc1ncn(-c2cc(Cl)c(C(=O)NC[C@@H](c3ccc(F)cc3)c3nc4c(F)ccc(C)c4c(=O)[nH]3)c(Cl)c2)n1]

(R)-2,6-dichloro-N-(2-(8-fluoro-5-methyl-4-oxo-3,4-dihydroquinazolin-2-yl)-2-(4-fluorophenyl)ethyl)-4-(3-methyl-1H-1,2,4-triazol-1-yl)benzamide FIXa IC50=4.6 nM Step A: ethyl 3-(((benzyloxy)carbonyl)amino)-2-(4-fluorophenyl)propanoate To the stirred solution of ethyl 3-amino-2-(4-fluorophenyl)propanoate, HCl (3000 mg, 12.11 mmol) in dry DCM (50 ml) were added 4-methylmorpholine (2.695 g, 26.6 mmol), DMAP (148 mg, 1.211 mmol) and then CBZ-Cl (1.815 ml, 12.72 mmol) at 0° C. The mixture was stirred at room temperature overnight, then concentrated, and purified by ISCO CombiFlash system using 120 g ISCO RediSep silica gel column, and 0-50% EtOAc in hexane as eluenting solvent. The product was collected. LC-Mass (M+H) calc.=346.14; found=346.19 (M+H); 368.17 (M+Na).

Step B: 3-(((benzyloxy)carbonyl)amino)-2-(4-fluorophenyl)propanoic acid

To the stirred solution of ethyl 3-(((benzyloxy)carbonyl)amino)-2-(4-fluorophenyl)propanoate (3.19 g, 9.24 mmol) in dioxane (20 mL)-water (20 mL) was added LiOH (0.885 g, 36.9 mmol). The mixture was stirred at room temperature overnight, then partitioned between EtOAc (50 mL) and 1N HCl in water (20 mL). The aqueous was extracted with EtOAc for additional three times. The organic phases were combined, washed with sat. NaCl, dried over Na$_2$SO$_4$, filtered and concentrated in vacuo to give the desired product.

LC-Mass (M+H) calc.=318.11; found=318.14 (M+H); 340.09 (M+Na). $^1$H NMR (500 MHz, CD$_3$OD): δ 7.34-7.28 (m, 7H); 7.10-7.03 (m, 2H); 5.05 (s, 2H); 3.87 (t, J=7.5 Hz, 1H); 3.68-3.63 (m, 1H); 3.48-3.42 (m, 1H)

Step C: benzyl (2-(8-fluoro-5-methyl-4-oxo-3,4-dihydroquinazolin-2-yl)-2-(4-fluorophenyl)ethyl) carbamate Step C1: benzyl (3-((2-carbamoyl-6-fluoro-3-methylphenyl)amino)-2-(4-fluorophenyl)-3-oxopropyl) carbamate The suspension of 3-(((benzyloxy)carbonyl)amino)-2-(4-fluorophenyl)propanoic acid (2.6 g, 8.19 mmol) in SOCl$_2$ (23.9 mL, 328 mmol) was stirred at 40° C. for 1 h. LC-MS in MeOH showed good conversion of methyl ester (LC-Mass (M+H) calc.=332.13; found=332.13). The volatile was evaporated, and the residue was redissolved in dry DMA (25 mL), followed by addition of 2-amino-3-fluoro-6-methylbenzamide (1.52 g, 9.01 mmol). The mixture was stirred at 50° C. for 30 min, then stirred at room temperature for 3 h. LC-MS showed formation of the titled compound. LC-Mass (M+Na) calc.=490.14; found=490.11 (M+Na)$^+$.

Step C2: benzyl (2-(8-fluoro-5-methyl-4-oxo-3,4-dihydroquinazolin-2-yl)-2-(4-fluorophenyl)ethyl) carbamate To the crude mixture from step C1 was added MeOH (25 mL) and potassium 2-methylpropan-2-olate in t-BuOH (1 M, 24.6 mL, 24.6 mmol). The mixture was stirred at room temperature for 4 h, then was quenched with addition of acetic acid (1.41 mL, 24.6 mmol). The mixture was partitioned between EtOAc and sat. NaCl aq. The aqueous was extracted with EtOAc three more times. Organic phases were combined, dried over Na$_2$SO$_4$, filtered and concentrated, and then purified by chromatography (ISCO CombiFlash Rf system, 120 g Isco RediSep silica gel column, and 0-60% EtOAc in hexane as eluent) to give the title compound. LC-Mass (M+H) calc.=450.16; found=450.11. $^1$H NMR (500 MHz, CD$_3$OD): δ 7.44-7.39 (m, 3H); 7.32-7.26 (m, 5H); 7.21-7.17 (m, 1H); 7.04 (t, J=8.5 Hz, 2H); 5.06 (dd, J=4.5 Hz, J=13 Hz, 2H); 4.21 (t, J=7.0 Hz, 1H); 3.94 (dd, J=7.5 Hz, J=13.5 Hz, 1H); 3.72 (dd, J=7.0 Hz, J=13.5 Hz, 1H); 2.74 (s, 3H).

Step D: (R)-benzyl (2-(8-fluoro-5-methyl-4-oxo-3,4-dihydroquinazolin-2-yl)-2-(4-fluorophenyl)ethyl) carbamate The racemic product from step C (2.43 g, 5.41 mmol) was then resolved by SFC separation (conditions listed below) to give peak-1 (enantiomer A, presumed as "R" enantiomer based on the FIXa activity of resulting final compounds, as the more potent enantiomer) and peak-2 (enantiomer B).

| Preparative Method: | Analytical Method: |
|---|---|
| AS-H (2 × 15 cm) | AS-H (25 × 0.46 cm) |
| 20% methanol/CO$_2$, 100 bar | 20% methanol(DEA)/CO$_2$, 100 bar |
| 70 mL/min, 220 nm | 3 mL/min, 220 and 254 nm |
| inj vol.: 0.8 mL, 20 mg/mL methanol | |

For Enantiomer A (the Titled Compound):
LC-Mass (M+H) calc.=450.16; found=450.19. $^1$H NMR (500 MHz, CD$_3$OD): same as the racemic product from step C.
For Enantiomer B:
LC-Mass (M+H) calc.=450.16; found=450.16. $^1$H NMR (500 MHz, CD$_3$OD): same as enantiomer A and the racemic compound.

Step E: (R)-2-(2-amino-1-(4-fluorophenyl)ethyl)-8-fluoro-5-methylquinazolin-4(3H)-one To a 100 mL round bottom flask with (R)-benzyl (2-(8-fluoro-5-methyl-4-oxo-3,4-dihydroquinazolin-2-yl)-2-(4-fluorophenyl)ethyl)carbamate (400 mg, 0.89 mmol) and Pd/C (10%, 142 mg, 0.133 mmol) was added EtOH (30 ml), then equipped with a H$_2$ balloon. The reaction flask was degassed and flushed with H$_2$ twice, then the mixture was stirred at room temperature in the presence of H$_2$ for 2 h. The catalyst was removed by filtration, and the filtrate was concentrated in vacuo to give the title compound. LC-Mass (M+H) calc.=316.12; found=316.17. $^1$H NMR (500 MHz, CD$_3$OD): δ 7.43-7.39 (m, 3H); 7.20 (dd, J=4.5 Hz, J=8.0 Hz, 1H); 7.08 (t, J=8.5 Hz, 2H); 4.02 (dd, J=5.0 Hz, J=8.5 Hz, 1H); 3.45 (dd, J=8.5 Hz, J=13.0 Hz, 1H); 3.10 (dd, J=5.5 Hz, J=13.0 Hz, 1H); 2.75 (s, 3H).

Step F: (R)-2,6-dichloro-N-(2-(8-fluoro-5-methyl-4-oxo-3,4-dihydroquinazolin-2-yl)-2-(4-fluorophenyl) ethyl)-4-(3-methyl-1H-1,2,4-triazol-1-yl)benzamide To the stirred solution of 2,6-dichloro-4-(3-methyl-1H-1,2,4-triazol-1-yl)benzoic acid, HCl (86 mg, 0.317 mmol) in DMA (1 mL) was added HOAt (51.8 mg, 0.318 mmol), and EDC (79 mg, 0.412 mmol). The mixture was stirred at room temperature for 2 min, then DIEA (0.055 ml, 0.317 mmol) was added, and the mixture was stirred at room temperature for additional 10 min, then (R)-2-(2-amino-1-(4-fluorophenyl)ethyl)-8-fluoro-5-methylquinazolin-4(1H)-one was added. The mixture was stirred at room temperature for additional 4 h, followed by addition of water (0.1 mL) and TFA (0.024 mL, 0.317 mmol). The reaction mixture was purified by reversed HPLC (Gilson system) using column: Waters Sunfire prep C18, 19×100 mm, 5 um and 10-95% acetonitrile (with 0.05% TFA)-water (with 0.05% TFA) as eluting solvent. The title compound (Step F) was collected after lyophilization.

LC-Mass (M+H) calc.=569.10; found=569.15. $^1$H NMR (500 MHz, CD$_3$OD): δ 9.05 (s, 1H); 7.89 (s, 2H); 7.57 (dd, J=5.5 Hz, J=8.5 Hz, 2H); 7.41 (dd, J=8.5 Hz, J=10.0 Hz, 1H); 7.19 (dd, J=5.0 Hz, J=8.5 Hz, 1H); 7.11 (t, J=8.5 Hz, 2H); 4.50 (dd, J=6.0 Hz, J=9.5 Hz, 1H); 4.23 (dd, J=9.5 Hz, J=13.0 Hz, 1H); 4.00 (dd, J=6.0 Hz, J=13.5 Hz, 1H); 2.75 (s, 3H); 2.42 (s, 3H).

Example 94

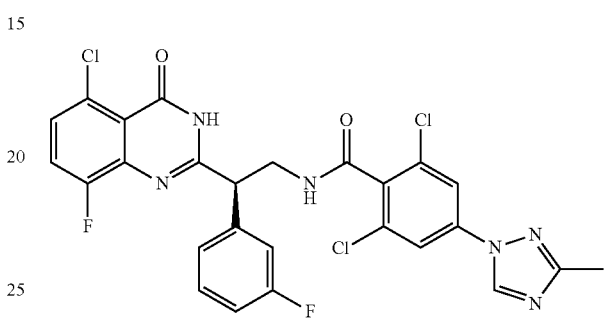

(R)-2,6-dichloro-N-(2-(5-chloro-8-fluoro-4-oxo-3,4-dihydroquinazolin-2-yl)-2-(3-fluorophenyl)ethyl)-4-(3-methyl-1H-1,2,4-triazol-1-yl)benzamide FIXa IC50=3.5 nM Step A: ethyl 3-(2,6-dichloro-4-(3-methyl-1H-1,2,4-triazol-1-yl)benzamido)-2-(3-fluorophenyl)propanoate To the stirred solution of 2,6-dichloro-4-(3-methyl-1H-1,2,4-triazol-1-yl)benzoic acid, HCl salt (659 mg, 2.42 mmol) in dry DMA (6 mL) was added HOAt (363 mg, 2.66 mmol), and EDC (557, 2.91 mmol). The mixture was stirred at room temperature for 0.5 h, then was added the solution of ethyl 3-amino-2-(3-fluorophenyl)propanoate, HCl and Hunig's base (0.812 mL) in DMA (2 mL). The mixture was stirred at room temperature overnight, then diluted with EtOAc and partitioned between EtOAc and sat. NaHCO$_3$. The aqueous was extracted with EtOAc two times, and organic phases were combined, washed with water, dried over Na$_2$SO$_4$, and concentrated in vacuo. The residue was purified by chromatography (ISCO CombiFlash Rf system) using 0-100% EtOAc in hexane as eluent to give the product. LC-Mass (M+H) calc.=465.08; found=465.16.

Step B: 3-(2,6-dichloro-4-(3-methyl-1H-1,2,4-triazol-1-yl)benzamido)-2-(3-fluorophenyl)propanoic acid To the stirred solution of ethyl 3-(2,6-dichloro-4-(3-methyl-1H-1,2,4-triazol-1-yl)benzamido)-2-(3-fluorophenyl)propanoate (995 mg, 2.14 mmol) in dioxane (10 mL)-water (10 mL) was added LiOH (205 mg, 8.55 mmol). The mixture was stirred at room temperature overnight, acidified with the addition of 4N HCl in dioxane (2.14 mL), and then purified by reversed HPLC (ISCO CombiFlash) using neutral conditions (5-60% acetonitrile in water) on column: 150 g HP C18 Gold RediSepRf column in two runs to give the product as a white solid after lyophilization (600 mg, 64%). LC-Mass (M+H) calc.=437.05; found=437.11.

Step C: 2,6-dichloro-N-(2-(5-chloro-8-fluoro-4-oxo-3,4-dihydroquinazolin-2-yl)-2-(3-fluorophenyl)ethyl)-4-(3-methyl-1H-1,2,4-triazol-1-yl)benzamide Step C-1

The suspension of 3-(2,6-dichloro-4-(3-methyl-1H-1,2,4-triazol-1-yl)benzamido)-2-(3-fluorophenyl)propanoic acid (290 mg, 0.663 mmol) in thionyl chloride (2.42 mL, 33.2 mmol) was stirred at 50° C. for 2 h. LCMS in methanol showed good conversion to methyl ester. LC-Mass (M+H) calc.=451.07; found=451.12. The reaction mixture was evaporated to dryness, and was used for next step without further purification.

Step C-2

To the above residue was added dry DMA (3 mL), followed by 2-amino-6-chloro-3-fluorobenzamide (150 mg, 0.796 mmol). The mixture was stirred at 50° C. for 2 h, and then at room temperature for additional 6 h. Crude LCMS showed the desired product as the major product. LC-Mass calc.=607.06; found=607.26 (M+H)$^+$.

Step C-3

To the reaction mixture from step C-2 was added MeOH (3 mL) and potassium 2-methylpropan-2-olate in tBuOH (1.0 M, 2.65 mL, 2.65 mmol), and stirred at room temperature overnight. The reaction mixture was neutralized with addition of AcOH (~0.24 mL), diluted with DMSO, and purified by reversed HPLC (ISCO CombiFlash system, 150 g HP C18 Gold RediSepRf column) using acetonitrile in water (20-100%) (no TFA) as eluting solvent as eluent in two runs to afford the product after lyophilization. LCMS calc.=589.04; found=589.30 (M+H)$^+$. $^1$H NMR (500 MHz, CD$_3$OD): δ 9.05 (s, 1H); 7.90 (s, 2H); 7.53-7.31 (m, 5H); 7.07-7.04 (m, 1H); 4.52 (dd, J=6 Hz, J=9 Hz, 1H); 4.22 (dd, J=9 Hz, J=13 Hz, 1H); 4.03 (dd, J=6 Hz, J=13.5 Hz, 1H); 2.43 (s, 3H).

Step D: (R)-2,6-dichloro-N-(2-(5-chloro-8-fluoro-4-oxo-3,4-dihydroquinazolin-2-yl)-2-(3-fluorophenyl)ethyl)-4-(3-methyl-1H-1,2,4-triazol-1-yl)benzamide The racemic product from step C (300 mg, 0.51 mmol) was resolved by SFC separation technique using the conditions as shown below to give both enationmers as white solid after concentration and lyophilization in high recovery yield (peak-1). The slow eluting enantiomer (2$^{nd}$ peak) was presumed as "R" isomer based on its FIXa activity.

| Preparative Method: | Analytical Method: |
|---|---|
| IA (2 × 15 cm) | IA (15 × 0.46 cm) |
| 30% ethanol/CO$_2$, 100 bar | 30% ethanol/CO$_2$, 100 bar |
| 60 mL/min, 220 nm | 3 mL/min, 220 and 254 nm |
| inj vol.: 1 mL, 4 mg/mL methanol:DCM | |

For Enantiomer B (the Title Compound):
LCMS calc.=589.04; found=589/591.09 (M+H)$^+$. $^1$H NMR (500 MHz, CD$_3$OD): δ 9.05 (s, 1H); 7.90 (s, 2H); 7.51 (t, J=9 Hz, 1H); 7.46-7.31 (m, 4H); 7.07-7.03 (m, 1H); 4.52 (dd, J=5.5 Hz, J=9 Hz, 1H); 4.22 (dd, J=9 Hz, J=13 Hz, 1H); 4.03 (dd, J=6 Hz, J=13.5 Hz, 1H); 2.43 (s, 3H).
For Enantiomer A:
LCMS calc.=589.04; found=589/591.09 (M+H)$^+$. 591.13. $^1$H NMR (500 MHz, CD$_3$OD): comparable to enantiomer B.

The following compounds (Table 7) were synthesized using methods analogous to those described for EXAMPLES 91-94 from commercially available materials or intermediates whose syntheses are described above.

TABLE 7

| Example | Structure | Calc. (M + H)$^+$ | LCMS (M + H)$^+$ | hFIXa IC50 (nM) |
|---|---|---|---|---|
| 95 | 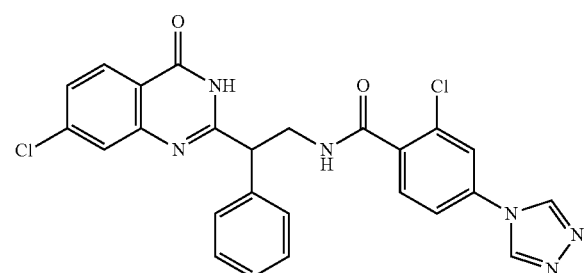 | 505.09 | 505.07 | 802.8 |
| 96 | 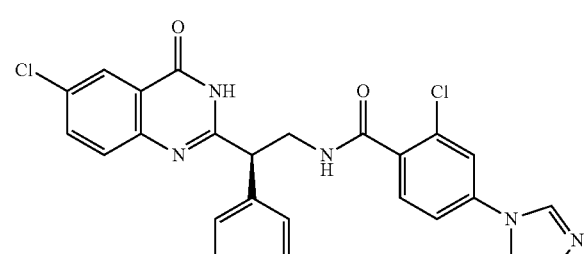 | 505.09 | 505.07 | 188.4 |

TABLE 7-continued

| Example | Structure | Calc. (M + H)+ | LCMS (M + H)+ | hFIXa IC50 (nM) |
|---|---|---|---|---|
| 97 | 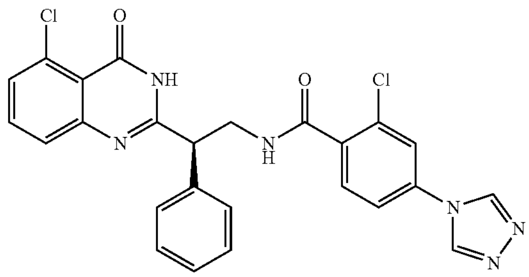 | 505.09 | 505.12 | 51.53 |
| 98 | 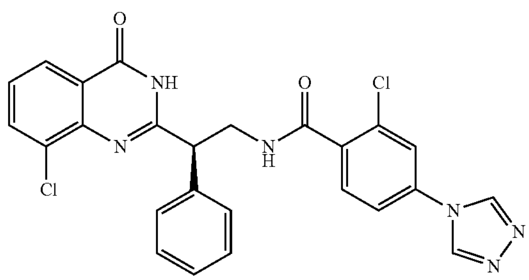 [SMILES: O=C(NC[C@@H](c1ccccc1)c1nc2c(Cl)cccc2c(=O)[nH]1)c1ccc(-n2cnnc2)cc1Cl] | 505.09 | 505.15 | 177.8 |
| 99 | 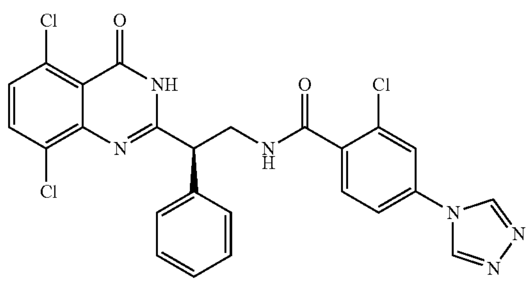 [SMILES: O=C(NC[C@@H](c1ccccc1)c1nc2c(Cl)ccc(Cl)c2c(=O)[nH]1)c1ccc(-n2cnnc2)cc1Cl] | 539.06 | 539/541.11 | 43.1 |
| 100 | 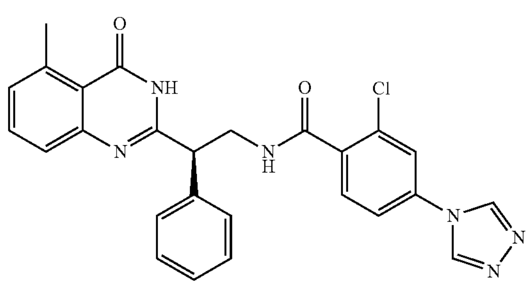 [SMILES: Cc1cccc2nc([C@@H](CNC(=O)c3ccc(-n4cnnc4)cc3Cl)c3ccccc3)[nH]c(=O)c12] | 485.15 | 485.19 | 16.79 |
| 101 | 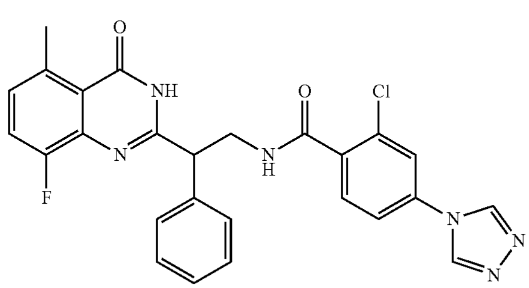 [SMILES: Cc1ccc(F)c2nc(C(CNC(=O)c3ccc(-n4cnnc4)cc3Cl)c3ccccc3)[nH]c(=O)c12] | 503.14 | 503.19 | 6.676 |

TABLE 7-continued

| Example | Structure | Calc. (M + H)+ | LCMS (M + H)+ | hFIXa IC50 (nM) |
|---|---|---|---|---|
| 102 | 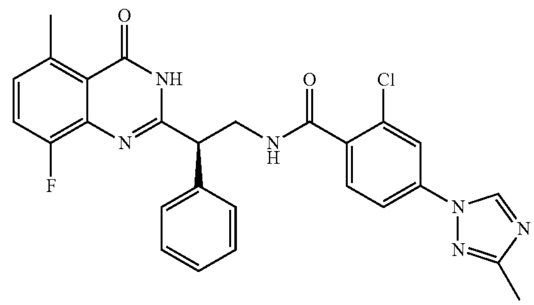 [SMILES: Cc1ncn(-c2ccc(C(=O)NC[C@@H](c3ccccc3)c3nc4c(F)ccc(C)c4c(=O)[nH]3)c(Cl)c2)n1] | 517.16 | 517.27 | 10.67 |
| 103 | 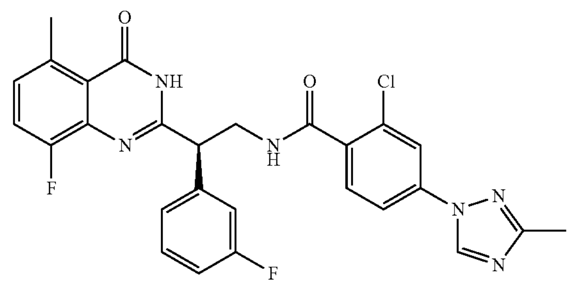 [SMILES: Cc1ncn(-c2ccc(C(=O)NC[C@@H](c3cccc(F)c3)c3nc4c(F)ccc(C)c4c(=O)[nH]3)c(Cl)c2)n1] | 535.15 | 535.32 | 6.352 |
| 104 | 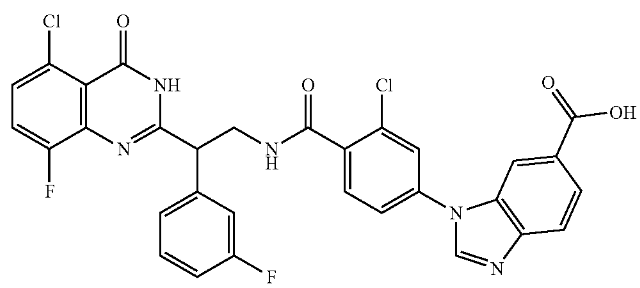 [SMILES: O=C(O)c1ccc2ncn(-c3ccc(C(=O)NCC(c4cccc(F)c4)c4nc5c(F)ccc(Cl)c5c(=O)[nH]4)c(Cl)c3)c2c1] | 634.09 | 634.18 | 1.97 |
| 105 | 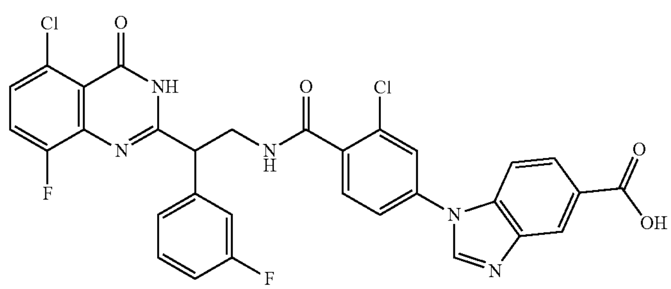 [SMILES: O=C(O)c1ccc2c(c1)ncn2-c1ccc(C(=O)NCC(c2cccc(F)c2)c2nc3c(F)ccc(Cl)c3c(=O)[nH]2)c(Cl)c1] | 634.09 | 634.35 | 3.319 |
| 106 | 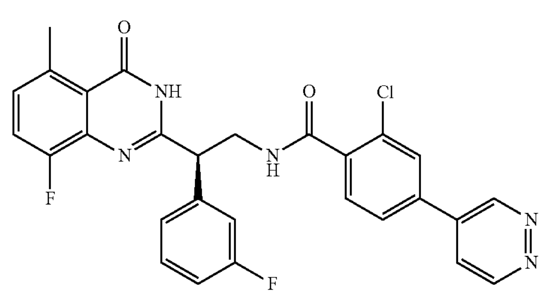 [SMILES: Cc1ccc(F)c2nc([C@@H](CNC(=O)c3ccc(-c4ccnnc4)cc3Cl)c3cccc(F)c3)[nH]c(=O)c12] | 532 | 532 | 8.5 |

TABLE 7-continued

| Example | Structure | Calc. (M + H)+ | LCMS (M + H)+ | hFIXa IC50 (nM) |
|---|---|---|---|---|
| 107 | 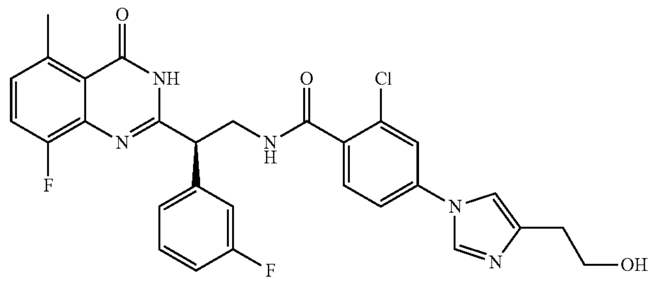 [SMILES: Cc1ccc(F)c2nc([C@@H](CNC(=O)c3ccc(-n4cnc(CCO)c4)cc3Cl)c3cccc(F)c3)[nH]c(=O)c12] | 564 | 564 | 7.3 |
| 108 | 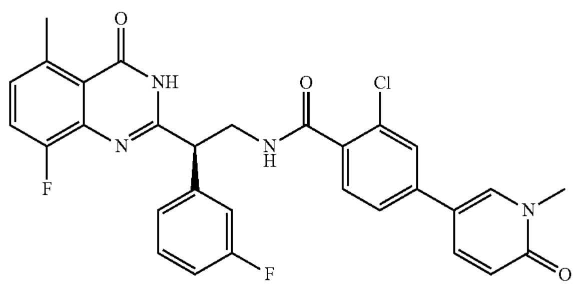 [SMILES: Cc1ccc(F)c2nc([C@@H](CNC(=O)c3ccc(-c4ccc(=O)n(C)c4)cc3Cl)c3cccc(F)c3)[nH]c(=O)c12] | 561 | 561 | 9.2 |
| 109 | 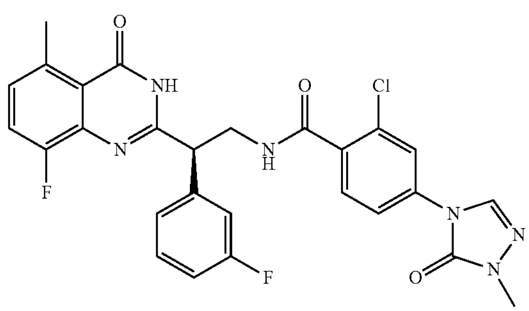 [SMILES: Cc1ccc(F)c2nc([C@@H](CNC(=O)c3ccc(-n4cnn(C)c4=O)cc3Cl)c3cccc(F)c3)[nH]c(=O)c12] | 551 | 551 | 1.8 |
| 110 | 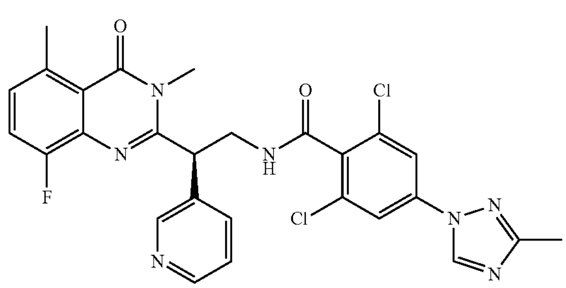 [SMILES: Cc1ncn(-c2cc(Cl)c(C(=O)NC[C@@H](c3cccnc3)c3nc4c(F)ccc(C)c4c(=O)n3C)c(Cl)c2)n1] | 566 | 566 | 8.9 |
| 111 | 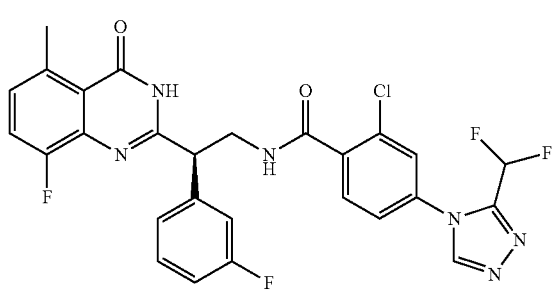 [SMILES: Cc1ccc(F)c2nc([C@@H](CNC(=O)c3ccc(-n4cnnc4C(F)F)cc3Cl)c3cccc(F)c3)[nH]c(=O)c12] | 571 | 571 | 9.6 |

Example 112

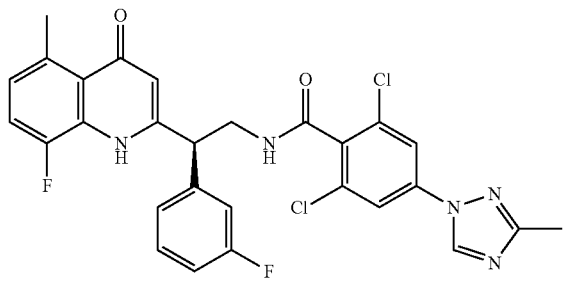 [SMILES: Cc1ncn(-c2cc(Cl)c(C(=O)NC[C@@H](c3cccc(F)c3)c3cc(=O)c4c(C)ccc(F)c4[nH]3)c(Cl)c2)n1]

Presumed (R)-2,6-dichloro-N-(2-(8-fluoro-5-methyl-4-oxo-1,4-dihydroquinolin-2-yl)-2-(3-fluorophenyl)ethyl)-4-(3-methyl-1H-1,2,4-triazol-1-yl)benzamide

Step A: (±)-2-(8-fluoro-4-((4-methoxybenzyl)oxy)-5-methylquinolin-2-yl)-2-(3-fluorophenyl)acetonitrile

*J. Org. Chem, Vol. 68, No. 21, 2003,* 8007

The reactor was charged with palladium(II) acetate (10.15 mg, 0.045 mmol), 2,8,9-triisobutyl-2,5,8,9-tetraaza-1-phosphabicyclo[3.3.3]undecane (32.3 μL, 0.090 mmol), and Intermediate 26 (150 mg, 0.452 mmol). The vessel was evacuated and refilled with $N_2$ for 3 cycles and degassed toluene (904 μL) was added, followed by NaHMDS (633 μL, 0.633 mmol). The reaction was stirred at 25° C. for 20 min before 2-(3-fluorophenyl)acetonitrile (73.3 mg, 0.543 mmol) was added. The reaction was then capped and heated at 100° C. for 2 h, cooled to room temperature, and quenched with sat $NH_4Cl$ aq. The aqueous layer was extracted with EtOAc (3×), dried over $MgSO_4$, and the filtrate was concentrated in vacuo. The crude material was purified by chromatography on silica gel (eluent: 0-20% EtOAc in Hexanes). LCMS calc.=431.15, found=430.96 $(M+H)^+$.

Step B: (±)-2-(8-fluoro-4-((4-methoxybenzyl)oxy)-5-methylquinolin-2-yl)-2-(3-fluorophenyl)ethanamine

*Synth. Comm.* 32(8), 1265-69 (2002).

Under $N_2$, to the product from step A (144 mg, 0.335 mmol), anhydrous nickel(II) chloride (43.4 mg, 0.335 mmol) in anhydrous ethanol (836 μL) and THF (836 μL) was added sodium borohydride (76 mg, 2.007 mmol). The reaction was stirred vigorously at 25° C. for 10 h. The reaction mixture was filtered through a celite pad. The filtered nickel boride precipitate was washed with methanol. The combined filtrate was concentrated then diluted with water and extracted with EtOAc. The combined extract was dried over $MgSO_4$, filtered and concentrated in vacuo. The crude product was purified by column chromatography over silica gel (eluent: 0-100% then 100% A in B. A: 10% MeOH in DCM; B: DCM.). LCMS calc.=435.18, found=434.99 $(M+H)^+$. $^1H$ NMR (499 MHz, Acetone-d6): δ 7.54-7.50 (m, 2H); 7.36-7.26 (m, 4H); 7.21-7.10 (m, 2H); 7.00-6.95 (m, 3H); 5.30-5.19 (m, 2H); 4.66 (t, J=7.1 Hz, 1H); 4.37 (dd, J=13.6, 8.2 Hz, 1H); 3.91-3.74 (m, 3H); 3.36-3.30 (m, 1H), 2.97 (brs, 2H), 2.70-2.63 (m, 3H).

Step C: (±)-2,6-dichloro-N-(2-(8-fluoro-4-((4-methoxybenzyl)oxy)-5-methylquinolin-2-yl)-2-(3-fluorophenyl)ethyl)-4-(3-methyl-1H-1,2,4-triazol-1-yl)benzamide To INTERMEDIATE 12 (47.0 mg, 0.173 mmol), EDC (39.7 mg, 0.207 mmol) and 1-hydroxy-7-azabenzotriazole (28.2 mg, 0.207 mmol) were added THF (1 mL). The mixture was stirred at 40° C. for 10 min and cooled back to room temperature. The product from step B (75 mg, 0.173 mmol) in THF (700 uL) was added and the reaction was stirred at 25° C. overnight. The reaction was quenched with sat $NaHCO_3$ aq, and extracted with EtOAc. The combined extract was dried over $MgSO_4$, filtered and concentrated in vacuo. The crude product was purified by column chromatography over silica gel (eluent: 0-100% EtOAc in Hexanes). LCMS calc.=688.16, found=687.96 $(M+H)^+$.

Step D: Presumed (R)-2,6-dichloro-N-(2-(8-fluoro-5-methyl-4-oxo-1,4-dihydroquinolin-2-yl)-2-(3-fluorophenyl)ethyl)-4-(3-methyl-1H-1,2,4-triazol-1-yl)benzamide To step C product (125 mg, 0.182 mmol) was added DCM and TFA, and the reaction was stirred at 25° C. for 1 h before quenched with sat $NaHCO_3$ aq (10 mL) and extracted with EtOAc (3×). The combined extract was dried over $MgSO_4$, filtered and concentrated in vacuo. The crude product was purified by column chromatography over silica gel (eluent: 0-100% EtOAc in Hexanes). LCMS calc.=568.10, found=567.86 $(M+H)^+$. $^1H$ NMR (500 MHz, Acetone-d6): δ 9.01 (s, 1H); 8.39 (s, 1H); 7.85 (s, 2H); 7.47-7.35 (m, 3H); 7.28 (dd, J=10.8, 8.2 Hz, 1H); 7.08 (t, J=8.2 Hz, 1H); 6.96 (s, 1H); 6.31 (s, 1H); 4.79 (t, J=7.8 Hz, 1H); 4.17 (t, J=6.6 Hz, 2H); 3.32 (s, 1H); 2.77 (s, 3H), 2.37 (s, 3H).

Chiral separation: AD column, 30×250 mm, 50% MeOH (0.2% NH4OH)/CO2, 70 mL/min, 120 bar, 12 mg/ml in MeOH/DCM, 35 C, 220 nM.

Fast eluent, enantiomer A; Slow eluent, enantiomer B. Title compound is enantiomer B.

The following compounds (Table 8) were synthesized using methods analogous to those described for EXAMPLE 112 from commercially available materials or intermediates whose syntheses are described above.

TABLE 8

| Example | Structure | Calc. (M + H)+ | LCMS (M + H)+ | hFIXa IC50 (nM) |
|---|---|---|---|---|
| 113 | 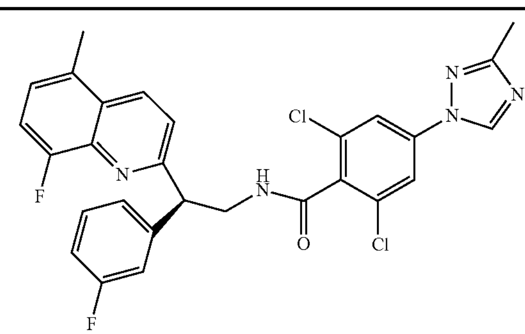 | 552.12 | 552.00/ 553.97 | 10.41 |

TABLE 8-continued

| Example | Structure | Calc. (M + H)+ | LCMS (M + H)+ | hFIXa IC50 (nM) |
|---|---|---|---|---|
| 114 | 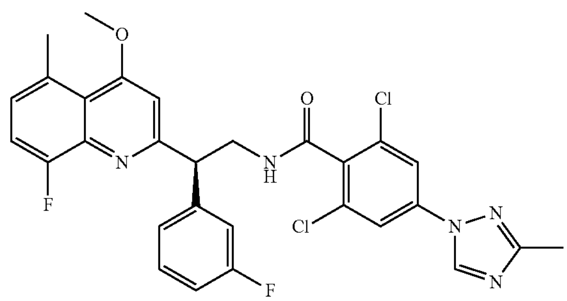 [SMILES: COc1cc([C@@H](CNC(=O)c2c(Cl)cc(-n3cnc(C)n3)cc2Cl)c2cccc(F)c2)nc2c(F)ccc(C)c12] | 582.13 | 581.94/ 583.96 | 52.19 |

Example 115

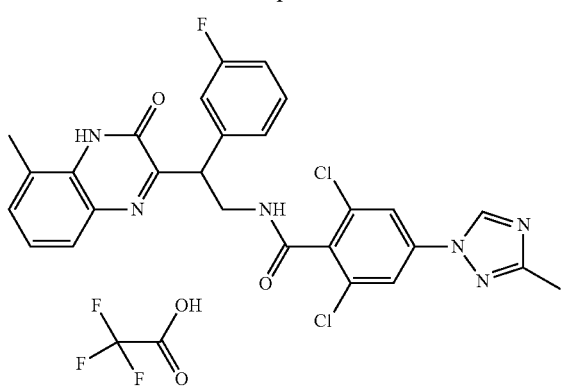

(R or S) 2,6-Dichloro-N-(2-(3-fluorophenyl)-2-(5-methyl-3-oxo-3,4-dihydroquinoxalin-2-yl)ethyl)-4-(3-methyl-1H-1,2,4-triazol-1-yl)benzamide 2,2,2-trifluoroacetate Step A: Ethyl 3-(2,6-dichloro-4-(3-methyl-1H-1,2,4-triazol-1-yl)benzamido)-2-(3-fluorophenyl)propanoate Ethyl 3-amino-2-(3-fluorophenyl)propanoate hydrochloride (4 g, 16.15 mmol), 1-(4-carboxy-3,5-dichlorophenyl)-3-methyl-1H-1,2,4-triazol-4-ium chloride (INTERMEDIATE 12) (4.98 g, 16.15 mmol), 1-hydroxy-7-azabenzotriazole (2.198 g, 16.15 mmol), EDC (3.10 g, 16.15 mmol), acetonitrile (108 ml) and Hunig's base (8.46 mL, 48.4 mmol) were stirred at room temperature overnight. Volatiles were removed under reduced pressure. The residue was partioned between water and ethyl acetate. The combined extracts were dried over Na$_2$SO$_4$, filtered and evaporated in vacuo. This oil mixture was purified by flash chromatography (SiO$_2$, 80 g cartridge). The column was eluted by a MeOH/CH$_2$Cl$_2$ mixture (0% to 25%). Related fractions were pooled and evaporated in vacuo to afford the title compound. LCMS calc.=465.08; found=465.04 (M+H)+.

Step B: 3-(2,6-Dichloro-4-(3-methyl-1H-1,2,4-triazol-1-yl)benzamido)-2-(3-fluorophenyl)propanoic acid Ethyl 3-(2,6-dichloro-4-(3-methyl-1H-1,2,4-triazol-1-yl)benzamido)-2-(3-fluorophenyl)propanoate (5.6069 g, 12.05 mmol) was stirred with 1,4-dioxane (30 mL) and lithium hydroxide monohydrate (36.1 ml, 36.1 mmol) at room temperature overnight. The crude mixture was acidified by 1N HCl (36.1 mL, 36.1 mmol). The crude mixture was partitioned between water and ethyl acetate. The combined extracts were dried over Na$_2$SO$_4$, filtered and evaporated in vacuo to afford the title compound. LCMS calc.=437.05; found=437.00 (M+H)+.

Step C: 2,6-Dichloro-N-(4-cyano-2-(3-fluorophenyl)-3-oxo-4-(triphenylphosphoranylidene)butyl)-4-(3-methyl-1H-1,2,4-triazol-1-yl)benzamide DMAP (0.069 g, 0.568 mmol) was added to a stirred, room temperature mixture of 3-(2,6-dichloro-4-(3-methyl-1H-1,2,4-triazol-1-yl)benzamido)-2-(3-fluorophenyl)propanoic acid (1.2417 g, 2.84 mmol), (triphenylphosphoranylidene)acetonitrile (0.856 g, 2.84 mmol) and EDC (0.544 g, 2.84 mmol) in DCM (30 mL) and the mixture was stirred at room temperature overnight. The crude mixture was partitioned between water and DCM. The combined extracts were dried over Na$_2$SO$_4$, filtered and evaporated in vacuo. The resulting crude mixture was purified by flash chromatography (SiO$_2$, 80 g cartridge). The column was eluted by a MeOH/CH$_2$Cl$_2$ mixture (0% to 20%). Related fractions were pooled and evaporated in vacuo to afford the desired product and a solid foam as impure fractions. This oil was further purified by flash chromatography (SiO$_2$, 80 g cartridge). The column was eluted by a short gradient of Hex/EtOAc then 100% EtOAc. Related fractions were pooled and combined with the pure fractions from the 1st column and evaporated in vacuo to afford the title compound. LCMS calc.=720.14; found=720.18 (M+H)+.

Step D: Methyl 4-(2,6-dichloro-4-(3-methyl-1H-1,2,4-triazol-1-yl)benzamido)-3-(3-fluorophenyl)-2-oxobutanoate 2,6-Dichloro-N-(4-cyano-2-(3-fluorophenyl)-3-oxo-4-(triphenylphosphoranylidene)butyl)-4-(3-methyl-1H-1,2,4-triazol-1-yl)benzamide (785 mg, 1.089 mmol) was ozonized at −40° C. (ref: JOC, 1994, 4364-4366) and quenched by dimethyl sulfide. The crude was purified by preparative HPLC (reverse phase, YMC-Pack ODS C-18 100×20 mm) eluting with acetonitrile/water 0.05% TFA. Related fractions were pooled and evaporated under reduced pressure to afford the title compound. LCMS calc.=479.06; found=478.99 (M+H)+.

Step E: 4-(2,6-Dichloro-4-(3-methyl-1H-1,2,4-triazol-1-yl)benzamido)-3-(3-fluorophenyl)-2-oxobutanoic acid Methyl 4-(2,6-dichloro-4-(3-methyl-1H-1,2,4-triazol-1-yl)benzamido)-3-(3-fluorophenyl)-2-oxobutanoate (189.9 mg, 0.396 mmol) was stirred with 1,4-dioxane (1.5 mL) and lithium hydroxide monohydrate (0.4 mL, 0.400 mmol) (turned dark purple immediately) at room temperature for 30 min. The crude mixture was neutralized by HCl (0.4 mL, 0.400 mmol). The crude was purified by preparative HPLC (reverse phase, YMC-Pack ODS C-18 100×20 mm) eluting with acetonitrile/water (0% to 45% organic in 10 min, then to 100% in 2 min, 20 mL/min). Related fractions were pooled and evaporated under reduced pressure to afford the title compound. LCMS calc.=465.05; found=464.94 (M+H)$^+$.

Step F: (R or S) 2,6-Dichloro-N-(2-(3-fluorophenyl)-2-(5-methyl-3-oxo-3,4-dihydroquinoxalin-2-yl)ethyl)-4-(3-methyl-1H-1,2,4-triazol-1-yl)benzamide 2,2,2-trifluoroacetate Hunig's base (0.085 mL, 0.487 mmol) was added to a stirred, room temperature mixture of 4-(2,6-dichloro-4-(3-methyl-1H-1,2,4-triazol-1-yl)benzamido)-3-(3-fluorophenyl)-2-oxobutanoic acid (75.6 mg, 0.162 mmol), 2,3-diaminotoluene (19.85 mg, 0.162 mmol) and HATU (61.8 mg, 0.162 mmol) in DMF (0.5 mL) and the mixture was stirred at room temperature for 2 h. AcOH (0.5 mL) was added to the reaction and heated to 100° C. for 8 h then allowed to cooled to ambient temperature overnight. The crude reaction was purified by preparative HPLC (reverse phase, YMC-Pack ODS C-18 100×20 mm) eluting with acetonitrile/water/0.1% TFA (10% to 80% organic in 10 min, then to 100% in 2 min, 20 mL/min). Volatiles were removed under reduced pressure. The resulting aqueous mixture was partitioned between aq sodium hydrogen carbonate and ethyl acetate. The combined organic extracts were back washed with water, separated, dried over Na$_2$SO$_4$, filtered and evaporated in vacuo. This was submitted for chiral resolution (OJ-H). The 2nd peak of 28 mg as one of the enantiomer. The 1st, 3rd and 4th peaks were further purified by preparative HPLC (reverse phase, YMC-Pack ODS C-18 100×20 mm) eluting with acetonitrile/water/0.1% TFA (15% to 85% organic in 10 min, then to 100% in 2 min, 20 mL/min). Related peaks were pooled and concentrated under reduced pressure and lyophilized to afford the 1st peak, 4th peak as another isomer and the 3rd peak as the title compound. LCMS calc.=551.11; found=551.10 (M+H)+. $^1$H NMR (499 MHz, DMSO-d6): 11.73 (s, 1H); δ 9.24 (s, 1H); 8.83 (d, J=5.8 Hz, 1H); 7.91 (s, 2H); 7.33-7.37 (m, 2H); 7.18-7.24 (m, 3H); 7.06 (d, J=2.6 Hz, 2H); 5.00 (t, J=7.7 Hz, 1H); 4.00 (t, J=6.8 Hz, 2H); 2.39 (s, 3H); 2.34 (s, 3H).

| Preparative Method: | Analytical Method: |
|---|---|
| OJ-H (2 × 25 cm) | OJ-H (25 × 0.46 cm) |
| 35% methanol/CO$_2$, 100 bar | 40% methanol/CO$_2$, 100 bar |
| 60 mL/min, 220 nm | 3 mL/min, 220 and 254 nm |

The following compound (Table 9) was synthesized using methods analogous to those described for EXAMPLE 115 from commercially available materials or intermediates whose syntheses are described above.

TABLE 9

| Example | Structure | Calc. (M + H)$^+$ | LCMS (M + H)$^+$ | hFIXa IC50 (nM) |
|---|---|---|---|---|
| 116 | 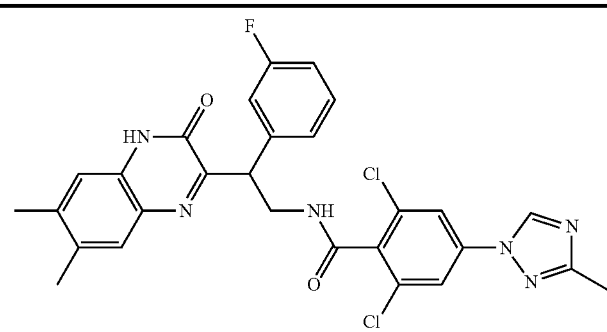 | 565.13 | 565.12 | 51.1 |

Determination of Inhibitory Activity Against Factor IXa

Formation of a clot to stem bleeding at a site of blood vessel injury involves the coordinated activity of a group of plasma proteins that initiate and propagate fibrin formation and subsequently protect fibrin from premature degradation. Factor IX is a key component of the plasma system that forms a fibrin clot at a site of vascular injury. The activity of Factor IXa is measured by monitoring the cleavage of the fluorescent peptide, CH$_3$SO$_2$-D-CHG-Gly-Arg-AFC.AcOH ("CHG" is cyclohexyl-glycine and "AFC" is trifluoro aminomethyl coumarin). Factor IXa cleaves the amide bond between Arg and AFC, thereby releasing the AFC fluorophore. The free AFC can be detected with a fluorescence detector at an excitation wavelength of 405 nM and emission wavelength of 510 nM.

What is claimed is:
1. A compound of Formula I:

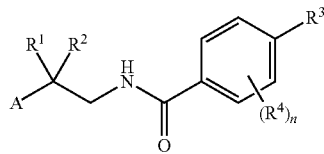

wherein A is selected from:

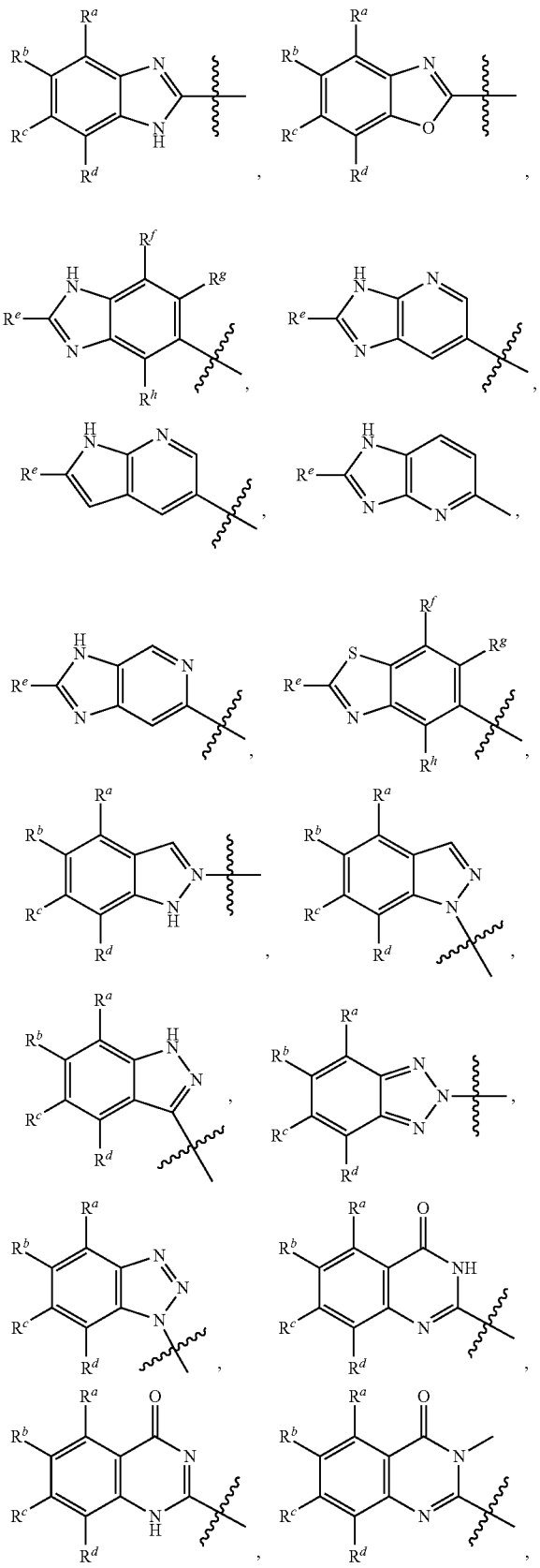

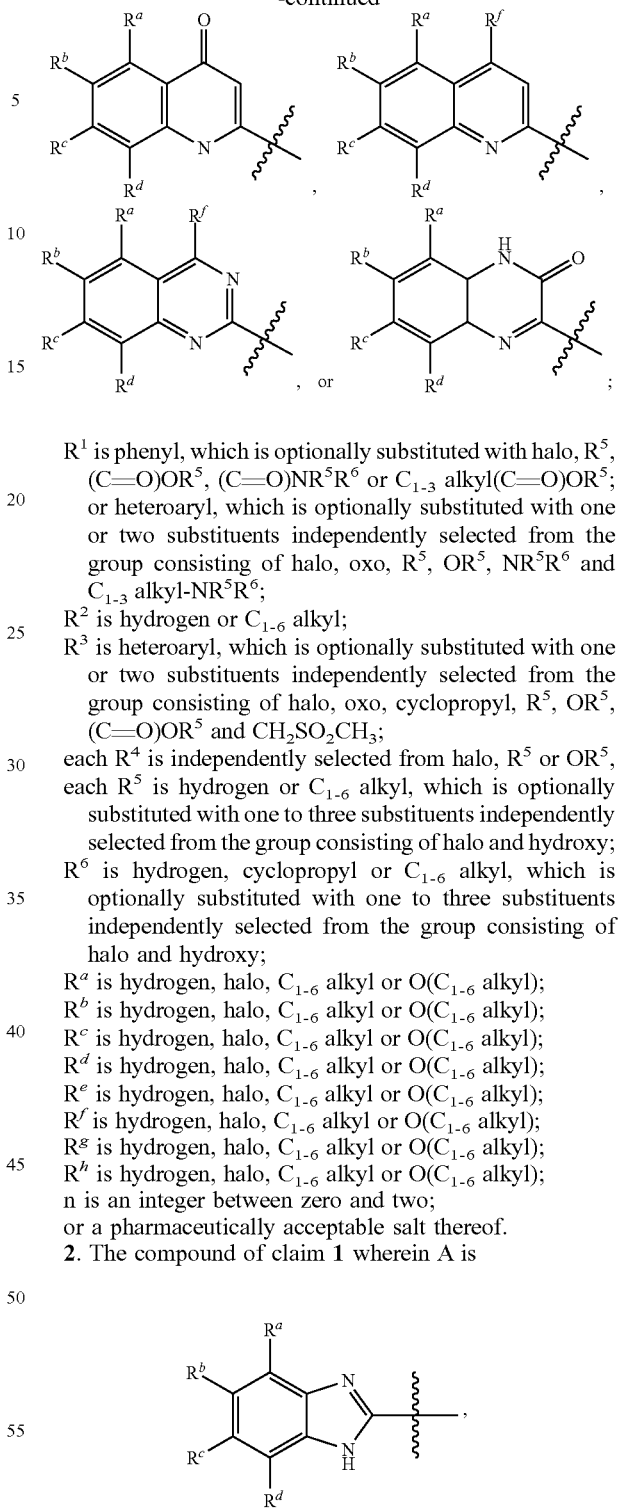

$R^1$ is phenyl, which is optionally substituted with halo, $R^5$, (C=O)OR$^5$, (C=O)NR$^5$R$^6$ or $C_{1-3}$ alkyl(C=O)OR$^5$; or heteroaryl, which is optionally substituted with one or two substituents independently selected from the group consisting of halo, oxo, $R^5$, OR$^5$, NR$^5$R$^6$ and $C_{1-3}$ alkyl-NR$^5$R$^6$;

$R^2$ is hydrogen or $C_{1-6}$ alkyl;

$R^3$ is heteroaryl, which is optionally substituted with one or two substituents independently selected from the group consisting of halo, oxo, cyclopropyl, $R^5$, OR$^5$, (C=O)OR$^5$ and CH$_2$SO$_2$CH$_3$;

each $R^4$ is independently selected from halo, $R^5$ or OR$^5$;

each $R^5$ is hydrogen or $C_{1-6}$ alkyl, which is optionally substituted with one to three substituents independently selected from the group consisting of halo and hydroxy;

$R^6$ is hydrogen, cyclopropyl or $C_{1-6}$ alkyl, which is optionally substituted with one to three substituents independently selected from the group consisting of halo and hydroxy;

$R^a$ is hydrogen, halo, $C_{1-6}$ alkyl or O($C_{1-6}$ alkyl);
$R^b$ is hydrogen, halo, $C_{1-6}$ alkyl or O($C_{1-6}$ alkyl);
$R^c$ is hydrogen, halo, $C_{1-6}$ alkyl or O($C_{1-6}$ alkyl);
$R^d$ is hydrogen, halo, $C_{1-6}$ alkyl or O($C_{1-6}$ alkyl);
$R^e$ is hydrogen, halo, $C_{1-6}$ alkyl or O($C_{1-6}$ alkyl);
$R^f$ is hydrogen, halo, $C_{1-6}$ alkyl or O($C_{1-6}$ alkyl);
$R^g$ is hydrogen, halo, $C_{1-6}$ alkyl or O($C_{1-6}$ alkyl);
$R^h$ is hydrogen, halo, $C_{1-6}$ alkyl or O($C_{1-6}$ alkyl);
n is an integer between zero and two;
or a pharmaceutically acceptable salt thereof.

2. The compound of claim 1 wherein A is or a pharmaceutically acceptable salt thereof.

3. The compound of claim 1 wherein $R^1$ is phenyl, which is optionally substituted with halo, (C=O)OR$^5$, (C=O)NR$^5$R$^6$ or $C_{1-3}$ alkyl(C=O)OR$^5$, or a pharmaceutically acceptable salt thereof.

4. The compound of claim 1 wherein $R^1$ is phenyl, which is optionally substituted with halo, or a pharmaceutically acceptable salt thereof.

5. The compound of claim 1 wherein $R^2$ is hydrogen, or a pharmaceutically acceptable salt thereof.

6. The compound of claim 1 wherein $R^4$ is halo; n is 2; or a pharmaceutically acceptable salt thereof.

7. The compound of claim 1 wherein $R^3$ is 1,2,3-triazolyl, 1,2,4-triazolyl, imidazolyl, tetrazolyl, pyridyl, pyrimidinyl, pyrazolyl, pyridazinyl, quinolinyl, triazolopyridinyl, triazolonyl, pyridinyl or benzoimidazolyl, wherein said groups are optionally substituted with halo, oxo, cyclopropyl, $R^5$, $OR^5$, (C=O)$OR^5$ or $CH_2SO_2CH_3$, or a pharmaceutically acceptable salt thereof.

8. A compound selected from
- (R)-2,6-Dichloro-N-(2-(5,6-dimethyl-1H-benzo[d]imidazol-2-yl)-2-phenylethyl)-4-(4-(2-hydroxyethyl)-1H-1,2,3-triazol-1-yl)benzamide;
- (R)-2,6-dichloro-N-[2-(5,6-dimethyl-1H-benzimidazol-2-yl)-2-phenylethyl]-4-(1H-tetrazol-1-yl)benzamide;
- (R)-2-chloro-N-[2-(5,6-dimethyl-1H-benzimidazol-2-yl)-2-phenylethyl]-4-[4-(2-hydroxyethyl)-1H-1,2,3-triazol-1-yl]benzamide;
- (R)-2-chloro-N-[2-(5,6-dimethyl-1H-benzimidazol-2-yl)-2-phenylethyl]-4-(3-methyl-1H-1,2,4-triazol-1-yl)-6-(trifluoromethyl)benzamide;
- (R)-2-chloro-N-[2-(5,6-dimethyl-1H-benzimidazol-2-yl)-2-phenylethyl]-4-(4H-1,2,4-triazol-4-yl)-6-(trifluoromethyl)benzamide;
- (R)-2,6-dichloro-N-[2-(5,6-dimethyl-1H-benzimidazol-2-yl)-2-phenylethyl]-4-(3-methyl-1H-1,2,4-triazol-1-yl)benzamide;
- (R)-2,6-dichloro-N-[2-(5,6-dimethyl-1H-benzimidazol-2-yl)-2-phenylethyl]-4-(4H-1,2,4-triazol-4-yl)benzamide;
- (R)-2-chloro-N-[2-(5,6-dimethyl-1H-benzimidazol-2-yl)-2-phenylethyl]-6-methyl-4-(3-methyl-1,2,4-triazol-1-yl)benzamide;
- (R)-2-chloro-N-[2-(5,6-dimethyl-1H-benzimidazol-2-yl)-2-phenylethyl]-6-methoxy-4-(4H-1,2,4-triazol-4-yl)benzamide;
- (R)-2-chloro-N-[2-(5,6-dimethyl-1H-benzimidazol-2-yl)-2-phenylethyl]-6-fluoro-4-(4H-1,2,4-triazol-4-yl)benzamide;
- (R)-2-chloro-N-[2-(5,6-dimethyl-1H-benzimidazol-2-yl)-2-phenylethyl]-6-methyl-4-(4H-1,2,4-triazol-4-yl)benzamide;
- (R)-2-chloro-N-[2-(5,6-dimethyl-1H-benzimidazol-2-yl)-2-phenylethyl]-4-(1H-tetrazol-1-yl)benzamide;
- (R)-2-chloro-N-[2-(6-chloro-1H-benzimidazol-2-yl)-2-(3-fluorophenyl)ethyl]-4-(3-methoxy-1H-1,2,4-triazol-1-yl)benzamide;
- (R)-2-chloro-N-[2-(5,6-dimethyl-1H-benzimidazol-2-yl)-2-phenylethyl]-4-(4H-1,2,4-triazol-4-yl)-6-(trifluoromethoxy)benzamide;
- (R)-2-chloro-N-[2-(6-chloro-4-methyl-1H-benzimidazol-2-yl)-2-(3-fluorophenyl)ethyl]-4-(3-methyl-4H-1,2,4-triazol-4-yl)benzamide;
- (±)-4-(3,5-dichloro-4-{[2-(5,6-dimethyl-1H-benzimidazol-2-yl)-2-phenylethyl]carbamoyl}phenyl)pyridine-2-carboxylic acid;
- (±)-2,6-dichloro-N-[2-(5,6-dimethyl-1H-benzimidazol-2-yl)-2-phenylethyl]-4-pyrimidin-5-ylbenzamide;
- (±)-2,6-dichloro-N-[2-(5,6-dimethyl-1H-benzimidazol-2-yl)-2-phenylethyl]-4-{-[(methyl sulfonyl)methyl]-1H-pyrazol-4-yl}benzamide;
- (±)-ethyl 4-(3,5-dichloro-4-{[2-(5,6-dimethyl-1H-benzimidazol-2-yl)-2-phenylethyl]carbamoyl}phenyl)pyridine-2-carboxylate;
- (±)-2,6-dichloro-N-[2-(5,6-dimethyl-1H-benzimidazol-2-yl)-2-phenylethyl]-4-(7-oxo-5,6,7,8-tetrahydro-1,8-naphthyridin-3-yl)benzamide;
- (±)-2,6-dichloro-N-[2-(5,6-dimethyl-1H-benzimidazol-2-yl)-2-phenylethyl]-4-[2-(2-fluoroethoxy)pyrimidin-5-yl]benzamide;
- (±)-2,6-dichloro-N-[2-(5,6-dimethyl-1H-benzimidazol-2-yl)-2-phenylethyl]-4-[5-(1-hydroxy-1-methylethyl)pyridin-3-yl]benzamide;
- (±)-methyl 5-(3,5-dichloro-4-{[2-(5,6-dimethyl-1H-benzimidazol-2-yl)-2-phenylethyl]carbamoyl}phenyl)pyridine-2-carboxylate;
- (±)-2,6-dichloro-N-[2-(5,6-dimethyl-1H-benzimidazol-2-yl)-2-phenylethyl]-4-(7-oxo-6,7-dihydro-5H-pyrrolo[3,4-b]pyridin-3-yl)benzamide;
- (±)-2,6-dichloro-N-[2-(5,6-dimethyl-1H-benzimidazol-2-yl)-2-phenylethyl]-4-quinolin-3-ylbenzamide;
- (±)-5-(3,5-dichloro-4-{[2-(5,6-dimethyl-1H-benzimidazol-2-yl)-2-phenylethyl]carbamoyl}phenyl)pyridine-2-carboxylic acid;
- (±)-2,6-dichloro-N-[2-(5,6-dimethyl-1H-benzimidazol-2-yl)-2-phenylethyl]-4-[1,2,4]triazolo[4,3-a]pyridin-6-ylbenzamide;
- (±)-2,6-dichloro-N-[2-(5,6-dimethyl-1H-benzimidazol-2-yl)-2-phenylethyl]-4-[1,2,4]triazolo[1,5-a]pyridin-7-ylbenzamide;
- (±)-2,6-dichloro-4-(2-cyclopropylpyrimidin-5-yl)-N-[2-(5,6-dimethyl-1H-benzimidazol-2-yl)-2-phenylethyl]benzamide;
- (±)-ethyl 4-(3-chloro-4-{[2-(5,6-dimethyl-1H-benzimidazol-2-yl)-2-phenylethyl]carbamoyl}phenyl)pyridine-2-carboxylate;
- (±)-2,6-dichloro-N-[2-(5,6-dimethyl-1H-benzimidazol-2-yl)-2-phenylethyl]-4-[1-(2-hydroxyethyl)-1H-pyrazol-4-yl]benzamide;
- (±)-2,6-dichloro-N-[2-(5,6-dimethyl-1H-benzimidazol-2-yl)-2-phenylethyl]-4-(1H-pyrazol-4-yl)benzamide;
- (±)-4-(3-chloro-4-{[2-(5,6-dimethyl-1H-benzimidazol-2-yl)-2-phenylethyl]carbamoyl}phenyl)pyridine-2-carboxylic acid;
- (±)-2,6-dichloro-N-[2-(5,6-dimethyl-1H-benzimidazol-2-yl)-2-phenylethyl]-4-[5-(hydroxymethyl)pyridin-3-yl]benzamide;
- (±)-2,6-dichloro-N-[2-(5,6-dimethyl-1H-benzimidazol-2-yl)-2-phenylethyl]-4-[6-(hydroxymethyl)pyridin-3-yl]benzamide;
- (±)-2,6-dichloro-N-[2-(5,6-dimethyl-1H-benzimidazol-2-yl)-2-phenylethyl]-4-[2-(hydroxymethyl)pyridin-4-yl]benzamide;
- (R)-2-chloro-N-[2-(5,6-dimethyl-1H-benzimidazol-2-yl)-2-phenylethyl]-4-(4H-1,2,4-triazol-4-yl)benzamide;
- (R)-2,6-dichloro-N-[2-(5,6-dimethyl-1H-benzimidazol-2-yl)-2-(5-fluoropyridin-3-yl)ethyl]-4-(4H-1,2,4-triazol-4-yl)benzamide;
- (±)-2,6-dichloro-N-[2-(6-chloro-1H-benzimidazol-2-yl)-2-(6-oxo-1,6-dihydropyridin-3-yl)ethyl]-4-(3-methyl-1H-1,2,4-triazol-1-yl)benzamide;
- (±)-2,6-Dichloro-N-(2-(6-chloro-1H-benzo[d]imidazol-2-yl)-2-(6-methoxypyridin-3-yl)ethyl)-4-(3-methyl-1H-1,2,4-triazol-1-yl)benzamide;
- (R)-4-(1-(6-Chloro-4-methyl-1H-benzo[d]imidazol-2-yl)-2-(2,6-dichloro-4-(3-methyl-1H-1,2,4-triazol-1-yl)benzamido)ethyl)benzoic acid;
- (R)-4-(1-(6-Chloro-4-methyl-1H-benzo[d]imidazol-2-yl)-2-(2,6-dichloro-4-(3-methyl-1H-1,2,4-triazol-1-yl)benzamido)ethyl)benzoic acid;

(R)-2,6-Dichloro-N-(2-(6-chlorobenzo[d]oxazol-2-yl)-2-(4-fluorophenyl)ethyl)-4-(4H-1,2,4-triazol-4-yl)benzamide;
(±)-2-chloro-N-[2-(5-methyl-1H-benzimidazol-2-yl)-2-phenylethyl]-4-(4H-1,2,4-triazol-4-yl)benzamide;
(±)-2-chloro-N-[2-(4-methyl-1H-benzimidazol-2-yl)-2-phenylethyl]-4-(4H-1,2,4-triazol-4-yl)benzamide;
(R)-2,6-dichloro-N-[2-(6-chloro-1H-benzimidazol-2-yl)-2-(3-fluorophenyl)ethyl]-4-(3-methyl-1H-1,2,4-triazol-1-yl)benzamide;
(R)-2,6-dichloro-N-[2-(6-chloro-4-methyl-1H-benzimidazol-2-yl)-2-(3-fluorophenyl)ethyl]-4-(3-methyl-1H-1,2,4-triazol-1-yl)benzamide;
(R)-2,6-dichloro-N-[2-(6-chloro-5-methoxy-1H-benzimidazol-2-yl)-2-(3-fluorophenyl)ethyl]-4-(3-methyl-1H-1,2,4-triazol-1-yl)benzamide;
(R)-2,6-dichloro-N-[2-(3-fluorophenyl)-2-(6-methoxy-1H-benzimidazol-2-yl)ethyl]-4-(3-methyl-1H-1,2,4-triazol-1-yl)benzamide;
(R)-2-chloro-N-[2-(5,6-dimethyl-1H-benzimidazol-2-yl)-2-(3-fluorophenyl)ethyl]-4-(4H-1,2,4-triazol-4-yl)benzamide;
(R)-2-chloro-N-[2-(5,6-dimethyl-1H-benzimidazol-2-yl)-2-(2-fluorophenyl)ethyl]-4-(4H-1,2,4-triazol-4-yl)benzamide;
(R)-2-chloro-N-[2-(5,6-dimethyl-1H-benzimidazol-2-yl)-2-(4-fluorophenyl)ethyl]-4-(4H-1,2,4-triazol-4-yl)benzamide;
(R)-2,6-dichloro-N-[2-(5,6-dimethyl-1H-benzimidazol-2-yl)-2-(4-fluorophenyl)ethyl]-4-(4H-1,2,4-triazol-4-yl)benzamide;
(R)-2,6-dichloro-N-[2-(6-chloro-5-methoxy-1H-benzimidazol-2-yl)-2-(3-fluorophenyl)ethyl]-4-(3-methyl-1H-1,2,4-triazol-1-yl)benzamide;
(±)-2-chloro-N-{2-(5,6-dimethyl-1H-benzimidazol-2-yl)-2-[6-(trifluoromethyl)pyridin-3-yl]ethyl}-4-(3-methyl-1H-1,2,4-triazol-1-yl)benzamide;
(R)-2-chloro-N-[2-(5,6-dimethyl-1H-benzimidazol-2-yl)-2-pyridin-3-ylethyl]-4-(4H-1,2,4-triazol-4-yl)benzamide;
(R)-2,6-dichloro-N-{2-(6-chloro-5-methoxy-1H-benzimidazol-2-yl)-2-[2-(dimethylamino)pyrimidin-5-yl]ethyl}-4-(3-methyl-1H-1,2,4-triazol-1-yl)benzamide;
(R)—N-[2-(4-carbamoylphenyl)-2-(6-chloro-5-methoxy-1H-benzimidazol-2-yl)ethyl]-2,6-dichloro-4-(3-methyl-1H-1,2,4-triazol-1-yl)benzamide;
(R)-3-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]benzoic acid;
(R)-4-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]benzoic acid;
(R)-2,6-dichloro-N-{2-(6-chloro-5-methoxy-1H-benzimidazol-2-yl)-2-[3-(methylcarbamoyl)phenyl]ethyl}-4-(3-methyl-1H-1,2,4-triazol-1-yl)benzamide;
(R)-{3-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]phenyl}acetic acid;
(R)-2,6-dichloro-N-{2-(6-chloro-5-methoxy-1H-benzimidazol-2-yl)-2-[4-(dimethylcarbamoyl)phenyl]ethyl}-4-(3-methyl-1H-1,2,4-triazol-1-yl)benzamide;
(R)-methyl {3-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]phenyl}acetate;
(R)-ethyl 4-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]benzoate;
(R)-ethyl 3-[1-(6-chloro-5-methoxy-1H-benzimidazol-2-yl)-2-({[2,6-dichloro-4-(3-methyl-1H-1,2,4-triazol-1-yl)phenyl]carbonyl}amino)ethyl]benzoate;
(R)-2,6-dichloro-N-{2-(6-chloro-5-methoxy-1H-benzimidazol-2-yl)-2-[3-(cyclopropylcarbamoyl)phenyl]ethyl}-4-(3-methyl-1H-1,2,4-triazol-1-yl)benzamide;
(±)-2-chloro-N-[2-[5,6-dimethyl-1,3-benzoxazol-2-yl]-2-(3-fluorophenyl)ethyl]-4-(4H-1,2,4-triazol-4-yl)benzamide;
(R)-2-chloro-N-(2-(5,6-dimethyl-1H-benzo[d]imidazol-2-yl)-2-phenylpropyl)-4-(4H-1,2,4-triazol-4-yl)benzamide;
((R)-2,6-Dichloro-N-(2-(5,6-dimethyl-1H-benzo[d]imidazol-2-yl)-2-(4-fluorophenyl)propyl)-4-(4H-1,2,4-triazol-4-yl)benzamide;
(±)-2,6-Dichloro-N-(2-(6-chloro-5-methoxy-1H-benzo[d]imidazol-2-yl)-2-(4-(hydroxymethyl)-1H-1,2,3-triazol-1-yl)ethyl)-4-(3-methyl-1H-1,2,4-triazol-1-yl)benzamide;
(±)-6-dichloro-N-[2-(6-chloro-5-methoxy-1H-benzimidazol-2-yl)-2-{4-[(dimethylamino)methyl]-1H-1,2,3-triazol-1-yl}ethyl]-4-(3-methyl-1H-1,2,4-triazol-1-yl)benzamide;
(±)-2,6-dichloro-N-{2-(6-chloro-5-methoxy-1H-benzimidazol-2-yl)-2-[4-(1-hydroxy-1-methylethyl)-1H-1,2,3-triazol-1-yl]ethyl}-4-(3-methyl-1H-1,2,4-triazol-1-yl)benzamide;
(R)-2,6-dichloro-N-(2-(5,6-dimethyl-1H-indol-2-yl)-2-phenylethyl)-4-(4H-1,2,4-triazol-4-yl)benzamide;
(R)-2,6-dichloro-N-(2-(3-fluorophenyl)-2-(2-methyl-1H-benzo[d]imidazol-5-yl)ethyl)-4-(3-methyl-1H-1,2,4-triazol-1-yl)benzamide;
(S)-2,6-dichloro-N-[2-(3-fluorophenyl)-2-(2-methyl-3H-imidazo[4,5-b]pyridin-6-yl)ethyl]-4-(3-methyl-1H-1,2,4-triazol-1-yl)benzamide;
(S)-2,6-dichloro-N-[2-(3-fluorophenyl)-2-(2-methyl-1H-pyrrolo[2,3-b]pyridin-5-yl)ethyl]-4-(3-methyl-1H-1,2,4-triazol-1-yl)benzamide;
(S)-2,6-dichloro-N-[2-(4-fluoro-2-methyl-1H-benzimidazol-5-yl)-2-(3-fluorophenyl)ethyl]-4-(3-methyl-1H-1,2,4-triazol-1-yl)benzamide;
(S)-2,6-dichloro-N-[2-(7-fluoro-2-methyl-1H-benzimidazol-5-yl)-2-(3-fluorophenyl);
(R)-2,6-dichloro-N-[2-(3-fluorophenyl)-2-(2-methyl-1H-imidazo[4,5-b]pyridin-5-yl)ethyl]-4-(3-methyl-1H-1,2,4-triazol-1-yl)benzamide;
(±)-2,6-dichloro-N-[2-(3-fluorophenyl)-2-(2-methyl-3H-imidazo[4,5-c]pyridin-6-yl)ethyl]-4-(3-methyl-1H-1,2,4-triazol-1-yl)benzamide;
(S)-2,6-dichloro-N-[2-(2,7-dimethyl-1H-benzimidazol-5-yl)-2-(3-fluorophenyl)ethyl]-4-(3-methyl-1H-1,2,4-triazol-1-yl)benzamide;
(R)-2,6-dichloro-N-(2-(3-fluorophenyl)-2-(2-methyl-benzo[d]thiazol-5-yl)ethyl)-4-(3-methyl-1H-1,2,4-triazol-1-yl)benzamide;
(R)-2-chloro-N-(2-(5-methyl-2H-indazol-2-yl)-2-phenylethyl)-4-(4H-1,2,4-triazol-4-yl)benzamide;
(S)-2-chloro-N-(2-(5-methyl-1-indazol-1-yl)-2-phenylethyl)-4-(4H-1,2,4-triazol-4-yl)benzamide;
(R)-2,6-dichloro-4-(4-(2-hydroxyethyl)-1H-1,2,3-triazol-1-yl)-N-(2-(5-methyl-1H-indazol-1-yl)-2-(oxazol-5-yl)ethyl)benzamide;
(R)-2-chloro-N-[2-(3-fluorophenyl)-2-(6-methyl-1H-indol-3-yl)ethyl]-4-(4H-1,2,4-triazol-4-yl)benzamide;

(S)-2-chloro-N-(2-(6-methyl-1H-indazol-3-yl)-2-phenylethyl)-4-(4H-1,2,4-triazol-4-yl)benzamide;

(R)-2,6-dichloro-N-(2-(5-methyl-2H-benzo[d][1,2,3]triazol-2-yl)-2-phenylethyl)-4-(4H-1,2,4-triazol-4-yl)benzamide;

(S)-2,6-dichloro-N-(2-(5-methyl-1H-benzo[d][1,2,3]triazol-1-yl)-2-phenylethyl)-4-(4H-1,2,4-triazol-4-yl)benzamide;

(R)-2-Chloro-N-(2-(6-methyl-4-oxo-3,4-dihydroquinazolin-2-yl)-2-phenylethyl)-4-(4H-1,2,4-triazol-4-yl)benzamide;

(R)-2,6-dichloro-N-(2-(8-fluoro-5-methyl-4-oxo-3,4-dihydroquinazolin-2-yl)-2-(3-fluorophenyl)ethyl)-4-(3-methyl-1H-1,2,4-triazol-1-yl)benzamide;

(R)-2,6-dichloro-N-(2-(8-fluoro-5-methyl-4-oxo-3,4-dihydroquinazolin-2-yl)-2-(4-fluorophenyl)ethyl)-4-(3-methyl-1H-1,2,4-triazol-1-yl)benzamide;

(R)-2,6-dichloro-N-(2-(5-chloro-8-fluoro-4-oxo-3,4-dihydroquinazolin-2-yl)-2-(3-fluorophenyl)ethyl)-4-(3-methyl-1H-1,2,4-triazol-1-yl)benzamide;

(±)-2-chloro-N-[2-(7-chloro-4-oxo-3,4-dihydroquinazolin-2-yl)-2-phenylethyl]-4-(4H-1,2,4-triazol-4-yl)benzamide;

(R)-2-chloro-N-[2-(6-chloro-4-oxo-3,4-dihydroquinazolin-2-yl)-2-phenylethyl]-4-(4H-1,2,4-triazol-4-yl)benzamide;

(R)-2-chloro-N-[2-(5-chloro-4-oxo-3,4-dihydroquinazolin-2-yl)-2-phenylethyl]-4-(4H-1,2,4-triazol-4-yl)benzamide;

(R)-2-chloro-N-[2-(8-chloro-4-oxo-3,4-dihydroquinazolin-2-yl)-2-phenylethyl]-4-(4H-1,2,4-triazol-4-yl)benzamide;

(R)-2-chloro-N-[2-(5,8-dichloro-4-oxo-3,4-dihydroquinazolin-2-yl)-2-phenylethyl]-4-(4H-1,2,4-triazol-4-yl)benzamide;

(R)-2-chloro-N-[2-(5-methyl-4-oxo-3,4-dihydroquinazolin-2-yl)-2-phenylethyl]-4-(4H-1,2,4-triazol-4-yl)benzamide;

(±)-2-chloro-N-[2-(8-fluoro-5-methyl-4-oxo-3,4-dihydroquinazolin-2-yl)-2-phenylethyl]-4-(4H-1,2,4-triazol-4-yl)benzamide;

(R)-2-chloro-N-[2-(8-fluoro-5-methyl-4-oxo-3,4-dihydroquinazolin-2-yl)-2-phenylethyl]-4-(3-methyl-1H-1,2,4-triazol-1-yl)benzamide;

(R)-2-chloro-N-[2-(8-fluoro-5-methyl-4-oxo-3,4-dihydroquinazolin-2-yl)-2-(3-fluorophenyl)ethyl]-4-(3-methyl-1H-1,2,4-triazol-1-yl)benzamide;

(R)-1-(3-chloro-4-{[2-(5-chloro-8-fluoro-4-oxo-3,4-dihydroquinazolin-2-yl)-2-(3-fluorophenyl)ethyl]carbamoyl}phenyl)-1H-benzimidazole-6-carboxylic acid;

(R)-1-(3-chloro-4-{[2-(5-chloro-8-fluoro-4-oxo-3,4-dihydroquinazolin-2-yl)-2-(3-fluorophenyl)ethyl]carbamoyl}phenyl)-1H-benzimidazole-5-carboxylic acid;

(R)-2,6-dichloro-N-(2-(8-fluoro-5-methyl-4-oxo-1,4-dihydroquinolin-2-yl)-2-(3-fluorophenyl)ethyl)-4-(3-methyl-1H-1,2,4-triazol-1-yl)benzamide;

(R)-2,6-dichloro-N-[2-(8-fluoro-5-methylquinolin-2-yl)-2-(3-fluorophenyl)ethyl]-4-(3-methyl-1H-1,2,4-triazol-1-yl)benzamide;

(R)-2,6-dichloro-N-[2-(8-fluoro-4-methoxy-5-methylquinolin-2-yl)-2-(3-fluorophenyl)ethyl]-4-(3-methyl-1H-1,2,4-triazol-1-yl)benzamide;

(R or S)-2,6-Dichloro-N-(2-(3-fluorophenyl)-2-(5-methyl-3-oxo-3,4-dihydroquinoxalin-2-yl)ethyl)-4-(3-methyl-1H-1,2,4-triazol-1-yl)benzamide 2,2,2-trifluoroacetate;

(R or S)-2,6-dichloro-N-[2-(6,7-dimethyl-3-oxo-3,4-dihydroquinoxalin-2-yl)-2-(3-fluorophenyl)ethyl]-4-(3-methyl-1H-1,2,4-triazol-1-yl)benzamide;

(R)-2-chloro-N-(2-(8-fluoro-5-methyl-4-oxo-3,4-dihydroquinazolin-2-yl)-2-(3-fluorophenyl)ethyl)-4-(pyridazin-4-yl)benzamide (R)-2-chloro-N-(2-(8-fluoro-5-methyl-4-oxo-3,4-dihydroquinazolin-2-yl)-2-(3-fluorophenyl)ethyl)-4-(4-(2-hydroxyethyl)-1H-imidazol-1-yl)benzamide (R)-2-chloro-N-(2-(8-fluoro-5-methyl-4-oxo-3,4-dihydroquinazolin-2-yl)-2-(3-fluorophenyl)ethyl)-4-(1-methyl-6-oxo-1,6-dihydropyridin-3-yl)benzamide (R)-2-chloro-N-(2-(8-fluoro-5-methyl-4-oxo-3,4-dihydroquinazolin-2-yl)-2-(3-fluorophenyl)ethyl)-4-(1-methyl-5-oxo-1,5-dihydro-4H-1,2,4-triazol-4-yl)benzamide (R)-2,6-dichloro-N-(2-(8-fluoro-3,5-dimethyl-4-oxo-3,4-dihydroquinazolin-2-yl)-2-(pyridin-3-yl)ethyl)-4-(3-methyl-1H-1,2,4-triazol-1-yl)benzamide (R)-2-chloro-4-(3-(difluoromethyl)-4H-1,2,4-triazol-4-yl)-N-(2-(8-fluoro-5-methyl-4-oxo-3,4-dihydroquinazolin-2-yl)-2-(3-fluorophenyl)ethyl)benzamide or a pharmaceutically acceptable salt thereof.

9. A pharmaceutical composition comprising a compound of claim 1 or a pharmaceutically acceptable salt thereof and a pharmaceutically acceptable carrier.

10. A method for inhibiting thrombus formation in blood or treating thrombus formation in blood comprising administering a composition of claim 9 to a mammal in need of thereof.

11. A method of treating venous thromboembolism and pulmonary embolism in a mammal comprising administering a composition of claim 9 to a mammal in need thereof.

12. A method of treating deep vein thrombosis in a mammal comprising administering a composition of claim 9 to a mammal in need thereof.

13. A method of treating thromboembolic stroke in a human comprising administering a composition of claim 9 to a mammal in need thereof.

14. A method of inhibiting Factor IXa comprising administering a composition of Compound 9 to a mammal in need thereof.

* * * * *